United States Patent
Sinclair et al.

(10) Patent No.: US 11,957,703 B2
(45) Date of Patent: Apr. 16, 2024

(54) MODULATING NUDIX HOMOLOGY DOMAIN (NHD) WITH NICOTINAMIDE MONONUCLEOTIDE ANALOGS AND DERIVATIVES OF SAME

(71) Applicants: President and Fellows of Harvard College, Cambridge, MA (US); Metro International Biotech, LLC, Worcester, MA (US)

(72) Inventors: David A. Sinclair, Chestnut Hill, MA (US); Jun Li, Brookline, MA (US); Karl D. Normington, Prides Crossing, MA (US)

(73) Assignees: President and Fellows of Harvard College, Cambridge, MA (US); Metro International Biotech, LLC, Worcester, MA (US)

( * ) Notice: Subject to any disclaimer, the term of this patent is extended or adjusted under 35 U.S.C. 154(b) by 0 days.

(21) Appl. No.: 17/737,541

(22) Filed: May 5, 2022

(65) Prior Publication Data
US 2023/0293569 A1 Sep. 21, 2023

Related U.S. Application Data

(63) Continuation of application No. 16/475,832, filed as application No. PCT/US2018/012182 on Jan. 3, 2018, now abandoned.

(60) Provisional application No. 62/442,247, filed on Jan. 4, 2017.

(51) Int. Cl.
*A61K 31/7084* (2006.01)
*A61K 31/706* (2006.01)

(52) U.S. Cl.
CPC ........ *A61K 31/7084* (2013.01); *A61K 31/706* (2013.01)

(58) Field of Classification Search
None
See application file for complete search history.

(56) References Cited

FOREIGN PATENT DOCUMENTS

| WO | WO-2006/105440 A2 | 10/2006 |
|---|---|---|
| WO | WO-2014/059034 A2 | 4/2014 |
| WO | WO-2015/070280 A1 | 5/2015 |
| WO | WO-2018/129039 A1 | 7/2018 |
| WO | WO-2018/129040 A1 | 7/2018 |

OTHER PUBLICATIONS

Chini, Eduardo Nunes, et al. "Deleted in breast cancer-1 (DBC-1) in the interface between metabolism, aging and cancer." Bioscience reports 33.4 (2013): e00058.*
Fang et al., "NAD+ Replenishment Improves Lifespan and Healthspan in Ataxia Telangiectasia Models via Mitophagy and DNA Repair," Cell Metabolism 24(4):566-581 (2016).
International Preliminary Report on Patentability for International Application No. PCT/US2018/012181 dated Jul. 9, 2019.
International Preliminary Report on Patentability for International Application No. PCT/US2018/012182 dated Jul. 9, 2019.
International Search Report and Written Opinion for Internationak Application No. PCT/US2018/012181 dated May 30, 2018.
International Search Report and Written Opinion for International Application No. PCT/US2018/012182 dated May 30, 2018.
Li et al., "A Conserved NAD + Binding Pocket that Regulates Protein-Protein Interactions During Aging," Science 355(6331): 1312-1317 (2017).
Luna et al., "SIRT1/PARP1 Crosstalk: Connecting DNA Damage and Metabolism," Genome Integrity 4(1):6 (2013).
Mendelshon et al., "The NAD+/PARP1/SIRT1 Axis in Aging," Rejunenation Research 20(3): 244-247 (2017).
Wang et al., "NAD+ administration decreases doxorubicin-induced liver damage of mice by enhancing antioxidation capacity and decreasing DNA damage," Chemico-Biological Interactions, 212: 65-71 (2014).
Yuan et al., "Regulation of SIRT1 Activity by Genotoxic Stress." Genes and Development 26(8):791-796 (2012).

* cited by examiner

*Primary Examiner* — Patrick T Lewis
(74) *Attorney, Agent, or Firm* — Foley Hoag LLP; DeAnn F. Smith; Allison L. Gilder

(57) ABSTRACT

The invention provides methods of modulating and regulating NHD protein-protein interactions through nicotinamide mononucleotide, analogs and derivatives thereof, such as $NAD^+$. Such modulation may be useful in methods of treating and preventing cancer, aging, cell death, radiation damage, radiation exposure, among others, may improve DNA repair, cell proliferation, cell survival, among others, and may increase the life span of a cell or protect it against certain stresses, among others.

15 Claims, 55 Drawing Sheets
Specification includes a Sequence Listing.

Homology model of DBC1-NHD

FIG. 9B

| Lane | Protein | Number of Spectra | Number of unique peptides | Coverage (%) |
|---|---|---|---|---|
| 5 | PARP1 | 79 | 44 | 46.2 |
|   | DBC1 | 28 | 15 | 40.7 |
| 11 | PARP1 | 52 | 34 | 40.0 |
|   | DBC1 | 19 | 14 | 35.0 |
|   | MACROD1 | 28 | 16 | 30.8 |
| 12 | MACROD1 | 26 | 14 | 24.9 |

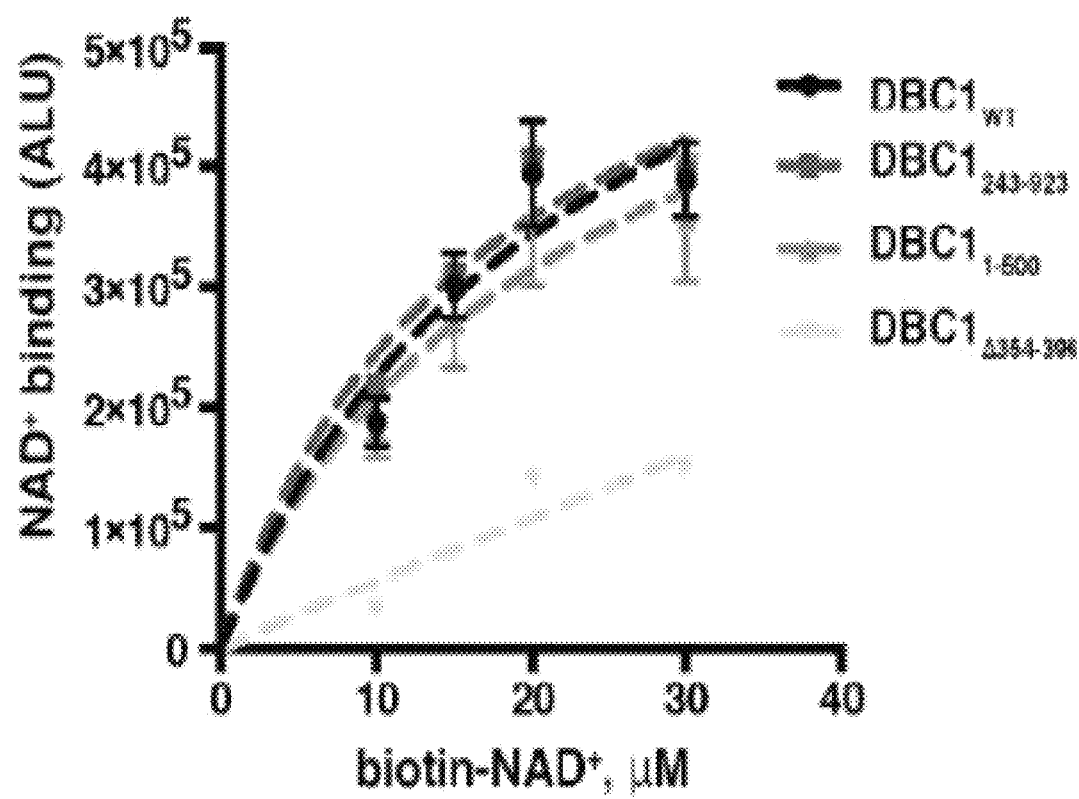

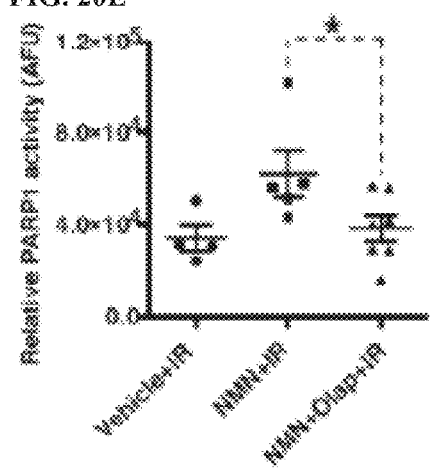

SEQUENCE LISTING

<160> NUMBER OF SEQ ID NOS: 40

<210> SEQ ID NO 1
<211> LENGTH: 264
<212> TYPE: PRT
<213> ORGANISM: Homo sapiens

<400> SEQUENCE: 1

Ser Asp Pro Ala Tyr Ser Ser Lys Val Leu Leu Leu Ser Ser Pro Gly

```
1               5                   10                  15
Leu Glu Glu Leu Tyr Arg Cys Cys Met Leu Phe Val Asp Asp Met Ala
                20                  25                  30

Glu Pro Arg Glu Thr Pro Glu His Pro Leu Lys Gln Ile Lys Phe Leu
            35                  40                  45

Leu Gly Arg Lys Glu Glu Ala Val Leu Val Gly Gly Glu Trp Ser
        50                  55                  60

Pro Ser Leu Asp Gly Leu Asp Pro Gln Ala Asp Pro Gln Val Leu Val
65                  70                  75                  80

Arg Thr Ala Ile Arg Cys Ala Gln Ala Gln Thr Gly Ile Asp Leu Ser
                85                  90                  95

Gly Cys Thr Lys Trp Trp Arg Phe Ala Glu Phe Gln Tyr Leu Gln Pro
                100                 105                 110

Gly Pro Pro Arg Arg Leu Gln Thr Val Val Tyr Leu Pro Asp Val
            115                 120                 125

Trp Thr Ile Met Pro Thr Leu Glu Glu Trp Glu Ala Leu Cys Gln Gln
            130                 135                 140

Lys Ala Glu Ala Ala Pro Pro Thr Gln Glu Ala Gln Gly Glu Thr
145                 150                 155                 160

Glu Pro Thr Glu Gln Ala Pro Asp Ala Leu Glu Gln Ala Ala Asp Thr
                165                 170                 175

Ser Arg Arg Asn Ala Glu Thr Pro Glu Ala Thr Thr Gln Gln Glu Thr
            180                 185                 190

Asp Thr Asp Leu Pro Glu Ala Pro Pro Pro Leu Glu Pro Ala Val
            195                 200                 205

Ile Ala Arg Pro Gly Cys Val Asn Leu Ser Leu His Gly Ile Val Glu
            210                 215                 220

Asp Arg Arg Pro Lys Glu Arg Ile Ser Phe Glu Val Met Val Leu Ala
225                 230                 235                 240

Glu Leu Phe Leu Glu Met Leu Gln Arg Asp Phe Gly Tyr Arg Val Tyr
                245                 250                 255

Lys Met Leu Leu Ser Leu Pro Glu
                260

<210> SEQ ID NO 2
<211> LENGTH: 266
<212> TYPE: PRT
<213> ORGANISM: Monodelphis domestica

<400> SEQUENCE: 2

Ser Asp Met Thr Tyr Ser Ala Lys Val Leu Leu Ser Ser Pro Gly
1               5                   10                  15

Leu Glu Glu Leu Tyr Arg Cys Cys Leu Leu Phe Val Glu Asp Met Ala
                20                  25                  30

Glu Pro Arg Glu Ser Pro Glu His Pro Leu Lys Gln Ile Lys Phe Leu
            35                  40                  45

Leu Arg Arg Lys Glu Asp Glu Ala Val Met Val Gly Gly Glu Trp Ser
        50                  55                  60

Pro Ser Leu Asp Gly Pro Asp Pro Lys Ala Asp Pro Gln Val Leu Val
65                  70                  75                  80

Arg Thr Ala Ile Arg Cys Ala Arg Ala Gln Thr Gly Ile Asp Leu Ser
                85                  90                  95

Asn Cys Thr Lys Trp Trp Arg Ile Ala Glu Phe Arg Tyr Ile Gln Leu
            100                 105                 110
```

```
Gly Pro Pro Arg Arg Gln Arg Thr Val Val Tyr Leu Pro Asp Ile
            115                 120                 125

Trp Thr Leu Met Pro Ser Leu Glu Glu Trp Glu Ala Leu Cys Gln Gln
130                 135                 140

Lys Val Ala Glu Thr Val Ala Pro Leu Gln Asp Thr Val Met Glu Ala
145                 150                 155                 160

Glu Ala Ser Val Glu Glu Thr Asn Ser Ser Glu Leu Gly Ala Ala Ala
                165                 170                 175

Glu Ala Ser Glu Gln Asp Pro Glu Asn Pro Glu Leu Ser Leu Gln Gln
            180                 185                 190

Glu Met Asp Pro Ser Leu Pro Glu Ala Pro Pro Pro Leu Glu Pro
            195                 200                 205

Val Ile Ile Ala Gln Pro Gly Cys Thr Asn Phe Ser Leu His Ala Leu
    210                 215                 220

Leu Glu Asp Arg Arg Pro Arg Glu Lys Ile Ser Phe Glu Val Met Val
225                 230                 235                 240

Leu Ala Ala Leu Phe Gln Glu Met Leu Gln Arg Asp Phe Gly Tyr Lys
                245                 250                 255

Ile Tyr Lys Met Leu Leu Ser Leu Pro Glu
            260                 265

<210> SEQ ID NO 3
<211> LENGTH: 277
<212> TYPE: PRT
<213> ORGANISM: Anolis carolinensis

<400> SEQUENCE: 3

Thr Asn Ser Ser Phe Ser Ala Lys Val Leu Leu Ser Ser Pro Gly
1               5                   10                  15

Leu Glu Glu Phe Tyr Arg His Cys Leu Gln Tyr Ile Asp Asp Pro Ser
                20                  25                  30

Asp Gln Arg Glu Ser Pro Glu His Pro Ala Lys Gln Ile Lys Phe Leu
            35                  40                  45

Leu Gly Lys Lys Ala Asp Glu Thr Val Leu Ile Gly Gly Glu Trp Ser
50                  55                  60

Pro Ser Leu Asp Gly Pro Asp Pro Ala Ala Asn Pro Met Val Leu Ile
65                  70                  75                  80

Arg Thr Ala Ile Arg Cys Thr Lys Val Gln Thr Gly Leu Asp Leu Thr
                85                  90                  95

Gly Cys Thr Lys Trp Leu Arg Phe Ala Glu Phe Arg Tyr Leu Arg Glu
            100                 105                 110

Gly Asn Pro Ser His Gln Glu Gln Thr Val Val Phe Leu Pro Asp Val
        115                 120                 125

Trp Ser Cys Met Pro Ser Leu Glu Glu Trp Glu Ala Leu Cys Lys Gln
130                 135                 140

Lys Ala Glu Lys Asn Pro Ser Ala Pro Pro Gln Glu Glu Thr Ala Val
145                 150                 155                 160

Met Glu Glu Ala Glu Gln Ser Ser Glu Thr Gly Leu Glu Gln Glu Thr
                165                 170                 175

Glu Thr Ser Glu Gln Glu Ala Glu Thr Ala Asp Pro Ala Pro Glu Pro
            180                 185                 190

Gly Val Glu Thr Ser Pro Ser Glu Pro Glu Ala Ser Ser Pro Pro Leu
        195                 200                 205

Glu Pro Ala Ile Ile Ala Ser Pro Lys Pro Ala Leu Gln Gly Gly Gln
    210                 215                 220
```

Pro Ser Cys Thr Asn Leu Ser Leu Trp Thr Leu Glu Tyr Arg Arg
225                 230                 235                 240

Gln Arg Glu Lys Leu Ser Phe Glu Val Ala Val Ala Ala Glu Phe Phe
            245                 250                 255

Gln Glu Met Met Gln Arg Asp Phe Gly Tyr Lys Leu Tyr Lys Ala Leu
        260                 265                 270

Leu Ala Leu Pro Glu
        275

<210> SEQ ID NO 4
<211> LENGTH: 268
<212> TYPE: PRT
<213> ORGANISM: Chelonia mydas

<400> SEQUENCE: 4

Ala Asp Pro Ala Phe Ser Ala Lys Val Met Leu Leu Ser Ser Pro Gly
1               5                   10                  15

Leu Glu Glu Leu Tyr Arg His Cys Leu Leu Tyr Ile Glu Glu Pro Ser
            20                  25                  30

Glu Gln Lys Glu Ser Pro Glu His Pro Thr Lys Gln Ile Lys Phe Leu
        35                  40                  45

Leu Gly Arg Lys Glu Asp Glu Ala Val Leu Ile Gly Gly Glu Trp Ser
    50                  55                  60

Pro Ser Leu Asp Gly Pro Glu Pro Asp Ser Asp Pro Met Val Leu Val
65                  70                  75                  80

Arg Thr Ala Ile Arg Cys Thr Lys Ala Gln Thr Gly Leu Asp Leu Ser
                85                  90                  95

Ala Cys Thr Lys Trp Phe Arg Phe Ala Glu Phe Arg Tyr Leu Arg Arg
            100                 105                 110

Gly Asp Pro Leu Gln Arg Glu Thr Ala Val Ile Phe Leu Pro Asp Val
        115                 120                 125

Trp Ser Cys Met Pro Ser Leu Glu Glu Trp Ala Leu Cys Gln Gln
    130                 135                 140

Lys Ala Glu Lys Ala Pro Leu Pro Ser Pro Ser Pro Glu Glu Lys Ala
145                 150                 155                 160

Glu Met Asp Val Glu Ile Pro Glu Ala Ala Pro Asp Gln Glu Met Glu
                165                 170                 175

Ala Asn Ala Gln Glu Val Asn Ala Thr Asp Ala Ala Ala Glu Pro Glu
            180                 185                 190

Ala Pro Thr Pro Pro Leu Glu Pro Ala Ile Val Ala Pro Pro Lys Lys
        195                 200                 205

Pro Ala Met Gln Gly Gly Gln Pro Ser Cys Ser Asn Leu Ser Leu Cys
    210                 215                 220

Thr Leu Leu Glu Tyr Arg Arg Gln Arg Glu Lys Leu Ser Phe Glu Val
225                 230                 235                 240

Ala Val Met Ala Glu Leu Phe Gln Glu Met Leu Gln Arg Asp Phe Gly
                245                 250                 255

Tyr Arg Leu Tyr Lys Ala Leu Leu Ala Leu Pro Glu
            260                 265

<210> SEQ ID NO 5
<211> LENGTH: 211
<212> TYPE: PRT
<213> ORGANISM: Danio rerio

<400> SEQUENCE: 5

Thr Asp Asp Ala Phe Ala Val Arg Val Leu Leu Phe Ser Met Pro Cys
1               5                   10                  15

Leu Glu Asp Val Tyr Ser Gln Cys Cys Asn Leu Ser Asn Asp Gly Gln
            20                  25                  30

Thr Gln Lys Glu Ala Val His Pro Ser Thr Leu Leu Lys Phe Leu Ile
        35                  40                  45

Val Asp Ser Gly Gly Glu Gln Arg Leu Pro Gly Gly His Trp Ser Pro
50                  55                  60

Glu Ala Asp Gly Ala Asn Pro Ala Lys Asp Ser Leu Thr Leu Val Asn
65                  70                  75                  80

Thr Ala Val Arg Cys Leu Lys Glu Gln Ala Gly Leu Asp Leu Ser Ala
                85                  90                  95

Cys Thr Gln Trp Tyr Lys Met Ala Glu Leu Arg Tyr Leu Ser Gly Asp
            100                 105                 110

Lys Val Glu Thr Val Val Leu Met Pro Asp Val Trp Asn Leu Val
        115                 120                 125

Pro Ser Glu Glu Glu Trp Ala Ser Leu Gln Leu Glu Asp Asp Leu Ser
        130                 135                 140

Leu Pro Glu Ser Pro Ser Val Val Phe His Pro Ser Ala Gly Leu Asn
145                 150                 155                 160

Leu Ser Ala Val Ser Leu Ser Ser Leu Leu Glu Pro Gln Thr Leu Gln
                165                 170                 175

Thr Arg Asp Ser Cys Glu Val Ser Leu Ile Ala Glu Met Phe Ser Glu
            180                 185                 190

Met Leu Gln Arg Asp Phe Gly Leu Gln Leu Tyr Arg Cys Leu Cys Ser
        195                 200                 205

Leu Pro Gln
        210

<210> SEQ ID NO 6
<211> LENGTH: 355
<212> TYPE: PRT
<213> ORGANISM: Homo sapiens

<400> SEQUENCE: 6

Ala Asp His Leu Tyr Ser Ala Lys Val Met Leu Met Ala Ser Pro Ser
1               5                   10                  15

Met Glu Asp Leu Tyr His Lys Ser Cys Ala Leu Ala Glu Asp Pro Gln
            20                  25                  30

Glu Leu Arg Asp Gly Phe Gln His Pro Ala Arg Leu Val Lys Phe Leu
        35                  40                  45

Val Gly Met Lys Gly Lys Asp Glu Ala Met Ala Ile Gly Gly His Trp
50                  55                  60

Ser Pro Ser Leu Asp Gly Pro Asp Pro Glu Lys Asp Pro Ser Val Leu
65                  70                  75                  80

Ile Lys Thr Ala Ile Arg Cys Cys Lys Ala Leu Thr Gly Ile Asp Leu
                85                  90                  95

Ser Val Cys Thr Gln Trp Tyr Arg Phe Ala Glu Ile Arg Tyr His Arg
            100                 105                 110

Pro Glu Glu Thr His Lys Gly Arg Thr Val Pro Ala His Val Glu Thr
        115                 120                 125

Val Val Leu Phe Phe Pro Asp Val Trp His Cys Leu Pro Thr Arg Ser
130                 135                 140

Glu Trp Glu Thr Leu Ser Arg Gly Tyr Lys Gln Gln Leu Val Glu Lys

```
                 145                 150                 155                 160
Leu Gln Gly Glu Arg Lys Glu Ala Asp Gly Glu Gln Asp Glu Glu
                165                 170                 175
Lys Asp Asp Gly Glu Ala Lys Glu Ile Ser Thr Pro Thr His Trp Ser
                180                 185                 190
Lys Leu Asp Pro Lys Thr Met Lys Val Asn Asp Leu Arg Lys Glu Leu
                195                 200                 205
Glu Ser Arg Ala Leu Ser Ser Lys Gly Leu Lys Ser Gln Leu Ile Ala
                210                 215                 220
Arg Leu Thr Lys Gln Leu Lys Val Glu Glu Lys Glu Gln Lys
225                 230                 235                 240
Glu Leu Glu Lys Ser Glu Lys Glu Asp Glu Asp Asp Arg Lys
                245                 250                 255
Ser Glu Asp Asp Lys Glu Glu Glu Arg Lys Arg Gln Glu Glu Ile
                260                 265                 270
Glu Arg Gln Arg Arg Glu Arg Arg Tyr Ile Leu Pro Asp Glu Pro Ala
                275                 280                 285
Ile Ile Val His Pro Asn Trp Ala Ala Lys Ser Gly Lys Phe Asp Cys
                290                 295                 300
Ser Ile Met Ser Leu Ser Val Leu Leu Asp Tyr Arg Leu Glu Asp Asn
305                 310                 315                 320
Lys Glu His Ser Phe Glu Val Ser Leu Phe Ala Glu Leu Phe Asn Glu
                325                 330                 335
Met Leu Gln Arg Asp Phe Gly Val Arg Ile Tyr Lys Ser Leu Leu Ser
                340                 345                 350
Leu Pro Glu
        355

<210> SEQ ID NO 7
<211> LENGTH: 354
<212> TYPE: PRT
<213> ORGANISM: Monodelphis domestica

<400> SEQUENCE: 7

Ala Asp His Leu Tyr Ser Ala Lys Val Met Leu Met Ala Ser Pro Ser
1               5                   10                  15
Met Glu Asp Leu Tyr His Lys Ser Cys Ala Leu Ala Glu Asp Pro Gln
                20                  25                  30
Glu Leu Arg Asp Gly Phe Gln His Pro Ala Arg Leu Val Lys Phe Leu
                35                  40                  45
Val Gly Met Lys Gly Lys Asp Glu Ala Met Ala Ile Gly Gly His Trp
            50                  55                  60
Ser Pro Ser Leu Asp Gly Pro Asp Pro Glu Lys Asp Pro Ser Val Leu
65                  70                  75                  80
Ile Lys Thr Ala Ile Arg Cys Cys Lys Ala Leu Thr Gly Ile Asp Leu
                85                  90                  95
Ser Val Cys Thr Gln Trp Tyr Arg Phe Ala Glu Ile Arg Tyr His Arg
                100                 105                 110
Pro Glu Glu Thr His Lys Gly Arg Thr Val Pro Ala His Val Glu Thr
                115                 120                 125
Val Val Leu Phe Phe Pro Asp Val Trp His Cys Leu Pro Thr Arg Ser
            130                 135                 140
Glu Trp Glu Thr Leu Ser Arg Gly Tyr Lys Gln Gln Leu Ala Glu Lys
145                 150                 155                 160
```

Leu Gln Gly Glu Arg Lys Glu Ala Asp Gly Gln Asp Glu Glu Lys
            165                 170                 175

Asp Asp Gly Glu Ala Lys Glu Ile Ser Thr Pro Thr His Trp Ser Lys
        180                 185                 190

Leu Asp Pro Lys Thr Met Lys Val Asn Asp Leu Arg Lys Glu Leu Glu
            195                 200                 205

Ser Arg Ala Leu Ser Ser Lys Gly Leu Lys Ser Gln Leu Ile Ala Arg
        210                 215                 220

Leu Thr Lys Gln Leu Lys Val Glu Glu Gln Lys Glu Gln Lys Glu
225                 230                 235                 240

Leu Glu Lys Ser Glu Lys Glu Glu Glu Glu Asp Arg Lys Ser
                245                 250                 255

Glu Asp Asp Lys Glu Glu Glu Arg Lys Arg Gln Glu Glu Met Glu
            260                 265                 270

Arg Gln Arg Arg Glu Arg Arg Tyr Ile Leu Pro Asp Glu Pro Ala Ile
        275                 280                 285

Ile Val His Pro Asn Trp Ala Ala Lys Ser Gly Lys Phe Asp Cys Ser
            290                 295                 300

Ile Met Ser Leu Ser Val Leu Leu Asp Tyr Arg Leu Glu Asp Asn Lys
305                 310                 315                 320

Glu His Ser Phe Glu Val Ser Leu Phe Ala Glu Leu Phe Asn Glu Met
                325                 330                 335

Leu Gln Arg Asp Phe Gly Val Arg Ile Tyr Lys Ser Leu Ile Ser Leu
            340                 345                 350

Pro Glu

<210> SEQ ID NO 8
<211> LENGTH: 355
<212> TYPE: PRT
<213> ORGANISM: Anolis carolinensis

<400> SEQUENCE: 8

Thr Asp His Leu Tyr Ser Ala Lys Val Met Leu Met Ala Ser Pro Ser
1               5                   10                  15

Met Glu Asp Leu Tyr His Lys Ser Cys Ala Leu Ala Glu Asp Pro Gln
            20                  25                  30

Glu Val Arg Asp Gly Phe Gln His Pro Ala Arg Leu Ile Lys Phe Leu
        35                  40                  45

Val Gly Met Lys Gly Lys Asp Glu Ala Met Ala Ile Gly Gly His Trp
    50                  55                  60

Ser Pro Ser Leu Asp Gly Pro Asp Pro Glu Lys Asp Pro Ser Val Leu
65                  70                  75                  80

Ile Lys Thr Ala Ile Arg Cys Cys Arg Ala Leu Thr Gly Ile Asp Leu
                85                  90                  95

Ser Val Cys Thr Gln Trp Tyr Arg Phe Ala Glu Ile Arg Tyr His Arg
            100                 105                 110

Pro Glu Glu Thr His Lys Gly Arg Thr Val Pro Ala His Val Glu Thr
        115                 120                 125

Val Val Leu Phe Phe Pro Asp Val Trp His Cys Leu Pro Thr Arg Ser
    130                 135                 140

Glu Trp Glu Thr Leu Ser Arg Gly Tyr Lys Gln Gln Leu Ala Glu Lys
145                 150                 155                 160

Leu Gln Gly Glu Arg Lys Glu Ala Asp Gly Glu Gln Asp Glu Glu
                165                 170                 175

Lys Asp Asp Gly Glu Ala Lys Glu Ile Ser Thr Pro Thr His Trp Ser
              180                 185                 190

Lys Leu Asp Pro Lys Ala Met Lys Val Asn Asp Leu Arg Lys Glu Leu
              195                 200                 205

Glu Ser Arg Thr Leu Ser Ser Lys Gly Leu Lys Ser Gln Leu Ile Ala
        210                 215                 220

Arg Leu Thr Lys Gln Leu Lys Val Glu Glu Lys Glu Glu Gln Lys
225                 230                 235                 240

Glu Leu Glu Lys Ser Lys Glu Asp Glu Glu Glu Glu Arg Lys
                    245                 250                 255

Ser Glu Asp Asp Lys Glu Glu Glu Arg Lys Arg Leu Glu Glu Val
            260                 265                 270

Glu Arg Gln Arg Arg Glu Arg Tyr Ile Leu Pro Asp Glu Pro Ala
        275                 280                 285

Ile Ile Val His Pro Asn Trp Ala Ala Lys Ser Gly Lys Phe Asp Cys
        290                 295                 300

Ser Ile Met Ser Leu Ser Val Leu Leu Asp Tyr Arg Leu Glu Asp Asn
305                 310                 315                 320

Lys Glu His Ser Phe Glu Val Ser Leu Phe Ala Glu Leu Phe Asn Glu
                325                 330                 335

Met Leu Gln Arg Asp Phe Gly Val Arg Ile Tyr Arg Ser Leu Leu Ser
            340                 345                 350

Leu Pro Glu
        355

<210> SEQ ID NO 9
<211> LENGTH: 355
<212> TYPE: PRT
<213> ORGANISM: Chelonia mydas

<400> SEQUENCE: 9

Ala Asp His Leu Tyr Ser Ala Lys Val Met Leu Met Ala Ser Pro Ser
1               5                   10                  15

Met Glu Asp Leu Tyr His Lys Ser Cys Ala Leu Ala Glu Asp Pro Gln
            20                  25                  30

Glu Leu Arg Asp Gly Phe Gln His Pro Ala Arg Leu Val Lys Phe Leu
        35                  40                  45

Val Gly Met Lys Gly Lys Asp Glu Ala Met Ala Ile Gly Gly His Trp
    50                  55                  60

Ser Pro Ser Leu Asp Gly Pro Asp Pro Glu Lys Asp Pro Ser Val Leu
65                  70                  75                  80

Ile Lys Thr Ala Ile Arg Cys Cys Lys Ala Leu Thr Gly Ile Asp Leu
                85                  90                  95

Ser Val Cys Thr Gln Trp Tyr Arg Phe Ala Glu Ile Arg Tyr His Arg
            100                 105                 110

Pro Glu Glu Thr His Lys Gly Arg Thr Val Pro Ala His Val Glu Thr
        115                 120                 125

Val Val Leu Phe Phe Pro Asp Val Trp His Cys Leu Pro Thr Arg Ser
    130                 135                 140

Glu Trp Glu Thr Leu Ser Arg Gly Tyr Lys Gln Gln Leu Val Glu Lys
145                 150                 155                 160

Leu Gln Gly Glu Arg Lys Glu Ala Asp Gly Glu Gln Asp Glu Glu
                165                 170                 175

Lys Asp Asp Gly Glu Ala Lys Glu Ile Ser Thr Pro Thr His Trp Ser
            180                 185                 190

```
Lys Leu Asp Pro Lys Thr Met Lys Val Asn Asp Leu Arg Lys Glu Leu
            195                 200                 205

Glu Ser Arg Thr Leu Ser Ser Lys Gly Leu Lys Ser Gln Leu Ile Ala
        210                 215                 220

Arg Leu Thr Lys Gln Leu Lys Val Glu Glu Lys Glu Glu Gln Lys
225                 230                 235                 240

Glu Leu Glu Lys Ser Glu Lys Glu Asp Glu Glu Glu Asp Arg Lys
                245                 250                 255

Ser Glu Asp Asp Lys Glu Glu Glu Arg Lys Arg Gln Glu Glu Met
            260                 265                 270

Glu Arg Gln Arg Arg Glu Arg Arg Tyr Ile Leu Pro Asp Glu Pro Ala
                275                 280                 285

Ile Ile Val His Pro Asn Trp Ala Ala Lys Ser Gly Lys Phe Asp Cys
290                 295                 300

Ser Ile Met Ser Leu Ser Val Leu Leu Asp Tyr Arg Leu Glu Asp Asn
305                 310                 315                 320

Lys Glu His Ser Phe Glu Val Ser Leu Phe Ala Glu Leu Phe Asn Glu
                325                 330                 335

Met Leu Gln Arg Asp Phe Gly Val Arg Ile Tyr Lys Ala Leu Ile Ser
            340                 345                 350

Leu Pro Glu
        355

<210> SEQ ID NO 10
<211> LENGTH: 356
<212> TYPE: PRT
<213> ORGANISM: Danio rerio

<400> SEQUENCE: 10

Ala Asn His Thr Tyr Ser Ala Lys Val Met Leu Leu Ala Asn Pro Ser
1               5                   10                  15

Leu Asp Glu Leu Tyr His Lys Ser Cys Ala Leu Ser Glu Asp Pro Ala
            20                  25                  30

Glu Leu Arg Asp Ser Phe Gln His Pro Ala Arg Leu Ile Lys Phe Leu
        35                  40                  45

Val Gly Met Arg Gly Lys Asp Glu Ala Met Ala Ile Gly Gly His Trp
50                  55                  60

Ser Pro Ser Leu Asp Gly Ala Asp Pro Glu His Asp Ala Ser Val Leu
65                  70                  75                  80

Ile Lys Thr Ala Val Arg Cys Cys Lys Ala Leu Thr Gly Ile Asp Leu
                85                  90                  95

Ser Leu Cys Thr Gln Trp Tyr Arg Phe Ala Glu Ile Arg Tyr His Arg
            100                 105                 110

Pro Glu Glu Thr His Lys Gly Arg Thr Val Pro Ala His Val Glu Thr
        115                 120                 125

Val Val Leu Phe Leu Pro Asp Val Trp His Cys Leu Pro Thr Arg Ser
130                 135                 140

Glu Trp Glu Glu Leu Ser Arg Gly Leu Lys Glu Gln Leu Ala Glu Lys
145                 150                 155                 160

Leu Leu Ala Glu Arg Lys Glu Ala Asp Gly Glu Gln Glu Glu Glu Asp
                165                 170                 175

Lys Asp Glu Asp Asp Ser Lys Glu Val Thr Thr Pro Thr His Trp Ser
            180                 185                 190

Lys Leu Asp Pro Lys Ser Met Lys Val Ser Asp Leu Arg Lys Glu Leu
```

```
                195                 200                 205
Glu Ser Arg Ser Leu Ser Ser Lys Gly Leu Lys Ser Gln Leu Ile Ala
    210                 215                 220

Arg Leu Thr Lys Gln Leu Lys Val Glu Glu Gln Val Glu Glu Ser Lys
225                 230                 235                 240

Glu Pro Glu Lys Pro Glu Pro Pro Ser Val Glu Asp Glu Ser Cys
                245                 250                 255

Arg Leu Glu Asp Asp Arg Glu Glu Glu Arg Lys Arg Gln Glu Glu
            260                 265                 270

Gln Glu Arg Gln Arg Arg Glu Arg Tyr Val Leu Pro Asp Glu Pro
        275                 280                 285

Thr Ile Ile Val His Pro Asn Trp Ala Ala Lys Asn Gly Lys Phe Asp
    290                 295                 300

Cys Ser Ile Met Ser Leu Ser Val Leu Leu Asp Tyr Arg Leu Glu Asp
305                 310                 315                 320

Asn Lys Glu His Ser Phe Glu Val Ser Leu Phe Ala Glu Leu Phe Asn
                325                 330                 335

Glu Met Leu Gln Arg Asp Phe Gly Tyr Arg Ile Tyr Lys Ala Leu Ala
            340                 345                 350

Ser Leu Pro Thr
        355

<210> SEQ ID NO 11
<211> LENGTH: 356
<212> TYPE: PRT
<213> ORGANISM: Maylandia zebra

<400> SEQUENCE: 11

Ala Asn His Thr Tyr Ser Ala Lys Val Met Leu Leu Ala Asn Pro Ser
1               5                   10                  15

Ile Glu Glu Leu Tyr His Lys Ser Cys Ala Leu Ala Glu Asp Pro Gln
            20                  25                  30

Glu Val Arg Asp Ser Phe Gln His Pro Ala Arg Leu Ile Lys Phe Leu
        35                  40                  45

Val Gly Met Arg Gly Lys Asp Glu Ala Met Ala Ile Gly Gly His Trp
    50                  55                  60

Ser Pro Ser Leu Asp Gly Ala Asp Pro Glu Lys Asp Pro Ser Val Leu
65                  70                  75                  80

Ile Lys Thr Ala Ile Arg Cys Cys Lys Ala Leu Thr Gly Ile Asp Leu
                85                  90                  95

Ser Leu Cys Thr Gln Trp Tyr Arg Phe Ala Glu Ile Arg Tyr His Arg
            100                 105                 110

Pro Glu Glu Thr His Lys Gly Arg Thr Val Pro Ala His Val Glu Thr
        115                 120                 125

Val Val Leu Phe Leu Pro Asp Val Trp His Cys Leu Pro Thr Arg Ser
    130                 135                 140

Glu Trp Glu Val Leu Ser Arg Arg Leu Arg Glu Gln Leu Ala Glu Lys
145                 150                 155                 160

Leu Ser Ala Glu Arg Lys Glu Ala Asp Gly Glu Gln Glu Glu Glu Glu
                165                 170                 175

Lys Asp Asp Asp Ser Lys Asp Val Ser Thr Pro Thr His Trp Ala
            180                 185                 190

Lys Leu Asp Pro Lys Ser Met Lys Val Asn Asp Leu Arg Arg Glu Leu
        195                 200                 205
```

Asp Cys Arg Ser Leu Ser Ser Lys Gly Leu Lys Ser Gln Leu Ile Ala
210                 215                 220

Arg Leu Thr Lys Gln Leu Lys Val Glu Glu Gln Val Glu Glu Ser Lys
225                 230                 235                 240

Glu Pro Glu Lys Val Glu Thr Lys Asp Val Glu Glu Glu Pro Ala
            245                 250                 255

Arg Thr Glu Asp Asp Arg Glu Glu Glu Lys Lys Arg Gln Glu Glu
            260                 265                 270

Leu Glu Arg Gln Arg Arg Glu Arg Arg Tyr Ile Leu Pro Asp Glu Pro
                275                 280                 285

Thr Ile Leu Val His Pro Asn Trp Ala Ala Lys Asn Gly Lys Phe Asp
290                 295                 300

Cys Ser Val Met Ser Leu Ser Val Leu Leu Asp Tyr Arg Leu Glu Asp
305                 310                 315                 320

Asn Lys Glu His Ser Phe Glu Val Ser Leu Phe Ala Glu Leu Phe Asn
                325                 330                 335

Glu Met Leu Gln Arg Asp Phe Gly Tyr Arg Ile Tyr Lys Ala Leu Ala
                340                 345                 350

Ala Leu Pro Thr
            355

<210> SEQ ID NO 12
<211> LENGTH: 355
<212> TYPE: PRT
<213> ORGANISM: Xenopus laevis

<400> SEQUENCE: 12

Ala Asp His Thr Tyr Ser Ala Lys Val Met Leu Leu Ala Ser Pro Ser
1               5                   10                  15

Leu Glu Glu Leu Tyr His Lys Ser Cys Ala Leu Ala Glu Asp Pro Ile
            20                  25                  30

Glu Val Arg Glu Gly Phe Gln His Pro Ala Arg Leu Ile Lys Phe Leu
        35                  40                  45

Val Gly Met Lys Gly Lys Asp Glu Ala Met Ala Ile Gly Gly His Trp
50                  55                  60

Ser Pro Ser Leu Asp Gly Pro Asn Pro Asp Lys Asp Pro Ser Val Leu
65                  70                  75                  80

Ile Arg Thr Ala Val Arg Cys Cys Lys Ala Leu Thr Gly Ile Glu Leu
                85                  90                  95

Ser Leu Cys Thr Gln Trp Tyr Arg Phe Ala Glu Ile Arg Tyr His Arg
            100                 105                 110

Pro Glu Glu Thr His Lys Gly Arg Thr Val Pro Ala His Val Glu Thr
        115                 120                 125

Val Val Leu Phe Phe Pro Asp Val Trp His Cys Leu Pro Thr Arg Ser
130                 135                 140

Glu Trp Glu Asn Leu Cys His Gly Tyr Lys Gln Gln Leu Val Asp Lys
145                 150                 155                 160

Leu Gln Gly Asp Arg Lys Glu Ala Asp Gly Glu Gln Glu Glu Glu Asp
                165                 170                 175

Lys Glu Asp Gly Asp Ala Lys Glu Ile Ser Thr Pro Thr His Trp Ser
            180                 185                 190

Lys Leu Asp Pro Lys Ile Met Lys Val Asn Asp Leu Arg Lys Glu Leu
        195                 200                 205

Glu Ser Arg Thr Leu Ser Ser Lys Gly Leu Lys Ser Gln Leu Ile Ala
210                 215                 220

```
Arg Leu Thr Lys Gln Leu Arg Ile Glu Glu Gln Lys Glu Glu Gln Lys
225                 230                 235                 240

Glu Leu Glu Lys Cys Glu Lys Glu Glu Glu Glu Glu Glu Glu Arg Lys
                245                 250                 255

Ser Glu Asp Asp Lys Glu Glu Glu Arg Lys Arg Gln Glu Glu Leu
            260                 265                 270

Glu Arg Gln Arg Arg Glu Lys Arg Tyr Met Leu Pro Asp Glu Pro Ala
            275                 280                 285

Ile Ile Val His Pro Asn Trp Ser Ala Lys Asn Gly Lys Phe Asp Cys
            290                 295                 300

Ser Ile Met Ser Leu Ser Val Leu Leu Asp Tyr Arg Ile Glu Asp Asn
305                 310                 315                 320

Lys Glu His Ser Phe Glu Val Ser Leu Phe Ala Glu Leu Phe Asn Glu
                325                 330                 335

Met Leu Gln Arg Asp Phe Gly Val Arg Ile Tyr Arg Glu Leu Leu Ala
                340                 345                 350

Leu Pro Glu
        355

<210> SEQ ID NO 13
<211> LENGTH: 401
<212> TYPE: PRT
<213> ORGANISM: Strongylocentrotus purpuratus

<400> SEQUENCE: 13

Ala Asn Tyr Ser Tyr Cys Ala Lys Val Met Leu Met Thr Ser Val Ser
1               5                   10                  15

Gln Asp Glu Leu Tyr Glu Lys Cys Cys Ala Arg Ala Gln Asp Ser Ser
                20                  25                  30

Asp Ile Arg Glu Asn Phe Gln His Pro Thr Arg Leu Ile Asn Phe Leu
            35                  40                  45

Val Gly Gln Lys Gly Lys Asn Glu Val Met Ala Ile Gly Gly Pro Trp
        50                  55                  60

Ser Pro Ser Leu Asp Gly Ala Asp Pro Val Asn Asp Thr Ser Val Leu
65                  70                  75                  80

Ile Lys Thr Ala Ile Arg Thr Thr Lys Ala Leu Ala Gly Ile Asp Leu
                85                  90                  95

Thr Ala Cys Thr Gln Trp Tyr Arg Phe Leu Glu Leu Ser Tyr Tyr Arg
                100                 105                 110

Pro Glu Glu Ile His Lys Gly Arg Val Ile Pro Ala Arg Val Glu Thr
            115                 120                 125

Val Val Ile Phe Val Pro Asp Val Trp His Ile Leu Pro Thr Lys Val
        130                 135                 140

Glu Trp Glu Ser Leu Ala Asp Leu Tyr Arg Lys Thr Leu Ser Asn Lys
145                 150                 155                 160

Leu Ala Ala Val Asp Ser Arg Asp Lys Lys Thr Glu Asp Pro Thr Pro
                165                 170                 175

Thr Gln Glu Glu Pro Ala Ala Val Lys Glu Glu Glu Glu Glu Glu Val
            180                 185                 190

Glu Glu Gln Glu His Gln Thr Pro Thr Asn Trp Lys Glu Leu Asp Pro
        195                 200                 205

Lys Asn Met Lys Val Asn Glu Leu Arg Gln Glu Leu Glu Ile Arg Gly
210                 215                 220

Leu Asn Ser Lys Gly Leu Lys Ser Gln Leu Ile Ala Arg Leu Thr Lys
```

```
            225                 230                 235                 240
Met Leu Lys Thr Glu Gln Glu Met Glu Asp Ala Glu Pro Ala Ala Met
                245                 250                 255

Glu Thr Asp Ala Ala Thr Glu Asn Ala Ser Lys Glu Glu Pro Lys Asp
                260                 265                 270

Ala Pro Lys Glu Glu Val Ser Glu Lys Asp Lys Glu Lys Glu Lys
            275                 280                 285

Lys Asp Lys Glu Glu Lys Glu Lys Lys Asp Lys Glu Asp Glu Lys Lys
            290                 295                 300

Lys Glu Ile Val Glu Glu Lys Lys Arg Gln Arg Glu Arg Glu Lys
305                 310                 315                 320

Arg Asp Leu Glu Ser Arg Tyr Thr Met Pro Asp Gly Pro Val Ile Leu
                325                 330                 335

Val His Pro Ser Pro Ile Ala Lys Ser Gly Lys Phe Asp Cys Thr Gln
                340                 345                 350

Gln Ser Leu Ser Val Leu Leu Asp Tyr Arg Val Glu Asp Asn Lys Glu
                355                 360                 365

His Ser Phe Glu Val Phe Leu Phe Ala Glu Leu Phe Asn Glu Met Leu
                370                 375                 380

Gln Arg Asp Phe Ala Phe Asn Met Tyr Lys Ala Ile Phe Arg Ala Pro
385                 390                 395                 400

Glu

<210> SEQ ID NO 14
<211> LENGTH: 363
<212> TYPE: PRT
<213> ORGANISM: Saccoglossus kowalevskii

<400> SEQUENCE: 14

Ala Asp His Leu Tyr Ser Ala Lys Val Met Leu Met Ala Ser Pro Pro
1               5                   10                  15

Leu Gln Glu Leu Tyr Gln Arg Ser Cys Ala Leu Ala Glu Asp Pro Gln
                20                  25                  30

Glu Leu Lys Asp Asn Phe Gln His Pro Thr Arg Leu Ile Gln Phe Leu
            35                  40                  45

Val Gly Met Lys Gly Lys Asn Glu Ala Ile Ala Ile Gly Gly Pro Trp
        50                  55                  60

Ser Pro Ser Ile Asp Gly Glu Asn Pro Glu Ser Asp Asp Arg Val Leu
65                  70                  75                  80

Ile Asn Thr Ala Ile Arg Thr Cys Arg Ser Leu Thr Gly Ile Asp Leu
                85                  90                  95

Ser Ser Cys Thr His Trp Trp Arg Phe Ala Glu Val Arg Tyr His Arg
                100                 105                 110

Ala Glu Glu Ile Tyr Lys Gly Arg Leu Val Pro Ala Arg Val Glu Thr
            115                 120                 125

Val Val Ile Phe Leu Pro Asp Val Trp His Cys Leu Pro Thr Arg Leu
        130                 135                 140

Glu Trp Glu Gly Leu Ser Ala Asp Tyr Lys Lys Gln Leu Val Asp Lys
145                 150                 155                 160

Ile Ala Glu Lys His Glu Asp Val Ala Glu Gln Leu Gln Glu Ala Gly
                165                 170                 175

Thr Asp Ala Val Glu Asp Asp Asp Phe Glu Asn Pro Thr His His
            180                 185                 190

Lys Leu Leu Asp Pro Arg Asn Met Lys Val Gly Asp Leu Arg Lys Glu
```

```
                195                 200                 205
Leu Glu Ala Arg Gly Ile Asn Ser Lys Gly Leu Lys Ser Gln Leu Ile
    210                 215                 220

Ala Arg Leu Thr Lys Ala Leu Lys Thr Glu Ala Glu Ser Glu Glu Gln
225                 230                 235                 240

Glu Asp Ile Ala Asp Glu Asp Pro Glu Glu Phe Val Glu Ala Lys Thr
                245                 250                 255

Glu Val Glu Glu Ile Glu Met Asn Ser Glu Asp Lys Lys Glu Glu Glu
            260                 265                 270

Glu Lys Arg Lys Gln Glu Glu Lys Asp Arg Leu Ile Lys Glu Lys Arg
        275                 280                 285

His Thr Leu Pro Glu Asp Pro Ala Ile Ile Val His Pro Ser Thr Thr
    290                 295                 300

Ala Lys Gly Gly Lys Phe Asp Cys Ser Val Val Ser Leu Ser Val Leu
305                 310                 315                 320

Leu Asp Tyr Arg Met Glu Asp Asn Lys Glu His Ser Phe Glu Val Ser
                325                 330                 335

Leu Phe Ala Glu Leu Phe Asn Glu Met Leu Gln Arg Asp Phe Gly Phe
            340                 345                 350

Asn Ile Tyr Lys Ser Leu Leu Lys Ile Pro Glu
        355                 360

<210> SEQ ID NO 15
<211> LENGTH: 353
<212> TYPE: PRT
<213> ORGANISM: Branchiostoma floridae

<400> SEQUENCE: 15

Val Met Leu Met Ala Cys Pro Ser Ala Glu Glu Leu Tyr His Arg Ser
1               5                   10                  15

Cys Ala Leu Ala Glu Asp Ala Ser Asp Val Arg Glu Thr Phe Gln His
            20                  25                  30

Pro Thr Arg Leu Ile Gln Phe Leu Val Gly Met Lys Gly Lys Asn Glu
        35                  40                  45

Ala Val Ala Ile Gly Gly Pro Trp Ser Pro Ser Leu Asp Gly Pro Asn
    50                  55                  60

Pro Asp Thr Asp Pro Ser Val Leu Ile Lys Thr Ala Ile Arg Thr Thr
65                  70                  75                  80

Lys Ala Leu Thr Gly Ile Asp Leu Lys Asn Cys Thr Gln Trp Tyr Arg
                85                  90                  95

Phe Ala Glu Val Arg Tyr His Arg Ala Ala Glu Thr Tyr Lys Gly Lys
            100                 105                 110

Thr Ile Pro Glu Arg Val Glu Thr Thr Val Met Phe Leu Pro Asp Val
        115                 120                 125

His His Cys Leu Pro Pro Arg Leu Asp Trp Ala Asn Val Ser Ala Gly
    130                 135                 140

Tyr Arg Ala Gln Leu Ala Arg Lys Ala Ala Asp Glu Lys Ser Glu Glu
145                 150                 155                 160

Ala Gly Glu Ser Gln Glu Glu Glu Gly Gly Glu Asp Glu Ser Gly
                165                 170                 175

Lys Lys Ala Pro Thr His His Thr Glu Leu Asp Pro Lys Thr Met Lys
            180                 185                 190

Val Asn Glu Leu Arg Ala Glu Leu Glu Ala Arg Gly Leu Asn Ser Lys
        195                 200                 205
```

```
Gly Leu Lys Ser Gln Leu Ile Ala Arg Leu Thr Lys Ala Leu Lys Met
    210                 215                 220
Glu Val Glu Lys Glu Glu Glu Lys Glu Ala Lys Asp Glu Ala Lys
225                 230                 235                 240
Glu Glu Glu Glu Glu Lys Glu Glu Val Glu Glu Asp Lys Glu
                245                 250                 255
Lys Lys Glu Glu Glu Arg Lys Lys Gln Glu Glu Arg Glu Arg
            260                 265                 270
Lys Thr Arg Glu Arg Arg Tyr Thr Leu Pro Asp Asn Pro Ala Ile Ile
        275                 280                 285
Val His Pro Ser Thr Thr Ala Lys Gly Gly Lys Phe Asp Cys Ala Val
290                 295                 300
Met Ser Leu Ser Val Leu Leu Asp Tyr Arg Val Glu Asp Asn Lys Glu
305                 310                 315                 320
His Ser Phe Glu Val Ser Leu Phe Ala Glu Leu Leu Asn Glu Met Leu
                325                 330                 335
Gln Arg Asp Phe Ala Phe Lys Ile Tyr Arg Ala Leu Met Val Ala Pro
            340                 345                 350
Glu

<210> SEQ ID NO 16
<211> LENGTH: 365
<212> TYPE: PRT
<213> ORGANISM: Bombus impatiens

<400> SEQUENCE: 16

Ala Asp Tyr Leu Phe Ser Ala Lys Val Met Leu Ile Ser Met Pro Ala
1               5                   10                  15
Met Glu Glu Ile Tyr Lys Arg Cys Cys Gly Val Ser Glu Asp Arg Asp
                20                  25                  30
Pro Asp Arg Asp Tyr Val His Pro Thr Arg Leu Ile Asn Phe Leu Val
            35                  40                  45
Gly Leu Arg Gly Lys Asn Glu Thr Met Ala Ile Gly Gly Pro Trp Ser
    50                  55                  60
Pro Ser Leu Asp Gly Pro Asn Pro Glu Lys Asp Pro Ser Val Leu Ile
65                  70                  75                  80
Arg Thr Ala Val Arg Thr Cys Lys Ala Leu Thr Gly Ile Asp Leu Ser
                85                  90                  95
Ser Cys Thr Gln Trp Tyr Arg Phe Leu Glu Leu Tyr Arg Arg Ala
            100                 105                 110
Glu Thr Thr His Lys Ser Gly Arg Val Val Pro Ser Arg Val Glu Thr
        115                 120                 125
Val Ile Leu Phe Leu Pro Asp Val Trp Ser Cys Val Pro Thr Lys Leu
130                 135                 140
Glu Trp Asp Gly Leu Gln Leu Asn Tyr Lys Lys Gln Leu Glu Arg Lys
145                 150                 155                 160
Leu Leu Arg Ala Ala Ser Ser Pro Asp Asp Leu Asp Ala Ala Asn Glu
                165                 170                 175
Thr Asp Glu Ala Ala Asp Asp Pro Val Pro Glu Lys Lys Asp Pro Thr
            180                 185                 190
His Tyr Ser Glu Leu Asp Pro Lys Ser Met Asn Val Asn Glu Leu Arg
        195                 200                 205
Gln Glu Leu Ala Ala Arg Asn Leu Asn Cys Lys Gly Leu Lys Ser Gln
    210                 215                 220
```

```
Leu Leu Ala Arg Leu Met Lys Thr Ile Thr Ser Glu Gln Ala Lys Glu
225                 230                 235                 240

Glu Gly Arg Gln Asp Asp Ile Asp Glu Asn Glu Lys Asp Ile Ser Pro
            245                 250                 255

Pro Pro Lys Glu Glu Asp Lys Lys Phe Lys Asp Ile Lys Asp His
        260                 265                 270

Asp Glu Asp Arg Arg Lys Leu Cys Glu Arg Glu Ala Ala Leu Glu
        275                 280                 285

Lys Arg Tyr Thr Leu Pro Glu Ser Ser His Ile Ile Val His Pro Ser
290                 295                 300

Arg Met Ala Lys Ser Gly Lys Phe Asp Cys Thr Val Met Ser Leu Ser
305                 310                 315                 320

Val Leu Leu Asp Tyr Arg Pro Glu Asp Thr Lys Glu His Ser Phe Glu
                325                 330                 335

Val Ser Leu Phe Ala Glu Leu Phe Asn Glu Met Leu Met Arg Asp Phe
                340                 345                 350

Gly Phe Arg Ile Tyr Arg Ala Leu Cys Ser Leu Pro Glu
            355                 360                 365

<210> SEQ ID NO 17
<211> LENGTH: 339
<212> TYPE: PRT
<213> ORGANISM: Dendroctonus ponderosae

<400> SEQUENCE: 17

Ala Asp Tyr Arg Phe Ser Ala Lys Val Met Leu Met Ser Val Pro Val
1               5                   10                  15

Ile Glu Glu Ile Tyr Gln Lys Cys Cys Ala Ile Ala Glu Asp Lys Asp
                20                  25                  30

Ser Arg Asp Arg Glu Ser Glu Asp Arg Asp His Ile His Pro Thr Arg
            35                  40                  45

Met Ile Asn Phe Leu Val Gly Leu Arg Gly Lys Asn Glu Thr Met Ala
        50                  55                  60

Ile Gly Gly Pro Trp Ser Pro Ser Leu Asp Gly Glu Asn Pro Glu Lys
65                  70                  75                  80

Asp Pro Ala Val Leu Ile Lys Thr Ala Ile Arg Thr Cys Lys Ala Leu
                85                  90                  95

Thr Gly Ile Asp Leu Ser Asn Cys Thr Gln Trp Tyr Arg Phe Val Glu
            100                 105                 110

Leu Tyr Tyr Arg Arg Gly Glu Thr Thr His Lys Gly Lys Ala Ile Pro
        115                 120                 125

Ala Arg Val Glu Thr Val Val Ile Phe Leu Pro Asp Val Trp Ser Cys
130                 135                 140

Leu Pro Thr Arg Leu Glu Trp Glu Glu Glu Asp Asn Glu Glu Val
145                 150                 155                 160

Leu Glu Pro Thr Leu His Ser Glu Leu Asn Pro Lys Ala Met Thr Val
                165                 170                 175

Val Gln Leu Arg Thr Glu Leu Lys Ala Arg Lys Leu Asp Phe Lys Gly
            180                 185                 190

Leu Lys Ala Gln Leu Val Ala Arg Leu Thr Lys Ala Leu Lys Ser Glu
        195                 200                 205

Ala Asp Arg Glu Glu Glu Asp Pro Arg Glu Lys Pro Asn Ser Asp Gly
210                 215                 220

Glu Ala Glu Cys Glu Lys Asp Asp Ala Pro Glu Ala Ser Pro Ser Ala
225                 230                 235                 240
```

```
Glu Lys Asp Lys Lys Ser Glu Pro Glu Lys Lys Leu Asp Glu Val
            245                 250                 255

Gln Lys Arg Arg Leu Glu Lys Gln Tyr Thr Leu Pro Asp Gln Pro His
            260                 265                 270

Leu Ile Val His Pro Ser Lys Val Ala Lys Ser Gly Lys Phe Asp Cys
            275                 280                 285

Thr Ser Met Ser Leu Ser Leu Leu Asp Tyr Arg Pro Glu Asp Thr
290                 295                 300

Lys Glu His Ser Phe Glu Val Ser Leu Phe Ala Glu Leu Phe Asn Glu
305                 310                 315                 320

Met Leu Met Arg Asp Phe Gly Phe Asn Ile Phe Lys Ala Leu Tyr Gln
            325                 330                 335

Val Pro Glu

<210> SEQ ID NO 18
<211> LENGTH: 509
<212> TYPE: PRT
<213> ORGANISM: Culex quinquefasciatus

<400> SEQUENCE: 18

Ala Asp Tyr Leu Tyr Ser Ala Lys Val Met Leu Met Ala Thr Pro Pro
1               5                   10                  15

Met Ala Glu Phe Tyr Gln Lys Cys Phe Ala Thr Ala Glu Asp Arg Asp
            20                  25                  30

Arg Tyr Glu Asp Leu Val His Pro Thr Arg Leu Ile Ser Phe Leu Val
        35                  40                  45

Gly Ile Arg Gly Lys Gly Glu Thr Met Ser Ile Gly Gly Pro Trp Ser
    50                  55                  60

Pro Ser Leu Asp Gly Glu Asn Pro Gln Ser Asp Pro Asn Val Leu Ile
65                  70                  75                  80

Lys Thr Ala Ile Arg Thr Cys Lys Gly Leu Thr Gly Ile Asp Leu Ser
            85                  90                  95

Asn Cys Ser Arg Trp Tyr Arg Phe Val Glu Leu Tyr Tyr Arg Arg Ser
            100                 105                 110

Glu Thr Tyr His Lys Gly Arg Leu Ile Pro Ala Arg Ile Glu Thr Val
        115                 120                 125

Val Ile Phe Leu Pro Asp Ile Arg Ser Cys Gln Pro Thr Arg Pro Glu
    130                 135                 140

Trp Asp Glu Leu His Leu Ser Tyr Lys Ser His Leu Glu Arg Ile Ile
145                 150                 155                 160

Asn Ser Gln Ser Ser Asp Ser Pro Val Pro Pro Ala Val Ala Ala Ala
            165                 170                 175

Pro Ser Thr Glu Glu Pro Glu Pro Ala Ala Ser Thr Val Thr Ala Asp
            180                 185                 190

Ser Pro Ser Pro Pro Ala Ala Ala Thr Ala Ala Glu Pro Ala Ala
        195                 200                 205

Ala Ala Asp Glu Glu Ser Thr Asp Lys Pro Val Asp Thr Ala Pro Ser
    210                 215                 220

Ser Thr Ser Asp Ile Val Lys Pro Ser Ala Glu Pro Ala Glu Pro Ala
225                 230                 235                 240

Ala Ala Pro Lys Asp Asp Thr Glu Asp Lys Ala Ala Asp Asp Val
            245                 250                 255

Val Glu Glu Glu Pro Glu Val Val Ile Leu Asp Glu Ser Asp Glu Glu
            260                 265                 270
```

```
Glu Pro Lys Lys Glu Pro Thr Pro Tyr Ala Gln Leu Asp Val Lys Lys
            275                 280                 285

Leu Lys Val Pro Glu Leu Arg Thr Glu Leu Gln Ala Arg Asp Leu Pro
        290                 295                 300

Thr Asp Gly Val Lys Asn Val Leu Val Thr Arg Leu Thr Lys Ala Leu
305                 310                 315                 320

Lys Glu Glu Gln Glu Glu Ala Glu Lys Gln Ala Pro Glu Ala Ala
                325                 330                 335

Thr Gly Glu Ala Lys Ser Val Asp Lys Pro Ala Ala Asp Glu Glu Thr
                340                 345                 350

Pro Ala Gln Glu Glu Lys Lys Pro Ala Glu Glu Lys Ser Ala Glu Lys
            355                 360                 365

Asp Ser Ala Asp Ala Ala Ala Pro Glu Asp Thr Ala Asn Pro Val Glu
        370                 375                 380

Lys Glu Ala Glu Glu Asp Phe Glu Thr Met Asp Asn Val Asp Met Ser
385                 390                 395                 400

Glu Val Thr Val Ile Asp Glu Tyr Asp Ser Lys Ala Glu Lys Thr
                    405                 410                 415

Lys Pro Glu Gln Val Lys Leu Thr Glu Lys Glu Cys Gln Leu Leu Glu
            420                 425                 430

Lys Arg Tyr Ser Leu Pro Glu Gln Pro His Ile Ile Val His Pro Ser
        435                 440                 445

Arg Thr Ala Lys Ser Gly Lys Phe Asp Cys Ala Val Met Ser Leu Ser
    450                 455                 460

Val Leu Leu Asp Tyr Arg Gln Glu Asp Ser Lys Glu His Ser Phe Glu
465                 470                 475                 480

Val Ser Leu Phe Ala Glu Leu Phe Asn Glu Met Leu Thr Arg Asp Phe
                485                 490                 495

Gly Phe Asn Ile Tyr Lys Ala Leu His Met Leu Pro Ala
                500                 505

<210> SEQ ID NO 19
<211> LENGTH: 494
<212> TYPE: PRT
<213> ORGANISM: Ceratitis capitata

<400> SEQUENCE: 19

Ala Asn Tyr Leu Tyr Ser Ala Lys Val Met Leu Met Ala Cys Pro Pro
1               5                   10                  15

Ile Ala Asp Leu Tyr Gln Lys Cys Phe Glu Asp Glu Glu Asn Glu Asn
            20                  25                  30

Glu Gln His Thr Val His Pro Ser Arg Leu Ile Ser Phe Leu Val Gly
        35                  40                  45

Thr Arg Gly Arg Asn Glu Pro Met Ala Ile Gly Gly Pro Trp Ser Pro
    50                  55                  60

Ser Leu Asp Gly Glu Asn Pro Asp Lys Asp Pro Ala Val Leu Ile Arg
65                  70                  75                  80

Thr Ala Ile Arg Thr Cys Lys Ala Leu Thr Gly Ile Asp Leu Ser Gln
                85                  90                  95

Cys Thr Gln Trp Tyr Arg Phe Val Glu Leu Gln Tyr His Arg Gln Asp
            100                 105                 110

His Lys Lys Lys Asp Ala Ala Ala Arg Ile Glu Thr Val Val Ile Tyr
        115                 120                 125

Leu Pro Asp Val His Ser Cys Met Pro Asn Ala Thr Gln Trp Gln Glu
```

```
              130                 135                 140
Leu Asn Gln Val Tyr Lys Asn Ala Val Glu Asn Leu Ile Ala Arg Lys
145                 150                 155                 160

Ser Ala Ala Lys Ala Ala Ala Thr Ser Asn Thr Thr Gly Gly
                165                 170                 175

Gly Thr Glu Glu Gly Thr Ser Ser Pro Lys Ala Glu Val Gly Gly
                180                 185                 190

Glu Gly Asp Asp Ala Thr Ala Ala Asp Thr Ser Asn Ala Asp Val Thr
                195                 200                 205

Lys Asp Asp Ala Asn Lys Ser Val Val Asp Glu Gly Ala Thr Ala Glu
                210                 215                 220

Ser Gly Asp Ile Ser Thr Thr Asn Gly Glu Ala Asp Ala Asp Ala Asp
225                 230                 235                 240

Ser Ala Ala Asp Thr Ser Ala Glu Val Ile Ala Ile Glu Glu Asn Asp
                245                 250                 255

Gln Lys Glu Pro Thr His Tyr Ser Lys Leu Asp Leu Lys Ser Met Lys
                260                 265                 270

Val Arg Glu Met Arg Asp Glu Leu Glu Ala Arg Asn Leu Pro Ser Lys
                275                 280                 285

Gly Ala Arg His Ile Ile Met Ala Arg Leu Ala Lys Ala Leu Asn Thr
                290                 295                 300

Glu Lys Ala Glu Asp Lys Ser Ser Lys Lys Ala Thr Pro Lys Ser Glu
305                 310                 315                 320

Pro Ala Lys Ser Glu Ala Ala Lys Gly Lys Pro Ala Asn Ala Lys Pro
                325                 330                 335

Ala Lys Val Ala Glu Ala Asn Asp Lys Lys Val Glu Gln Gln Lys Glu
                340                 345                 350

Thr Lys Lys Glu Thr Val Glu Ile Lys Glu Asp Ile Asp Lys Ser
                355                 360                 365

Asn Asp Glu Glu Gln Glu Asp Gln Gly Glu Trp Asn Asp Val Asp Val
370                 375                 380

Asp Met Ser Asp Ile Val Ile Leu Asp Glu Tyr Asp Ser Ser Lys Asn
385                 390                 395                 400

Pro Glu Glu Thr Pro Lys Glu Leu Asn Glu Lys Lys Asn Gln Leu
                405                 410                 415

Ile Arg Arg Tyr Lys Leu Pro Thr Lys Glu His Ile Ile Val His Pro
                420                 425                 430

Asn Lys Thr Ala Lys Gly Gly Lys Phe Asp Cys Ser Ile Met Ser Leu
                435                 440                 445

Ser Val Leu Leu Asp Tyr Gly Pro Ala Asp Thr Lys Glu Arg Phe Phe
450                 455                 460

Glu Val Ser Ile Phe Ala Glu Leu Phe Asn Glu Met Leu Met Arg Asp
465                 470                 475                 480

Phe Gly Phe Asn Ile Tyr Lys Glu Met Tyr Leu Phe Lys Glu
                485                 490

<210> SEQ ID NO 20
<211> LENGTH: 427
<212> TYPE: PRT
<213> ORGANISM: Danaus plexippus

<400> SEQUENCE: 20

Ala Asp Tyr Arg Phe Ser Ala Lys Val Met Leu Ile Ser Met Pro Ser
1               5                   10                  15
```

```
Leu Glu Thr Leu Tyr Gln Lys Cys Gly Leu Thr Lys Val Asp Glu Lys
             20                  25                  30

Asp Lys Arg Thr Ser Ser Lys Thr Pro Leu His Pro Thr Arg Leu Ile
         35                  40                  45

Lys Phe Leu Val Gly Gln Lys Gly Lys Gly Glu Asn Phe Ala Ile
     50                  55                  60

Gly Gly Pro Trp Ser Pro Ser Leu Asp Gly Glu His Pro Glu Thr Asp
65                  70                  75                  80

Pro Gly Val Leu Val Lys Thr Ala Ile Arg Thr Cys Lys Ala Leu Thr
                 85                  90                  95

Gly Val Asp Leu Ser Asn Cys Thr Gln Trp Tyr Arg Val Val Glu Phe
                100                 105                 110

Tyr Tyr Trp Arg Glu Gly Gly Arg Ser Arg Leu Glu Cys Val Val
             115                 120                 125

Leu Phe Leu Pro Asp Val Trp Ser Ala Arg Pro Ser Arg Val Glu Trp
    130                 135                 140

Thr Thr Val Gln Asp Gln Tyr Lys Ala Ala Arg Asp Ala Ala Leu Arg
145                 150                 155                 160

Arg Leu Leu Gly Gly Glu Ser Pro Arg Arg Ser Asp Ser Pro Asp
                165                 170                 175

Arg Ser Pro Ile Glu Asn Leu Asp Ala Asn Ala Ser Thr Ile Thr Ile
                180                 185                 190

Asp Glu Asn Asp Asp Asp Asp Cys Lys Pro Glu Ala Thr His Tyr
                195                 200                 205

Ser Asn Ile Asp Leu Arg Thr Ile Lys Val Asp Gln Leu Arg Gln Glu
210                 215                 220

Leu Arg Ala Arg Asn Val Ser Cys Lys Gly Leu Arg Ser Gln Leu Val
225                 230                 235                 240

Ser Arg Leu Ser Lys Leu Ile Lys Ala Glu Glu Lys Asp Thr Lys
                245                 250                 255

Asn Glu Asp Val Met Glu Val Val Asp Asp Gln Glu Asp Lys Lys
                260                 265                 270

Asp Thr Thr Asp Thr Val Glu Ile Thr Asp Asp Thr Thr Asn Asp Lys
                275                 280                 285

Glu Lys Pro Val Glu Asp Lys Ile Glu Lys Asn Asp Ala Asn Asp Ser
290                 295                 300

Lys Pro Asn Asp Lys Ser Lys Asp Gly Glu Ser Lys Glu Ser Asp Gly
305                 310                 315                 320

Val Ser Glu Glu Arg Lys Asp Arg Pro Lys Thr Glu Lys Glu Ile Glu
                325                 330                 335

Glu Glu Lys Lys Arg Leu Glu Arg Glu Arg Gln Ser Leu Met Thr Arg
                340                 345                 350

Tyr Glu Leu Pro Ala Ser Pro His Val Val His Ala Ser Gly Ser
             355                 360                 365

Ala Arg Ala Gly Arg Phe Ala Cys Ser Val Ala Ser Leu Ser Leu Leu
    370                 375                 380

Leu Asp Tyr Arg Val Thr Asp Asn Lys Glu His Ser Phe Glu Leu Phe
385                 390                 395                 400

Val Phe Ala Glu Leu Phe Asn Glu Met Leu Met Arg Asp Phe Gly Phe
                405                 410                 415

Tyr Val Tyr Lys Thr Leu Tyr Thr Leu Pro Glu
             420                 425
```

-continued

<210> SEQ ID NO 21
<211> LENGTH: 320
<212> TYPE: PRT
<213> ORGANISM: Daphnia pulex

<400> SEQUENCE: 21
```

Ala Asp Tyr Ala Tyr Ser Ala Lys Val Met Leu Leu Ser Leu Leu Pro
1               5                   10                  15

Met Asp Glu Phe Leu Arg Lys Cys Cys Pro Glu Asp Glu Lys Glu Asp
            20                  25                  30

Phe Val His Pro Ala Arg Leu Ile Arg Phe Leu Val Gly His Arg Gly
        35                  40                  45

Lys Asn Glu Thr Met Ala Ile Gly Gly Pro Trp Ser Pro Ser Leu Asp
    50                  55                  60

Gly Ala Asp Pro Lys Ser Asp Pro Gln Val Leu Ile Arg Thr Ala Ile
65                  70                  75                  80

Arg Thr Cys Lys Ala Leu Thr Gly Ile Asp Leu Ser Ser Cys Thr Gln
                85                  90                  95

Trp Tyr Arg Met Ala Glu Ile Arg Tyr His Arg Val Ser Ser Met Lys
            100                 105                 110

Ser Arg Ile Glu Ser Val Leu Leu Phe Val Pro Asp Val Trp Ser Cys
        115                 120                 125

Val Pro Thr Ala Ser Gln Trp Glu Thr Ile Val His Ser Tyr Met Gln
    130                 135                 140

Pro Ser Ser Glu Pro Met Glu Glu Glu Thr Lys Glu Glu Thr Val Val
145                 150                 155                 160

Asp Pro Leu Lys Glu Ala Ser His His Ser Lys Leu Glu Pro Lys Ser
                165                 170                 175

Leu Lys Phe Ser Glu Leu Lys Thr Glu Leu Glu Ala Arg Asn Leu Ser
            180                 185                 190

Ser Lys Gly Met Arg Thr Gln Leu Ile Pro Arg Leu Thr Ile Ala Leu
        195                 200                 205

Lys Gly Glu Ala Glu Glu Glu Lys Arg Lys Arg Glu Asp Ala Gln Leu
    210                 215                 220

Asn Glu Glu Glu Gln Gln Gln Gln Glu Ser Ser Arg Glu Asp Ser Leu
225                 230                 235                 240

Pro Ala Asp Asp Val Asp Ser Ile His Arg Leu Asp Phe Val Ala Ser
                245                 250                 255

Pro Gln Ile Leu Val His Pro Ser Arg Thr Ala Lys Ala Gly Lys Phe
            260                 265                 270

Ser Cys Ser Leu Val Ser Leu Ser Val Leu Leu Asp Tyr Arg Leu Glu
        275                 280                 285

Asp Thr Lys Glu His Thr Phe Glu Val Ser Leu Phe Ser Glu Leu Phe
    290                 295                 300

Asn Glu Met Leu Met Arg Asp Phe Gly Ala Leu Val Tyr Arg Ser Val
305                 310                 315                 320

```
<210> SEQ ID NO 22
<211> LENGTH: 355
<212> TYPE: PRT
<213> ORGANISM: Ixodes scapularis

<400> SEQUENCE: 22
```

Leu Asp Phe Ser Phe Ser Ala Lys Val Met Leu Leu Ser Ala Pro Ala
1               5                   10                  15

Leu Glu Glu Leu Tyr Gln Gln Ser Cys Ala Leu Ala Glu Glu Ser Glu
```

```
                20                  25                  30

Glu Gly Arg Leu Gly Ser Met His Pro Ala Arg Ile Leu Ser Phe Leu
            35                  40                  45

Val Gly Leu Lys Gly Lys Ser Glu Thr Val Ala Leu Gly Gly Pro Trp
 50                  55                  60

Ser Pro Ser Leu Asp Gly Pro Asn Pro Ser Asp Pro Arg Val Leu
 65                  70                  75                  80

Ile Arg Thr Ala Val Arg Thr Cys Arg Ala Leu Thr Gly Ile Asp Leu
                    85                  90                  95

Ser Ala Cys Thr Gln Trp Tyr Arg Phe Ala Glu Ile Cys Tyr Arg Arg
                100                 105                 110

Glu Ser Ser Ser Ser Cys Ala Thr Leu Glu Arg Val Val Leu Phe
            115                 120                 125

Phe Pro Asp Val Trp Arg Cys Met Pro Thr Arg Gln Glu Trp Ala Asp
        130                 135                 140

Leu Glu Leu Arg Leu Arg Ser Ile Ser Leu Cys Gly Thr Glu Asp Pro
145                 150                 155                 160

Ala Gly Asp Ala Pro Ala Gln Ala Leu Asp Thr Leu Pro Thr Thr Pro
                165                 170                 175

Pro Leu Ala Arg Arg Cys Cys Gln Leu Pro Thr His Pro Ser Glu Pro
            180                 185                 190

Ala Cys Ala Leu Arg Leu Gln Val Gly Asp Leu Arg Thr Glu Leu Glu
        195                 200                 205

Ala Arg Gly Leu Leu Thr Lys Gly Leu Lys Ser Gln Leu Val Ala Arg
    210                 215                 220

Leu Ala Lys Ala Leu Lys Ala Glu Ala Glu Gln Glu Glu Glu Glu Glu
225                 230                 235                 240

Glu Glu Glu Val Glu Glu Glu Ala Glu Glu Met Glu Glu Gly Gly Glu
                245                 250                 255

Val Val Asp Glu Ala Asn Glu Glu Glu Glu Val Glu Ala Val Glu
            260                 265                 270

Glu Glu Ala Pro Glu Ser Glu Pro Glu Glu Glu Lys Pro Arg Pro Thr
        275                 280                 285

Ile Leu Val Tyr Pro Ser Arg Lys Ala Lys Gly Gly Arg Phe Asp Cys
290                 295                 300

Ser Val Met Ser Leu Ser Val Leu Leu Asp Tyr Arg Gln Glu Asp Asn
305                 310                 315                 320

Lys Glu His Ser Phe Glu Val Ser Leu Phe Ala Glu Leu Phe Asn Glu
                325                 330                 335

Met Leu Ile Arg Asp Cys Ala Phe Asn Ile Tyr Arg Ala Leu Leu Glu
            340                 345                 350

Ala Pro Glu
        355

<210> SEQ ID NO 23
<211> LENGTH: 442
<212> TYPE: PRT
<213> ORGANISM: Caenorhabditis elegans

<400> SEQUENCE: 23

Ala Asp His Arg His Gln Val Lys Val Leu Leu Leu Ser His Ala Gly
 1               5                  10                  15

Lys Ser Glu Val Val Lys Lys Ala Phe Cys Leu Met Ala Asp Gly Thr
            20                  25                  30
```

```
Thr Asp Asp His Gln Glu Pro Gln Ser Leu Leu Lys Asn Leu His Phe
         35                  40                  45
Leu Val Gly Ala Arg Gly Lys Glu Thr Met Gly Ile Gly Gly Ser Trp
 50                  55                  60
Ser Pro Ser Gln Asp Gly Ala Asp Pro Asn Ser Ala Thr Thr Met Ile
 65                  70                  75                  80
Arg Thr Ala Val Arg Thr Thr Lys Ser Leu Thr Gly Ile Asp Leu Ser
                 85                  90                  95
Ser Val Ser Gln Trp Phe Ser Met Val Gln Ile Arg Tyr Tyr Arg Ala
                100                 105                 110
Asp Lys Gln Arg Ile Asp His Val Asn Tyr Leu Leu Pro Asp Thr Gln
                115                 120                 125
Ser Leu Ala Leu Asp Asp Ala Gln Trp Met Leu Ala Glu Thr Lys Ile
        130                 135                 140
Ala Glu Gln Leu Lys Ala Lys Leu Ala Asn Val Asp Ala Leu Lys Ile
145                 150                 155                 160
Glu Glu Asp Glu Pro Pro Val Val Met Met Val Glu Glu Ser Glu Ser
                165                 170                 175
Val Val Ala Ala Ala Ala Ala Ala Asp Val Val Pro Glu Gln Ser
                180                 185                 190
Ile Pro Asp Val Lys Lys Glu Glu Leu Gln Ala Glu Glu Pro Lys
        195                 200                 205
Val Leu Asp Asn Val Lys Ala Glu Glu Ser Asp Val Val Ala Asp Val
        210                 215                 220
Ser Met Asn Ser Thr Thr Asp Ala Asp Asn Ser Glu Ala Pro Ala Ala
225                 230                 235                 240
Glu Asn Gly Gln Gly Pro Thr Asn Trp Ser Asn Leu Asp Pro Lys Ser
                245                 250                 255
Met Lys Val Ala Glu Leu Arg Val Glu Leu Glu Leu Arg Gly Leu Glu
                260                 265                 270
Thr Lys Gly Ile Lys Thr Leu Leu Val Gln Arg Leu Gln Thr Ala Leu
                275                 280                 285
Asp Thr Glu Lys Ala Ala Glu Ala Ser Val Ala Ala Arg Asp Val Glu
        290                 295                 300
Met Arg Asp Ala Ala Glu Asn Ala Val Lys Gln Glu Gly Gly Glu Glu
305                 310                 315                 320
Asn Pro Ala Ala Phe Ile Ala Pro Ser Ile Glu Glu Thr Lys Ala Lys
                325                 330                 335
Thr Glu Ala Glu Ala Lys Lys Glu Ala Glu Ala Glu Lys Arg Lys
        340                 345                 350
Lys Lys Glu Glu Gln Leu Glu Lys Glu Lys Lys Glu Lys Arg Glu Ala
        355                 360                 365
Leu Glu Lys His Tyr Gln Leu Pro Lys Asp Lys Lys Ile Leu Val Phe
        370                 375                 380
Pro Ser Lys Ser Phe Lys Ser Gly Lys Phe Asp Cys Lys Val Leu Ser
385                 390                 395                 400
Leu Ser Ser Leu Leu Asp Tyr Arg His Asp Asp Asn Lys Glu Asn Gln
                405                 410                 415
Phe Glu Val Ser Leu Phe Ala Glu Ala Phe Lys Glu Met Ile Glu Arg
                420                 425                 430
Asn Ala Ala Phe Thr Ile Tyr Glu Thr Leu
                435                 440
```

```
<210> SEQ ID NO 24
<211> LENGTH: 436
<212> TYPE: PRT
<213> ORGANISM: Caenorhabditis briggsae

<400> SEQUENCE: 24
```

| | | | | | | | | | | | | | | | |
|---|---|---|---|---|---|---|---|---|---|---|---|---|---|---|---|
| Ala | Asp | His | Arg | His | Gln | Val | Lys | Val | Leu | Leu | Ser | His | Ala | Gly |
| 1 | | | | 5 | | | | | 10 | | | | | 15 |
| Lys | Thr | Glu | Val | Val | Lys | Lys | Ser | Phe | Cys | Leu | Met | Ala | Asp | Gly | Thr |
| | | | 20 | | | | | 25 | | | | | 30 | | |
| Thr | Asp | Asp | His | Gln | Glu | Pro | Gln | Ser | Leu | Leu | Lys | Asn | Leu | His | Phe |
| | | | 35 | | | | | 40 | | | | | 45 | | |
| Leu | Val | Gly | Ala | Arg | Gly | Lys | Glu | Thr | Met | Gly | Ile | Gly | Gly | Ser | Trp |
| | 50 | | | | | 55 | | | | | 60 | | | | |
| Ser | Pro | Ser | Leu | Asp | Gly | Ala | Asp | Pro | Thr | Ser | Thr | Thr | Thr | Met | Ile |
| 65 | | | | | 70 | | | | | 75 | | | | | 80 |
| Arg | Thr | Ala | Val | Arg | Thr | Thr | Arg | Ala | Leu | Thr | Gly | Ile | Asp | Leu | Ser |
| | | | | 85 | | | | | 90 | | | | | 95 | |
| Ser | Val | Ser | Gln | Trp | Phe | Ser | Met | Val | Gln | Ile | Arg | Tyr | Tyr | Arg | Ala |
| | | | 100 | | | | | 105 | | | | | 110 | | |
| Asp | Lys | Gln | Arg | Ile | Asp | His | Val | Asn | Phe | Leu | Leu | Pro | Asp | Thr | Gln |
| | | | 115 | | | | | 120 | | | | | 125 | | |
| Ser | Leu | Ala | Leu | Asp | Asp | Ala | Thr | Trp | Ser | Ser | Ala | Glu | Ala | Ser | Ile |
| 130 | | | | | 135 | | | | | 140 | | | | | |
| Gly | Glu | Gln | Leu | Lys | Ala | Lys | Leu | Ala | Glu | Val | Asp | Ala | Leu | Lys | Ile |
| 145 | | | | | 150 | | | | | 155 | | | | | 160 |
| Glu | Glu | Glu | Pro | Glu | Val | Val | Glu | Met | Val | Gly | Ala | Val | Glu | Pro | Ala |
| | | | | 165 | | | | | 170 | | | | | 175 | |
| Ala | Glu | Val | Val | Val | Thr | Pro | Glu | Ala | Ala | Val | Val | Thr | Ala | Glu | Thr |
| | | | 180 | | | | | 185 | | | | | 190 | | |
| Val | Ala | Ala | Pro | Glu | Asp | Ala | Pro | Ser | Asp | Val | Lys | Glu | Ser | Ile | Val |
| | | | 195 | | | | | 200 | | | | | 205 | | |
| Leu | Leu | Tyr | Met | Val | Glu | Asn | Glu | Asn | Asp | Val | Ser | Met | Asn | Ser | Glu |
| 210 | | | | | 215 | | | | | 220 | | | | | |
| Thr | Gly | Glu | Ala | Asp | Lys | Pro | Ile | Val | Ala | Gly | Gln | Gly | Pro | Thr | Asn |
| 225 | | | | | 230 | | | | | 235 | | | | | 240 |
| Trp | Ser | Lys | Leu | Asp | Pro | Lys | Ser | Met | Lys | Val | Ala | Glu | Leu | Arg | Val |
| | | | | 245 | | | | | 250 | | | | | 255 | |
| Glu | Leu | Glu | Leu | Arg | Gly | Leu | Glu | Thr | Lys | Gly | Ile | Lys | Thr | Leu | Leu |
| | | | 260 | | | | | 265 | | | | | 270 | | |
| Val | Gln | Arg | Leu | Gln | Thr | Ala | Leu | Asp | Ser | Glu | Lys | Ser | Thr | Glu | Ala |
| | | | 275 | | | | | 280 | | | | | 285 | | |
| Ala | Ala | Ser | Lys | Asp | Val | Glu | Met | Lys | Asp | Val | Lys | Asp | Glu | Val | Lys |
| 290 | | | | | 295 | | | | | 300 | | | | | |
| Gln | Glu | Ala | Gly | Ala | Val | Ala | Gly | Glu | Glu | Asn | Pro | Ala | Ala | Phe | Ile |
| 305 | | | | | 310 | | | | | 315 | | | | | 320 |
| Ala | Pro | Pro | Ile | Glu | Glu | Thr | Lys | Ala | Lys | Thr | Glu | Ala | Glu | Ala | Lys |
| | | | | 325 | | | | | 330 | | | | | 335 | |
| Lys | Glu | Gln | Glu | Glu | Ala | Asp | Lys | Lys | Lys | Lys | Glu | Glu | Gln | Leu |
| | | | 340 | | | | | 345 | | | | | 350 | | |
| Glu | Lys | Glu | Lys | Lys | Asp | Lys | Arg | Asp | Ala | Leu | Glu | Lys | His | Tyr | Gln |
| | | | 355 | | | | | 360 | | | | | 365 | | |
| Leu | Pro | Lys | Asp | Lys | Lys | Val | Leu | Val | Phe | Pro | Ser | Lys | Thr | Phe | Lys |
| | 370 | | | | | 375 | | | | | 380 | | | | |

```
Ser Gly Lys Phe Asp Cys Lys Val Leu Ser Leu Ser Ser Leu Leu Asp
385                 390                 395                 400

Tyr Arg His Asp Asp Asn Lys Glu Ser Gln Phe Glu Val Ser Leu Phe
                405                 410                 415

Ala Glu Ala Phe Lys Glu Met Ile Glu Arg Asn Ser Ala Phe Thr Ile
                420                 425                 430

Tyr Glu Thr Leu
        435

<210> SEQ ID NO 25
<211> LENGTH: 398
<212> TYPE: PRT
<213> ORGANISM: Brugia malayi

<400> SEQUENCE: 25

Ala Asp Cys Arg Phe Ser Val Lys Ile Val Leu Met Ser His Gln Gly
1               5                   10                  15

Leu Ser Leu Val His Gln Lys Ala Phe Gly Leu Leu Val Asp Gly Ser
                20                  25                  30

Ile Asp Glu Asn Val Asp Ser Val Ser Leu Lys Arg Cys Leu Asn Phe
            35                  40                  45

Val Val Gly Thr Arg Asn Lys Glu Met Met Ala Ile Gly Gly Ala Trp
50                  55                  60

Ser Pro Ser Leu Asp Gly Asp Asn Pro Glu Thr Asp Pro Gln Val Phe
65                  70                  75                  80

Val Arg Thr Ala Ile Arg Thr Val Arg Ala Leu Ile Gly Val Asp Leu
                85                  90                  95

Ser Arg Cys Pro Arg Trp Tyr Lys Met Ala Glu Ile Arg Tyr Tyr Arg
                100                 105                 110

Ala Glu Lys Asp Arg Met Asp Thr Cys Cys Leu Phe Leu Pro Asp Thr
                115                 120                 125

Ser Gly Leu Met Pro Thr Glu Asp Cys Tyr Gln Gln Leu Leu Ala Thr
            130                 135                 140

Leu Lys Asp Gln Leu Gly Asn Lys Leu Ala Ala Val Asp Ala Gln Lys
145                 150                 155                 160

Leu Val Leu Pro Ser Thr Val Ala Val Thr Ala Thr Asp Cys Gly Asp
                165                 170                 175

Ala Gly Glu Gly Ala Thr Val Thr Thr Glu Pro Met Ala Pro Ala Gly
                180                 185                 190

Asp Thr Gln Gln Gln Leu Gln Gln Gly Gln Gln Gln Ser Asp Val Asn
                195                 200                 205

Lys Glu Gln Val Gln Glu Val Glu Glu Asp Asp Glu Asp Leu Asn
            210                 215                 220

Pro Thr His Trp Ser Lys Leu Asp Ile Arg Thr Met Lys Val Ala Glu
225                 230                 235                 240

Leu Arg Gln Glu Leu Met Ala Arg Asp Leu Glu Thr Lys Gly Val Lys
                245                 250                 255

Ser Val Leu Cys Ala Arg Leu Gln Glu Ala Leu Asp Gln Glu Lys Thr
                260                 265                 270

Lys Asp Glu Asp Lys Glu Asp Val Cys Leu Lys Thr Ala Val Gly Met
            275                 280                 285

Ile Glu Val Ala Lys Pro Gln Glu Gly Asn Glu Glu Lys Glu Leu Thr
290                 295                 300

Asp Glu Asp Lys Lys Ala Val Glu Lys Phe Glu Lys Glu Lys Lys Glu
305                 310                 315                 320
```

```
Lys Lys Ala Ser Leu Glu Arg His Phe Thr Ile Pro Lys Glu Pro Gly
                325                 330                 335

Ile Leu Val Tyr Pro Asn Arg Met Ala Lys Gly Gly Lys Phe Asp Cys
                340                 345                 350

Lys Ile Val Ser Leu His Thr Met Leu Asp Tyr Arg Ile Glu Asp Asn
                355                 360                 365

Lys Glu His Ser Phe Glu Leu Ala Val Met Ala Glu Cys Ile Ser Glu
                370                 375                 380

Met Leu Asp Arg Ser Gln Ala Phe Ile Ala Tyr Lys Thr Leu
385                 390                 395

<210> SEQ ID NO 26
<211> LENGTH: 391
<212> TYPE: PRT
<213> ORGANISM: Loa loa

<400> SEQUENCE: 26

Ala Asp Tyr Arg Phe Ser Val Lys Val Val Leu Met Ser His Gln Gly
1               5                   10                  15

Leu Ser Leu Val His Gln Lys Ala Phe Gly Leu Gln Val Asp Gly Ser
                20                  25                  30

Ile Asp Glu Asn Ile Asp Pro Ala Ser Leu Lys Arg Cys Ile Asn Phe
                35                  40                  45

Val Val Gly Thr Arg Asn Lys Glu Met Met Ala Ile Gly Gly Ala Trp
            50                  55                  60

Ser Pro Ser Leu Asp Gly Asp Asn Pro Glu Ser Asp Pro Gln Val Phe
65                  70                  75                  80

Val Arg Thr Ala Val Arg Thr Val Arg Ala Leu Ile Gly Val Asp Leu
                85                  90                  95

Ser Lys Cys Pro Arg Trp Tyr Lys Met Ala Glu Ile Arg Tyr Tyr Arg
                100                 105                 110

Ala Glu Lys Asp Arg Met Asp Thr Cys Cys Leu Phe Leu Pro Asp Thr
                115                 120                 125

Ser Gly Leu Met Pro Thr Glu Asp Cys Tyr Gln Gln Leu Leu Ala Thr
            130                 135                 140

Leu Lys Asp Gln Leu Gly Asn Lys Leu Ala Ala Leu Asp Ala Gln Lys
145                 150                 155                 160

Leu Val Leu Pro Ser Thr Val Ala Ala Leu Ala Thr Asp Ser Gly Asp
                165                 170                 175

Ala Gly Glu Gly Thr Thr Thr Thr Glu Pro Val Ala Gln Ala Gly
                180                 185                 190

Asp Thr Gln Gln Gln Leu Gln Gln Gly Gln Gln Gln Ile Asp Ala Asn
                195                 200                 205

Lys Glu Gln Val Gln Glu Val Glu Asp Asp Glu Asp Leu Asn
            210                 215                 220

Pro Thr His Trp Ser Lys Leu Asp Ile Arg Thr Met Lys Val Ala Glu
225                 230                 235                 240

Leu Arg Gln Glu Leu Met Ala Arg Asp Leu Glu Thr Lys Gly Val Lys
                245                 250                 255

Ser Val Leu Cys Ala Arg Leu Gln Glu Ala Leu Asp His Glu Lys Thr
                260                 265                 270

Lys Asp Glu Asp Lys Gly Asp Lys Ala Glu Val Ala Lys Val Lys Glu
                275                 280                 285

Glu Glu Lys Glu Glu Lys Glu Leu Thr Asp Glu Asp Lys Lys Ala Ile
```

```
                290                 295                 300
Glu Lys Phe Glu Lys Glu Lys Glu Lys Lys Ala Ser Leu Glu Arg
305                 310                 315                 320

His Phe Thr Ile Pro Lys Glu Leu Gly Ile Leu Val His Pro Asn Arg
                325                 330                 335

Met Ala Lys Gly Gly Lys Phe Asp Cys Lys Ile Val Ser Leu His Thr
                340                 345                 350

Met Leu Asp Tyr Arg Thr Glu Asp Asn Lys Glu His Ser Phe Glu Leu
                355                 360                 365

Ala Val Met Ala Glu Cys Ile Ser Glu Met Leu Asp Arg Ser Gln Ala
                370                 375                 380

Phe Val Ala Tyr Lys Thr Leu
385                 390

<210> SEQ ID NO 27
<211> LENGTH: 377
<212> TYPE: PRT
<213> ORGANISM: Schistosoma mansoni

<400> SEQUENCE: 27

Ala Asp Tyr Ser Tyr Ser Ala Arg Val Met Leu Met Ala Cys Pro Gln
1               5                   10                  15

Leu Gly Glu Leu Tyr Lys Asn Thr Cys Arg Met Ala Asp Asp Ala Asn
                20                  25                  30

Gly Ala Gly Lys Val Leu Pro Asp Lys Ser Ile His Phe Leu Val Gly
            35                  40                  45

Gly Arg Ala Lys Ser Glu Thr Met Ala Leu Gly Gly Pro Trp Ser Pro
50                  55                  60

Ser Leu Asp Gly Pro Asp Pro Gln Gly Asn Pro Met Thr Leu Ile Lys
65                  70                  75                  80

Thr Ala Ile Arg Thr Phe Lys Gly Leu Thr Gly Leu Asp Leu Ser Ser
                85                  90                  95

Cys Thr Glu Trp Val Arg Phe Met Glu Leu Lys Tyr Tyr Arg Met Pro
                100                 105                 110

Asp Thr Lys Ala Pro Ala Phe Thr Glu Ala Glu Glu Arg Glu Ile
            115                 120                 125

Thr Ser Glu Arg Pro Glu Val Val Phe Phe Ile Pro Asn Ala Ala
130                 135                 140

His Leu Ile Pro Ser Glu Glu Gln Trp Ala Lys Thr Lys Glu Tyr Tyr
145                 150                 155                 160

Asn Ser Ile Leu Gln Lys Gln Leu Thr Val Glu Lys Val Glu Asp Glu
                165                 170                 175

Ser Met Val Glu Gln Gln Asp Gly Asp Met Ser Val Ala Asp Val Ser
            180                 185                 190

Val Glu Glu Pro Glu Glu Ser Ile Ala Arg Ser Asp Ile Glu Pro Thr
195                 200                 205

His Tyr Ser Lys Leu Asp Val Asn Thr Leu Lys Val Ser Asp Leu Arg
            210                 215                 220

Asn Glu Leu Ala Ala Arg Lys Leu Asp Thr Lys Gly Leu Lys Val Asn
225                 230                 235                 240

Leu Val Ala Arg Leu Gln Ser Ala Leu Asp Glu Lys Lys Ala Asp
                245                 250                 255

Ala Pro Glu Asp Ile Lys Ile Asp Glu Glu Ile Lys Ala Glu Gln Thr
            260                 265                 270
```

```
Pro Asn Lys Ile Ser Ser Pro Ser Ala Thr Gln Pro Lys Asp Asp Ser
        275                 280                 285

Lys Asp Leu Ser Glu Lys Asp Arg Arg Leu Glu Arg Leu Tyr Arg
    290                 295                 300

Leu Gly Asp Lys Pro Ala Ile Val Ile His Pro Asn Lys Ser Ala Lys
305                 310                 315                 320

Gly Gly Arg Phe Asp Cys His Arg Val Ser Leu Phe Ser Leu Leu Asp
                325                 330                 335

Tyr His Thr Glu Asp Gln Lys Glu His Asn Phe Glu Val Ser Leu Phe
                340                 345                 350

Ala Glu Gln Phe His Glu Met Leu Gln Arg Asp Ala Ala Phe Thr Ile
            355                 360                 365

Phe Lys Ala Ile His Asp Ala Pro Glu
    370                 375
```

<210> SEQ ID NO 28
<211> LENGTH: 378
<212> TYPE: PRT
<213> ORGANISM: Clonorchis_sinensis

<400> SEQUENCE: 28

```
Ala Asp Tyr Ser Tyr Ser Ala Arg Val Met Leu Met Ala Cys Pro Gln
1               5                   10                  15

Leu Ala Glu Leu Tyr Lys Asn Thr Cys His Met Ala Asp Asp Val Ser
            20                  25                  30

Gly Thr Asp Lys Val Pro Pro Gly Lys Asn Ile His Phe Leu Val Gly
        35                  40                  45

Gly Arg Ala Lys Ser Glu Thr Met Ala Ile Gly Gly Pro Trp Ser Pro
50                  55                  60

Ser Met Asp Gly Ala Asp Pro Cys Gly Asp Pro Arg Thr Leu Ile Asn
65                  70                  75                  80

Thr Ala Ile Arg Thr Phe Lys Gly Tyr Thr Gly Leu Asp Leu Ser Ser
                85                  90                  95

Cys Thr Glu Trp Ile Arg Phe Met Glu Ile Arg Tyr Tyr Arg Phe Ala
            100                 105                 110

Asp Thr Lys Ala Pro Ala Phe Thr Gly Asp Asp Glu Arg Leu Val
        115                 120                 125

Thr Thr Glu Arg Pro Glu Val Val Val Phe Phe Ile Pro Asn Ala Ser
    130                 135                 140

His Leu Ile Pro Ser Asp Glu Glu Trp Ala Lys Val Lys Glu His Tyr
145                 150                 155                 160

Thr Ser Val Leu Gln Ala Leu Leu Ser Pro Glu Gln Lys Pro Glu Val
                165                 170                 175

Glu Ala Thr Pro Gly Ala Asp Ala Thr Glu Val Glu Thr Ser Val Val
            180                 185                 190

Asp Ala Ser Met Asp Asp Gly Asp Glu Ala Gly Thr Arg Ser Asp Met
        195                 200                 205

Glu Pro Thr His Tyr Ser Lys Leu Asp Ala Asn Ser Leu Lys Val Asn
    210                 215                 220

Glu Leu Arg Asn Glu Leu Ala Ala Arg Asn Leu Asp Thr Lys Gly Leu
225                 230                 235                 240

Lys Val Asn Leu Val Ala Arg Leu Gln Ala Ala Leu Asp Glu Glu Lys
                245                 250                 255

Lys Ala Asp Thr Pro Glu Glu Thr Lys Ala Ala Glu Asp Ser Lys Ala
            260                 265                 270
```

```
Glu Glu Thr Pro Ala Lys Ala Thr Thr Pro Thr Gln Ser Lys Asp Glu
            275                 280                 285

Ser Lys Asp Leu Ser Glu Lys Glu Arg Arg Leu Glu Arg Leu Tyr
    290                 295                 300

Arg Leu Asn Asp Lys Pro Ala Ile Ile Ile His Pro Asn Lys Ser Ala
305                 310                 315                 320

Arg Gly Gly Arg Phe Asp Cys His Arg Val Ser Leu Phe Ser Leu Leu
                325                 330                 335

Asp Tyr Arg Thr Glu Glu Gln Lys Glu Gln Asn Phe Glu Val Ser Leu
                340                 345                 350

Phe Ala Glu Gln Phe His Glu Met Leu Gln Arg Asp Cys Ala Phe Thr
                355                 360                 365

Ile Phe Lys Ala Ile Asn Asp Ala Pro Glu
            370                 375

<210> SEQ ID NO 29
<211> LENGTH: 436
<212> TYPE: PRT
<213> ORGANISM: Clonorchis_sinensis

<400> SEQUENCE: 29

Ala Glu Thr Gly Phe Tyr Val Asn Val Leu Leu Ser Met Pro Ser
1               5                   10                  15

Ile Pro Thr Leu Gln Asp Lys Thr Thr Val Arg Ala Glu Ser Ser Asp
            20                  25                  30

Arg Glu Lys Val Pro Leu Arg Lys Tyr Ile Lys Ile Leu Ala Leu Ser
        35                  40                  45

Lys Thr Asn Glu Arg Phe Lys Ala Ile Gly Gly Pro Trp Asn Pro Asp
50                  55                  60

Leu Asp Gly Gln Asp Pro Val Gly Asp Ser Arg Ala Leu Ile Asn Ala
65                  70                  75                  80

Ala Ile Arg Ile Cys Lys Glu Gln Leu Gly Leu Asp Leu Ser Tyr Cys
                85                  90                  95

Thr Gln Trp His Arg Phe Leu Glu Phe Arg Tyr Ser Arg Thr Glu Gly
            100                 105                 110

Ser Thr Ala Arg Pro Ala Ser Val Leu Phe Pro Gly Ser Gln Leu Trp
        115                 120                 125

Gly Arg Ser Phe Pro Glu Ser Ala Asn Ser Lys Ser Ala Thr Pro Ser
130                 135                 140

Lys Pro Tyr His Arg Ile Val Val Tyr Phe Leu Pro Asp Ile Trp Ser
145                 150                 155                 160

Leu Met Pro Ser Thr Gly Asp Trp Ala Asn Val Lys Arg Ser Met Glu
                165                 170                 175

Asn Ala Leu Ser Arg Lys Leu Pro Gln Leu Phe Pro Met Ser Gln Ala
            180                 185                 190

Glu Ile Asn Ala Leu Ser Asp Ala Thr Ser Thr Gly Ala Ser Ser Asp
        195                 200                 205

Asp Ala Lys Asn Lys Ser Asn Pro Thr Cys Pro Thr Gly Val Thr
210                 215                 220

Ala Thr Ala Leu Gly Asp Thr Thr Thr Ser Thr Ala Gly Asp Ser
225                 230                 235                 240

Gln Asn Asn Pro Thr Ala Ala Pro Lys Pro Asp Gln Ser Asp Ser Met
                245                 250                 255

Leu Asp Thr Ser Ala Arg Glu Ile Gly Asp Glu Gly Leu Gln Ser Pro
```

```
                260                 265                 270
Thr Arg Ala Ser Gly Gly Asp Lys Asn Asp Ser Ser Gln Glu Val Ser
            275                 280                 285

Glu Leu Arg Glu Gln Leu Lys Val Arg Asn Leu Pro Ala Asp Gly Ile
        290                 295                 300

Lys Ala Gln Leu Leu Ser Arg Leu Lys Thr Ala Val Glu Lys Glu Ala
305                 310                 315                 320

Glu Gln Ala Arg Lys Glu Glu Glu Arg Lys Lys Glu Lys Glu
            325                 330                 335

Met Gln Glu Ala Leu Ala Ala Lys Glu Glu Asp Lys Lys Arg Glu
        340                 345                 350

Ser Ser Lys Pro Thr Ile Glu Ile Ser Ala Thr Pro Lys Ala Asp Ala
            355                 360                 365

Cys Ile Ala Leu Arg Asn Tyr Pro Ser Ile Ile Val Gln Lys Arg Leu
        370                 375                 380

Thr Asp Asp Tyr Thr Leu Gln Thr Val Ser Leu Asp Ser Val Leu Glu
385                 390                 395                 400

Ser Lys Ser Asp Phe Met Asp Ala Arg Ser Tyr Glu Leu Val Ile Cys
                405                 410                 415

Val His Asn Leu Phe Asp Met Val Arg Arg Asp Phe Ile Phe Thr Leu
            420                 425                 430

Phe Arg Ala Leu
            435

<210> SEQ ID NO 30
<211> LENGTH: 466
<212> TYPE: PRT
<213> ORGANISM: Schistosoma mansoni

<400> SEQUENCE: 30

Asn Asp Ser Gly Phe Ala Ala Tyr Val Leu Leu Ser Leu Pro Ala
1               5                   10                  15

Met Ala Glu Leu Met Glu Lys Ile Val Val Arg Ala Glu Ser Pro Ser
            20                  25                  30

Arg Met Arg Gly Ser Leu Arg Lys Tyr Ile Lys Ile Leu Ala Ala Gly
        35                  40                  45

Lys Val Asp Glu Arg Leu Lys Ala Ile Gly Gly Ser Trp Ser Arg Asp
    50                  55                  60

Leu Asp Gly Pro Asp Pro Ala Thr Asn Pro Gln Thr Leu Val Asn Thr
65                  70                  75                  80

Ala Ile Arg Val Cys Lys Gln Leu Ile Gly Leu Asp Leu Ser Tyr Cys
                85                  90                  95

Thr Gln Trp His Arg Phe Leu Glu Phe Arg Tyr Ser Arg Thr Glu Gly
            100                 105                 110

Ser Thr Ala Gln Pro Thr Ser Val Leu Phe Pro Gly Ser Gln Leu Trp
        115                 120                 125

Gly Arg Pro Val Thr Glu Ser Pro Glu Ser Asp Met Ile Pro Pro Ser
    130                 135                 140

Lys Pro Phe His Gln Ile Val Val Tyr Phe Ile Pro Asn Val Trp Ser
145                 150                 155                 160

Leu Met Pro Thr Asp Glu Glu Trp Ser Thr Ile Lys Leu Ala Tyr Glu
                165                 170                 175

Asn Ile Leu Ala Ser Lys Glu Pro Lys Val Phe Pro Met Ser Pro Ser
            180                 185                 190
```

```
Asn Leu Lys Lys Phe Ser Gly Leu Glu Ser Ala Ser Lys Gly Thr Gly
            195                 200                 205

Asp Gly Lys Leu Asn Val Val Ser Glu Leu Asp Ser Asn Leu Leu Lys
        210                 215                 220

Ser Pro Thr Gln Asp Asn Ala His Glu Asp Ser Asn Val Ser Lys Met
225                 230                 235                 240

Asp Glu Gly Asn Lys Ser Thr Val Gln Ala Pro Val Glu Phe His Arg
                245                 250                 255

Ser Ser Pro Tyr Leu Ala Gly Gln Glu Thr Val Pro Lys Val Ala Ala
            260                 265                 270

Ile Ser Glu Thr Glu Asp Gly Phe Glu Ser Val Asp Leu Ala Ala Gln
        275                 280                 285

Gly Asn Pro Asn Gln Glu Gly Thr Asp Lys Cys Gln Lys Leu His
    290                 295                 300

Thr Glu Leu Asn Leu Ala Ser Met Lys Val Ser Glu Leu Arg Glu Gln
305                 310                 315                 320

Leu Lys Ala Arg Asn Leu Pro Thr Glu Gly Val Arg Ala Gln Leu Leu
                325                 330                 335

Thr Arg Leu Lys Thr Ala Ile Gln Glu Glu Glu Lys Glu Ser Ala
            340                 345                 350

Lys Lys Ala Glu Lys Glu Lys Met Glu Gln Glu Lys Thr Leu Gln Ser
        355                 360                 365

Val Thr Ile Asp Lys Ser Pro Gln Val Ser Glu Gln Ile Lys Pro
    370                 375                 380

Leu Asn Thr Glu Ser Gly Ser Lys Ser Trp Thr Asp Ala Pro Lys Leu
385                 390                 395                 400

Thr Leu Arg Asp Leu Pro Ser Ile Ile Val Leu Arg Lys Lys Thr Val
                405                 410                 415

Asp Phe Thr Val Gln Ser Val Gly Leu Asp Val Val Met Asp Ser Lys
            420                 425                 430

Ser Asp Phe Met Asp Cys Arg Ser Tyr Glu Phe Met Phe Cys Ile His
        435                 440                 445

Thr Ile Phe Asp Met Leu Arg Arg Asp Ser Val Phe Thr Leu Phe Arg
    450                 455                 460

Ala Leu
465

<210> SEQ ID NO 31
<211> LENGTH: 467
<212> TYPE: PRT
<213> ORGANISM: Schistosoma japonicum

<400> SEQUENCE: 31

Ser Asp Ser Gly Phe Ala Ala Tyr Val Leu Leu Ser Leu Pro Ala
1               5                   10                  15

Met Ala Glu Leu Met Glu Lys Ile Val Val Arg Ala Glu Ser Pro Ser
            20                  25                  30

Arg Val Arg Gly Ser Leu Arg Lys Tyr Ile Lys Ile Leu Ala Val Gly
        35                  40                  45

Lys Val Asp Glu Arg Leu Lys Ala Ile Gly Gly Ser Trp Asn Pro Asp
    50                  55                  60

Leu Asp Gly Ser Asp Pro Ala Thr Asn Pro Gln Thr Leu Ile Asn Thr
65                  70                  75                  80

Ala Ile Arg Asn Cys Lys Gln Leu Ile Gly Leu Asp Leu Ser Tyr Cys
                85                  90                  95
```

Thr Gln Trp His Arg Phe Leu Glu Phe Arg Tyr Ser Arg Thr Glu Gly
            100                 105                 110

Ser Thr Ala Gln Pro Thr Ser Val Leu Phe Pro Gly Ser Gln Leu Trp
            115                 120                 125

Gly Arg Pro Ala Thr Glu Ser Asn Asp Val Ile Pro Pro Ser Lys Pro
130                 135                 140

Phe His Gln Ile Val Val Tyr Phe Ile Pro Asn Val Trp Ser Leu Met
145                 150                 155                 160

Pro Ala Asp Glu Glu Trp Ser Thr Ile Lys Leu Ala Tyr Glu Asn Val
                165                 170                 175

Leu Ala Ser Lys Glu Pro Asn Val Phe Pro Leu Ala Pro Ser Ser Leu
            180                 185                 190

Lys Lys Phe Ser Gly Leu Glu Ser Ala Ser Lys Glu Thr Ser Asp Gly
            195                 200                 205

Lys Leu Lys Leu Val Val Glu Met Asp Ser Asn Ser Leu Lys Ser Pro
        210                 215                 220

Ala Gln Asp Asn Leu Cys Glu Asp Pro Asn Ala Ser Lys Met Asp Glu
225                 230                 235                 240

Gly Asn Lys Ser Ile Leu Gln Ala Pro Val Glu His Asp Gly Ser Ala
                245                 250                 255

Leu Ser Thr Ala Asp Gln Glu Ser Val Ser Lys Ile Ala Asn Thr Pro
            260                 265                 270

Glu Ala Glu Asp Gly Phe Glu Ser Met Gly Pro Lys Asn Ile Ser Ile
        275                 280                 285

Gln Gly Asn Pro Asn Gln Glu Gly Thr Glu Lys Cys Gln Lys Lys Leu
        290                 295                 300

His Thr Glu Ile Asn Leu Ala Asn Met Lys Val Ser Glu Leu Arg Glu
305                 310                 315                 320

Gln Leu Lys Ala Arg Asn Leu Pro Thr Glu Gly Val Arg Ala Gln Leu
                325                 330                 335

Leu Thr Arg Leu Lys Met Ala Ile Gln Glu Glu Glu Lys Glu Ser
            340                 345                 350

Ala Ile Lys Ala Glu Lys Glu Lys Met Glu Gln Ala Lys Ala Leu Gln
            355                 360                 365

Leu Val Thr Ile Asp Lys Ser Pro Gln Val Pro Glu Glu Gln Val Lys
        370                 375                 380

Pro Val Asn Ala Glu Ser Gly Ser Lys Leu Lys Thr Asp Val Pro Lys
385                 390                 395                 400

Leu Ala Leu Arg Asp Leu Pro Ser Ile Ile Leu Arg Lys Lys Asn
                405                 410                 415

Ala Asp Phe Thr Val Gln Ser Val Gly Leu Asp Val Val Met Asp Ser
            420                 425                 430

Lys Ser Asp Phe Met Asp Ser Arg Ser Tyr Glu Phe Met Phe Cys Ile
            435                 440                 445

His Thr Ile Phe Asp Met Leu Arg Arg Asp Ser Val Phe Thr Leu Phe
            450                 455                 460

Arg Ala Leu
465

<210> SEQ ID NO 32
<211> LENGTH: 372
<212> TYPE: PRT
<213> ORGANISM: Guillardia theta

<400> SEQUENCE: 32

```
Phe Thr Val Lys Tyr Asn Ala Lys Val Met Leu Leu Gln Gly Leu Pro
1               5                   10                  15

Asp Leu Trp Trp Glu Ala Gly Gly Thr Ser Lys Ala His Leu Gly Lys
            20                  25                  30

Met Ile Lys Phe Leu Cys Val Lys Ser Gln Lys His Gly Leu Phe Cys
        35                  40                  45

Met Gly Gly Met Trp Met Glu Glu Lys Asp Gly Gly Ser Thr Gly
    50                  55                  60

Pro Asp Thr Glu Ala Leu Ile Arg Thr Ala Ile Arg Cys Val Lys Glu
65                  70                  75                  80

Thr Ile Asp Val Asp Leu Ser Gly Val Lys Lys Trp His Arg Phe Met
                85                  90                  95

Glu Ile Gln Tyr Asn Arg Pro Ala Glu Met Tyr Lys Gly Gln Trp Tyr
            100                 105                 110

Pro Glu Gln Glu Glu His Thr Ile Ile Phe Leu Pro Glu Leu Glu Gly
        115                 120                 125

Ala Met Pro Asp Arg Glu Gln Phe Thr Ser Ser Ile Ser Asn Leu Glu
    130                 135                 140

Asp Glu Leu Asn Ser Lys Ala His Ala Ala Trp Glu Lys Asp Met Glu
145                 150                 155                 160

Glu Arg Arg Arg Ala Ala Lys Glu Ala Glu Ile Lys Arg Ala Ala Ala
                165                 170                 175

Ala Ala Ala Ala Ala Glu Ala Ala Lys Leu Ala Ala Ala Ala Ala Ala
            180                 185                 190

Ala Ala Ala Ala Lys Ala Ala Glu Ala Glu Ala Ala Ala Glu
            195                 200                 205

Ser Ile Ser Thr Gly Asp Arg Lys Thr Pro Ala Gly Ala Gly Asn Ile
    210                 215                 220

Asn Glu Ala Gly Gln Pro Gly Asp Gly Lys Ser Ala Glu Val Lys Leu
225                 230                 235                 240

Glu Ser Val Val Pro Ala Thr Ser Ser Gly Val Gln Gln Asp Ala Asp
                245                 250                 255

Ala Ser Gly Gln Leu Ala Thr Ser Thr Gly Glu Val Lys Thr Glu Gln
            260                 265                 270

Glu Gly Gly Gly His Gly Val Lys Glu Val Lys Gly Pro Pro
        275                 280                 285

Pro Pro Glu Pro Ile Lys Leu Asp Phe Pro Glu Glu Pro Cys Ile Leu
    290                 295                 300

Val Arg Pro Lys Trp Glu Gly Gly Asp Gly Lys Gly Gln Ile Lys
305                 310                 315                 320

Ala Ser Leu Ile Ser Leu Asp Gly Leu Leu Asp Tyr Asn Leu Asp Asp
                325                 330                 335

Val Leu Glu Lys Asn Phe Glu Val Ser Leu Phe Ala Glu Phe His
            340                 345                 350

Glu Met Leu Glu His Met Phe Ala Ser Arg Ile Leu Lys Asp Ile Gln
        355                 360                 365

Asp Arg Ala Arg
    370
```

<210> SEQ ID NO 33
<211> LENGTH: 286
<212> TYPE: PRT
<213> ORGANISM: Dictyostelium fasciculatum

<400> SEQUENCE: 33

Asn Gly Val Lys Tyr Asn Ala Lys Val Met Leu Phe Gln Gln Leu Pro
1               5                   10                  15

Val Asp Ser Thr Thr Pro Thr Asn Leu Cys Lys Arg Leu Lys Phe Leu
            20                  25                  30

Val Ala Lys Glu Asn Lys Asp Ile Cys Cys Ile Gly Gly Thr Trp Ser
        35                  40                  45

Pro Ser Leu Asp Gly Gln Asp Ile Asp Asn Pro Gln Thr Leu Ile Asn
    50                  55                  60

Thr Ala Ile Arg Thr Thr Lys Glu Tyr Thr Gln Phe Asp Leu Ser Lys
65                  70                  75                  80

Cys Val Lys Trp Ile Lys Phe Met Glu Val His Tyr Arg Pro Pro
                85                  90                  95

Thr Glu Lys Asn Gln Gln Tyr Gln Glu Val Thr Val Ile Phe Val Pro
            100                 105                 110

Asp Ile Ser Asn Ile Thr Pro Asn Glu Ile Asn His Ser Leu Leu Gln
        115                 120                 125

Gln Asp Lys Pro Ser Glu Lys Glu Gly Glu Asp His His Gln
    130                 135                 140

Gln Gln Gln Gln Gln Gln Gln Gln Gln Gln Gln Gln Gln Glu Glu
145                 150                 155                 160

Gly Thr Asn Glu Tyr Asp Pro Glu Asn Gln Gly Glu Lys Gln Asp
                165                 170                 175

Ser Ser Asn Asp Pro Ala Gln Thr Asp Ala Lys Ile Ser Ile Thr Ser
            180                 185                 190

Glu Thr Ser Ser Glu Arg Lys Thr Thr Ser Pro Asn Pro Ala Pro Leu
            195                 200                 205

Val Ala Leu Pro Lys Glu Leu Gln Ser Cys Phe Ile Ile Thr Thr Pro
        210                 215                 220

Leu Ser Asp Thr Ser Ser Ile Lys Tyr Arg Ala Met Met Leu Ser Leu
225                 230                 235                 240

Asp Gly Leu Leu Asp Tyr Glu Glu Ser Asp Lys Phe Glu Gly Thr Phe
                245                 250                 255

Glu Ala Ser Leu Phe Gly Glu Leu Phe Tyr Leu Met Leu Ala Thr Glu
            260                 265                 270

Met Gly Asn Ile Val Met Gln Ala Leu Leu Asp Phe Thr Pro
            275                 280                 285

<210> SEQ ID NO 34
<211> LENGTH: 286
<212> TYPE: PRT
<213> ORGANISM: Dictyostelium discoideum

<400> SEQUENCE: 34

Thr His Ile Lys Tyr Asn Ser Lys Val Met Leu Tyr Ser Phe Tyr Ser
1               5                   10                  15

Asn Ile Glu Asp Pro Ser Ile Thr Lys Lys Ile Lys Phe Leu Val Ser
            20                  25                  30

Lys Glu Asp Lys Asp Ile Ser Cys Ile Gly Gly Thr Trp Leu Pro Asp
        35                  40                  45

Leu Asp Gly Glu Asp Val Asn Asp His Pro Gln Thr Leu Ile Asn Thr
    50                  55                  60

Ala Ile Arg Thr Thr Lys Glu Tyr Thr Gln Ile Asp Leu Ser Gly Cys
65                  70                  75                  80

```
Lys Lys Trp Tyr Lys Phe Met Glu Val His Tyr Tyr Arg Pro Pro Thr
                85                  90                  95

Glu Glu Gln Ser Tyr Tyr Gln Glu Ile Thr Val Ile Tyr Val Pro Asp
            100                 105                 110

Ile Thr Asp Ile Gln Pro Met Asp Val Asp Ser Leu Leu Lys Val Pro
        115                 120                 125

Thr Val Ser Glu Thr Thr Pro Ser Ala Pro Val Gly Val Thr Thr Ala
    130                 135                 140

Thr Thr Lys Thr Thr Glu Glu Glu Glu Glu Asp Gln Ala Pro Lys
145                 150                 155                 160

Asp His Val Ser Lys Asp Phe Asp Asn Asp Glu Thr Ser Ser Asn Thr
                165                 170                 175

Glu Gln Asn Gln Pro Pro Lys Ser Ser Thr Thr Ser Asn Thr Thr Lys
            180                 185                 190

Pro Ala Ala Ala Val Pro Thr Thr Thr Ala Ala Thr Ala Thr Thr Thr
        195                 200                 205

His Gly Ser Leu His Leu Pro Lys Ala Ser Lys Phe Tyr Asn Val Ile
    210                 215                 220

Thr Pro Ser Ser Glu Gly Asn Arg Tyr Lys Ala Met Met Leu Ser Leu
225                 230                 235                 240

Asp Gly Leu Leu Asp Tyr Asp Glu Ser Asp Thr His Glu Gly Thr Phe
                245                 250                 255

Glu Ala Ser Leu Phe Ser Glu Leu Phe Tyr Leu Met Leu Cys Arg Asp
            260                 265                 270

Met Gly Thr Asn Ile Leu Thr Ser Ile Val Asn Tyr Arg Pro
        275                 280                 285

<210> SEQ ID NO 35
<211> LENGTH: 316
<212> TYPE: PRT
<213> ORGANISM: Polysphondylium pallidum

<400> SEQUENCE: 35

Asp Asn Ile Lys Tyr Asn Ala Lys Val Met Met Phe Gln Gln Val Thr
1               5                   10                  15

Pro Val Asn Gln Thr Ala Pro Leu His Ile Asn Lys Arg Leu Lys Phe
            20                  25                  30

Leu Val Ala Lys Glu Asn Lys Asp Ile Ser Cys Ile Gly Gly Ser Trp
        35                  40                  45

Asn Pro Thr Leu Asp Gly Asn Asp Ile Asn Asp Pro Gln Thr Leu Ile
    50                  55                  60

Asn Thr Ala Ile Arg Thr Thr Lys Glu Tyr Thr Gln Ile Asp Leu Ser
65                  70                  75                  80

Arg Cys Asn Arg Trp Val Lys Phe Met Glu Ile His Tyr Tyr Arg Pro
                85                  90                  95

Pro Thr Glu Ala Met Ala Gln Phe Gln Glu Ile Thr Val Ile Phe Val
            100                 105                 110

Pro Asp Leu Thr Asn Ile Thr Pro Phe Asp Gly Lys Glu His Met Lys
        115                 120                 125

Asn Lys Val Thr Thr Ala Ser Pro Thr Glu Lys Ser Thr Glu Ser Asn
    130                 135                 140

Asn Glu His His Glu Glu Thr Asp Asp Gly Glu Glu Asn His Pro Pro
145                 150                 155                 160

Ala Gly Asn Asp Thr Gly Asp Ser Glu Lys Pro Ala Ala Ser Asp Glu
```

```
             165                 170                 175
Ile Val Gly Glu Val Thr Gly Glu Pro Lys Asp Lys Asp Glu Met Glu
            180                 185                 190

Met Ala Pro Ser Ser Val Ser Ala Ser Ser Asn Asp Gln Glu Ser
        195                 200                 205

His His His Asn Gln Thr Ser Gly Gly Ile Gln Ser Pro Asn Ser Ser
    210                 215                 220

Ser Ser Gln Ser Val Ser Ala Ser Thr Ala Thr Ala Ile Ser Thr Ala
225                 230                 235                 240

Ala Asn Gly Ser Asp Asp Ser His Ser Cys Phe Ser Val Thr Thr Pro
                245                 250                 255

Lys Ser Glu Asn Met Lys Tyr Arg Ser Met Met Leu Ser Leu Asp Gly
                260                 265                 270

Leu Leu Glu Tyr Asp Glu Ser Asp Lys Phe Glu Gly Thr Phe Glu Ala
                275                 280                 285

Ser Leu Phe Gly Glu Leu Phe Tyr Leu Met Leu Cys Arg Asp Phe Gly
                290                 295                 300

Ser Leu Ile Leu Gln Ser Ile Leu Tyr Phe Asn Pro
305                 310                 315

<210> SEQ ID NO 36
<211> LENGTH: 222
<212> TYPE: PRT
<213> ORGANISM: Dictyostelium purpureum

<400> SEQUENCE: 36

Asn Cys Ile Lys Tyr Asn Ala Lys Val Met Leu Tyr Ser Tyr Tyr Ser
1               5                   10                  15

Asn Ser Glu Asp Pro Ser Ile Ser Lys Arg Leu Lys Phe Leu Val Ala
                20                  25                  30

Lys Glu Asp Lys Asp Ile Ser Cys Ile Gly Gly Ser Trp Asn Pro Glu
            35                  40                  45

Leu Asp Gly Glu Asp Ile Asn Asp Pro Gln Thr Leu Ile Asn Thr Ala
    50                  55                  60

Ile Arg Thr Thr Lys Glu Tyr Thr Gln Ile Asp Leu Ser Ser Val Lys
65                  70                  75                  80

Lys Trp Val Lys Phe Met Glu Val His Tyr Tyr Arg Pro Pro Thr Asp
                85                  90                  95

Glu Phe Ser Phe Tyr Gln Glu Ile Thr Val Val Tyr Ile Pro Asn Ile
                100                 105                 110

Ser Glu Ile Pro Pro Leu Asp Val Glu Thr Leu Met Lys Asn Asn Ser
            115                 120                 125

Lys Gly Leu Glu Thr Asp Lys Gln Gly Glu Gln Ser Thr Ile Thr
    130                 135                 140

Pro Asn Thr Ile Leu Pro His Asn Ser Lys Lys Phe Tyr Thr Val Thr
145                 150                 155                 160

Thr Pro Ser Ser Asp Gly Asn Lys Phe Lys Ala Met Met Leu Ser Leu
                165                 170                 175

Asp Gly Leu Leu Asp Tyr Asp Glu Thr Asp Val His Glu Ser Thr Phe
                180                 185                 190

Glu Ala Ser Leu Phe Ser Glu Leu Phe Tyr Leu Met Leu Ala Arg Asp
            195                 200                 205

Met Gly Thr Thr Ile Leu Asn Thr Ile Ile Asn Tyr Arg Thr
    210                 215                 220
```

```
<210> SEQ ID NO 37
<211> LENGTH: 293
<212> TYPE: PRT
<213> ORGANISM: Chlorella variabilis

<400> SEQUENCE: 37

Gly Ser Val Val Tyr Asn Ala Lys Val Met Phe Thr Thr Gly Leu Gly
1               5                   10                  15

Glu Gly Glu Val Ala Ala Leu Leu Ala Gly Ala Ala Asp Lys Ala Gly
            20                  25                  30

Asp His Leu Cys Arg Leu Leu Lys Phe Val Val Ala Arg Ala Asp Arg
        35                  40                  45

Asn Gly Asp Lys Ser Gly Ile Phe Cys Leu Gly Arg Cys Asp Pro
    50                  55                  60

Ala Met Asp Gly Asp Pro Thr Gln Gly Asp Ala Ala Leu Val Ala Ala
65                  70                  75                  80

Ala Arg Arg His Val Ala Ala Gln Ala Arg Leu Glu Leu Pro Pro Ala
                85                  90                  95

Gly Ala Gly Ala Trp Leu Arg Phe Ile Glu Val His Tyr Thr Arg Leu
            100                 105                 110

Asp Arg Asn Asp Val Glu His His Gln Val Thr Val Val Phe Met
        115                 120                 125

Val Asp Ala Ser Arg Cys Leu Pro Ser Ala Ala Asp Trp Pro His Val
130                 135                 140

Trp Gln Gln Gln Gln Lys Pro Val Leu Leu Gln Lys Leu Ala Ala Glu
145                 150                 155                 160

Arg Ala Ala Lys Gln Glu Ala Ala Ala Lys Glu Pro Lys Pro Ala
                165                 170                 175

Ala Ala Gly Gly Leu Lys Glu Gly Gly Glu Gly Glu Arg Lys Glu
            180                 185                 190

Gly Gly Glu Glu Gly Glu Lys Glu Gly Glu Val Ala Ala Ala Arg Ala
            195                 200                 205

Val Glu Glu Gln Glu Glu Glu Ala Leu Pro Glu Pro Glu Met Pro
210                 215                 220

Ala Arg Pro Gln Leu Gln Leu Val Gly Leu His Thr Asp Lys Leu Arg
225                 230                 235                 240

Leu Lys Thr Ala Ala Val Ser Leu Asp Gly Leu Leu Asp Tyr Asn Thr
                245                 250                 255

Ser Asp Lys Asp Glu Cys Thr Phe Glu Leu Ser Leu Phe Ala Glu Ala
            260                 265                 270

Phe His Glu Ala Leu Met Arg Asp Ala Gly Cys Thr Ile Leu Ala Glu
        275                 280                 285

Leu Tyr Arg Gln Arg
    290

<210> SEQ ID NO 38
<211> LENGTH: 365
<212> TYPE: PRT
<213> ORGANISM: Volvox carteri

<400> SEQUENCE: 38

Gly Ser Leu Thr Leu Gly Gly Gln Val Leu Leu Val Gln Gly Leu Ser
1               5                   10                  15

Pro Ser Leu Arg Met Asp Val Leu Val Gly Pro His Glu Gly Gly
            20                  25                  30
```

-continued

```
Ala His Leu Val His Ala Leu Lys Phe Val Ala Ala Arg Phe Ser Arg
         35                  40                  45

Ser Gln Pro Ser Ala Gly Ala Glu Arg Glu Gly Lys Asp Lys Glu
 50                  55                  60

Gly Gly Lys Asp Arg Gln Arg Gly Val Leu Gly Ala Leu Gly Gly Thr
 65                  70                  75                  80

Trp Asp Pro Glu Leu Asp Gly Gly Asp Pro Glu Ser Glu Asp Gly Gly
                 85                  90                  95

Leu Ile Arg Thr Cys Ile Arg His Val Lys Asn Gln Ala Gly Val Asp
            100                 105                 110

Leu Ser Ala Cys Ala His Trp Leu Arg Val Cys Asp Ile Thr Tyr Met
        115                 120                 125

Arg Ala Ala Ser Ser Pro Thr Ser Gly Ser Gly Asp Ala Ala Ser Ala
    130                 135                 140

Gly Gln Leu Ser Ser Ser Ile Ser Asp Pro Gln Leu Arg Glu Val Val
145                 150                 155                 160

Val Val Phe Ala Ala Val Pro Asp Ala Cys Met Ala Gly Pro Asp Ala
                165                 170                 175

Trp Pro Glu Glu Ala Arg Gln Gln Gln Ala Phe Lys Gln Gln Arg Ile
            180                 185                 190

Ala Leu Glu Ser Glu Ala Arg Lys Lys Glu Asp Ala Ala Thr Ala Arg
        195                 200                 205

Lys Asp Lys Asp Val Val Thr Glu Lys Glu Lys Thr Lys Asp Glu Lys
    210                 215                 220

Arg Asp Lys Arg Glu Glu Glu Thr Asn Pro Gly Ala Glu Ala Ser Lys
225                 230                 235                 240

Asp Lys Asp Val Asp Asp Pro Leu Lys Gly Ala Gly Lys Asp Lys Asp
                245                 250                 255

Lys Asp Ser Asn Asp Asn Asn Lys Glu Ala Asp Gly Asp Ser Ser Lys
            260                 265                 270

Ala Glu Pro Glu Ala Ala Pro Val Arg Glu Val Pro Leu Pro Glu Glu
        275                 280                 285

Pro Gly Ile Gln Leu Arg Gly Arg Ala Ser Gly Leu Thr Ala Gly Ala
    290                 295                 300

Gly Leu Gly Gly Tyr Glu Arg Ile Lys Thr Phe Ser Ile Ser Leu His
305                 310                 315                 320

Gly Leu Leu Asp Tyr Asp Glu Thr Asp Arg Asp Glu Pro Thr Phe Glu
                325                 330                 335

Leu Ser Val Phe Thr Glu Cys Phe Gln Asp Met Leu Ser Arg Glu Tyr
            340                 345                 350

Gly Gly Thr Ile Tyr Ala Ala Leu Val Ala Glu Arg Ser
        355                 360                 365

<210> SEQ ID NO 39
<211> LENGTH: 326
<212> TYPE: PRT
<213> ORGANISM: Coccomyxa subellipsoidea

<400> SEQUENCE: 39

Gly Ala Val Lys Trp Asn Ala Arg Val Val Leu Leu Ser Gly Leu Asp
 1               5                  10                  15

Asp Asp Ala Arg Lys Glu Leu Leu Lys Gly Val His His Gly Gln
             20                  25                  30

His Leu His Gln Leu Leu Lys Phe Leu Thr Val Arg Thr Glu Thr Asp
         35                  40                  45
```

```
Lys Asp Asp Gly Arg Val Glu Arg Ser Gly Ile Thr Ala Ile Gly Gly
     50                  55                  60

Gln His Asp Pro Ser Leu Asp Gly Pro Ile Thr Asp Ala Ser Lys Ser
 65                  70                  75                  80

Thr Glu Pro Leu Ile Ala Thr Cys Val Arg His Ala Lys Lys Leu Leu
                     85                  90                  95

Gly Val Asp Leu Ser Ala Cys Lys Glu Trp Leu Pro Val Ile Glu Val
                 100                 105                 110

His Tyr Gln Arg Pro Pro Ser Ser Leu Ser Pro Asp Ala Thr Glu Ser
                 115                 120                 125

Thr Glu Ile Thr Val Ile Phe Leu Ala Ile Ala Arg Arg Val Met Pro
            130                 135                 140

Glu Asp Trp Gln Ser Thr Trp Lys Glu Gln Glu Ala Trp Leu Lys Gly
145                 150                 155                 160

Lys Ala Ala Arg Glu Glu Ala Val Thr Lys Lys Glu Glu Glu Lys
                165                 170                 175

Ala Ser Lys Ala Lys Ala Val Glu Glu Lys Ala Lys Pro Glu Glu Ala
                180                 185                 190

Thr Lys Ala Glu Gly Ala Ala Val Lys Asp Asp Glu Pro Ala Gly Ala
            195                 200                 205

Glu Lys Pro Ala Lys Arg Ala Lys Thr Gly Asp Val Glu Glu Glu Lys
        210                 215                 220

Lys Lys Asp His Gly Lys Val Val Asp Thr Asp Ile Lys Asp Ala Asp
225                 230                 235                 240

Asn Lys Ala Pro Glu Ala Pro Gln Glu Ala Glu Thr Asp Ala Lys Val
                245                 250                 255

Pro Glu Val Pro Arg Leu Leu Phe Arg Gly Lys Arg Ser Ala Lys Glu
                260                 265                 270

Arg Trp Arg Ser Ala Ser Ile Ser Leu Asp Gly Leu Leu Asp Tyr Asp
            275                 280                 285

Glu Glu Asp Arg Asp Glu Ser Thr Met Glu Leu Ser Leu Phe Ala Glu
        290                 295                 300

Gly Phe Gln Glu Met Leu Ala Arg Asp Tyr Gly Glu Arg Ile Leu Lys
305                 310                 315                 320

Ser Leu Tyr Ala Glu Arg
                325

<210> SEQ ID NO 40
<211> LENGTH: 287
<212> TYPE: PRT
<213> ORGANISM: Selaginella moellendorffii

<400> SEQUENCE: 40

Gly Ser Thr Val Trp Asn Val Lys Val Met Leu Met Ser Gly Leu Thr
 1                   5                  10                  15

Glu Glu Tyr Val Ala Asp Leu Leu Ser Asp Lys Pro Ser Asp Lys Pro
                 20                  25                  30

Thr Ser Phe Gln Lys Met Leu Lys Phe Val Ala Leu Arg Lys Asp Arg
             35                  40                  45

Asn Ala Ile Met Ala Ala Gly Thr Arg Trp Asp Lys Ser Leu Asp Gly
             50                  55                  60

Gly Asp Pro Thr Val Asp Asp Ser Gly Leu Ile Arg Ala Ala Val Arg
 65                  70                  75                  80

Ser Leu Lys Glu Leu Ile Gln Leu Asp Leu Ser Glu Cys Lys Asp Trp
```

-continued

```
            85                  90                  95
Phe Arg Phe Ala Glu Val His Tyr Glu Arg Val Asp Glu Asp Gly Phe
            100                 105                 110
Pro Ser His Arg Glu Ile Ser Val Ile Phe Phe Pro Asp Met Ser Ser
            115             120                 125
Cys Val Pro Ser Phe Glu Asn Trp Cys Leu Gln Trp Asn Gln Arg Lys
    130                 135                 140
Gln Ala Lys Leu Glu Arg Glu Gly Gln Ser Lys Lys Glu Val Lys Pro
145                 150                 155                 160
Ser Glu Lys Lys Asp Ala Ala Glu Lys Glu Ser Ile Ser Glu Gly Thr
                165                 170                 175
Pro Glu Thr Asp Val Asn Asn Gly Glu Pro Val Ala Ala Lys Glu Glu
            180                 185                 190
Glu Lys Lys Glu Lys Glu Lys Lys Glu Lys Asp Pro Pro Lys Asp
        195                 200                 205
Ser Glu Val Lys Lys Asp Glu Ala Pro Glu His Pro Gly Phe Leu Leu
    210                 215                 220
Met Thr Lys Arg Thr Lys Ala Ser Lys Leu Arg Ser Met Thr Ile Ser
225                 230                 235                 240
Leu Asp Gly Leu Leu Asp Tyr Asp Glu Asn Asp Lys Asp Glu Cys Thr
                245                 250                 255
Phe Glu Leu Ser Leu Phe Ala Glu Ala Phe Ala Glu Met Ile Gln Phe
                260                 265                 270
Arg Lys Gly Ser Gln Ile Leu Ala Ser Leu Glu Asn Leu Arg Arg
            275                 280                 285
```

MODULATING NUDIX HOMOLOGY DOMAIN (NHD) WITH NICOTINAMIDE MONONUCLEOTIDE ANALOGS AND DERIVATIVES OF SAME

RELATED APPLICATIONS

This application is a continuation of U.S. application Ser. No. 16/475,832 filed Jul. 3, 2019, which is a § 371 national-stage application based on PCT/US18/012182 filed Jan. 3, 2018 which claims the benefit of priority to U.S. Provisional Application No. 62/442,247 filed Jan. 4, 2017, each of which is hereby incorporated by reference in its entirety.

GOVERNMENT INTEREST

This invention was made with Government support under National Institutes of Health Grant AG019719 and AG028730. The Government has certain rights in the invention.

SEQUENCE LISTING

The instant application contains a Sequence Listing which has been submitted electronically in ASCII format and is hereby incorporated by reference in its entirety. Said ASCII copy, created on May 4, 2018, is named HMV_27426_ST.txt and is 124 kbytes in size.

BACKGROUND OF THE INVENTION

Nicotinamide adenine dinucleotide ($NAD^+$) is critical for redox reactions and as a substrate for signaling by the poly(ADP-ribose) polymerases (PARPs) and the sirtuins (SIRT1-7) in the regulation of DNA repair, energy metabolism, cell survival, circadian rhythms, among others (R. H. Houtkooper et al. *Endocr. Rev.* 31, 194-223 (2010); M. S. Bonkowski et al. *Nat. Rev. Mol. Cell Biol.* 17, 679-690 (2016); S. Imai et al. *Trends Cell Biol.* 24, 464-471 (2014)). Raising $NAD^+$ concentrations or directly activating the sirtuins delays aging in yeast, flies, and mice (L. Mouchiroud et al. *Cell* 154, 430-441 (2013); J. Yoshino et al. *Cell Metab.* 14, 528-536 (2011); K. S. Bhullar et al. *Biochim. Biophys. Acta* 1852, 1209-1218 (2015)). Increased amounts of sirtuin and PARP1 activity are also associated with improved health and longevity in humans (L. Mouchiroud et al. *Cell* 154, 430-441 (2013); K. Grube et al. *Proc. Natl. Acad. Sci. U.S.A.* 89, 11759-11763 (1992)). How cells modulate $NAD^+$ and PARP1 activity may impact diabetes, cancer, and possibly aging (S. Imai et al. *Trends Cell Biol.* 24, 464-471 (2014); M. C. Haigis et al. *Annu. Rev. Pathol.* 5, 253-295 (2010)). Whether $NAD^+$ has a third role in cells as a direct regulator of protein-protein interactions is a matter of speculation (V. Anantharaman et al. *Cell cycle* 7, 1467-1472 (2008)). Numerous proteins possess Nudix homology domains (NHDs) that have no known function. Understanding the mechanism and interplay of NAD+ and NHDs may shed light on the regulation of DNA repair, energy metabolism, cell survival, among others, and provide novel methods and therapies for major diseases such as cancer, radiation, and aging, among others.

SUMMARY OF THE INVENTION

The present invention is based, at least in part, on the discovery that Nudix homology domains (NHDs) are nicotinamide adenine dinucleotide ($NAD^+$) binding domains that regulate protein-protein interactions. Through NHDs, $NAD^+$ may directly regulate protein-protein interactions, the modulation of which may be useful in methods of recovering from, treating, and preventing cancer, aging, cell death, radiation damage, radiation exposure, among others, may improve DNA repair, cell proliferation, cell survival, among others, and may increase the life span of a cell or protect it against certain stresses, among others.

One aspect of the invention relates to a method for recovering from, treating, or preventing cancer in a subject in need thereof comprising administering an effective amount of a) nicotinamide mononucleotide, or an analog or derivative thereof; b) an agent that increases the level of nicotinamide mononucleotide, or an analog or derivative thereof; or c) both a) and b); to the subject to thereby modulate the activity of a biologically active polypeptide comprising a Nudix homology domain (NHD), or fragment thereof, or a nucleic acid encoding same.

Another aspect of the invention relates to a method for recovering from, treating, or preventing aging or cell death in a subject in need thereof comprising administering an effective amount of a) nicotinamide mononucleotide, or an analog or derivative thereof; b) an agent that increases the level of nicotinamide mononucleotide, or an analog or derivative thereof; or c) both a) and b); to the subject to thereby modulate the activity of a biologically active polypeptide comprising a Nudix homology domain (NHD), or fragment thereof, or a nucleic acid encoding same.

Another aspect of the invention relates to a method for recovering from, treating, or preventing radiation damage or radiation exposure or in a subject in need thereof comprising administering an effective amount of a) nicotinamide mononucleotide, or an analog or derivative thereof; b) an agent that increases the level of nicotinamide mononucleotide, or an analog or derivative thereof; or c) both a) and b); to the subject to thereby modulate the activity of a biologically active polypeptide comprising a Nudix homology domain (NHD), or fragment thereof, or a nucleic acid encoding same.

Another aspect of the invention relates to a method for recovering from, treating, or preventing chemotherapy-induced damage or cellular senescence in a subject in need thereof comprising administering an effective amount of a) nicotinamide mononucleotide, or an analog or derivative thereof; b) an agent that increases the level of nicotinamide mononucleotide, or an analog or derivative thereof; or c) both a) and b); to the subject to thereby modulate the activity of a biologically active polypeptide comprising a Nudix homology domain (NHD), or fragment thereof, or a nucleic acid encoding same.

Another aspect of the invention relates to a method for modulating DNA repair in a subject in need thereof comprising administering an effective amount of a) nicotinamide mononucleotide, or an analog or derivative thereof; b) an agent that increases the level of nicotinamide mononucleotide, or an analog or derivative thereof; or c) both a) and b); to the subject to thereby modulate the activity of a biologically active polypeptide comprising a Nudix homology domain (NHD), or fragment thereof, or a nucleic acid encoding same.

Another aspect of the invention relates to a method for modulating cell proliferation or cell survival in a subject in need thereof comprising administering an effective amount of a) nicotinamide mononucleotide, or an analog or derivative thereof; b) an agent that increases the level of nicotinamide mononucleotide, or an analog or derivative thereof; or c) both a) and b); to the subject to thereby modulate the activity of a biologically active polypeptide comprising a Nudix homology domain (NHD), or fragment thereof, or a nucleic acid encoding same.

In some embodiments of any of the aforementioned methods, said biologically active polypeptide comprising a Nudix homology domain (NHD), or fragment thereof, binds nicotinamide dinucleotide, or an analog or derivative thereof.

In some embodiments of any of the aforementioned methods, said nicotinamide mononucleotide, or an analog or derivative thereof is nicotinamide adenine dinucleotide (NAD+).

In some embodiments of any of the aforementioned methods, said biologically active polypeptide comprising a Nudix homology domain (NHD), or fragment thereof, comprises the NHD domain of a protein from Deleted Breast Cancer 1 (DBC1), or a protein set forth in Table 3.

In some embodiments of any of the aforementioned methods, said biologically active polypeptide comprising a Nudix homology domain (NHD), or fragment thereof, has a defective, deleted, or mutated protein binding region which inhibits interaction with a protein involved in cancer, aging, radiation damage, DNA repair, cell proliferation, or cell survival.

In some embodiments of any of the aforementioned methods, said biologically active polypeptide comprising a Nudix homology domain (NHD), or fragment thereof, has a defective, deleted, or mutated protein binding region which inhibits interaction with a protein involved in regulating of gene expression, cell cycle, or both, wherein said protein comprises a protein set forth in Table 4.

In some embodiments, the protein involved in regulating of gene expression is selected from the group consisting of proteins involved in RNA processing, translation, transcription, RNA splicing, spliceosomal complex, signal transduction, chromatin remodeling, immune response, trafficking, transcriptional regulation, and circadian cycle.

In some embodiments, the protein involved in regulating cell cycle is selected from the group consisting of proteins involved in proliferation, chromosome condensation, chromosome segregation, DNA damage response, DNA replication, metabolism, nuclear trafficking, immune response.

In some embodiments of any of the aforementioned methods, said protein is selected from the group consisting of PARP1, HNRPLL, SON, SUGP2, WDR33, THOC5, PUS1, SYMPK, THOC2, SART3, LSM4, PLRG1, SF3B2, SNRNP40, XAB2, ZCCHC8, PRPF8, PRPF4, POLR3B, POLR1A, POLR2D, POLR2A, SUPTSH, SUPT6H, GT3C4, EXOSC7, EIF4H, GTF3C5, MRPS23, SEP15, FKBP5, MRPS34, TPX2, TRIM27, USP7, UBE2K, STAG2, PDSSB, SMC4, PDSSA, NCAPG2, AKAP8, NUMA1, CEP170, POGZ, CTR9, TBLXR1, G3BP1, TLE1, SPIN1, COPS3, TLE3, GPS1, CSNK2A1, PRKDC, MSH3, MSH6, POLA1, TMPO, FEN1, PRIM2, CHTF18, AKAP8L, MLF2, SPATA5, ZMPSTE24, SMARCA2, SIRT1, SMARCA4, ARID1A, SMARCC2, KDM3B, ADNP, HDAC3, VPRBP, LCP1, KPNA3, TOMM40, IPO9, TIMM13, COBRA1, SAFB2, PELP1, TCEB2, CDK9, TROVE2, SRRT, PSPC1, FAM98B, GK, TXNRD1, NADKD1, NDUFS2, PCK2, CISD1, CYC1, and UQCRFS1, or combination thereof.

In some embodiments of any of the aforementioned methods, said protein is selected from the group consisting of PARP1, MATR3, SRRT, NOP56, RIP1L1, UPF1, ZC3H14, HNRNPA0, LRPPRC, FARSA, EIF3D, MRPS22, NOP2, DNAJA2, NSUN2, DNAJA3, DDX5, DHX9, SFPQ, PPP1CB, PPP2R1A, BUB3, ILF3, ADAR, ISG15, NUP155, ZFR, ZC3H11A, KPNA4, KPNA1, KPNA3, KPNA6, ZNF326, SKIV2L2, SON, SUGP2, WTAP, PTBP1, PTBP3, CPSF1, RBM4, HNRNPUL2, SF1, SF3B1, PNN, ZCCHC8, SF3B3, CDC5L, PRPF8, SNRNP200, SAFB, PRMT5, WDR77, SUPT16H, SIRT1, SAP18, IKZF1, HCFC1, HDAC3, ZNF281, ZNF318, GIGYF2, RBM14, SAFB2, SPIN1, GTF21, MCM3, AKAP8L, TRIM28, PSMA2, PSME3, PSMB3, p53, USP11, SLC25A6, PFAS, CAD, SLC25A3, PFKL, ACLY, PPHLN1, RBM12B, and FLNA, or combination thereof.

In some embodiments of any of the aforementioned methods, the agent is an NAD+ precursor.

In some embodiments, the NAD+ precursor is nicotinamide mononucleotide (NMN) or a salt thereof, or a prodrug thereof, including crystalline and polymorphic form of same.

In some embodiments of any of the aforementioned methods, the agent decreases or reduces nicotinamide.

In some embodiments of any of the aforementioned methods, the agent increases the level or activity of an enzyme involved in NAD+ biosynthesis, or an enzymatically active fragment thereof, or a nucleic acid encoding an enzyme involved in NAD+ biosynthesis, or an enzymatically active fragment thereof.

In some embodiments, the enzyme is mononucleotide adenylyl transferase (NMNAT) or nicotinamide phosphoribosyl transferase (NAMPT or NAMPRT).

In some embodiments of any of the aforementioned methods, said method further comprises administering an inhibitor that blocks or prevents protein-protein interaction or binding of said biologically active polypeptide comprising a NHD, or fragment thereof, with said protein involved in cancer, aging, radiation damage, DNA repair, cell proliferation, or cell survival.

In some embodiments of any of the aforementioned methods, the agent is administered at a dose of between 0.5-5 grams per day.

In some embodiments of any of the aforementioned methods, the agent is administered conjointly, prior to, or subsequent to administrating the biologically active polypeptide comprising the NHD, or fragment thereof, or a nucleic acid encoding same.

In some embodiments of any of the aforementioned methods, the agent or the biologically active polypeptide comprising the NHD, or fragment thereof, or a nucleic acid encoding same is administered in a pharmaceutically effective amount.

In some embodiments, the pharmaceutically effective amount is provided as a pharmaceutical composition in combination with a pharmaceutically-acceptable excipient, diluent, or carrier.

In some embodiments, the subject is a mammal or non-mammal.

In some embodiments, the subject is a human.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 1A shows endogenous DBC1 and PARP1 interact. FIG. 1B shows that NAD$^+$ dissociates the PARP1-DBC1 interaction. FIG. 1A-shows the effect of NAD$^+$ and structurally related molecules on the PARP1-DBC1 interaction. Flag-DBC1 was incubated with molecules (200 μM) for 1 hr then probed for PARP1. FIG. 1D to FIG. 1F show the PARP1-DBC1 interaction after FK866 (FIG. 1D) or NMN (FIG. 1E) treatments for 24 hrs, or in cells overexpressing NMNAT1, an NAD salvage pathway gene (FIG. 1F) to raise NAD$^+$, mean±SEM, (FIG. 1D)) and (FIG. 1E), one-way ANOVA, Sidak's post-hoc correction; (FIG. 1F)), unpaired two-tailed t-test, *p<0.05, ****p<0.0001.

FIG. 2A shows the domains and crystallographic-based homology model of the NHD docked with NAD$^+$. Abbreviations: S1-like, ribosomal protein S1 OB-fold domain-like; EF, EF-hand; LZ, leucine zipper. Residues predicted to be in the vicinity of bound NAD$^+$ are highlighted. FIG. 2B shows the interaction of V5/His-tagged DBC1 mutants and PARP1. See FIG. 12 for additional mutants. Panels (FIG. 2C) and (FIG. 2D) show the direct binding of NAD$^+$ to the DBC1-NHD, assessed using a radiolabeled NAD$^+$ binding assay (FIG. 2C) or a biotin-NAD$^+$ binding assay (FIG. 2D), mean±SEM, one-way ANOVA, Sidak's post-hoc correction, ***p<0.001, n.s., not significant. FIG. 2E depicts the effect of NAD$^+$ on binding of DBC1-NHD mutants to PARP1.

FIG. 3A shows inhibition of PARP1 activity by DBC1 purified from 293T cells. FIG. 3B shows PAR (polyADP-ribose) abundance in 293T cells lacking DBC1. FIG. 3C shows opposing effects of re-introducing wild-type or DBC1$_{Q3914}$ into MCF-7 cells on mRNA of PARP1-regulated genes: TMSNB (Thymosin beta), PEG10 (Paternally expressed gene 10) and NELL2 (Neural EGFL-like 2). ABHD2 was a negative control. DBC1 and PARP1 abundance are shown in FIG. 14E. FIG. 3D shows γ-H2AX abundance in DBC1 knockdown cells after paraquat treatment (1 mM, 24 hrs). FIG. 3E shows DNA fragmentation after paraquat treatment (0.5 mM, 24 hrs) in DBC1 knockdown cells, assessed by a comet assay, >50 cells/group. See FIG. 15A. FIG. 3F shows DNA break repair (NHEJ and HR) in DBC1 knockdown cells treated with paraquat (1 mM) or 3-AB (5 mM), n=3 biological replicates. FIG. 3G shows protection of human primary fibroblasts from DNA damage (300 μM paraquat) by NMN (500 μM). 100±20 cells/condition, n=4 biological replicates (2 cell lines, 2× for each), 24 hrs treatment. See FIG. 16. Errors are SEM, one-way ANOVA (FIG. 3C and FIG. 3G) and two-way ANOVA (FIG. 3E and FIG. 3F), Sidak's post-hoc correction, *p<0.05, p<0.01, *p<0.001, ****p<0.0001, n.s., not significant.

FIG. 4A and FIG. 4B show NAD$^+$ concentrations and PARP1-DBC1 interactions in livers of young and old mice (6 vs. 22 months, n=3/group). FIG. 4C shows γH2AX foci (red arrow) in the livers of young (6 month, Y) and old mice (30 months, 0) (n=3/group) treated for 7 days with vehicle (PBS) or NMN (500 mg/kg/day i.p., n=3/group). FIG. 4D and FIG. 4E show NAD$^+$ concentrations and PARP1-DBC1 interactions in the livers of old mice (22 months) treated as in (FIG. 4C)). FIG. 4E shows γH2AX foci (red arrow) in the livers of young (6 month, Y) and old mice (30 months, O) (n=3/group) treated as in (FIG. 4C). FIG. 4, Panel (FIG. 4F) shows PARP1 activity in young (6 months, n=4) and old (26±4 months, n=8/group) mice. FIG. 4G shows PARP1 activity in 18-20 month old DBC1 knockout mice livers (n=3-4). FIG. 4H shows γH2AX abundance in the livers of 26-month olds after irradiation (IR) (7.5 Gy, $^{137}$CsCl) treated as in (FIG. 4C) (n=3/group). FIG. 4I shows blood counts of 23-month olds on the 7-8th days after irradiation (n=10 per group). See FIG. 22A and FIG. 22B. FIG. 4J shows blood metrics of 4-month olds with a single oral dose of NMN (2000 mg/kg) 1 hr after irradiation (8 Gy, $^{137}$CsCl) followed by another 7 days (2000 mg/kg/d, n=5-8/group). See FIG. 22C. Errors are SEM, FIG. 4A to FIG. 4D and FIG. 4G are unpaired two-tailed t-test; FIG. 4E), FIG. 4F) and FIG. 4H) are one-way ANOVA, Sidak's post-hoc correction; (FIG. 4I) and (FIG. 4J), Mann-Whitney U-test, *p<0.05, p<0.01, **p<0.0001.

FIG. 5A shows PARP1-DBC1 interaction in the presence the SIRT1 inhibitor EX527 (20 μM, 24 hrs). FIG. 5B shows the effect of SIRT1 knockdown on the PARP1-DBC1 complex. FIG. 5C shows the PARP1-DBC1 interaction in the presence of the PARP1 inhibitors PJ34 (1011M) or 3-AB (2 mM) for 24 hrs, bottom panel showing inhibitory effect of 3-AB (2 mM) on PAR induced by paraquat (0.5 mM). FIG. 5D shows the effect of overexpressing MACROD1 on the PARP1-DBC1 complex. DNA transfections: +=1 μg; ++=2 μg. FIG. 5E shows the interaction of catalytically inactive PARP1-E988K with DBC1, E988K lacks PAR modification ability, as tested in the bottom panel. All experiments were performed in 293T cells.

FIG. 6A, FIG. 6B and FIG. 6C show the PARP1-DBC1 interaction in the presence of molecules structurally related to NAD$^+$: NAM (500 μM) and its analogue 3-AB (2 mM), adenine (200 μM), adenosine (200 μM), ATP (200 μM), or ADP-ribose (low=200 μM; high=500 μM). Flag-DBC1 immunoprecipitates bound to M2 beads were incubated with the above molecules for 1 hr, followed by assessment of PARP1 binding by western blotting. FIG. 6D shows the effect of NAD$^+$ on the interaction between catalytically inactive PARP1-E988K and DBC1. FIG. 6E shows the effect of PARG (2 ng) or MACROD1 (1 μg) on the PARP1-DBC1 complex. The activity of self-purified MACROD1 was tested in the bottom panel: E988K-PARP1 was mono-ADPribosylated using biotin-NAD$^+$ as described (Z. Mao et al. (2011) *Science* 332, 1443-1446), then de-ADPribosylated by incubating with 1 ug MacroD1 for 30 min as described (F. Rosenthal et al. (2013) *Nat. Struc. Mol. Biol.* 20, 502-507). FIG. 6F shows the effect of carba-NAD, a non-hydrolysable NAD$^+$ analogue, on the PARP1-DBC1 complex.

FIG. 7A shows that the treatment of 293T cells with nicotinamide riboside (NR) raises cellular NAD$^+$ levels and dissociates PARP1-DBC1 complex (mean±SEM, unpaired two-tailed t-test, ***p<0.001). FIG. 7B shows the effect of paraquat treatment (24 hrs) on the PARP1-DBC1 complex. FIG. 7C-shows the effect of the NAMPT inhibitor FK866 (5 nM, 24 hrs) on the SIRT1-DBC1 interaction.

FIG. 8A shows the DBC1 deletion mutants. Yellow-colored mutants were expressed in 293T cells. Blue-colored mutants could not be expressed. FIG. 8B and FIG. 8C shows the expression of DBC1$_{(243-923)}$, DBC1$_{(1-500)}$, DBC1$_{(1-330)}$, DBC1$_{(1-269)}$ and DBC1$_{(243-462)}$ in 293T cells. FIG. 8D shows the interaction between PARP1 and DBC1$_{(\Delta 354-396)}$, a form of DBC1 lacking partially the NHD.

FIG. 9A-FIG. 9B shows direct binding of DBC1 to PARP1. FIG. 9A shows binding of recombinant human PARP1-ΔCAT (residues 1 to 654) to human DBC1 (residue 239 to 553) on blue native poly acrylamide gel electrophoresis in the presence or absence of PARG or MACROD1. FIG. 9B shows mass spectrometry on the three excised bands from lane 5, 11 and 12 at the position of the red arrow confirming PARP1-DBC1 complex.

FIG. 10A shows PARP1 and PARP2 structures. Zinc finger regions (ZnI and ZnII) and nuclear localization sequence (NLS) are shown. FIG. 10B shows the effect of deleting the BRCT domain on PARP1-DBC1 complex formation. FIG. 10C shows lack of an endogenous interaction between PARP2 and DBC1. FIG. 10D shows that DBC1 interacts with the PARP1-BRCT domain but not PARP1-CAT. Purified His-tagged recombinant proteins were incubated with Flag-DBC1 cell lysate (0.5 mg) overnight and immunoprecipitated using nickel resin and DBC1 was detected by western blotting. FIG. 10E shows the effect of deleting the BRCT domain on poly(ADP) ribose (PAR) levels. FIG. 10F shows the activity of PARP1 immunoprecipitated from 293T cells, mean±SEM, unpaired two-tailed t-test, **p<0.01.

FIG. 13A-FIG. 13E shows that DBC1 specifically binds to NAD$^+$, which requires its NHD domain. FIG. 13A shows the biotin-NAD$^+$ binding assay. FIG. 13B shows binding of NAD to DBC1. Each well was loaded with 0.2 mg of a cell lysate from 293T cells stably transfected with empty vector or Flag-DBC1. FIG. 13C shows competition of biotin-NAD$^+$ with unlabeled NAD$^+$. Flag-DBC1 from cell lysates (0.5 mg) was immobilized in each well and biotin-NAD$^+$ (20 μM) was competed off with unlabeled NAD$^+$ (0-500 μM). FIG. 13D shows effects of NAD$^+$, NADH and NMN on binding of biotin-NAD$^+$ to DBC1. Unlabeled NAD$^+$, NADH or NMN (200 μM) was competed against biotin-NAD$^+$ (20 μM). FIG. 13E shows binding curves of DBC1$_{WT}$, DBC1$_{243-923}$, DBC1$_{1-500}$, and DBC1$_{\Delta 354-396}$. Kd constants were 22.2, 16.9, 20.6 and 378.7 respectively, determined by GraphPad using "one site, specific binding" formula. Errors are SEM, one-way ANOVA with Sidak's post-hoc correction, *p<0.05, **p<0.01, n.s., not significant.

FIG. 14A shows the PAR levels in DBC1 knockout MEFs were determined by western blotting. FIG. 14B, FIG. 14C, and FIG. 14D show the effect of DBC1 knockdown in 293T cells on PAR levels under normal conditions and after treatment with FIG. 14B paraquat (0.5 mM, 24 hr), FIG. 14C H$_2$O$_2$ (0.2 mM, 30 min) or (FIG. 14D) etoposide (25 μM, 24 hr). PARG (2 ng) was added into cell lysates to digest PAR for 30 min (*). FIG. 14E shows assessment of DBC1 protein levels in MCF-7 cells knocked down for DBC1 and reconstituted with mutants from FIG. 3C. FIG. 14F shows the effect of re-introducing wild-type DBC1 and DBC1-Q391A on PAR levels.

FIG. 15A shows representative images of the comet assay performed on DBC1 knockdown 293T cells after paraquat treatment (0.5 mM, 24 hrs). Images are at 200× magnification. FIG. 15B shows the effect of DBC1 knockdown on survival after paraquat treatment (24 hrs), mean±SEM, unpaired two-tailed t-test, **p<0.01. FIG. 15C shows the effect of knocking down DBC1 on DNA damage response pathways in 293T cells treated with paraquat (0.5 mM, 24 hrs). Western blotting was used to detect phosphor-Chk2 (Thr68), Chk2, phosphor-Chk1 (Ser345), Chk1, phosphor-p53 (Ser15), p53, DBC1. GAPDH served as a loading control.

FIG. 20A-FIG. 20F shows that PARP1 activity decreases with age and is reversed by NMN or genetically ablating DBC1. FIG. 20A shows that the enzymatic activity of PARP1 decreases with age. PARP1 was immunoprecipitated from 6-, 22- and 30-month old mouse liver extracts and assayed for maximum activity in the presence of nuclease-treated DNA (n=5 each group, one-way ANOVA with Sidak's post-hoc correction). FIG. 20B shows that PARP1 activation in livers of young and old mice after irradiation. Young (10 month) and old (20 month) mice were exposed to a sub-lethal dose of ionizing radiation (+IR, 7.5 Gy). PAR levels are quantified on the right. FIG. 20C shows that the PAR levels are higher in DBC1 knockout mice livers than wild-type at 18-20 months of age. Quantification of PAR is shown on the right. FIG. 20D shows that the PAR levels in 30-month old mouse livers after NMN treatment as in FIG.

4C. FIG. 20E and FIG. 20F show that the effect of NMN depends on PARP1 activity. The old mice (20 month) were injected intraperitoneally (i.p.) with vehicle (PBS with 10% 2-hydroxypropyl-β-cyclodextrin), NMN (500 mg/kg/d) alone or with PARP1 inhibitor olaparib (100 mg/kg/d) for 7 days. Two hours after the last injection, mice were irradiated with 7.5 Gy and killed 2 hrs later. Equal amounts of liver cell lysates from each group were assayed for PARP1 maximal activity—and PAR levels by western blot). Errors are SEM, unpaired two-tailed t-test except (A), $*p<0.05$, $p<0.01$, $*p<0.001$, n.s., not significant.

FIG. 21A shows PAR levels in 6-, 22- and 30-month-old mouse livers. FIG. 21B shows $NAD^+$ levels (n=3 each group) and (FIG. 21C) the DNA damage marker 8-OHdG (n=3 or 4) in the livers of 26-month old mice after NMN treatment as in FIG. 4C, mean±SEM, unpaired two-tailed t-test, $*p<0.05$.

FIG. 22A Experimental design of experiments in FIG. 4I. Two groups of 23-month old mice were pretreated with PBS or NMN (i.p. 500 mg/kg/day) for 7 days then exposed to a single dose of ionizing radiation (7.5 Gy). Mice received injections for 2 more days and blood cell counts were conducted on day 7 and 8. (FIG. 22B) Continued from FIG. 4L Neutrophils, monocyte, red blood cell and platelet counts. (FIG. 22C) Continued from FIG. 4J: changes in body weight (n=20/group) and white blood cell, red blood cell and platelet counts. Errors are SEM, Mann-Whitney U-test, n.s., not significant.

Figure 1A:
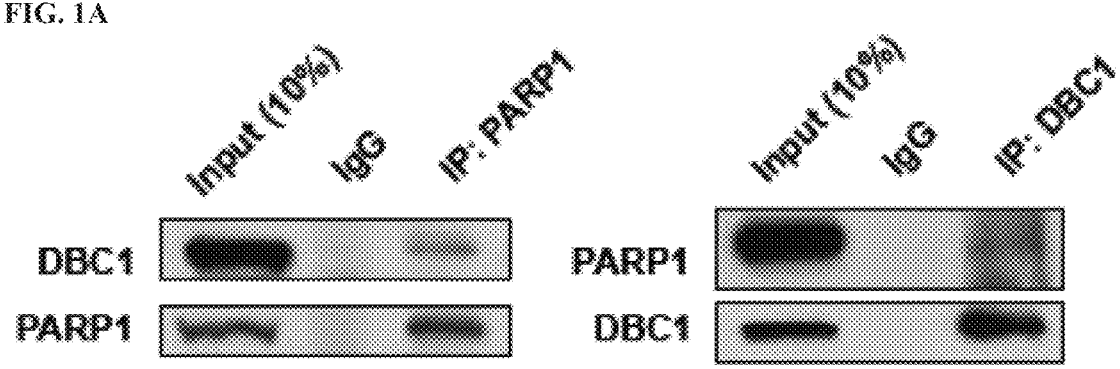
FIG. 1A-FIG. 1F depicts regulation of the PARP1-DBC1 interactions by NAD$^+$.

Note that for every figure containing a histogram, the bars from left to right for each discreet measurement correspond to the figure boxes from top to bottom in the figure legend as indicated.

DETAILED DESCRIPTION OF THE INVENTION

The present invention is based, at least in part, on the discovery that NHDs are $NAD^+$ binding domains that regulate protein-protein interactions. As provided herein, the binding of $NAD^+$ to the NHD domain of Deleted in Breast Cancer 1 (DBC1) prevents it from inhibiting poly (ADP ribose) polymerase (PARP1), a critical DNA repair protein. As mammals age and $NAD^+$ concentrations decline, DBC1 is increasingly bound to PARP1, causing DNA damage to accumulate, a process rapidly reversed by restoring the abundance of $NAD^+$. In this way, $NAD^+$ may directly regulate protein-protein interactions, the modulation of which may protect against cancer, radiation damage, and aging.

Definitions

As used herein, the following terms and phrases shall have the meanings set forth below. Unless defined otherwise, all technical and scientific terms used herein have the same meaning as commonly understood to one of ordinary skill in the art to which this invention belongs.

The singular forms "a," "an," and "the" include plural reference unless the context clearly dictates otherwise.

Recitation of ranges of values herein are merely intended to serve as a shorthand method of referring individually to each separate value falling within the range, unless otherwise indicated herein, each individual value is incorporated into the specification as if it were individually recited herein. Ranges may be expressed herein as from "about" (or "approximate") one particular value, and/or to "about" (or "approximate") another particular value. When such a range is expressed, another embodiment includes from the one particular value and/or to the other particular value. Similarly, when values are expressed as approximations, by use of the antecedent "about" or "approximate" it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that is "less than or equal to the value" or "greater than or equal to the value" possible ranges between these values are also disclosed, as appropriately understood by the skilled artisan. For example, if the value "10" is disclosed the "less than or equal to 10" as well as "greater than or equal to 10" is also disclosed.

All methods described herein can be performed in any suitable order unless otherwise indicated herein or otherwise clearly contradicted by context. Further, all methods described herein and having more than one step can be performed by more than one person or entity. Thus, a person or an entity can perform step (a) of a method, another person or another entity can perform step (b) of the method, and a yet another person or a yet another entity can perform step (c) of the method, etc. The use of any and all examples, or exemplary language (e.g. "such as") provided herein is intended merely to better illuminate the invention and does not pose a limitation on the scope of the invention otherwise claimed.

Units, prefixes, and symbols are denoted in their Système International de Unites (SI) accepted form. Unless otherwise indicated, nucleic acids are written left to right in 5' to 3' orientation; amino acid sequences are written left to right in amino to carboxy orientation.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

The headings used herein are for organizational purposes only and are not meant to be used to limit the scope of the description or the claims, which can be had by reference to the specification as a whole. Accordingly, the terms defined immediately below are more fully defined by reference to the specification in its entirety.

Illustrations are for the purpose of describing a preferred embodiment of the invention and are not intended to limit the invention thereto.

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); The Cambridge Dictionary of Science and Technology (Walker ed., 1988); *The Glossary of Genetics,* 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used herein, the term "about" refers to a range of values of plus or minus 10% of a specified value. For example, the phrase "about 200" includes plus or minus 10% of 200, or from 180 to 220, unless clearly contradicted by context.

As used herein, the term "administering" means the actual physical introduction of a composition into or onto (as appropriate) a host or cell. Any and all methods of introducing the composition into the host or cell are contemplated according to the invention; the method is not dependent on any particular means of introduction and is not to be so construed. Means of introduction are well-known to those skilled in the art, and also are exemplified herein.

As used herein, administration "in combination" refers to both simultaneous and sequential administration of two or more compositions. Concurrent or combined administration, as used herein, means that two or more compositions are administered to a subject either (a) simultaneously, or (b) at different times during the course of a common treatment schedule. In the latter case, the two or more compositions are administered sufficiently close in time to achieve the intended effect.

The terms "cancer" or "tumor" or "hyperproliferative disorder" refer to the presence of cells possessing characteristics typical of cancer-causing cells, such as uncontrolled proliferation, immortality, metastatic potential, rapid growth and proliferation rate, and certain characteristic morphological features. Cancer is generally associated with uncontrolled cell growth, invasion of such cells to adjacent tissues, and the spread of such cells to other organs of the body by vascular and lymphatic means. Cancer invasion occurs when cancer cells intrude on and cross the normal boundaries of adjacent tissue, which can be measured by assaying cancer cell migration, enzymatic destruction of basement membranes by cancer cells, and the like. In some embodiments, a particular stage of cancer is relevant and such stages can include the time period before and/or after angiogenesis, cellular invasion, and/or metastasis. Cancer cells are often in the form of a solid tumor, but such cells may exist alone within an animal, or may be a non-tumorigenic cancer cell, such as a leukemia cell. Cancers include, but are not limited to, B cell cancer, e.g., multiple myeloma, Waldenstrom's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglubulinemia, and heavy chain disease. In some embodiments, the cancer whose phenotype is determined by the method of the present invention is an epithelial cancer such as, but not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, brenner, or undifferentiated. In some embodiments, the present invention is used in the treatment, diagnosis, and/or prognosis of melanoma and its subtypes.

As used herein, "DBC1" refers to the protein Deleted in Breast Cancer 1. DBC1 is one of the most abundant, yet enigmatic proteins in mammals (M. Wang et al. *Proteomics* 15, 3163-3168 (2015); S. M. Armour et al. *Mol. Cell. Biochem.* 33, 1487-1502 (2013)), with a conserved domain similar to Nudix hydrolases that hydrolyze nucleoside diphosphates but lacking catalytic activity due to the absence of key catalytic residues (V. Anantharaman et al. *Cell cycle* 7, 1467-1472 (2008); A. S. Mildvan et al. *Arch. Biochem. Biophys.* 433, 129-143 (2005); J. P. Gagne et al. *Nucleic Acids Res.* 36, 6959-6976 (2008)). DBC1 may encompass any of the amino acid sequences set forth in GenBank (Accession: Q8N163.2 GI: 85701135); (Accession: O60477.2 GI: 85700960); (Accession: EHH64042.1 GI: 355779566); (Accession: EHH28342.1 GI: 355697794).

As used herein, the term "DNA repair deficiency disorder" refers to a disorder in a subject in which one or more components of the DNA repair pathway(s) is underexpressed, mutated, or less functional than the same component in a wild-type organism. A DNA repair deficiency disorder may refer to a subject in which at least a cell has a mutation. Examples of DNA repair deficiency disorders include, but are not limited to, Ataxia Telangiectasia (A-T), Xeroderma Pigmentosum (XP), Fanconi's Anemia (FA), Li Fraumeni syndrome, Nijmegen breakage syndrome (NBS), A-T-like disorder (ATLD), Werner's syndrome, Bloom's syndrome, Rothmund-Thompson syndrome, Cockayne's syndrome (CS), Trichothiodystrophy, ATR-Seckel syndrome, LIG4 syndrome, Human immunodeficiency with microcephaly, Spinocerebellar ataxia with axonal neuropathy, Ataxia with oculomotor apraxia 1, Ataxia with oculomotor apraxia 2, Diamond Blackfan anemia, Rapadilino syndrome, Turcot Syndrome, Seckle Syndrome, Lynch syndrome, NBS-like syndrome, and RIDDLE Syndrome.

As used herein, "DNA repair proteins" encompass any number of proteins involved in replication, recombination, or homologous recombination. These include, but not limited to, AKT1, BAX, BAG1, ARF1, CDK1/2/4, DAPS, BSG, H-RAS, RAC1, PARP1, S11, and REL. There is also an upregulation of mTOR signaling components AKT, HRAS, R-RAS, MAPK1, RAC1, and RHO A/C/G/J/T2.

As used herein, the terms "effective amount," "effective dose," "sufficient amount," "amount effective to," "therapeutically effective amount," or grammatical equivalents thereof mean a dosage sufficient to produce a desired result, to ameliorate, or in some manner, reduce a symptom or stop or reverse progression of a condition and provide either a subjective relief of a symptom(s) or an objectively identifiable improvement as noted by a clinician or other qualified observer. Amelioration of a symptom of a particular condition by administration of a pharmaceutical composition described herein refers to any lessening, whether permanent or temporary, lasting or transit that can be associated with the administration of the pharmaceutical composition. With respect to "effective amount," "effective dose," "sufficient amount," "amount effective to," or "therapeutically effective amount" of a probiotic microorganism, the dosing range varies with the probiotic microorganism used, the route of administration and the potency of the particular probiotic microorganism.

As used herein, the term "genetic instability" refers to a mutation in a nucleic acid caused by exposure of a subject to radiation, to a carcinogen, to a virus, etc., preferably radiation.

The terms "individual," "subject," "host," and "patient," used interchangeably herein, refer to a mammal, including, but not limited to, murines, simians, felines, canines, equines, bovines, mammalian farm animals, mammalian sport animals, and mammalian pets and humans. Preferred is a human. More preferred is a human exposed to radiation or a human at risk of being exposed to radiation.

As used herein, the terms "mutation" or "DNA damage," used interchangeably herein, mean a change in a nucleic acid sequence (in comparison to a wildtype or normal nucleic acid sequence) that alters or eliminates the function of an encoded polypeptide, that alters or eliminates the amount of an encoded polypeptide produced, or that alters or eliminates a regulatory function of the nucleic acid having acquired a mutation. Mutations or DNA damage include, but are not limited to, point mutations, deletions, insertions, inversions, duplications, single-stranded DNA breaks, double-stranded DNA breaks, and DNA lesions as as known in the art.

As used herein, nicotinamide adenine dinucleotide (NAD) and its derivative compounds are known as essential coenzymes in cellular redox reactions in all living organisms. Several lines of evidence have also shown that NAD participates in a number of important signaling pathways in mammalian cells, including poly(ADP-ribosyl)ation in DNA repair (Menissier de Murcia et al., *EMBO J.*, (2003) 22, 2255-2263), mono-ADP-ribosylation in the immune response and G protein-coupled signaling (Corda and Di Girolamo, *EMBO J.*, (2003) 22, 1953-8), and the synthesis of cyclic ADP-ribose and nicotinate adenine dinucleotide phosphate (NAADP) in intracellular calcium signaling (Lee, *Annu. Rev. Pharmacol. Toxicol.*, (2001) 41, 317-345). Recently, it has also been shown that NAD and its derivatives play an important role in transcriptional regulation (Lin and Guarente, *Curr. Opin. Cell. Biol.*, (2003) 15, 241-246). In particular, the discovery of Sir2 NAD-dependent deacetylase activity (e.g., Imai et al., *Nature*, (2000) 403, 795-800; Landry et al., *Biochem. Biophys. Res. Commun.*, (2000) 278, 685-690; Smith et al., *Proc. Natl. Acad. Sci. USA*, (2000) 97, 6658-6663) drew attention to this new role of NAD.

The NAD biosynthesis pathways have been characterized in prokaryotes by using *Escherichia coli* and *Salmonella typhimurium* (Penfound and Foster, Biosynthesis and recycling of NAD, in *Escherichia coli* and *Salmonella*: Cellular and Molecular Biology, p. 721-730, ed. Neidhardt, F. C., 1996, ASM Press: Washington, D.C.) and recently in yeast (Lin and Guarente, *Curr. Opin. Cell. Biol.*, (2003) 15, 241-246; Denu, *Trends Biochem. Sci.*, (2003) 28, 41-48). In prokaryotes and lower eukaryotes, NAD is synthesized by the de novo pathway via quinolinic acid and by the salvage pathway via nicotinic acid (Penfound and Foster, Id.) In yeast, the de novo pathway begins with tryptophan, which is converted to nicotinic acid mononucleotide (NaMN) through six enzymatic steps and one non-enzymatic reaction (Lin and Guarente, *Curr. Opin. Cell. Biol.*, (2003) 15, 241-246). Two genes, BNA1 and QPT1, have been characterized in this pathway in yeast. At the step of NaMN synthesis, the de novo pathway converges with the salvage pathway. The salvage pathway begins with the breakdown of NAD into nicotinamide and O-acetyl-ADP-ribose, which is mainly catalyzed by the Sir2 proteins in yeast. Nicotinamide is then deamidated to nicotinic acid by a nicotinamidase encoded by the PNC1 gene. Nicotinic acid phosphoribosyltransferase (Npt), encoded by the NPT1 gene, converts nicotinic acid to NaMN, which is eventually converted to NAD through the sequential reactions of nicotinamide/nicotinic acid mononucleotide adenylyltransferase (encoded by NMA1 and/or NMA2) and NAD synthetase (encoded by QNS1).

Figure 11:
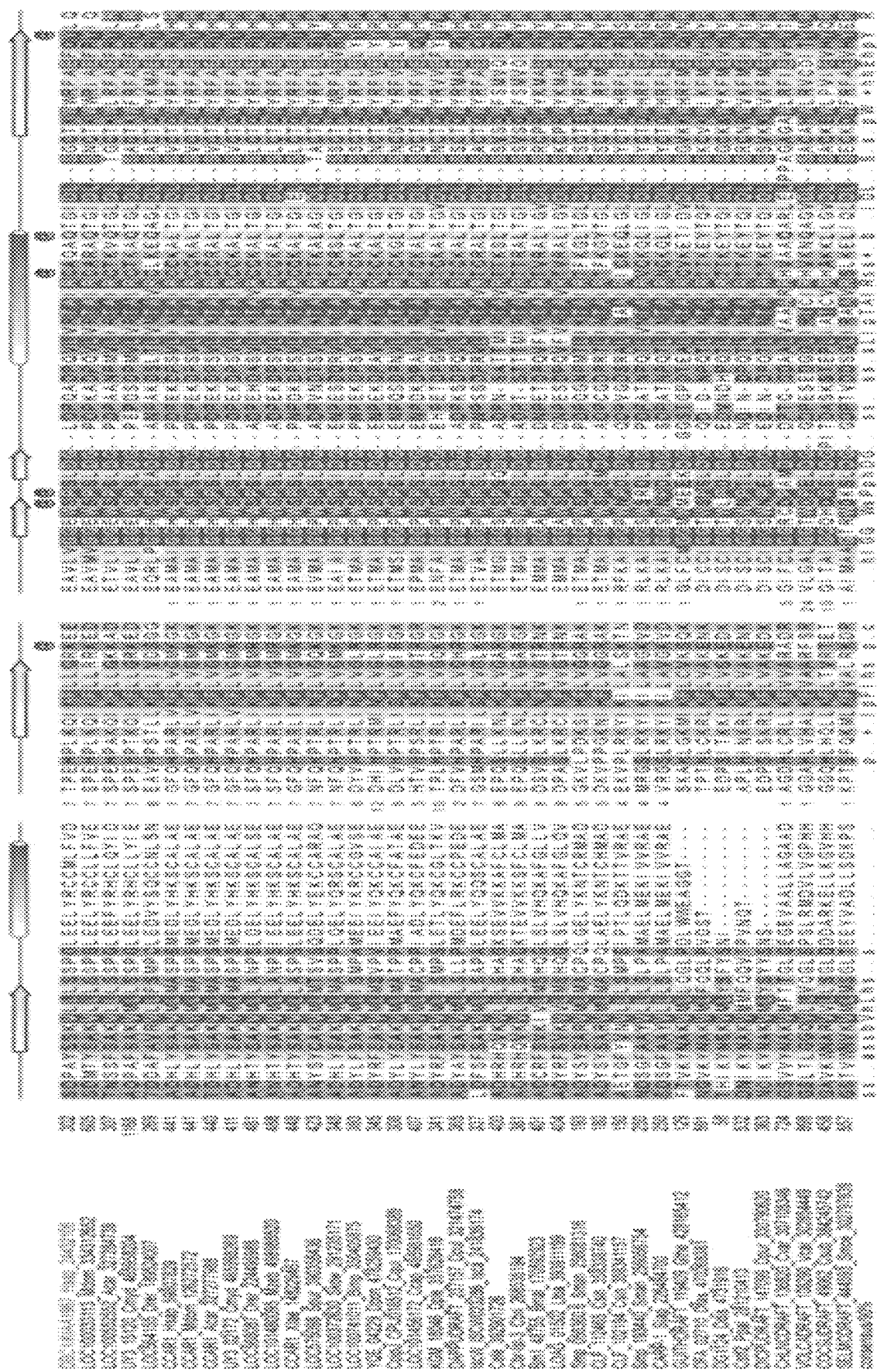
FIG. 11 shows multiple alignments of Nudix domains from various species. Putative ligand binding residues are indicated by @.
Figure 11:
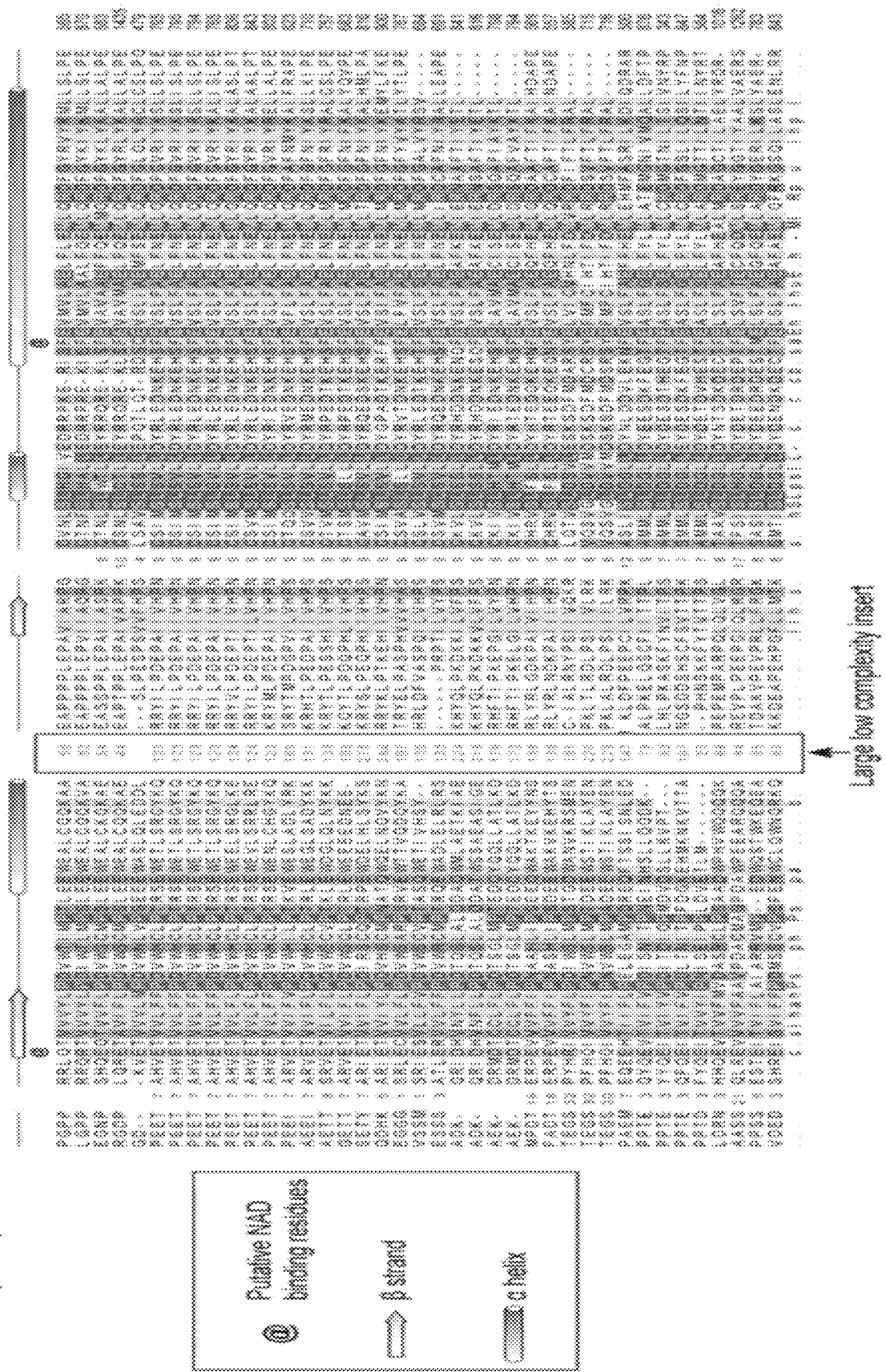

As used herein, "NHD" refers to Nudix homology domain which is conserved in numerous proteins, including but not limited to, DBC1; CCAR2 (KIAA1967_*Homo sapiens*_24432106); KIAA1967-like (LOC100033113_*Monodelphis domestica*_334312652; LOC100552552_*Anolis carolinensis*_327284738); UY3 (UY3_15120_*Chelonia mydas*_465958204); KIAA1967 homolog (L00564155_*Danio rerio*_189524007); CCAR1 (CCAR1_*Homo sapiens*_59807829; CCAR1_*Monodelphis domestica*_126272572; ccar1_*Anolis carolinensis*_327277988; UY3_02172_*Chelonia mydas*_465998269; L00568087_*Danio rerio*_224495988; LOC101480095_*Maylandia zebra*_498988520; ccar1_*Xenopus laevis*_148229467);

L00575098_Strongylocentrotus_purpuratus_390356436; CCAR1-like (LOC100372630_Saccoglossus kowalevskii_291235171); BRAFLDRAFT_124590_Branchiostoma floridae_260814428; CCAR1-like (LOC100741011_Bombus impatiens_350405875); YQE_04229_Dendroctonus ponderosae_478259430; CCAR1 (CpipJ_CPIJ018512_Culex quinquefasciatus_170068389); CCAR1-like isoform X2 (LOC101456172_Ceratitis capitata_498981650); CCAR1 (KGM_18046_Danaus plexippus_357626416); DAPPUDRAFT_237157_Daphnia pulex_321474758; CCAR1 putative (IscW_ISCW023286_Ixodes scapularis_241836174); LST-3, isoform a (Caenorhabditis elegans_392901726); CBR-LST-3 (Cbr-lst-3_Caenorhabditis briggsae_268535194); SAP domain containing protein (Bm1_48755_Brugia malayi_170592923); LOAG_01502 (LOAG_01502_Loa loa_393911199); P30 dbc protein (Smp_056360.6_Schistosoma mansoni_256081316); CCAR1 (CLF_112465_Clonorchis sinensis_358338740); CCAR1 (CLF_102194_Clonorchis sinensis_358341157); P30 dbc protein (Smp_193440_Schistosoma mansoni_256056754); CCAR1 (CARP-1_Schistosoma japonicum_226484700); GUITHDRAFT_119409_Guillardia theta CCMP2712_428165412; calcium-binding EF-hand domain-containing protein (DFA_02710_Dictyostelium fasciculatum_470268381); development protein DG1124 (DG1124_Dictyostelium discoideum_4731916); RNA-binding region RNP-1 domain-containing protein (cstf2_Polysphondylium pallidum PN500_281210413); DICPUDRAFT_147099_Dictyostelium purpureum_330790620; CHLNCDRAFT_136820_Chlorella variabilis_307105346; VOLCADRAFT_108290_Volvox carteri f. nagariensis_302854449; COCSUDRAFT_49062_Coccomyxa subellipsoidea C-169_384245742; or SELMODRAFT_444593_Selaginella moellendorffii_302797639. Multiple alignments of Nudix homology domains from the various species set forth above are shown in FIG. 11. Representative sequences are set forth below. The amino acid sequence information for the aforementioned proteins are well known in the art and readily available on publicly available databases, such as the National Center for Biotechnology Information (NCBI). For example, exemplary amino acid sequences derived from publicly available sequence databases are provided below in Table 3.

TABLE 3

Nudix homology domain (NHD) proteins
(bolded and underlined amino acids denote putative NAD ligand
binding residues KIAA1967_Homo_sapiens_24432106 (SEQ ID NO: 1) (264 aa)
SDPAYSSKVLLLSSPGLEELYRCCMLFVDDMAEPRETPEHPLKQIKFLLGRKEEEAV
LVGGEWSPSLDGLDPQADPQVLVRTAIRCAQAQTGIDLSGCTKWWRFAEFQYLQP
GPPRRLQTVVVYLPDVWTIMPTLEEWEALCQQKAAEAAPPTQEAQGETEPTEQAPD
ALEQAADTSRRNAETPEATTQQETDTDLPEAPPPPLEPAVIARPGCVNLSLHGIVEDR
RPKERISFEVMVLAELFLEMLQRDFGYRVYKMLLSLPE LOC100033113_Monodelphis_domestica_334312652 (SEQ ID NO: 2) (266 aa)
SDMTYSAKVLLLSSPGLEELYRCCLLFVEDMAEPRESPEHPLKQIKFLLRRKEDEAV
MVGGEWSPSLDGPDPKADPQVLVRTAIRCARAQTGIDLSNCTKWWRIAEFRYIQLG
PPRRQRTVVVYLPDIWTLMPSLEEWEALCQQKVAETVAPLQDTVMEAEASVEETNS
SELGAAAEASEQDPENPELSLQQEMDPSLPEAPPPPLEPVIIAQPGCTNFSLHALLEDR
RPREKISFEVMVLAALFQEMLQRDFGYKIYKMLLSLPE LOC100552552_Anolis_carolinensis_327284738 (SEQ ID NO: 3) (277 aa)
TNSSFSAKVLLLSSPGLEEFYRHCLQYIDDPSDQRESPEHPAKQIKFLLGKKADETVLI
GGEWSPSLDGPDPAANPMVLIRTAIRCTKVQTGLDLTGCTKWLRFAEFRYLREGNP
SHQEQTVVFLPDVWSCMPSLEEWEALCKQKAEKNPSAPPQEETAVMEEAEQSSETG
LEQETETSEQEAETADPAPEPGVETSPSEPEASSPPLEPAIIASPKPALQGGQPSCTNLS
LWTLLEYRRQREKLSFEVAVAAEFFQEMMQRDFGYKLYKALLALPE UY3_15120_Chelonia_mydas_465958204 (SEQ ID NO: 4) (268 aa)
ADPAFSAKVMLLSSPGLEELYRHCLLYIEEPSEQKESPEHPTKQIKFLLGRKEDEAVL
IGGEWSPSLDGPEPDSDPMVLVRTAIRCTKAQTGLDLSACTKWFRFAEFRYLRRGD
PLQRETAVIFLPDVWSCMPSLEEWEALCQQKAEKAPLPSPSPEEKAEMDVEIPEAAP
DQEMEANAQEVNATDAAAEPEAPTPPLEPAIVAPPKKPAMQGGQPSCSNLSLCTLLE
YRRQREKLSFEVAVMAELFQEMLQRDFGYRLYKALLALPE LOC564155_Danio_rerio_189524007 (SEQ ID NO: 5) (211 aa)
TDDAFAVRVLLFSMPCLEDVYSQCCNLSNDGQTQKEAVHPSTLLKFLIVDSGGEQR
LPGGHWSPEADGANPAKDSLTLVNTAVRCLKEQAGLDLSACTQWYKMAELRYLS
GDKVETVVVLMPDVWNLVPSEEEWASLQLEDDLSLPESPSVVFHPSAGLNLSAVSL
SSLLEPQTLQTRDSCEVSLIAEMFSEMLQRDFGLQLYRCLCSLPQ CCAR1_Homo_sapiens_59807829 (SEQ ID NO: 6) (355 aa)
ADHLYSAKVMLMASPSMEDLYHKSCALAEDPQELRDGFQHPARLVKFLVGMKGK
DEAMAIGGHWSPSLDGPDPEKDPSVLIKTAIRCCKALTGIDLSVCTQWYRFAEIRYH
RPEETHKGRTVPAHVETVVLFFPDVWHCLPTRSEWETLSRGYKQQLVEKLQGERKE
ADGEQDEEEKDDGEAKEISTPTHWSKLDPKTMKVNDLRKELESRALSSKGLKSQLI
ARLTKQLKVEEQKEEQKELEKSEKEEDEDDDRKSEDDKEEEERKRQEEIERQRRER
RYILPDEPAIIVHPNWAAKSGKFDCSIMSLSVLLDYRLEDNKEHSFEVSLFAELFNEM
LQRDFGVRIYKSLLSLPE CCAR1_Monodelphis_domestica_126272572 (SEQ ID NO: 7) (354 aa)
ADHLYSAKVMLMASPSMEDLYHKSCALAEDPQELRDGFQHPARLVKFLVGMKGK
DEAMAIGGHWSPSLDGPDPEKDPSVLIKTAIRCCKALTGIDLSVCTQWYRFAEIRYH TABLE 3-continued Nudix homology domain (NHD) proteins
(bolded and underlined amino acids denote putative NAD ligand
binding residues RPEETHKGRTVPAHVETVVLFFPDVWHCLPTRSEWETLSRGYKQQLAEKLQGERKE
ADGQDEEEKDDGEAKEISTPTHWSKLDPKTMKVNDLRKELESRALSSKGLKSQLIA
RLTKQLKVEEQKEEQKELEKSEKEEEEEEDRKSEDDKEEEERKRQEEMERQRRERR
YILPDEPAIIVHPNWAAKSGKFDCSIMSLSVLLDYRLEDNKEHSFEVSLFAELFNEML
QRDFGVRIYKSLISLPE

*ccar1_Anolis_carohnensis_327277988* (SEQ ID NO: 8) (355 aa)
TDHLYSAKVMLMASPSMEDLYHKSCALAEDPQEVRDGFQHPARLIKFLVGMKGKD
EAMAIGGHWSPSLDGPDPEKDPSVLIKTAIRCCRALTGIDLSVCTQWYRFAEIRYHR
PEETHKGRTVPAHVETVVLFFPDVWHCLPTRSEWETLSRGYKQQLAEKLQGERKEA
DGEQDEEEKDDGEAKEISTPTHWSKLDPKAMKVNDLRKELESRTLSSKGLKSQLIA
RLTKQLKVEEQKEEQKELEKSEKEDEEEEERKSEDDKEEEERKRLEEVERQRRERY
ILPDEPAIIVHPNWAAKSGKFDCSIMSLSVLLDYRLEDNKEHSFEVSLFAELFNEMLQ
RDFGVRIYRSLLSLPE UY3_02172_*Chelonia_mydas*_465998269 (SEQ ID NO: 9) (355 aa)
ADHLYSAKVMLMASPSMEDLYHKSCALAEDPQELRDGFQHPARLVKFLVGMKGK
DEAMAIGGHWSPSLDGPDPEKDPSVLIKTAIRCCKALTGIDLSVCTQWYRFAEIRYH
RPEETHKGRTVPAHVETVVLFFPDVWHCLPTRSEWETLSRGYKQQLVEKLQGERKE
ADGEQDEEEKDDGEAKEISTPTHWSKLDPKTMKVNDLRKELESRTLSSKGLKSQLIA
RLTKQLKVEEQKEEQKELEKSEKEDEEEEDRKSEDDKEEEERKRQEEMERQRRERR
YILPDEPAIIVHPNWAAKSGKFDCSIMSLSVLLDYRLEDNKEHSFEVSLFAELFNEML
QRDFGVRIYKALISLPE LOC568087_*Danio_rerio*_224495988 (SEQ ID NO: 10) (356 aa)
ANHTYSAKVMLLANPSLDELYHKSCALSEDPAELRDSFQHPARLIKFLVGMRGKDE
AMAIGGHWSPSLDGADPEHDASVLIKTAVRCCKALTGIDLSLCTQWYRFAEIRYHR
PEETHKGRTVPAHVETVVLFLPDVWHCLPTRSEWEELSRGLKEQLAEKLLAERKEA
DGEQEEEDKDEDDSKEVTTPTHWSKLDPKSMKVSDLRKELESRSLSSKGLKSQLIAR
LTKQLKVEEQVEESKEPEKPEPPSVEEDESCRLEDDREEEERKRQEEQERQRRERRY
VLPDEPTIIVHPNWAAKNGKFDCSIMSLSVLLDYRLEDNKEHSFEVSLFAELFNEML
QRDFGYRIYKALASLPT LOC101480095_*Maylandia_zebra*_498988520 (SEQ ID NO: 11) (356 aa)
ANHTYSAKVMLLANPSIEELYHKSCALAEDPQEVRDSFQHPARLIKFLVGMRGKDE
AMAIGGHWSPSLDGADPEKDPSVLIKTAIRCCKALTGIDLSLCTQWYRFAEIRYHRP
EETHKGRTVPAHVETVVLFLPDVWHCLPTRSEWEVLSRRLREQLAEKLSAERKEAD
GEQEEEEKDDDSKDVSTPTHWAKLDPKSMKVNDLRRELDCRSLSSKGLKSQLIAR
LTKQLKVEEQVEESKEPEKVETKDVEEEEPARTEDDREEEEKKRQEELERQRRERRY
ILPDEPTILVHPNWAAKNGKFDCSVMSLSVLLDYRLEDNKEHSFEVSLFAELFNEML
QRDFGYRIYKALAALPT

*ccar1_Xenopus_laevis*_148229467 (SEQ ID NO: 12) (355 aa)
ADHTYSAKVMLLASPSLEELYHKSCALAEDPIEVREGFQHPARLIKFLVGMKGKDE
AMAIGGHWSPSLDGPNPDKDPSVLIRTAVRCCKALTGIELSLCTQWYRFAEIRYHRP
EETHKGRTVPAHVETVVLFFPDVWHCLPTRSEWENLCHGYKQQLVDKLQGDRKEA
DGEQEEEDKEDGAKEISTPTHWSKLDPKIMKVNDLRKELESRTLSSKGLKSQLIAR
LTKQLRIEEQKEEQKELEKCEKEEEEEEERKSEDDKEEEERKRQEELERQRREKRYM
LPDEPAIIVHPNWSAKNGKFDCSIMSLSVLLDYRIEDNKEHSFEVSLFAELFNEMLQR
DFGVRIYRELLALPE LOC575098_*Strongylocentrotus_purpuratus* 390356436 (SEQ ID NO: 13)
(401 aa)
ANYSYCAKVMLMTSVSQDELYEKCCARAQDSSDIRENFQHPTRLINFLVGQKGKNE
VMAIGGPWSPSLDGADPVNDTSVLIKTAIRTTKALAGIDLTACTQWYRFLELSYYRP
EEIHKGRVIPARVETVVIFVPDVWHILPTKVEWESLADLYRKTLSNKLAAVDSRDKK
TEDPTPTQEEPAAVKEEEEEEVEEQEHQTPTNWKELDPKNMKVNELRQELEIRGLNS
KGLKSQLIARLTKMLKTEQEMEDAEPAAMETDAATENASKEEPKDAPKEEEVSEKD
KEKEKKDKEEKEKKDKEDEKKKEIVEEEKKRQREREKRDLESRYTMPDGPVILVHP
SPIAKSGKFDCTQQSLSVLLDYRVEDNKEHSFEVFLFAELFNEMLQRDFAFNMYKAI
FRAPE LOC100372630_*Saccoglossus_kowalevskii*_291235171 (SEQ ID NO: 14)
(363 aa)
ADHLYSAKVMLMASPPLQELYQRSCALAEDPQELKDNFQHPTRLIQFLVGMKGKN
EAIAIGGPWSPSIDGENPESDDRVLINTAIRTCRSLTGIDLSSCTHWWRFAEVRYHRA
EEIYKGRLVPARVETVVIFLPDVWHCLPTRLEWEGLSADYKQLVDKIAEKHEDVA
EQLQEAGTDAVEDDDDFENPTHHKLLDPRNMKVGDLRKELEARGINSKGLKSQLIA
RLTKALKTEAESEEQEDIADEDPEEFVEAKTEVEEIEMNSEDKKEEEEERKQEEKDR
LIKEKRHTLPEDPAIIVHPSTTAKGGKFDCSVVSLSVLLDYRMEDNKEHSFEVSLFAE
LFNEMLQRDFGNIYKSLLKIPE BRAFLDRAFT_124590_*Branchiostoma_floridae* 260814428 (SEQ ID NO: 15)
(353 aa)
VMLMACPSAEELYHRSCALAEDASDVRETFQHPTRLIQFLVGMKGKNEAVAIGGP
WSPSLDGPNPDTDPSVLIKTAIRTTKALTGIDLKNCTQWYRFAEVRYHRAAETYKG TABLE 3-continued Nudix homology domain (NHD) proteins
(bolded and underlined amino acids denote putative NAD ligand
binding residues KTIPERVETTVMFLPDVHHCLPPRLDWANVSAGYRAQLARKAADEKSEEAGESQEE
EEGGEDESGKKAPTHHTELDPKTMKVNELRAELEARGLNSKGLKSQLIARLTKALK
MEVEKEEEEKEAKDEAKEEEEEKEEEVEEDKEKKEEEERKKQEEERERKTRERRY
TLPDNPAIIVHPSTTAKGGKFDCAVMSLSVLLDYRVEDNKEHSFEVSLFAELLNEML
QRDFAFKIYRALMVAPE LOC100741011_Bombus_impatiens_350405875 (SEQ ID NO: 16) (365 aa)
ADYLFSAKVMLISMPAMEEIYKRCCGVSEDRDPDRDYVHPTRLINFLVGLRGKNET
MAIGGPWSPSLDGPNPEKDPSVLIRTAVRTCKALTGIDLSSCTQWYRFLELYYRRAE
TTHKSGRVVPSRVETVILFLPDVWSCVPTKLEWDGLQLNYKKQLERKLLRAASSPD
DLDAANETDEAADDPVPEKKDPTHYSELDPKSMNVNELRQELAARNLNCKGLKSQ
LLARLMKTITSEQAKEEGRQDDIDENEKDISPPPKEEEDKKFKDIKDHDEDRRKLCE
RERAALEKRYTLPESSHIIVHPSRMAKSGKFDCTVMSLSVLLDYRPEDTKEHSFEVSL
FAELFNEMLRDFGFRIYRALCSLPE YQE_04229_Dendroctonus_ponderosae_478259430 (SEQ ID NO: 17) (339 aa)
ADYRFSAKVMLMSVPVIEEIYQKCCAIAEDKDSRDRESEDRDHIHPTRMINFLVGLR
GKNETMAIGGPWSPSLDGENPEKDPAVLIKTAIRTCKALTGIDLSNCTQWYRFVELY
YYRRGETTHKGKAIPARVETVVIFLPDVWSCLPTRLEWEEEEDNEEVLEPTLHSELNP
KAMTVVQLRTELKARKLDFKGLKAQLVARLTKALKSEADREEEDPREKPNSDGEA
ECEKDDAPEASPSAEKDKKSEPEEKKLDEVQKRRLEKQYTLPDQPHLIVHPSKVAKS
GKFDCTSMSLSLLLDYRPEDTKEHSFEVSLFAELFNEMLRDFGFNIFKALYQVPE CpipJ_CPIJ018512_Culex_quinquefasciatus 170068389 (SEQ ID NO: 18)
(509 aa)
ADYLYSAKVMLMATPPMAEFYQKCFATAEDRDRYEDLVHPTRLISFLVGIRGKGET
MSIGGPWSPSLDGENPQSDPNVLIKTAIRTCKGLTGIDLSNCSRWYRFVELYYRRSE
TYHKGRLIPARIETVVIFLPDIRSCQPTRPEWDELHLSYKSHLERIINSQSSDSPVPPAV
AAAPSTEEPEPAASTVTADSPSPPAAAATAAEPAAAADEESTDKPVDTAPSSTSDIVK
PSAEPAEPAAAPKDDTEDDKAADDVVEEEPEVVILDESDEEEPKKEPTPYAQLDVKK
LKVPELRTELQARDLPTDGVKNVLVTRLTKALKEEQEEAEKKQAPEAATGEAKSVD
KPAADEETPAQEEKKPAEEKSAEKDSADAAAPEDTANPVEKEAEEDFETMDNVDM
SEVTVIDEYDSKAEEKTKPEQVKLTEKECQLLEKRYSLPEQPHIIVHPSRTAKSGKFD
CAVMSLSVLLDYRQEDSKEHSFEVSLFAELFNEMLTRDFGFNIYKALHMLPA LOC101456172_Ceratitis_capitata_498981650 (SEQ ID NO: 19) (494 aa)
ANYLYSAKVMLMACPPIADLYQKCFEDEENENEQHTVHPSRLISFLVGTRGRNEPM
AIGGPWSPSLDGENPDKDPAVLIRTAIRTCKALTGIDLSQCTQWYRFVELQYHRQDH
KKKDAAARIETVVIYLPDVHSCMPNATQWQELNQ**VYKNAVENLIARKSAAAKAAA
ATSNTTGGGTEEEGTSSPKAEVGGEGDDATAADTSNADVTKDDANKSVVDEGATA
ESGDISTTNGEADADADSAADTSAEVIAIEENDQKEPTHYSKLDLKSMKVREMRDE
LEARNLPSKGARHIIMARLAKALNTEKAEDKSSKKATPKSEPAKSEAAKGKPANAK
PAKVAEANDKKVEQQKETKKETVEIKEEDIDKSNDEEQEDQEEWNDVDVDMSDIVI
LDEYDSSKNPEETPKELNEKEKNQLIRRYKLPTKEHIIVHPNKTAKGGKFDCSIMSLS
VLLDYGPADTKERFFEVSIFAELFNEMLRDFGFNIYKEMYLFKE KGM_18046_Danaus_plexippus_357626416 (SEQ ID NO: 20) (427 aa)
ADYRFSAKVMLISMPSLETLYQKCGLTKVDEKDKRTSSKTPLHPTRLIKFLVGQKGK
GGENFAIGGPWSPSLDGEHPETDPGVLVKTAIRTCKALTGVDLSNCTQWYRVVEFY
YWREGGGRSRLECVVLFLPDVWSARPSRVEWTTVQDQYKAARDAALRRLLGGESP
RRSDDSPDRSPIENLDANASTITIDENDDDDDCKPEATHYSNIDLRTIKVDQLRQELR
ARNVSCKGLRSQLVSRLSKLIKAEEEKDTKNEDVMEVVDDEQEDKKDTTDTVEITD
DTTNDKEKPVEDKIEKNDANDSKPNDKSKDGESKESDGVSEERKDRPKTEKEIEEEK
KRLERERQSLMTRYELPASPHVVVHASGSARAGRFACSVASLSLLLDYRVTDNKEH
SFEELFVFAELFNEMLRDFGFYVYKTLYTLPE DAPPUDRAFT_237157_Daphnia_pulex_321474758 (SEQ ID NO: 21) (320 aa)
ADYAYSAKVMLLSLLPMDEFLRKCCPEDEKEDFVHPARLIRFLVGHRGKNETMAIG
GPWSPSLDGADPKSDPQVLIRTAIRTCKALTGIDLSSCTQWYRMAIRYHRVSSMKS
RIESVLLFVPDVWSCVPTASQWETIVHSYMQPSSEPMEEETKEETVVDPLKEASHES
KLEPKSLKFSELKTELEARNLSSKGMRTQLIPRLTIALKGEAEEEKRKREDAQLNEEE
QQQQESSREDSLPADDVDSIHRLDFVASPQILVHPSRTAKAGKFSCSLVSLSVLLDYR
LEDTKEHTFEVSLFSELFNEMLRDFGALVYRSV IscW_ISCW023286_Ixodes_scapularis_241836174 (SEQ ID NO: 22) (355 aa)
LDFSFSAKVMLLSAPALEELYQQSCALAEESEEGRLGSMHPARILSFLVGLKGKSET
VALGGPWSPSLDGPNPSSDPRVLIRTAVRTCRALTGIDLSACTQWYRFAEICYRRES
SSSSCATLERVVLFFPDVWRCMPTRQEWADLELRLRSISLCGTEDPAGDAPAQALDT
LPTTPPLARRCCQLPTHPSEPACALRLQVGDLRTELEARGLLTKGLKSQLVARLAKA
LKAEAEQEEEEEEEVEEEAEMEEGGEVVDEANEEEEEVEAVEEEAPESEPEEEKP
RPTILVYPSRKAKGGRFDCSVMSLSVLLDYRQEDNKEHSFEVSLFAELFNEMLIRDC
AFNIYRALLEAPE Caenorhabditis_elegans_392901726 (SEQ ID NO: 23) (442 aa)
ADHRHQVKVLLLSHAGKSEVVKKAFCLMADGTTDDHQEPQSLLKNLHFLVGARG
KETMGIGGSWSPSQDGADPNSATTMIRTAVRTTKSLTGIDLSSVSQWFSMVQIRYY

TABLE 3-continued

Nudix homology domain (NHD) proteins
(bolded and underlined amino acids denote putative NAD ligand
binding residues RADKQRIDHVNYLLPDTQSLALDDAQWMLAETKIAEQLKAKLANVDALKIEEDEPP
VVMMVEESESVVAAAAAADVVPEQSIPDVKKEEELQAEEPKVLDNVKAEESDVV
ADVSMNSTTDADNSEAPAAENGQGPTNWSNLDPKSMKVAELRVELELRGLETKGI
KTLLVQRLQTALDTEKAAEASVAARDVEMRDAAENAVKQEGGEENPAAFIAPSIEE
TKAKTEAEAKKEAEEAEKRKKKEEQLEKEKKEKREALEKHYQLPKDKKILVFPSKS
FKSGKFDCKVLSLSSLLDYRHDDNKENQFEVSLFAEAFKEMIERNAAFTIYETL Cbr-lst-3_Caenorhabditis_briggsae_268535194 (SEQ ID NO: 24) (436 aa)
ADHRHQVKVLLLSHAGKTEVVKKSFCLMADGTTDDHQEPQSLLKNLHFLVGARGK
ETMGIGGSWSPSLDGADPTSTTTMIRTAVRTTRALTGIDLSSVSQWFSMVQIRYYRA
DKQRIDHVNFLLPDTSLALDDATWSSAEASIGEQLKAKLAEVDALKIEEEPEVVEM
VEAVEPAAEVVVTPEAAVVTAETVAAPEDAPSDVKESIVLLYMVENENDVSMNSET
GEADKPIVAGQGPTNWSKLDPKSMKVAELRVELELRGLETKGIKTLLVQRLQTALD
SEKSTEAAASKDVEMKDVKDEVKQEAGAVAGEENPAAFIAPPIEETKAKTEAEAKK
EQEEADKKKKKEEQLEKEKKDKRDALEKHYQLPKDKKVLVFPSKTFKSGKFDCKV
LSLSSLLDYRHDDNKESQFEVSLFAEAFKEMIERNSAFTIYETL Bm1_48755_Brugia_malayi_170592923 (SEQ ID NO: 25) (398 aa)
ADCRFSVKIVLMSHQGLSLVHQKAFGLLVDGSIDENVDSVSLKRCLNFVVGTRNKE
NIMAIGGAWSPSLDGDNPETDPQVFVRTAIRTVRALIGVDLSRCPRWYKMAEIRYYR
AEKDRMDTCCLFLPDTSGLMPTEDCYQQLLATLKDQLGNKLAAVDAQKLVLPSTV
AVTATATDC**GDAGEGATVTTEPMAPAGDTQQQLQQGQQQSDVNKEQVQEVEEEDDE
DLNPTHWSKLDIRTMKVAELRQELMARDLETKGVKSVLCARLQEALDQEKTKDED
KEDVCLKTAVGMIEVAKPQEENEEKELTDEDKKAVEKFEKEKKEKKASLERHFTIP
KEPGILVYPNRMAKGGKFDCKIVSLHTMLDYRIEDNKEHSFELAVMAECISEMLDR
SQAFIAYKTL LOAG_01502_Loa_loa_393911199 (SEQ ID NO: 26) (391 aa)
ADYRFSVKVVLMSHQGLSLVHQKAFGLQVDGSIDENIDPASLKRCINFVVGTRNKE
MMAIGGAWSPSLDGDNPESDPQVFVRTAVRTVRALIGVDLSKCPRWYKMAEIRYY
RAEKDRMDTCCLFLPDTSGLMPTEDCYQQLLATLKDQLGNKLAALDAQKLVLPST
VAALATDSGDAGEGTTTTTEPVAQAGDTQQQLQQGQQQIDANKEQVQEVEEDDDE
DLNPTHWSKLDIRTMKVAELRQELMARDLETKGVKSVLCARLQEALDHEKTKDED
KGDKAEVAKVKEEEKEEKELTDEDKKAIEKFEKEKKEKKASLERHFTIPKELGILVH
PNRMAKGGKFDCKIVSLHTMLDYRTEDNKEHSFELAVMAECISEMLDRSQAFVAY
KTL Smp_056360.6_Schistosoma_mansoni_256081316 (SEQ ID NO: 27) (377 aa)
ADYSYSARVMLMACPQLGELYKNTCRMADDANGAGKVLPDKSIHFLVGGRAKSE
TMALGGPWSPSLDGPDPQGNPMTLIKTAIRTFKGLTGLDLSSCTEWVRFMELKYYR
MPDTKAPAFTEAEEEREITSERPEVVVFFIPNAAHLIPSEEQWAKTKEYYNSILQKQL
TVEKVEDESMVEQQDGDMSVADVSVEEPEESIARSDIEPTHYSKLDVNTLKVSDLR
NELAARKLDTKGLKVNLVARLQSALDEEKKADAPEDIKIDEEIKAEQTPNKISSPSAT
QPKDDSKDLSEKDRRRLERLYRLGDKPAIVIHPNKSAKGGRFDCHRVSLFSLLDYHT
EDQKEHNFEVSLFAEQFHEMLQRDAAFTIFKAIHDAPE CLF_112465_Clonorchis_sinensis_358338740 (SEQ ID NO: 28) (378 aa)
ADYSYSARVMLMACPQLAELYKNTCHMADDVSGTDKVPPGKNIHFLVGGRAKSET
MAIGGPWSPSMDGADPCGDPRTLINTAIRTFKGYTGLDLSSCTEWIRFMEIRYYRFA
DTKAPAFTGDDEERLVTTERPEVVVFFIPNASHLIPSDEEWAKVKEHYTSVLQALLS
PEQKPEVEATPGADATEVETSVVDASMDDGDEAGTRSDMEPTHYSKLDANSLKVN
ELRNELAARNLDTKGLKVNLVARLQAALDEEKKADTPEETKAAEDSKAEETPAKA
TTPTQSKDESKDLSEKERRRLERLYRLNDKPAIIIHPNKSARGGRFDCHRVSLFSLLD
YRTEEQKEQNFEVSLFAEQFHEMLQRDCAFTIFKAINDAPE CLF_102194_Clonorchis_sinensis_358341157 (SEQ ID NO: 29) (436 aa)
AETGFYVNVLLLSMPSIPTLQDKTTVRAESSDREKVPLRKYIKILALSKTNERFKAIG
GPWNPDLDGQDPVGDSRALINAAIRICKEQLGLDLSYCTQWHRFLEFRYSRTEGST
ARPASVLFPGSQLWGRSFPESANSKSATPSKPYHRIVVYFLPDIWSLMPSTGDWANV
KRSMENALSRKLPQLFPMSQAEINALSDATSTGASSDDAKNKSNPTTCPTGVTATAL
GDTATTSTAGDSQNNPTAAPKPDQSDSMLDTSAREIGDEGLQSPTRASGGDKNDSS
QEVSELREQLKVRNLPADGIKAQLLSRLKTAVEKEAEQARKEEEERKKKEKEMQEA
LAAKEEEDKKRESSKPTIEISATPKADACIALRNYPSIIVQKRLTDDYTLQTVSLDSVL
ESKSDFMDARSYELVICVHNLFDMVRRDFIFTLFRAL Smp_193440_Schistosoma_mansoni_256056754 (SEQ ID NO: 30) (466 aa)
NDSGFAAYVLLLSLPAMAELMEKIVVRAESPSRMRGSLRKYIKILAAGKVDERLKAI
GGSWSRDLDGPDPATNPQTLVNTAIRVCKQLIGLDLSYCTQWHRFLEFRYSRTEGST
AQPTSVLFPGSQLWGRPVTESPESDMIPPSKPFHQIVVYFIPNVWSLMPTDEEWSTIK
LAYENILASKEPKVFPMSPSNLKKFSGLESASKGTGDGKLNVVSELDSNLLKSPTQD
NAHEDSNVSKMDEGNKSTVQAPVEFHRSSPYLAGQETVPKVAAISETEDGFESVDL
AAQGNPNQEGTDKCQKKLHTELNLASMKVSELREQLKARNLPTEGVRAQLLTRLK
TAIQEEEEKESAKKAEKEKMEQEKTLQSVTIDKSPQVSEEQIKPLNTESGSKSWTDAP
KLTLRDLPSIIVLRKKTVDFTVQSVGLDVVMDSKSDFMDCRSYEFMFCIHTIFDMLR
RDSVFTLFRAL TABLE 3-continued Nudix homology domain (NHD) proteins
(bolded and underlined amino acids denote putative NAD ligand
binding residues CARP-1_Schistosoma_japonicum_226484700 (SEQ ID NO: 31) (467 aa)
SDSGFAAYVLLLSLPAMAELMEKIVVRAESPSRVRGSLRKYIKILAVGKVDERLKAI
GGSWNPDLDGSDPATNPQTLINTAIRNCKQLIGLDLSYCTQWHRFLEFRYSRTEGST
AQPTSVLFPGSQLWGRPATESNDVIPPSKPFHQIVVYFIPNVWSLMPADEE**WSTIKLA
YENVLASKEPNVFPLAPSSLKKFSGLESASKETSDGKLKLVVEMDSNSLKSPAQDNL
CEDPNASKMDEGNKSILQAPVEHDGSALSTADQESVSKIANTPEAEDGFESMGPKNI
SIQGNPNQEGTEKCQKKLHTEINLANIVIKVSELREQLKARNLPTEGVRAQLLTRLKM
AIQEEEEKESAIKAEKEKMEQAKALQLVTIDKSPQVPEEQVKPVNAESGSKLKTDVP
KLALRDLPSIIILRKKNADFTVQSVGLDVVMDSKSDFMDSRSYEFMFCIHTIFDMLRR
DSVFTLFRAL GUITHDRAFT_119409_Guillardia_theta_CCMP2712_428165412 (SEQ ID NO: 32)
(372 aa)
FTVKYNAKVMLLQGLPDLWWEAGGTSKAHLGKMIKFLCVKSQKHGLFCMGGMW
MEEKDGGGSTGPDTEALIRTAIRCVKETIDVDLSGVKKWHRFMEIQYNRPAEMYK
GQWYPEQEEHTIIFLPELEGAMPDREQFTSSISNLEDELNSKAHAAWEKDMEERRRA
AKEAEIKRAAAAAAAAEAAKLAAAAAAAAAAKAAEAEAAAAESISTGDRKTPAG
AGNINEAGQPGDGKSAEVKLESVVPATSSGVQQDADASGQLATSTGEVKTEQEGG
GGHGVKEEVKGPPPPEPIKLDFPEEPCILVRPKWEEGGDGKGQIKASLISLDGLLDYN
LDDVLEKNFEVSLFAEFFHEMLEHMFASRILKDIQDRAR DFA_02710_Dictyostelium_fasciculatum_470268381 (SEQ ID NO: 33)
(286 aa)
NGVKYNAKVMLFQQLPVDSTTPTNLCKRLKFLVAKENKDICCIGGTWSPSLDGQDI
DNPQTLINTAIRTTKEYTQFDLSKCVKWIKFMEVHYYRPPTEKNQQYQEVTVIFVPD
ISNITPNEINHSLLQQDKPSEKEEGEDDHHQQQQQQQQQQQQQQEEGTNEYDPEN
QGEDKQDSSNDPAQTDAKISITSETSSERKTTSPNPAPLVALPKELQSCFIITTPLSDTS
SIKYRAMMLSLDGLLDYEESDKFEGTFEASLFGELFYLMLATEMGNIVMQALLDFT
P DG1124_Dictyostelium_discoideum_4731916 (SEQ ID NO: 34) (287 aa)
THIKYNSKVMLYSFYSNIEDPSITKKIKFLVSKEDKDISCIGGTWLPDLDGEDVNDHP
QTLINTAIRTTKEYTQIDLSGCKKWYKFMEVHYYRPPTEEQSYYQEITVIYVPDITDI
QPMDVDSLLKVPTVSETTPSAPVGVTTATTKTTEEEEEEDQAPKDHVSKDFDND-
ETSSNTEQNQPPKSSTTSNTTKPAAAVPTTTAATATTTHGSLHLPKASKFYNVITPSS
EGNRYKAMMLSLDGLLDYDESDTHEGTFEASLFSELFYLMLCRDMGTNILTSIVNY
RP cstf2_Polysphondylium_fiallidum_PN500_281210413 (SEQ ID NO: 35)
(316 aa)
DNIKYNAKVMMFQQVTPVNQTAPLHINKRLKFLVAKENKDISCIGGSWNPTLDGN
DINDPQTLINTAIRTTKEYTQIDLSRCNRWVKFMEIHYYRPPTEAMAQFQEITVIFVP
DLTNITPFDGKEHMKNKVTTASPTEKSTESNNEHHEETDDGEENHPPAGNDTGDSE
KPAASDEIVGEVTGEPKDKDEMEMAPSSSVSASSNDQESHHHNQTSGGIQSPNSSSS
QSVSASTATAISTAANGSDDSHSCFSVTTPKSENMKYRSMMLSLDGLLEYDESDKFE
GTFEASLFGELFYLMLCRDFGSLILQSILYFNP DICPUDRAFT_147099_Dictyostelium_purpureum_330790620 (SEQ ID NO: 36)
(222 aa)
NCIKYNAKVMLYSYYSNSEDPSISKRLKFLVAKEDKDISCIGGSWNPELDGEDINDP
QTLINTAIRTTKEYTQIDLSSVKKWVKFMEVHYYRPPTDEFSFYQEITVVYIPNISEIP
PLDVETLMKNNSKGLETDKQGEEQSTITPNTILPHNSKKFYTVTTPSSDGNKFKAMM
LSLDGLLDYDETDVHESTFEASLFSELFYLMLARDMGTTILNTIINYRT CHLNCDRAFT_136820_Chlorella_variabilis_307105346 (SEQ ID NO: 37)
(293 aa)
GSVVYNAKVMFTTGLGEGEVAALLAGAADKAGDHLCRLLKFVVARADRNGDKSG
IFCLGGRCDPAMDGDPTQGDAALVAAARRHVAAQARLELPPAGAGAWLRFIEVHY
TRLDRNDVEHHQEVTVVFMVDASRCLPSAADWPHVWQQQQKPVLLQKLAAERAA
KQEAAAAKEPKPAAAGGLKEGGEEGERKEGGEEGEKEGEVAAARAVEEQEEEEAL
PEPEMPARPQLQLVGLHTDKLRLKTAAVSLDGLLDYNTSDKDECTFELSLFAEAFHE
ALMRDAGCTILAELYRQR VOLCADRAFT_108290_Volvox_carteri_f._nagariensis_302854449 (SEQ ID
NO: 38) (365 aa)
GSLTLGGQVLLVQGLSPSLRMDVLVGPHHEGGAHLVHALKFVAARFSRSQPSAGAE
EREGKDKEGGKDRQRGVLGALGGTWDPELDGGDPESEDGGLIRTCIRHVKNQAGV
DLSACAHWLRVCDITYMRAASSPTSGSGDAASAGQLSSSISDPQLREVVVVFAAVP
DACMAGPDAWPEEARQQQAFKQQRIALESEARKKEDAATARKDKDVVTEKEKTK
DEKRDKREEETNPGAEASKDKDVDDPLKGAGKDKDKDSNDNNKEADGDSSKAEPE
AAPVREVPLPEEPGIQLRGRASGLTAGAGLGGYERIKTFSISLHGLLDYDETDRDEPT
FELSVFTECFQDMLSREYGGTIYAALVAERS

TABLE 3-continued

Nudix homology domain (NHD) proteins
(bolded and underlined amino acids denote putative NAD ligand binding residues COCSUDRAFT_49062_Coccomyxa_subellipsoidea_C-169_384245742 (SEQ ID NO: 39) (326 aa)
GAVKWNARVVLLSGLDDDARKELLKGVHHGGQHLHQLLKFLTVRTETDKDDGRV
ERSGITAIGGQHDPSLDGPITDASKSTEPLIATCVRHAKKLLGVDLSACKEWLPVIEV
HYQRPPSSLSPDATESTEITVIFLAIARRVMPEDWQSTWKEQEAWLKGKAAREEAVT
KKEEEEKASKAKAVEEKAKPEEATKAEGAAVKDDEPAGAEKPAKRAKTGDVEEEK
KKDHGKVVDTDIKDADNKAPEAPQEAETDAKVPEVPRLLFRGKRSAKERWRSASIS
LDGLLDYDEEDRDESTMELSLFAEGFQEMLARDYGERILKSLYAER SELMODRAFT_444593_Selaginella_moellendortiii_302797639 (SEQ ID NO: 40) (287 aa)
GSTVWNVKVMLMSGLTEEYVADLLSDKPSDKPTSFQKMLKFVALRKDRNAIMAA
GTRWDKSLDGGDPTVDDSGLIRAAVRSLKELIQLDLSECKDWFRFAEVHYERVDED
GFPSHREISVIFFPDMSSCVPSFENWCLQWNQRKQAKLEREGQSKKEVKPSEKKDA
AEKESISEGTPETDVNNGEPVAAKEEEKKEKEEKKEKDPPKDSEVKKDEAPEHPGFL
LMTKRTKASKLRSMTISLDGLLDYDENDKDECTFELSLFAEAFAEMIQFRKGSQILA
SLENLRR In some embodiments, the following amino positions and/or residues of SEQ ID NO: 1 are preferably conserved for function and remaining positions can be modified. Positions (indicated in bolded-underlined text in Table 3 and @ in FIG. 11) believed to be involved in putative ligand (e.g., NAD or NAD analogs or derivatives thereof described infra) binding residues: 52, 64, 65, 86, 90, 109, 119, and/or 234, or any combination thereof.

In some embodiments, the following amino positions and/or residues of SEQ ID NO: 2 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 52, 64, 65, 86, 90, 109, 119, and/or 236, or any combination thereof.

In some embodiments, the following amino positions and/or residues of SEQ ID NO: 3 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 52, 64, 65, 86, 90, 109, 119, and/or 247, or any combination thereof.

In some embodiments, the following amino positions and/or residues of SEQ ID NO: 4 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 52, 64, 65, 86, 90, 109, 119, and/or 238, or any combination thereof.

In some embodiments, the following amino positions and/or residues of SEQ ID NO: 5 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 51, 63, 64, 85, 89, 108, 115, and/or 181, or any combination thereof.

In some embodiments, the following amino positions and/or residues of SEQ ID NO: 6 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 52, 65, 66, 87, 91, 110, 127, and/or 325, or any combination thereof.

In some embodiments, the following amino positions and/or residues of SEQ ID NO: 7 are preferably conserved for function and remaining positions can be modified. Positions believed to be involved in putative ligand (e.g., NAD or NAD analogs or derivatives thereof described infra) binding residues: 52, 65, 66, 87, 91, 110, 127, and/or 325, or any combination thereof.

In some embodiments, the following amino positions and/or residues of SEQ ID NO: 8 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 52, 65, 66, 87, 91, 110, 127, and/or 325, or any combination thereof.

In some embodiments, the following amino positions and/or residues of SEQ ID NO: 9 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 52, 65, 66, 87, 91, 110, 127, and/or 325, or any combination thereof.

In some embodiments, the following amino positions and/or residues of SEQ ID NO: 10 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 52, 65, 66, 87, 91, 110, 127, and/or 326, or any combination thereof.

In some embodiments, the following amino positions and/or residues of SEQ ID NO: 11 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 52, 65, 66, 87, 91, 110, 127, and/or 326, or any combination thereof.

In some embodiments, the following amino positions and/or residues of SEQ ID NO: 12 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 52, 65, 66, 87, 91, 110, 127, and/or 325, or any combination thereof.

In some embodiments, the following amino positions and/or residues of SEQ ID NO: 13 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 52, 65, 66, 87, 91, 110, 127, and/or 371, or any combination thereof.

In some embodiments, the following amino positions and/or residues of SEQ ID NO: 14 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 52, 65, 66, 87, 91, 110, 127, and/or 333, or any combination thereof.

In some embodiments, the following amino positions and/or residues of SEQ ID NO: 15 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 44, 57, 58, 80, 84, 102, 119, and/or 323, or any combination thereof.

In some embodiments, the following amino positions and/or residues of SEQ ID NO: 16 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 51, 64, 65, 86, 90, 109, 127, and/or 335, or any combination thereof.

In some embodiments, the following amino positions and/or residues of SEQ ID NO: 17 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 57, 70, 71, 92, 96, 115, 132, and/or 309, or any combination thereof.

In some embodiments, the following amino positions and/or residues of SEQ ID NO: 18 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 51, 64, 65, 86, 90, 109, 126, and/or 479, or any combination thereof.

In some embodiments, the following amino positions and/or residues of SEQ ID NO: 19 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 50, 63, 64, 85, 89, 108, 123, and/or 464, or any combination thereof.

In some embodiments, the following amino positions and/or residues of SEQ ID NO: 20 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 55, 69, 70, 91, 95, 114, 125, and/or 397, or any combination thereof.

In some embodiments, the following amino positions and/or residues of SEQ ID NO: 21 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 47, 60, 61, 82, 86, 105, 116, and/or 295, or any combination thereof.

In some embodiments, the following amino positions and/or residues of SEQ ID NO: 22 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 52, 65, 66, 87, 91, 110, 123, and/or 325, or any combination thereof.

In some embodiments, the following amino positions and/or residues of SEQ ID NO: 23 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 53, 65, 66, 86, 90, 109, 118, and/or 417, or any combination thereof.

In some embodiments, the following amino positions and/or residues of SEQ ID NO: 24 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 53, 65, 66, 86, 90, 109, 118, and/or 411, or any combination thereof.

In some embodiments, the following amino positions and/or residues of SEQ ID NO: 25 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 53, 65, 66, 87, 91, 110, 119, and/or 373, or any combination thereof.

In some embodiments, the following amino positions and/or residues of SEQ ID NO: 26 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 53, 65, 66, 87, 91, 110, 119, and/or 366, or any combination thereof.

In some embodiments, the following amino positions and/or residues of SEQ ID NO: 27 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 50, 63, 64, 85, 89, 108, 134, and/or 347, or any combination thereof.

In some embodiments, the following amino positions and/or residues of SEQ ID NO: 28 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 50, 63, 64, 85, 89, 108, 134, and/or 348, or any combination thereof.

In some embodiments, the following amino positions and/or residues of SEQ ID NO: 29 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 49, 62, 63, 84, 89, 107, 149, and/or 411, or any combination thereof.

In some embodiments, the following amino positions and/or residues of SEQ ID NO: 30 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 49, 62, 63, 84, 89, 107, 149, and/or 441, or any combination thereof.

In some embodiments, the following amino positions and/or residues of SEQ ID NO: 31 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 49, 62, 63, 84, 89, 107, 147, and/or 442, or any combination thereof.

In some embodiments, the following amino positions and/or residues of SEQ ID NO: 32 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 41, 54, 55, 77, 81, 100, 117, and/or 342, or any combination thereof.

In some embodiments, the following amino positions and/or residues of SEQ ID NO: 33 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 36, 48, 49, 69, 73, 92, 105, and/or 256, or any combination thereof.

In some embodiments, the following amino positions and/or residues of SEQ ID NO: 34 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 34, 46, 47, 68, 72, 91, 104, and/or 257, or any combination thereof.

In some embodiments, the following amino positions and/or residues of SEQ ID NO: 35 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 37, 49, 50, 70, 74, 93, 106, and/or 286, or any combination thereof.

In some embodiments, the following amino positions and/or residues of SEQ ID NO: 36 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 34, 46, 47, 67, 71, 90, 103, and/or 192, or any combination thereof.

In some embodiments, the following amino positions and/or residues of SEQ ID NO: 37 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 46, 63, 64, 84, 88, 109, 122, and/or 264, or any combination thereof.

In some embodiments, the following amino positions and/or residues of SEQ ID NO: 38 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 46, 82, 83, 104, 108, 127, 157, and/or 335, or any combination thereof.

In some embodiments, the following amino positions and/or residues of SEQ ID NO: 39 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 45, 67, 68, 72, 76, 114, 130, and/or 297, or any combination thereof.

In some embodiments, the following amino positions and/or residues of SEQ ID NO: 40 are preferably conserved for function and remaining positions can be modified. Positions (indicated in bolded-underline text in Table 3 and @ in FIG. 11) believed to be involved in putative ligand (e.g., NAD or NAD analogs or derivatives thereof described infra) binding residues: 46, 59, 60, 81, 85, 104, 117, and/or 27, or any combination thereof.

Included in Table 3 are variations of 1, 2, 3, 4, 5, 6, 7, 8, 9, 10, 11, 12, 13, 14, 15, 16, 17, 18, 19, 20, or more amino acids on the 5' end, on the 3' end, or on both the 5' and 3' ends, of the domain sequences as long as the sequence variations maintain the recited function and/or homology Included in Table 3 are polypeptide molecules comprising, consisting essentially of, or consisting of:
1) an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with a nucleic acid sequence of SEQ ID NO: 1-40, or a biologically active fragment thereof;
2) an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with a nucleic acid sequence of SEQ ID NO: 1-40, or a biologically active fragment thereof, comprising at least one or more (e.g., one, two, three, four, five, six, seven, eight, nine or ten) conserved ligand (e.g., NAD or NAD analogs or derivatives thereof described infra) binding residues set forth in Table 3;
3) an amino acid sequence having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3500, 4000, 4500, 5000, 5500, 6000, 6500, 7000, 7500, 8000, 8500, 9000, 9500, 10000, or more amino acids, or any range in between, inclusive such as between 200 and 600 amino acids;

4) an amino acid sequence having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2650, 2700, 2750, 2800, 2850, 2900, 2950, 3000, 3500, 4000, 4500, 5000, 5500, 6000, 6500, 7000, 7500, 8000, 8500, 9000, 9500, 10000, or more amino acids, or any range in between, inclusive such as between 200 and 600 amino acids, comprising at least one or more (e.g., one, two, three, four, five, six, seven, eight, nine or ten) conserved ligand (e.g., NAD or NAD analogs or derivatives thereof described infra) binding residues set forth in Table 3;

5) a biologically active fragment of an amino acid sequence of SEQ ID NO: 1-40 having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2625, or more amino acids, or any range in between, inclusive such as between 200 and 600 amino acids; or 6) a biologically active fragment of an amino acid sequence of SEQ ID NO: 1-40 having at least 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 400, 450, 500, 550, 600, 650, 700, 750, 800, 850, 900, 950, 1000, 1050, 1100, 1150, 1200, 1250, 1300, 1350, 1400, 1450, 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2625, or more amino acids, or any range in between, inclusive such as between 200 and 600 amino acids, comprising at least one or more (e.g., one, two, three, four, five, six, seven, eight, nine or ten) conserved ligand (e.g., NAD or NAD analogs or derivatives thereof described infra) binding residues set forth in Table 3.

As used herein, the term "radiation" refers to energy which may be selectively applied, including energy having a wavelength of between 10-14 and 104 meters including, for example, electron beam radiation, gamma radiation, x-ray radiation, light such as ultra-violet light, visible light, and infrared light, microwave radiation, cosmic or galactic radiation, and radio waves. The radiation is in particular an ionizing radiation which comprises subatomic particles and/or ions or electromagnetic waves which are energetic enough to ionize atoms or molecules. "Irradiation" refers to the application (exposure) of radiation to a subject, e.g., in radiation oncology for the treatment of cancer and/or during accidental or environmental radiation.

As used herein, the term "radiation-induced toxicity" or grammatical equivalents thereof means any damage to a cell, tissue, or any of its components, such as a nucleic acid (DNA or RNA), caused by radiation (e.g., as caused from X-ray exposure (during medical or dental visits), nuclear spills, nuclear clean-up).

As used herein, the term "radiation treatment" means a procedure including, but not limited to, radiotherapy, radiosurgery (i.e., radiation surgery) and/or any other (in particular) medical procedure, which uses ionizing radiation and in which a subject is treated by applying radiation to the subject's body. The radiation used for the treatment (the "treatment radiation") is effective for a particular part(s) of the body. Radiation treatment comprises a step of providing an energy value which depends on the radiation energy, in particular the energy of the treatment radiation, which is applied to the patient's body, and a step of controlling the period of time over which radiation treatment is performed in accordance with the energy value. The ionizing radiation can be emitted by an irradiation device such as an x-ray tube and/or a particle accelerator and/or an antenna and/or a radioactive material.

As used herein, the term "substantially decreased" and grammatical equivalents thereof refer to a level, amount, concentration of a parameter, such as a chemical compound, a metabolite, a nucleic acid, a polypeptide, a physical parameter (pH, temperature, viscosity, etc.), or a microorganism measured in a sample that has a decrease of at least 10%, preferably about 20%, more preferable about 40%, even more preferable about 50% and still more preferably a decrease of more than 75% when compared to the level, amount, or concentration of the same chemical compound, nucleic acid, polypeptide, physical parameter, or microorganism in a control sample. In some embodiments, the parameter is not detectable in a subject sample, while it is detectable in a control sample.

As used herein, the term "substantially increased" and grammatical equivalents thereof refer to a level, amount, concentration of a parameter, such as a chemical compound, a metabolite, a nucleic acid, a polypeptide, a physical parameter (pH, temperature, viscosity, etc.), or a microorganism measured in a sample that has an increase of at least 30%, preferably about 50%, more preferable about 75%, and still more preferably an increase of more than 100% when compared to the level, amount, or concentration of the same chemical compound, nucleic acid, polypeptide, physical parameter, or microorganism in a control sample. In some embodiments, the parameter is detectable in a subject sample, while it is not detectable in a control sample.

As used herein, the terms "treat," "treating," and "treatment" include: (1) preventing a pathological condition, disorder, or disease, i.e. causing the clinical symptoms of the pathological condition, disorder, or disease not to develop in a subject that may be predisposed to the pathological condition, disorder, or disease but does not yet experience any symptoms of the pathological condition, disorder, or disease; (2) inhibiting the pathological condition, disorder, or disease, i.e. arresting or reducing the development of the pathological condition, disorder, or disease or its clinical symptoms; or (3) relieving the pathological condition, disorder, or disease, i.e. causing regression of the pathological condition, disorder, or disease or its clinical symptoms. These terms encompass also prophylaxis, therapy and cure. Treatment means any manner in which the symptoms of a pathological condition, disorder, or disease are ameliorated or otherwise beneficially altered. Preferably, the subject in need of such treatment is a mammal, more preferable a human.

A "variant" or "biologically active fragment" of a polypeptide refers to a polypeptide having the amino acid sequence of the polypeptide in which is altered in one or more amino acid residues. The variant may have "conservative" changes, wherein a substituted amino acid has similar structural or chemical properties (e.g., replacement of leucine with isoleucine). A variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

The term "variant," when used in the context of a polynucleotide sequence, may encompass a polynucleotide sequence related to that of a particular gene or the coding sequence thereof. This definition may also include, for example, "allelic," "splice," "species," or "polymorphic" variants. A splice variant may have significant identity to a reference molecule, but will generally have a greater or lesser number of polynucleotides due to alternate splicing of exons during mRNA processing. The corresponding polypeptide may possess additional functional domains or an absence of domains. Species variants are polynucleotide sequences that vary from one species to another. The resulting polypeptides generally will have significant amino acid identity relative to each other. A polymorphic variation is a variation in the polynucleotide sequence of a particular gene between individuals of a given species. Polymorphic variants also may encompass "single nucleotide polymorphisms" (SNPs) in which the polynucleotide sequence varies by one base. The presence of SNPs may be indicative of, for example, a certain population, a disease state, or a propensity for a disease state.

1. Anti-NHD Antibodies

In certain embodiments, the present invention relates to antibodies and antigen binding fragments thereof that bind specifically to NHD and uses thereof. In some embodiments, the antibodies bind to a domain of NHD required for complex formation with c-Myc. Accordingly, in certain embodiments the antibodies described herein are able to inhibit complex formation between NHD (e.g., DBC1 or Table 3 proteins) and any of the proteins set forth in Table 4.

Table 4: NHD-Domain Containing Protein (e.g., DBC1) Interactors (See FIGS. 4 and 5 of Giguère, S et al. *Mol Cell Proteomics* (2016) 15(3):791-809)

PARP1, HNRPLL, SON, SUGP2, WDR33, THOC5, PUS1, SYMPK, THOC2, SART3, LSM4, PLRG1, SF3B2, SNRNP40, XAB2, ZCCHC8, PRPF8, PRPF4, POLR3B, POLR1A, POLR2D, POLR2A, SUPTSH, SUPT6H, GT3C4, EXOSC7, EIF4H, GTF3C5, MRPS23, SEP15, FKBP5, MRPS34, TPX2, TRIM27, USP7, UBE2K, STAG2, PDSSB, SMC4, PDSSA, NCAPG2, AKAP8, NUMA1, CEP170, POGZ, CTR9, TBLXR1, G3BP1, TLE1, SPIN1, COPS3, TLE3, GPS1, CSNK2A1, PRKDC, MSH3, MSH6, POLA1, TMPO, FEN1, PRIM2, CHTF18, AKAP8L, MLF2, SPATA5, ZMPSTE24, SMARCA2, SIRT1, SMARCA4, ARID1A, SMARCC2, KDM3B, ADNP, HDAC3, VPRBP, LCP1, KPNA3, TOMM40, IPO9, TIMM13, COBRA1, SAFB2, PELP1, TCEB2, CDK9, TROVE2, SRRT, PSPC1, FAM98B, GK, TXNRD1, NADKD1, NDUFS2, PCK2, CISD1, CYC1, UQCRFS1, MATR3, SRRT, NOP56, RIP1L1, UPF1, ZC3H14, HNRNPA0, LRPPRC, FARSA, EIF3D, MRPS22, NOP2, DNAJA2, NSUN2, DNAJA3, DDX5, DHX9, SFPQ, PPP1CB, PPP2R1A, BUB3, ILF3, ADAR, ISG15, NUP155, ZFR, ZC3H11A, KPNA4, KPNA1, KPNA3, KPNA6, ZNF326, SKIV2L2, SON, SUGP2, WTAP, PTBP1, PTBP3, CPSF1, RBM4, HNRNPUL2, SF1, SF3B1, PNN, ZCCHC8, SF3B3, CDCSL, PRPF8, SNRNP200, SAFB, PRMT5, WDR77, SUPT16H, SIRT1, SAP18, IKZF1, HCFC1, HDAC3, ZNF281, ZNF318, GIGYF2, RBM14, SAFB2, SPIN1, GTF21, MCM3, AKAP8L, TRIM28, PSMA2, PSME3, PSMB3, p53, USP11, SLC25A6, PFAS, CAD, SLC25A3, PFKL, ACLY, PPHLN1, RBM12B, or FLNA, or biologically active fragments thereof. Such antibodies can be polyclonal or monoclonal and can be, for example, murine, chimeric, humanized or fully human.

Polyclonal antibodies can be prepared by immunizing a suitable subject (e.g. a mouse) with a polypeptide immunogen (e.g., Table 3). The polypeptide antibody titer in the immunized subject can be monitored over time by standard techniques, such as with an enzyme linked immunosorbent assay (ELISA) using immobilized polypeptide. If desired, the antibody directed against the antigen can be isolated from the mammal (e.g., from the blood) and further purified by well-known techniques, such as protein A chromatography to obtain the IgG fraction.

At an appropriate time after immunization, e.g., when the antibody titers are highest, antibody-producing cells can be obtained from the subject and used to prepare monoclonal antibodies using standard techniques, such as the hybridoma technique originally described by Kohler and Milstein (1975) *Nature* 256:495-497) (see also Brown et al. (1981) *J. Immunol.* 127:539-46; Brown et al. (1980) *J. Biol. Chem.* 255:4980-83; Yeh et al. (1976) *Proc. Natl. Acad. Sci.* 76:2927-31; and Yeh et al. (1982) *Int. J. Cancer* 29:269-75), the more recent human B cell hybridoma technique (Kozbor et al. (1983) *Immunol. Today* 4:72), the EBV-hybridoma technique (Cole et al. (1985) *Monoclonal Antibodies and Cancer Therapy*, Alan R. Liss, Inc., pp. 77-96) or trioma techniques. The technology for producing monoclonal antibody hybridomas is well known (see generally Kenneth, R. H. in *Monoclonal Antibodies: A New Dimension In Biological Analyses*, Plenum Publishing Corp., New York, N.Y. (1980); Lerner, E. A. (1981) *Yale J. Biol. Med.* 54:387-402; Gefter, M. L. et al. (1977) *Somatic Cell Genet.* 3:231-36). Briefly, an immortal cell line (typically a myeloma) is fused to lymphocytes (typically splenocytes) from a mammal immunized with an immunogen as described above, and the culture supernatants of the resulting hybridoma cells are screened to identify a hybridoma producing a monoclonal antibody that binds to the polypeptide antigen, preferably specifically.

As an alternative to preparing monoclonal antibody-secreting hybridomas, a monoclonal specific for NHD and/or a polypeptide having an amino acid sequence selected from Table 3 can be identified and isolated by screening a recombinant combinatorial immunoglobulin library (e.g., an antibody phage display library or an antibody yeast display library) with the appropriate polypeptide (e.g., any of the proteins and sequences from Table 3) to thereby isolate immunoglobulin library members that bind the polypeptide.

Additionally, recombinant antibodies specific for NHD and/or a polypeptide having an amino acid sequence selected from Table 3, such as chimeric or humanized monoclonal antibodies, can be made using standard recombinant DNA techniques. Such chimeric and humanized monoclonal antibodies can be produced by recombinant DNA techniques known in the art, for example using methods described in U.S. Pat. Nos. 4,816,567; 5,565,332; Better et al. (1988) *Science* 240: 1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci.* 84:214-218; Nishimura et al. (1987) *Cancer Res.* 47:999-1005; Wood et al. (1985) *Nature* 314:446-449; and Shaw et al. (1988) *J. Natl. Cancer Inst.* 80: 1553-1559); Morrison, S. L. (1985) *Science* 229: 1202-1207; Oi et al. (1986) *Biotechniques* 4:214; Winter U.S. Pat. No. 5,225, 539; Jones et al. (1986) *Nature* 321:552-525); Verhoeyan et al. (1988) *Science* 239: 1534; and Beidler et al. (1988) *J. Immunol.* 141:4053-4060.

Human monoclonal antibodies specific for NHD and/or a polypeptide having an amino acid sequence selected from Table 3 can be generated using transgenic or transchromosomal mice carrying parts of the human immune system rather than the mouse system. For example, "HuMAb mice" which contain a human immunoglobulin gene miniloci that encodes unrearranged human heavy (μ and γ) and κ light chain immunoglobulin sequences, together with targeted mutations that inactivate the endogenous μ and κ chain loci (Lonberg, N. et al. (1994) *Nature* 368(6474): 856 859). Accordingly, the mice exhibit reduced expression of mouse IgM or κ, and in response to immunization, the introduced human heavy and light chain transgenes undergo class switching and somatic mutation to generate high affinity human IgGK monoclonal antibodies (Lonberg, N. et al. (1994), supra; reviewed in Lonberg, N. (1994) *Handbook of Experimental Pharmacology* 113:49 101; Lonberg, N. and Huszar, D. (1995) *Intern. Rev. Immunol.* Vol. 13: 65 93, and Harding, F. and Lonberg, N. (1995) *Ann. N. Y Acad. Sci* 764:536 546). The preparation of HuMAb mice is described in Taylor, L. et al. (1992) *Nucleic Acids Research* 20:6287 6295; Chen, J. et al. (1993) *International Immunology* 5: 647 656; Tuaillon et al. (1993) *Proc. Natl. Acad. Sci USA* 90:3720 3724; Choi et al. (1993) *Nature Genetics* 4: 117 123; Chen, J. et al. (1993) *EMBO J.* 12: 821 830; Tuaillon et al. (1994) *J. Immunol.* 152:2912 2920; Lonberg et al., (1994) *Nature* 368(6474): 856 859; Lonberg, N. (1994) *Handbook of Experimental Pharmacology* 113:49 101; Taylor, L. et al. (1994) *International Immunology* 6: 579 591; Lonberg, N. and Huszar, D. (1995) *Intern. Rev. Immunol.* Vol. 13: 65 93; Harding, F. and Lonberg, N. (1995) *Ann. N.Y. Acad. Sci* 764:536 546; Fishwild, D. et al. (1996) *Nature Biotechnology* 14: 845 851. See further, U.S. Pat. Nos. 5,545,806; 5,569,825; 5,625,126; 5,633,425; 5,789,650; 5,877,397; 5,661,016; 5,814,318; 5,874,299; 5,770,429; and 5,545,807.

In certain embodiments, the antibodies of the instant invention are able to bind to an epitope of NHD in a domain required for complex formation with PARP (e.g., a domain having an amino acid sequence selected from Table 3 with a dissociation constant of no greater than $10^{-6}$, $10^{-7}$, $10^{-8}$ or $10^{-9}$ M. Standard assays to evaluate the binding ability of the antibodies are known in the art, including for example, ELISAs, Western blots and RIAs. The binding kinetics (e.g., binding affinity) of the antibodies also can be assessed by standard assays known in the art, such as by Biacore analysis. In some embodiments, the binding of the antibody to NHD (e.g., DBC1 or Table 3 proteins) substantially inhibits the ability of any of the proteins set forth in Table 4 to form a complex with NHD (e.g., DBC1 or Table 3 proteins). As used herein, an antibody substantially inhibits the ability of any of the proteins set forth in Table 4 to form a complex with NHD (e.g., DBC1 or Table 3 proteins) when an excess of antibody reduces the quantity of complex formed to by at least about 20%, 40%, 60% or 80%, 85% or 90% (as measured in an in vitro competitive binding assay).

2. Inhibitors of NHD Complex Formation

Certain embodiments of the present invention relate to methods of recovering from, treating, or preventing cancer, aging, cell death, radiation damage, radiation exposure, among others, improving DNA repair, cell proliferation, cell survival, among others, and increasing the life span of a cell or protecting it against certain stresses, among others. These methods include administering agents that reduce NHDs ability to complex with any of the proteins set forth in Table 4. For example, in certain embodiments the agent inhibits complex formation between NHD (e.g., DBC1 or Table 3 proteins) and any of the proteins set forth in Table 4. In some embodiments, the agents induce a conformational change in NHD (e.g., DBC1 or Table 3 proteins) or any of the proteins set forth in Table 4 that abrogates their interaction and/or alters the ability of NHD (e.g., DBC1 or Table 3 proteins) to affect any of the proteins set forth in Table 4 activity, protein levels or cell localization.

In some embodiments, any agent that reduces inhibition of any of the proteins set forth in Table 4 by NHD (e.g., DBC1 or Table 3 proteins) can be used to practice the methods of the invention. In some embodiments, the agent inhibits complex formation between NHD and any of the proteins set forth in Table 4. Such agents can be those described herein or those identified through routine screening assays (e.g. the screening assays described herein).

In some embodiments, assays used to identify agents useful in the methods of the present invention include a reaction between a polypeptide comprising a sequence selected from Table 3 or a biologically active fragment thereof and one or more assay components. The other components may be either a test compound (e.g. the potential agent), or a combination of test compounds and any of the proteins set forth in Table 4 protein or fragment thereof. Agents identified via such assays, may be useful, for example, for recovering from, preventing, or treating cancer, aging, cell death, radiation damage, radiation exposure, among others, improving DNA repair, cell proliferation, cell survival, among others, and increasing the life span of a cell or protecting it against certain stresses, among others.

Agents useful in the methods of the present invention may be obtained from any available source, including systematic libraries of natural and/or synthetic compounds. Agents may also be obtained by any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann et al., 1994, *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam, 1997, Anticancer Drug Des. 12: 145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91: 11422; Zuckermann et al. (1994). *J. Med. Chem.* 37:2678; Cho et al. (1993)

Science 261: 1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37: 1233. Libraries of agents may be presented in solution (e.g., Houghten, 1992, *Biotechniques* 13:412-421), or on beads (Lam, 1991, *Nature* 354:82-84), chips (Fodor, 1993, *Nature* 364:555-556), bacteria and/or spores, (Ladner, U.S. Pat. No. 5,223,409), plasmids (Cull et al, 1992, *Proc Natl Acad Sci USA* 89: 1865-1869) or on phage (Scott and Smith, 1990, *Science* 249:386-390; Devlin, 1990, *Science* 249:404-406; Cwirla et al, 1990, *Proc. Natl. Acad. Sci.* 87:6378-6382; Felici, 1991, *J. Mol. Biol.* 222:301-310; Ladner, supra.).

Agents useful in the methods of the present invention may be identified, for example, using assays for screening candidate or test compounds which inhibit complex formation between NHD (e.g., DBC1 or Table 3 proteins) and any of the proteins set forth in Table 4.

The basic principle of the assay systems used to identify compounds that inhibit complex formation between NHD (e.g., DBC1 or Table 3 proteins), and any of the proteins set forth in Table 4, involves preparing a reaction mixture containing a NHD (e.g., DBC1 or Table 3 proteins) protein or fragment thereof, and any of the proteins set forth in Table 4, or fragment thereof under conditions and for a time sufficient to allow the NHD (e.g., DBC1 or Table 3 proteins) protein or fragment thereof to form a complex with any of the proteins set forth in Table 4 or fragment thereof. In order to test an agent for modulatory activity, the reaction mixture is prepared in the presence and absence of the test compound. The test compound can be initially included in the reaction mixture, or can be added at a time subsequent to the addition of the NHD (e.g., DBC1 or Table 3 proteins) protein or fragment thereof, and any of the proteins set forth in Table 4 or fragment thereof. Control reaction mixtures are incubated without the test compound or with a placebo. The formation of any complexes between the NHD (e.g., DBC1 or Table 3 proteins) protein or fragment thereof, and any of the proteins set forth in Table 4 or fragment thereof, is then detected. The formation of a complex in the control reaction, but less or no such formation in the reaction mixture containing the test compound, indicates that the compound interferes with the interaction of the NHD (e.g., DBC1 or Table 3 proteins) protein or fragment thereof, and any of the proteins set forth in Table 4 or fragment thereof.

The assay for compounds that modulate the interaction of the NHD (e.g., DBC1 or Table 3 proteins) protein or fragment thereof, and any of the proteins set forth in Table 4 or fragment thereof, may be conducted in a heterogeneous or homogeneous format. Heterogeneous assays involve anchoring either the NHD (e.g., DBC1 or Table 3 proteins) protein or fragment thereof, or any of the proteins set forth in Table 4 or fragment, thereof onto a solid phase and detecting complexes anchored to the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the NHD (e.g., DBC1 or Table 3 proteins) protein or fragment thereof, and any of the proteins set forth in Table 4 or fragment thereof (e.g., by competition), can be identified by conducting the reaction in the presence of the test substance, i.e., by adding the test substance to the reaction mixture prior to or simultaneously with the NHD (e.g., DBC1 or Table 3 proteins) protein or fragment thereof, and any of the proteins set forth in Table 4 or fragment thereof.

Alternatively, test compounds that disrupt preformed complexes, e.g., compounds with higher binding constants that displace one of the components from the complex, can be tested by adding the test compound to the reaction mixture after complexes have been formed. The various formats are briefly described below.

In a heterogeneous assay system, either the NHD (e.g., DBC1 or Table 3 proteins) protein or fragment thereof, or any of the proteins set forth in Table 4 protein or fragment thereof, is anchored onto a solid surface or matrix, while the other corresponding non-anchored component may be labeled, either directly or indirectly. In practice, microtitre plates are often utilized for this approach. The anchored species can be immobilized by a number of methods, either non-covalent or covalent, that are typically well known to one who practices the art. Non-covalent attachment can often be accomplished simply by coating the solid surface with a solution of the NHD (e.g., DBC1 or Table 3 proteins) protein or fragment thereof, or any of the proteins set forth in Table 4 or fragment thereof, and drying. Alternatively, an immobilized antibody specific for the assay component to be anchored can be used for this purpose.

In related assays, a fusion protein can be provided which adds a domain that allows one or both of the assay components to be anchored to a matrix. For example, glutathione-S-transferase/marker fusion proteins or glutathione-S-transferase/binding partner can be adsorbed onto glutathione sepharose beads (Sigma Chemical, St. Louis, MO) or glutathione derivatized microtiter plates, which are then combined with the test compound or the test compound and either the non-adsorbed the NHD (e.g., DBC1 or Table 3 proteins) protein or fragment thereof, or any of the proteins set forth in Table 4 or fragment thereof, and the mixture incubated under conditions conducive to complex formation (e.g., physiological conditions). Following incubation, the beads or microtiter plate wells are washed to remove any unbound assay components, the immobilized complex assessed either directly or indirectly, for example, as described above.

A homogeneous assay may also be used to identify inhibitors of complex formation. This is typically a reaction, analogous to those mentioned above, which is conducted in a liquid phase in the presence or absence of the test compound. The formed complexes are then separated from unreacted components, and the amount of complex formed is determined. As mentioned for heterogeneous assay systems, the order of addition of reactants to the liquid phase can yield information about which test compounds modulate (inhibit or enhance) complex formation and which disrupt preformed complexes.

In such a homogeneous assay, the reaction products may be separated from unreacted assay components by any of a number of standard techniques, including but not limited to: differential centrifugation, chromatography, electrophoresis and immunoprecipitation. In differential centrifugation, complexes of molecules may be separated from uncomplexed molecules through a series of centrifugal steps, due to the different sedimentation equilibria of complexes based on their different sizes and densities (see, for example, Rivas, G., and Minton, A. P., *Trends Biochem Sci* 1993 August; 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the complex as compared to the uncomplexed molecules may be exploited to differentially separate the complex from the remaining individual reactants, for example through the use of ion-exchange chromatography resins. Such resins and chromatographic techniques are well known to one skilled in the art (see, e.g., Heegaard, 1998, *J Mol. Recognit.* 11: 141-148; Hage and Tweed, 1997, *J. Chromatogr. B. Biomed. Sci. Appl.,* 699:499-525). Gel electrophoresis may also be employed to separate complexed molecules from unbound species (see, e.g., Ausubel et al. (eds.), In: *Current Protocols in Molecular Biology,* J. Wiley & Sons, New York. 1999). In this technique, protein or nucleic acid complexes are separated based on size or charge, for example. In order to maintain the binding interaction during the electrophoretic process, nondenaturing gels in the absence of reducing agent are typically preferred, but conditions appropriate to the particular interactants will be well known to one skilled in the art. Immunoprecipitation is another common technique utilized for the isolation of a protein-protein complex from solution (see, e.g., Ausubel et al. (eds.), In: *Current Protocols in Molecular Biology,* J. Wiley & Sons, New York. 1999). In this technique, all proteins binding to an antibody specific to one of the binding molecules are precipitated from solution by conjugating the antibody to a polymer bead that may be readily collected by centrifugation. The bound assay components are released from the beads (through a specific proteolysis event or other technique well known in the art which will not disturb the protein-protein interaction in the complex), and a second immunoprecipitation step is performed, this time utilizing antibodies specific for the correspondingly different interacting assay component. In this manner, only formed complexes should remain attached to the beads. Variations in complex formation in both the presence and the absence of a test compound can be compared, thus offering information about the ability of the compound to modulate interactions between the NHD (e.g., DBC1 or Table 3 proteins) protein or fragment thereof, and any of the proteins set forth in Table 4 or fragment thereof.

Agents useful in the methods described herein may also be identified, for example, using methods wherein a cell (e.g., a cell that expresses NHD (e.g., DBC1 or Table 3 proteins) and any of the proteins set forth in Table 4), such as a mammalian cell) is contacted with a test compound, and the expression level of any of the proteins set forth in Table 4 target gene or a reporter gene under the transcriptional control of the promoter of a c-Myc target gene is determined. In some embodiments, any of the proteins set forth in Table 4 reporter gene encodes a readily detectable protein (e.g., a fluorescent protein or a protein catalyzes a reaction that produces a change in color, luminescence and/or opacity). In some embodiments, the level of expression of the reporter gene in the presence of the test compound is compared to the level of expression of mRNA or protein in the absence of the candidate compound. If the expression of the mRNA or protein increases in the presence of the test compound, the test compound an agent useful in the methods described herein.

3. NAD+, Analogs and Derivatives Thereof

The advantages of the present invention include, without limitation, compositions of nicotinamide mononucleotide, encompassing analogs and derivatives thereof, (e.g., NAD+) and their use in the methods provided herein (e.g., methods of recovering from, treating, and preventing cancer, aging, cell death, radiation damage, radiation exposure, among others), may improve DNA repair, cell proliferation, cell survival, among others, and may increase the life span of a cell or protect it against certain stresses, among others). In some embodiments, the invention relates to pharmaceutical compositions and nutritional supplements containing nicotinamide mononucleotide derivatives. In further embodiments, the invention relates to methods of using nicotinamide mononucleotide derivatives that promote the increase of intracellular levels of nicotinamide adenine dinucleotide (NAD+) in cells and tissues for recovering from, treating, or preventing diseases (e.g., cancer, aging, radiation damage, radiation exposure) and improving DNA repair, cell and tissue survival.

One embodiment of the nicotinamide mononucleotide, encompassing analogs and derivatives thereof, is a compound, its stereoisomer, salt, hydrate, solvate, or crystalline or polymorphic form thereof, represented by formula II:

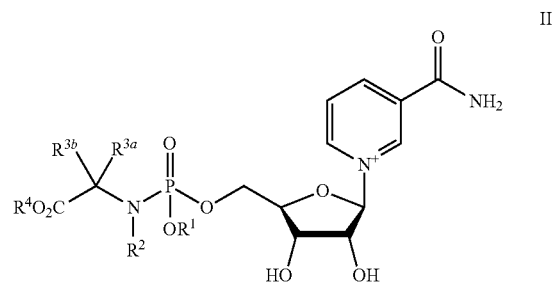

II wherein
(a) $R^1$ is hydrogen, n-alkyl; branched alkyl; cycloalkyl; or aryl, which includes, but is not limited to, phenyl or naphthyl, where phenyl or naphthyl are optionally substituted with at least one of $C_{1-6}$ alkyl, $C_{2-6}$ alkenyl, $C_{2-6}$ alkynyl, $C_{1-6}$ alkoxy, F, Cl, Br, I, nitro, cyano, $C_{1-6}$ haloalkyl, —N(R$^{1'}$)$_2$, $C_{1-6}$ acylamino, —NHSO$_2$C$_{1-6}$ alkyl, —SO$_2$N(R$^{1'}$)$_2$, COR$^{1''}$, and —SO$_2$C$_{1-6}$ alkyl; (R$^{1'}$ is independently hydrogen or alkyl, which includes, but is not limited to, $C_{1-20}$ alkyl, $C_{1-10}$ alkyl, or $C_{1-6}$ alkyl, R$^{1''}$ is —OR' or —N(R$^{1'}$)$_2$);
(b) $R^2$ is hydrogen, $C_{1-10}$ alkyl, $R^{3a}$ or $R^{3b}$ and $R^2$ together are (CH$_2$)$_n$ so as to form a cyclic ring that includes the adjoining N and C atoms, C(O)CR$^{3a}$R$^{3b}$NHR$^1$, where n is 2 to 4 and $R^1$, $R^{3a}$, and $R^{3b}$;
(c) $R^{3a}$ and $R^{3b}$ are (i) independently selected from hydrogen, $C_{1-10}$ alkyl, cycloalkyl, —(CH$_2$)$_c$(NR$^3$)$_2$, $C_{1-6}$ hydroxyalkyl, —CH$_2$SH, —(CH$_2$)$_2$S(O)$_d$Me, —(CH$_2$)$_3$NHC(=NH)NH$_2$, (1H-indol-3-yl)methyl, (1H-imidazol-4-yl)methyl, —(CH$_2$)$_e$COR$^{3''}$, aryl and aryl $C_{1-3}$ alkyl, said aryl groups optionally substituted with a group selected from hydroxyl, $C_{1-10}$ alkyl, $C_{1-6}$ alkoxy, halogen, nitro and cyano; (ii) $R^{3a}$ and $R^{3b}$ both are $C_{1-6}$ alkyl; (iii) $R^{3a}$ and $R^{3b}$ together are (CH$_2$)$_f$ so as to form a spiro ring; (iv) $R^{3a}$ is hydrogen and $R^{3b}$ and $R^2$ together are (CH$_2$)$_n$ so as to form a cyclic ring that includes the adjoining N and C atoms (v) $R^{3b}$ is hydrogen and $R^{3a}$ and $R^2$ together are (CH$_2$)$_n$ so as to form a cyclic ring that includes the adjoining N and C atoms, where c is 1 to 6, d is 0 to 2, e is 0 to 3, f is 2 to 5, n is 2 to 4, and where $R^3$ is independently hydrogen or $C_{1-6}$ alkyl and R$^{3''}$ is —OR' or —N(R$^3$)$_2$);
(vi) $R^{3a}$ is H and $R^{3b}$ is H, CH$_3$, CH$_2$CH$_3$, CH(CH$_3$)$_2$, CH$_2$CH(CH$_3$)$_2$, CH(CH$_3$)CH$_2$CH$_3$, CH$_2$Ph, CH$_2$-indol-3-yl, —CH$_2$CH$_2$SCH$_3$, CH$_2$CO$_2$H, CH$_2$C(O)NH$_2$, CH$_2$CH$_2$COOH, CH$_2$CH$_2$C(O)NH$_2$, CH$_2$CH$_2$CH$_2$CH$_2$NH$_2$, —CH$_2$CH$_2$CH$_2$NHC(NH) NH$_2$, CH$_2$-imidazol-4-yl, CH$_2$OH, CH(OH)CH$_3$, CH$_2$ ((4'-OH)-Ph), CH₂SH, or lower cycloalkyl; or (viii) $R^{3a}$ is CH₃, —CH₂CH₃, CH(CH₃)₂, CH₂CH(CH₃)₂, CH(CH₃)CH₂CH₃, CH₂Ph, CH₂-indol-3-yl, —CH₂CH₂SCH₃, CH₂CO₂H, CH₂C(O)NH₂, CH₂CH₂COOH, CH₂CH₂C(O)NH₂, CH₂CH₂CH₂CH₂NH₂, —CH₂CH₂CH₂NHC(NH)NH₂, CH₂-imidazol-4-yl, CH₂OH, CH(OH)CH₃, CH₂((4'-OH)-Ph), CH₂SH, or lower cycloalkyl and $R^{3b}$ is H, where $R^3$ is independently hydrogen or alkyl, which includes, but is not limited to, $C_{1-20}$ alkyl, $C_{1-10}$ alkyl, or $C_{1-6}$ alkyl, $R^{3'''}$ is —OR' or —N(R^{3'})₂); and (d) $R^4$ is hydrogen, $C_{1-10}$ alkyl, $C_{1-10}$ alkyl optionally substituted with a lower alkyl, alkoxy, di(lower alkyl)-amino, or halogen, $C_{1-10}$ haloalkyl, $C_{3-10}$ cycloalkyl, cycloalkyl alkyl, cycloheteroalkyl, aminoacyl, aryl, such as phenyl, heteroaryl, such as, pyridinyl, substituted aryl, or substituted heteroaryl.

Another embodiment of the nicotinamide mononucleotide, encompassing analogs and derivatives thereof, is a compound, its stereoisomer, salt, hydrate, solvate, or crystalline or polymorphic form thereof, wherein the compound is selected from the group consisting of

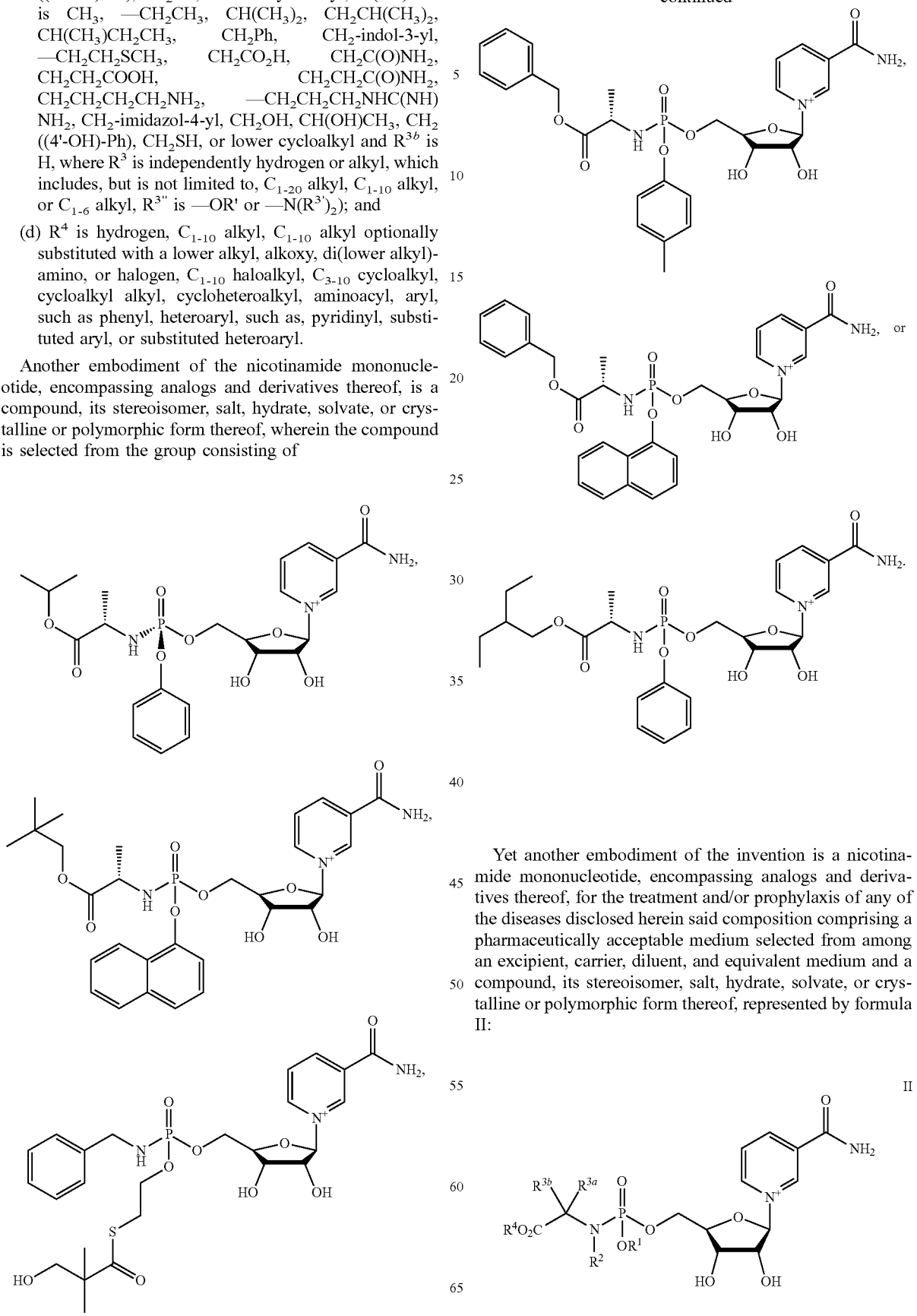

Yet another embodiment of the invention is a nicotinamide mononucleotide, encompassing analogs and derivatives thereof, for the treatment and/or prophylaxis of any of the diseases disclosed herein said composition comprising a pharmaceutically acceptable medium selected from among an excipient, carrier, diluent, and equivalent medium and a compound, its stereoisomer, salt, hydrate, solvate, or crystalline or polymorphic form thereof, represented by formula II:

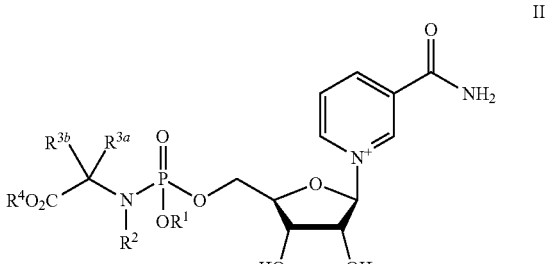

II wherein
(a) $R^1$ is hydrogen, n-alkyl; branched alkyl; cycloalkyl; or aryl, which includes, but is not limited to, phenyl or naphthyl, where phenyl or naphthyl are optionally substituted with at least one of $C_{1-6}$ alkyl, $C_{2-6}$ alkenyl, $C_{2-6}$ alkynyl, $C_{1-6}$ alkoxy, F, Cl, Br, I, nitro, cyano, $C_{1-6}$haloalkyl, —$N(R^{1'})_2$, $C_{1-6}$ acylamino, —$NHSO_2C_{1-6}$ alkyl, —$SO_2N(R^{1'})_2$, $COR^{1''}$, and —$SO_2C_{1-6}$ alkyl; ($R^{1'}$ is independently hydrogen or alkyl, which includes, but is not limited to, $C_{1-20}$ alkyl, $C_{1-10}$ alkyl, or $C_{1-6}$ alkyl, $R^{1''}$ is —OR' or —$N(R^1)_2$);
(b) $R^2$ is hydrogen, $C_{1-10}$ alkyl, $R^{3a}$ or $R^{3b}$ and $R^2$ together are $(CH_2)_n$ so as to form a cyclic ring that includes the adjoining N and C atoms, $C(O)CR^{3a}R^{3b}NHR^1$, where n is 2 to 4 and $R^1$, $R^{3a}$, and $R^{3b}$;
(c) $R^{3a}$ and $R^{3b}$ are (i) independently selected from hydrogen, $C_{1-10}$ alkyl, cycloalkyl, —$(CH_2)_c(NR^{3'})_2$, $C_{1-6}$ hydroxyalkyl, —$CH_2SH$, —$(CH_2)_2S(O)_dMe$, —$(CH_2)_3NHC(=NH)NH_2$, (1H-indol-3-yl)methyl, (1H-imidazol-4-yl)methyl, —$(CH_2)_eCOR^{3'''}$, aryl and aryl $C_{1-3}$ alkyl, said aryl groups optionally substituted with a group selected from hydroxyl, $C_{1-10}$ alkyl, $C_{1-6}$ alkoxy, halogen, nitro and cyano; (ii) $R^{3a}$ and $R^{3b}$ both are $C_{1-6}$ alkyl; (iii) $R^{3a}$ and $R^{3b}$ together are $(CH_2)_f$ so as to form a spiro ring; (iv) $R^{3a}$ is hydrogen and $R^{3b}$ and $R^2$ together are $(CH_2)_n$ so as to form a cyclic ring that includes the adjoining N and C atoms (v) $R^{3b}$ is hydrogen and $R^{3a}$ and $R^2$ together are $(CH_2)_n$ so as to form a cyclic ring that includes the adjoining N and C atoms, where c is 1 to 6, d is 0 to 2, e is 0 to 3, f is 2 to 5, n is 2 to 4, and where $R^3$ is independently hydrogen or $C_{1-6}$ alkyl and $R^{3''}$ is —OR' or —$N(R^{3'})_2$); (vi) $R^{3a}$ is H and $R^{3b}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl; or (viii) $R^{3a}$ is $CH_3$, —$CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl and $R^{3b}$ is H, where $R^3$ is independently hydrogen or alkyl, which includes, but is not limited to, $C_{1-20}$ alkyl, $C_{1-10}$ alkyl, or $C_{1-6}$ alkyl, $R^{3''}$ is —OR' or —$N(R^{3'})_2$); and
(d) $R^4$ is hydrogen, $C_{1-10}$ alkyl, $C_{1-10}$ alkyl optionally substituted with a lower alkyl, alkoxy, di(lower alkyl)-amino, or halogen, $C_{1-10}$ haloalkyl, $C_{3-10}$ cycloalkyl, cycloalkyl alkyl, cycloheteroalkyl, aminoacyl, aryl, such as phenyl, heteroaryl, such as, pyridinyl, substituted aryl, or substituted heteroaryl.

Another embodiment of the invention is method of treatment in a subject in need thereof, which comprises: administering a therapeutically effective amount of the compound represented by formula I to the subject; wherein the compound or its stereoisomer, salt, hydrate, solvate, or crystalline or polymorphic form thereof represented by formula II:

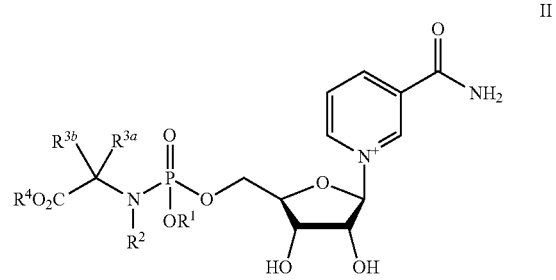

wherein
(a) $R^1$ is hydrogen, n-alkyl; branched alkyl; cycloalkyl; or aryl, which includes, but is not limited to, phenyl or naphthyl, where phenyl or naphthyl are optionally substituted with at least one of $C_{1-6}$ alkyl, $C_{2-6}$ alkenyl, $C_{2-6}$ alkynyl, $C_{1-6}$ alkoxy, F, Cl, Br, I, nitro, cyano, $C_{1-6}$ haloalkyl, —$N(R^{1'})_2$, $C_{1-6}$ acylamino, —$NHSO_2C_{1-6}$ alkyl, —$SO_2N(R^{1'})_2$, $COR^{1''}$, and —$SO_2C_{1-6}$ alkyl; ($R^{1'}$ is independently hydrogen or alkyl, which includes, but is not limited to, $C_{1-20}$ alkyl, $C_{1-10}$ alkyl, or $C_{1-6}$ alkyl, $R^{1''}$ is —OR' or —$N(R^{1'})_2$);
(b) $R^2$ is hydrogen, $C_{1-10}$ alkyl, $R^{3a}$ or $R^{3b}$ and $R^2$ together are $(CH_2)_n$ so as to form a cyclic ring that includes the adjoining N and C atoms, $C(O)CR^{3a}R^{3b}NHR^1$, where n is 2 to 4 and $R^1$, $R^{3a}$, and $R^{3b}$;
(c) $R^{3a}$ and $R^{3b}$ are (i) independently selected from hydrogen, $C_{1-10}$ alkyl, cycloalkyl, —$(CH_2)_c(NR^{3'})_2$, $C_{1-6}$ hydroxyalkyl, —$CH_2SH$, —$(CH_2)_2S(O)_dMe$, —$(CH_2)_3NHC(=NH)NH_2$, (1H-indol-3-yl)methyl, (1H-imidazol-4-yl)methyl, —$(CH_2)_eCOR^{3'''}$, aryl and aryl $C_{1-3}$ alkyl, said aryl groups optionally substituted with a group selected from hydroxyl, $C_{1-10}$ alkyl, $C_{1-6}$ alkoxy, halogen, nitro and cyano; (ii) $R^{3a}$ and $R^{3b}$ both are $C_{1-6}$ alkyl; (iii) $R^{3a}$ and $R^{3b}$ together are $(CH_2)_f$ so as to form a spiro ring; (iv) $R^{3a}$ is hydrogen and $R^{3b}$ and $R^2$ together are $(CH_2)_n$ so as to form a cyclic ring that includes the adjoining N and C atoms (v) $R^{3b}$ is hydrogen and $R^{3a}$ and $R^2$ together are $(CH_2)_n$ so as to form a cyclic ring that includes the adjoining N and C atoms, where c is 1 to 6, d is 0 to 2, e is 0 to 3, f is 2 to 5, n is 2 to 4, and where $R^3$ is independently hydrogen or $C_{1-6}$ alkyl and $R^{3''}$ is —OR' or —$N(R^{3'})_2$); (vi) $R^{3a}$ is H and $R^{3b}$ is H, $CH_3$, $CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl; or (viii) $R^{3a}$ is $CH_3$, —$CH_2CH_3$, $CH(CH_3)_2$, $CH_2CH(CH_3)_2$, $CH(CH_3)CH_2CH_3$, $CH_2Ph$, $CH_2$-indol-3-yl, —$CH_2CH_2SCH_3$, $CH_2CO_2H$, $CH_2C(O)NH_2$, $CH_2CH_2COOH$, $CH_2CH_2C(O)NH_2$, $CH_2CH_2CH_2CH_2NH_2$, —$CH_2CH_2CH_2NHC(NH)NH_2$, $CH_2$-imidazol-4-yl, $CH_2OH$, $CH(OH)CH_3$, $CH_2((4'-OH)-Ph)$, $CH_2SH$, or lower cycloalkyl and $R^{3b}$ is H, where $R^{3'}$ is independently hydrogen or alkyl, which includes, but is not limited to, $C_{1-20}$ alkyl, $C_{1-10}$ alkyl, or $C_{1-6}$ alkyl, $R^{3''}$ is —OR' or —$N(R^{3'})_2$); and
(d) $R^4$ is hydrogen, $C_{1-10}$ alkyl, $C_{1-10}$ alkyl optionally substituted with a lower alkyl, alkoxy, di(lower alkyl)-amino, or halogen, $C_{1-10}$ haloalkyl, $C_{3-10}$ cycloalkyl, cycloalkyl alkyl, cycloheteroalkyl, aminoacyl, aryl, such as phenyl, heteroaryl, such as, pyridinyl, substituted aryl, or substituted heteroaryl.

In yet another embodiment is a method of treatment, wherein the compound, its stereoisomer, salt, hydrate, solvate, or crystalline or polymorphic form thereof, wherein the compound is selected from the group consisting of

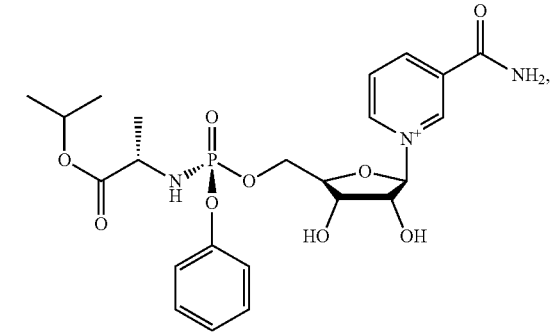

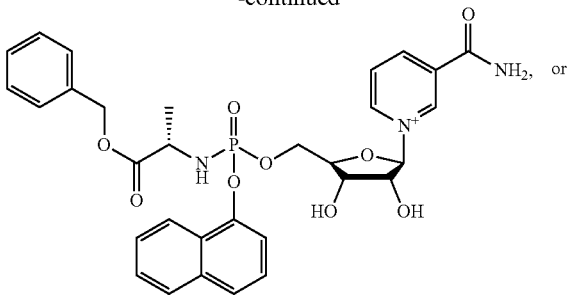

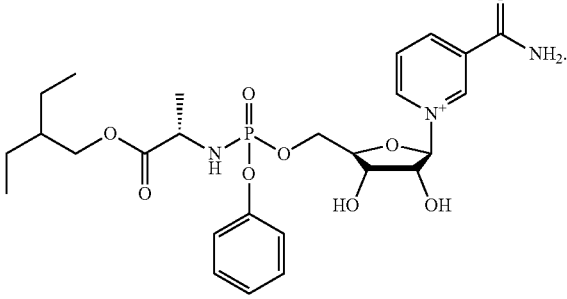

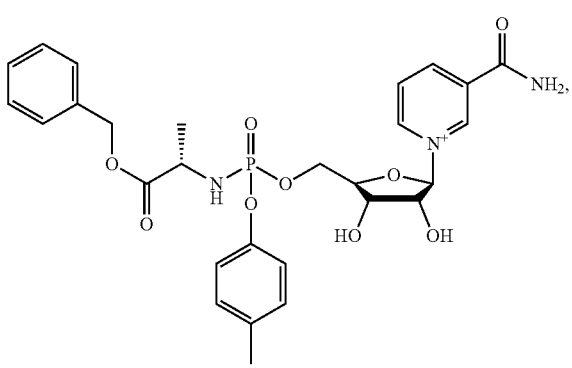

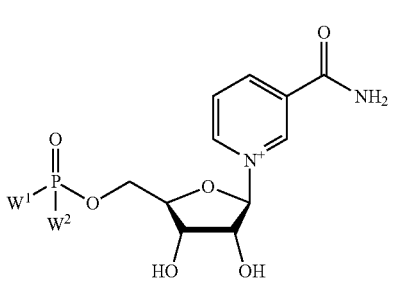

An embodiment of the current invention is a compound, its stereoisomer, salt, hydrate, solvate, or crystalline or polymorphic form thereof, represented by formula III:

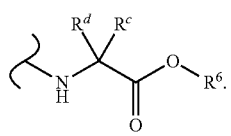

III

In which each $W^1$ and $W^2$ is independently

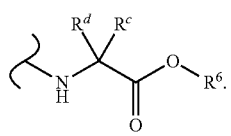

In an aspect of this embodiment, each $R^c$ or $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl $(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is S. In another aspect of this embodiment, each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is R. In another aspect of this embodiment, each $R^c$ is H and each $R^d$ is independently $(C_1-C_8)$alkyl. In another aspect of this embodiment, each $R^c$ is H and each $R^d$ is independently $(C_1-C_8)$alkyl wherein the chirality of the carbon to which said $R^c$ and $R^d$ is attached is S. In another aspect of this embodiment, each $R^c$ is H and each $R^d$ is independently $(C_1-C_8)$alkyl wherein the chirality of the carbon to which said $R^c$ and $R^d$ is attached is R. In another aspect of this embodiment, each

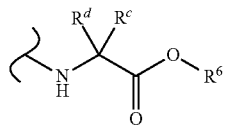

comprises a nitrogen-linked naturally occurring α-amino acid ester.

In another embodiment of Formula III, each $W^1$ and $W^2$ is independently

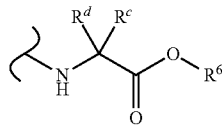

and each $R^6$ is independently $(C_1-C_8)$alkyl, $(C_2-C_8)$alkenyl, $(C_2-C_8)$alkynyl, $(C_3-C_8)$carbocyclyl or $(C_4-C_8)$carbocyclylalkyl. In another aspect of this embodiment, each $R^6$ is independently $(C_1-C_8)$alkyl. In another aspect of this embodiment, each $R^c$ or $R^d$ is independently H, $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is S. In another aspect of this embodiment, each $R^c$ is H and each $R^d$ is independently $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is R. In another aspect of this embodiment, each $R^c$ is H and each $R^d$ is independently $(C_1-C_8)$alkyl. In another aspect of this embodiment, each $R^c$ is H and each $R^d$ is independently $(C_1-C_8)$alkyl wherein the chirality of the carbon to which said $R^c$ and $R^d$ is attached is S. In another aspect of this embodiment, each $R^c$ is H and each $R^d$ is independently $(C_1-C_8)$alkyl wherein the chirality of the carbon to which said $R^c$ and $R^d$ is attached is R. In another aspect of this embodiment, each

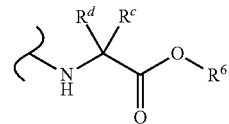

comprises a nitrogen-linked naturally occurring α-amino acid ester.

In one embodiment of Formula III, each $W^1$ and $W^2$ is independently

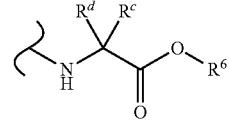

and each $R^6$ is independently $(C_1-C_8)$alkyl. In another aspect of this embodiment, each $R^6$ is independently secondary alkyl. In another aspect of this embodiment, each $R^6$ is 2-propyl. In another aspect of this embodiment, each $R^c$ is H and each $R^d$ is methyl. In another aspect of this embodiment, each $R^c$ is H and each $R^d$ is methyl wherein the chirality of the carbon to which said $R^c$ and $R^d$ is attached is S. In another aspect of this embodiment, each $R^c$ is H and each $R^d$ is methyl wherein the chirality of the carbon to which said $R^c$ and $R^d$ is attached is R. In another aspect of this embodiment, $R^1$ is H. In another aspect of this embodiment, $R^1$ is $(C_1-C_8)$alkyl. In another aspect of this embodiment, $R^1$ is methyl. In another aspect of this embodiment, $R^1$ is $(C_1-C_8)$alkyl and $R^2$ is OH. In another aspect of this embodiment, $R^1$ is $(C_1-C_8)$alkyl, $R^2$ is OH and $R^3$ is $(C_1-C_8)$alkyl. In another aspect of this embodiment, $R^1$ is methyl and $R^2$ is OH. In another aspect of this embodiment, $R^1$ is methyl, $R^2$ is OH and $R^3$ is $(C_1-C_8)$alkyl. In another aspect of this embodiment, each

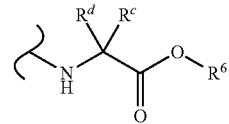

comprises a nitrogen-linked naturally occurring α-amino acid ester.

In one embodiment of Formula III, one of $W^1$ or $W^2$ is $OR^4$ and the other of $W^1$ or $W^2$ is

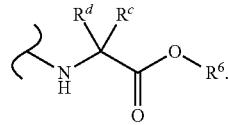

In another aspect of this embodiment, $R^4$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, $R^4$ is $(C_6-C_{20})$aryl, ($C_2$-$C_{20}$)heterocyclyl or heteroaryl. In another aspect of this embodiment, $R^4$ is ($C_6$-$C_{20}$)aryl. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $S(O)_nR^a$, $S(O)_2N(R^a)_2$, $S(O)_2NH(R^a)$, $S(O)_2NH_2$, $OR^a$ or $R^a$. In another aspect of this embodiment, each

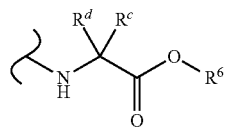

comprises a nitrogen-linked naturally occurring α-amino acid ester.

In one embodiment of Formula III, one of $W^1$ or $W^2$ is $OR^4$ and the other of $W^1$ or $W^2$ is

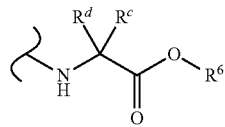

wherein $R^4$ is unsubstituted phenyl. In another aspect of this embodiment, $R^1$ is H. In another aspect of this embodiment, $R^1$ is ($C_1$-$C_8$)alkyl. In another aspect of this embodiment, $R^1$ is methyl. In another aspect of this embodiment, $R^1$ is ($C_1$-$C_8$)alkyl and $R^2$ is OH. In another aspect of this embodiment, $R^1$ is ($C_1$-$C_8$)alkyl, $R^2$ is OH and $R^3$ is ($C_1$-$C_8$)alkyl. In another aspect of this embodiment, $R^1$ is methyl and $R^2$ is OH. In another aspect of this embodiment, $R^1$ is methyl, $R^2$ is OH and $R^3$ is ($C_1$-$C_8$)alkyl. In another aspect of this embodiment, each $R^c$ or $R^d$ is independently H, ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl($C_1$-$C_8$)alkyl, heterocyclyl($C_1$-$C_8$)alkyl, ($C_6$-$C_{20}$)aryl, ($C_2$-$C_{20}$)heterocyclyl or heteroaryl. In another aspect of this embodiment, one of $R^c$ or $R^d$ is H and the other of $R^c$ or $R^d$ is ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl($C_1$-$C_8$)alkyl, heterocyclyl($C_1$-$C_8$)alkyl, ($C_6$-$C_{20}$)aryl, ($C_2$-$C_{20}$)heterocyclyl or heteroaryl. In another aspect of this embodiment, one of $R^c$ or $R^d$ is H and the other of $R^c$ or $R^d$ is ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl($C_1$-$C_8$)alkyl, heterocyclyl($C_1$-$C_8$)alkyl, ($C_6$-$C_{20}$)aryl, ($C_2$-$C_{20}$)heterocyclyl or heteroaryl wherein the chirality of the carbon to which said $R^c$ and $R^d$ is attached is S. In another aspect of this embodiment, one of $R^c$ or $R^d$ is H and the other of $R^c$ or $R^d$ is independently ($C_1$-$C_8$)alkyl, ($C_2$-$C_8$)alkenyl, ($C_2$-$C_8$)alkynyl, ($C_3$-$C_8$)carbocyclyl, ($C_4$-$C_8$)carbocyclylalkyl, aryl($C_1$-$C_8$)alkyl, heterocyclyl($C_1$-$C_8$)alkyl, ($C_6$-$C_{20}$)aryl, ($C_2$-$C_{20}$)heterocyclyl or heteroaryl wherein the chirality of the carbon to which said $R^c$ and $R^d$ is attached is R. In another aspect of this embodiment, one of $R^c$ or $R^d$ is H and the other of $R^c$ or $R^d$ is ($C_1$-$C_8$)alkyl. In another aspect of this embodiment, one of $R^c$ or $R^d$ is H and the other of $R^c$ or $R^d$ is ($C_1$-$C_8$)alkyl wherein the chirality of the carbon to which said $R^c$ and $R^d$ is attached is S. In another aspect of this embodiment, one of $R^c$ or $R^d$ is H and the other of $R^c$ or $R^d$ is ($C_1$-$C_8$)alkyl wherein the chirality of the carbon to which said $R^c$ and $R^d$ is attached is R. In another aspect of this embodiment, the chirality at phosphorus is S. In another aspect of this embodiment, the chirality at phosphorus is R. In another aspect of this embodiment, each

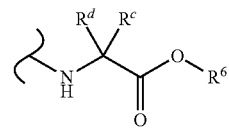

comprises a nitrogen-linked naturally occurring α-amino acid ester.

In one embodiment of Formula III, one of $W^1$ or $W^2$ is $OR^4$ and the other of W or $W^2$ is

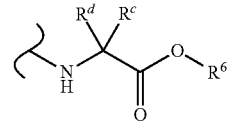

wherein one of $R^c$ or $R^d$ is H and the other of $R^c$ or $R^d$ is methyl. In another aspect of this embodiment, one of $R^c$ or $R^d$ is H and the other of $R^c$ or $R^d$ is methyl wherein the chirality of the carbon to which said $R^c$ and $R^d$ is attached is S. In another aspect of this embodiment, one of $R^c$ or $R^d$ is H and the other of $R^c$ or $R^d$ is methyl wherein the chirality of the carbon to which said $R^c$ and $R^d$ is attached is R. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $S(O)_nR^a$, $S(O)_2N(R^a)_2$, $S(O)_2NH(R^a)$, $S(O)_2NH_2$, $OR^a$ or $R^a$. In another aspect of this embodiment, $R^1$ is H. In another aspect of this embodiment, $R^1$ is ($C_1$-$C_8$)alkyl. In another aspect of this embodiment, $R^1$ is methyl. In another aspect of this embodiment, $R^1$ is ($C_1$-$C_8$)alkyl and $R^2$ is OH. In another aspect of this embodiment, $R^1$ is ($C_1$-$C_8$)alkyl, $R^2$ is OH and $R^3$ is ($C_1$-$C_8$)alkyl. In another aspect of this embodiment, $R^1$ is methyl and $R^2$ is OH. In another aspect of this embodiment, $R^1$ is methyl, $R^2$ is OH and $R^3$ is ($C_1$-$C_8$)alkyl. In another aspect of this embodiment, the chirality at phosphorus is S. In another aspect of this embodiment, the chirality at phosphorus is R. In another aspect of this embodiment, each

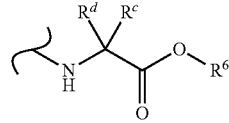

comprises a nitrogen-linked naturally occurring α-amino acid ester.

In one embodiment of Formula III, one of $W^1$ or $W^2$ is $OR^4$ and the other of $W^1$ or $W^2$ is

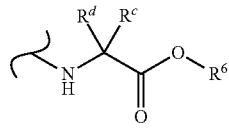

wherein $R^4$ is unsubstituted phenyl, one of $R^c$ or $R^d$ is H and the other of $R^c$ or $R^d$ is methyl. In another aspect of this embodiment, the chirality at phosphorous is R. In another aspect of this embodiment, the chirality at phosphorous is S. In another aspect of this embodiment, the chirality of the carbon to which said $R^c$ and $R^d$ is attached is S. In another aspect of this embodiment, the chirality of the carbon to which said $R^c$ and $R^d$ is attached is S and the chirality at phosphorus is S. In another aspect of this embodiment, the chirality of the carbon to which said $R^c$ and $R^d$ is attached is S and the chirality at phosphorus is R. In another aspect of this embodiment, the chirality of the carbon to which said $R^c$ and $R^d$ is attached is R. In another aspect of this embodiment, the chirality of the carbon to which said $R^c$ and $R^d$ is attached is R and the chirality at phosphorus is S. In another aspect of this embodiment, the chirality of the carbon to which said $R^c$ and $R^d$ is attached is R and the chirality at phosphorus is R. In another aspect of this embodiment, $R^1$ is H. In another aspect of this embodiment, $R^1$ is $(C_1-C_8)$ alkyl. In another aspect of this embodiment, $R^1$ is methyl. In another aspect of this embodiment, $R^1$ is $(C_1-C_8)$alkyl and $R^2$ is OH. In another aspect of this embodiment, $R^1$ is $(C_1-C_8)$alkyl, $R^2$ is OH and $R^3$ is $(C_1-C_8)$alkyl. In another aspect of this embodiment, $R^1$ is methyl and $R^2$ is OH. In another aspect of this embodiment, $R^1$ is methyl, $R^2$ is OH and $R^3$ is $(C_1-C_8)$alkyl. In another aspect of this embodiment, each

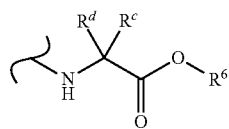

comprises a nitrogen-linked naturally occurring α-amino acid ester.

In one embodiment of Formula III, one of $W^1$ or $W^2$ is $OR^4$ and the other of $W^1$ or $W^2$ is

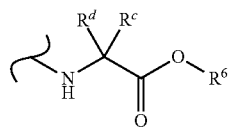

wherein $R^4$ is unsubstituted phenyl and $R^6$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl. In another aspect of this embodiment, $R^6$ is $(C_1-C_8)$alkyl. In another aspect of this embodiment, one of $R^c$ or $R^d$ is H and the other of $R^c$ or $R^d$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl. In another aspect of this embodiment, one of $R^c$ or $R^d$ is H and the other of $R^c$ or $R^d$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is S. In another aspect of this embodiment, one of $R^c$ or $R^d$ is H and the other of $R^c$ or $R^d$ is $(C_1-C_8)$alkyl, $(C_2-C_8)$alkenyl, $(C_2-C_8)$alkynyl, $(C_3-C_8)$carbocyclyl, $(C_4-C_8)$carbocyclylalkyl, aryl$(C_1-C_8)$alkyl, heterocyclyl$(C_1-C_8)$alkyl, $(C_6-C_{20})$aryl, $(C_2-C_{20})$heterocyclyl or heteroaryl wherein the chirality of the carbon to which said $R^c$ and $R^d$ is attached is R. In another aspect of this embodiment, one of $R^c$ or $R^d$ is H and the other of $R^c$ or $R^d$ is $(C_1-C_8)$alkyl. In another aspect of this embodiment, one of $R^c$ or $R^d$ is H and the other of $R^c$ or $R^d$ is $(C_1-C_8)$alkyl wherein the chirality of the carbon to which said $R^c$ and $R^d$ is attached is S. In another aspect of this embodiment, one of $R^c$ or $R^d$ is H and the other of $R^c$ or $R^d$ is $(C_1-C_8)$alkyl wherein the chirality of the carbon to which said $R^c$ and $R^d$ is attached is R. In another aspect of this embodiment, the chirality at phosphorus is S. In another aspect of this embodiment, the chirality at phosphorus is R. In another aspect of this embodiment, each

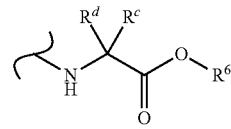

comprises a nitrogen-linked naturally occurring α-amino acid ester.

In one embodiment of Formula III, one of $W^1$ or $W^2$ is $OR^4$ and the other of $W^1$ or $W^2$ is

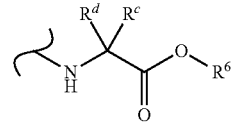

wherein one of $R^c$ or $R^d$ is H and the other of $R^c$ or $R^d$ is methyl and $R^6$ is $(C_1-C_8)$alkyl. In another aspect of this embodiment, $R^6$ is secondary alkyl. In another aspect of this embodiment, $R^6$ is 2-propyl. In another aspect of this embodiment, the chirality of the carbon to which said $R^c$ and $R^d$ is attached is S. In another aspect of this embodiment, chirality of the carbon to which said $R^c$ and $R^d$ is attached is R. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $S(O)_nR^a$, $S(O)_2N(R^a)_2$, $S(O)_2NH(R^a)$, $S(O)_2NH_2$, $OR^a$ or $R^a$. In another aspect of this embodiment, $R^1$ is H. In another aspect of this embodiment, $R^1$ is $(C_1-C_8)$alkyl. In another aspect of this embodiment, $R^1$ is methyl. In another aspect of this embodiment, $R^1$ is $(C_1-C_8)$alkyl and $R^2$ is OH. In another aspect of this embodiment, $R^1$ is $(C_1-C_8)$alkyl, $R^2$ is OH and $R^3$ is $(C_1-C_8)$alkyl. In another aspect of this embodiment, $R^1$ is methyl and $R^2$ is OH. In another aspect of this embodiment, $R^1$ is methyl, $R^2$ is OH and $R^3$ is $(C_1-C_8)$alkyl. In another aspect of this embodiment, the chirality at phosphorus is S. In another aspect of this embodiment, the chirality at phosphorus is R. In another aspect of this embodiment, each

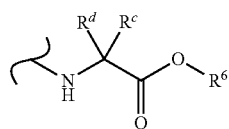

comprises a nitrogen-linked naturally occurring α-amino acid ester.

In one embodiment of Formula III, one of $W^1$ or $W^2$ is $OR^4$ and the other of $W^1$ or $W^2$ is

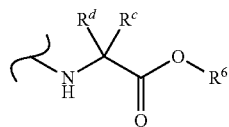

wherein $R^4$ is unsubstituted phenyl, one of $R^c$ or $R^d$ is H and the other of $R^c$ or $R^d$ is methyl and $R^6$ is $(C_1-C_8)$alkyl. In another aspect of this embodiment, $R^6$ is secondary alkyl. In another aspect of this embodiment, $R^6$ is 2-propyl. In another aspect of this embodiment, the chirality of the carbon to which said $R^c$ and $R^d$ is attached is S. In another aspect of this embodiment, chirality of the carbon to which said $R^c$ and $R^d$ is attached is R. In another aspect of this embodiment, $R^1$ is H. In another aspect of this embodiment, $R^1$ is $(C_1-C_8)$alkyl. In another aspect of this embodiment, $R^1$ is methyl. In another aspect of this embodiment, $R^1$ is $(C_1-C_8)$alkyl and $R^2$ is OH. In another aspect of this embodiment, $R^1$ is $(C_1-C_8)$alkyl, $R^2$ is OH and $R^3$ is $(C_1-C_8)$alkyl. In another aspect of this embodiment, $R^1$ is methyl and $R^2$ is OH. In another aspect of this embodiment, $R^1$ is methyl, $R^2$ is OH and $R^3$ is $(C_1-C_8)$alkyl. In another aspect of this embodiment, the chirality at phosphorus is S. In another aspect of this embodiment, the chirality at phosphorus is R. In another aspect of this embodiment, $R^8$ is halogen, $NR^{11}R^{12}$, $OR^{11}$, or $SR^{11}$. In another aspect of this embodiment, $R^8$ is halogen. In another aspect of this embodiment, $R^8$ is $NH_2$. In another aspect of this embodiment, $R^8$ is $OR^{11}$. In another aspect of this embodiment, $R^8$ is OH. In another aspect of this embodiment, $R^8$ is $SR^{11}$. In another aspect of this embodiment, $R^8$ is SH. In another aspect of this embodiment, $R^9$ is H, halogen, $NR^{11}R^{12}$, $OR^{11}$, or $SR^{11}$. In another aspect of this embodiment, $R^9$ is H. In another aspect of this embodiment, $R^9$ is halogen. In another aspect of this embodiment, $R^9$ is $NR^{11}R^{12}$. In another aspect of this embodiment, $R^9$ is $NH_2$. In another aspect of this embodiment, $R^9$ is $OR^{11}$. In another aspect of this embodiment, $R^9$ is OH. In another aspect of this embodiment, $R^9$ is $SR^{11}$. In another aspect of this embodiment, $R^9$ is SH. In another aspect of this embodiment, each

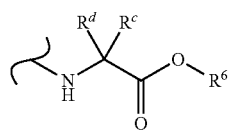

comprises a nitrogen-linked naturally occurring α-amino acid ester.

In another embodiment of Formula III, $R^8$ is halogen, $NR^{11}R^{12}$, $OR^{11}$, or $SR^{11}$. In another aspect of this embodiment, $R^8$ is halogen. In another aspect of this embodiment, $R^8$ is $NH_2$. In another aspect of this embodiment, $R^8$ is $OR^{11}$. In another aspect of this embodiment, $R^8$ is OH. In another aspect of this embodiment, $R^8$ is $SR^{11}$. In another aspect of this embodiment, $R^8$ is SH. In another aspect of this embodiment, $R^9$ is H, halogen, $NR^{11}R^{12}$, $OR^{11}$, or $SR^{11}$. In another aspect of this embodiment, $R^9$ is H. In another aspect of this embodiment, $R^9$ is halogen. In another aspect of this embodiment, $R^9$ is $NR^{11}R^{12}$. In another aspect of this embodiment, $R^9$ is $NH_2$. In another aspect of this embodiment, $R^9$ is $OR^{11}$. In another aspect of this embodiment, $R^9$ is OH. In another aspect of this embodiment, $R^9$ is $SR^{11}$. In another aspect of this embodiment, $R^9$ is SH.

In another embodiment of Formula III, $R^8$ is $NH_2$ and $R^9$ is H. In another aspect of this embodiment, $R^1$ is H. In another aspect of this embodiment, $R^1$ is $(C_1-C_8)$alkyl. In another aspect of this embodiment, $R^1$ is $(C_2-C_8)$alkenyl. In another aspect of this embodiment, $R^1$ is $(C_2-C_8)$alkynyl. In another aspect of this embodiment, $R^2$ is OH. In another aspect of this embodiment, $R^2$ is OH and $R^3$ is $(C_1-C_8)$alkyl. In another aspect of this embodiment, each $R^1$ is H and each $R^d$ is methyl. In another aspect of this embodiment, each $R^c$ is H and each $R^d$ is methyl wherein the chirality of the carbon to which each said $R^c$ and $R^d$ is attached is S. In another aspect of this embodiment, each $R^c$ is H and each $R^d$ is methyl wherein the chirality of the carbon to which each said $R^c$ and $R^d$ is attached is R. In another aspect of this embodiment, $R^4$ is phenyl wherein said phenyl is optionally substituted with one or more halo, hydroxy, CN, $N_3$, $N(R^a)_2$, $NH(R^a)$, $NH_2$, $C(O)N(R^a)_2$, $C(O)NH(R^a)$, $C(O)NH_2$, $OC(O)N(R^a)_2$, $OC(O)NH(R^a)$, $OC(O)NH_2$, $C(O)OR^a$, $OC(O)OR^a$, $S(O)_nR^a$, $S(O)_2N(R^a)_2$, $S(O)_2NH(R^a)$, $S(O)_2NH_2$, $OR^a$ or $R^a$.

In another embodiment of Formula III, $R^8$ is $NH_2$, $R^9$ is H and $R^1$ is $(C_1-C_8)$alkyl. In another aspect of this embodiment, $R^2$ is OH. In another aspect of this embodiment, $R^2$ is OH and $R^3$ is $(C_1-C_8)$alkyl. In another aspect of this embodiment, each $R^6$ is independently $(C_1-C_8)$alkyl. In another aspect of this embodiment, each $R^6$ is independently secondary alkyl. In another aspect of this embodiment, each $W^1$ and $W^2$ is independently

In another aspect of this embodiment, one of $W^1$ or $W^2$ is $OR^4$ and the other of $W^1$ or $W^2$ is

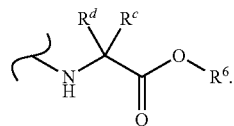

In another aspect of this embodiment, each

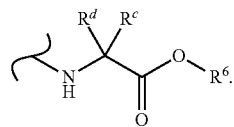

comprises a nitrogen-linked naturally occurring α-amino acid ester.

In another embodiment of Formula III, R$^8$ is NH$_2$, R$^9$ is H and one of W$^1$ or W$^2$ is OR$^4$ and the other of W$^1$ or W$^2$ is

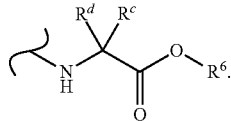

In another aspect of this embodiment, one of R$^c$ or R$^d$ is H and the other of R$^c$ or R$^d$ is methyl. In another aspect of this embodiment, one of R$^c$ or R$^d$ is H and the other of R$^c$ or R$^d$ is methyl wherein the chirality of the carbon to which said R$^c$ and R$^d$ is attached is S. In another aspect of this embodiment, one of R$^c$ or R$^d$ is H and the other of R$^c$ or R$^d$ is methyl wherein the chirality of the carbon to which said R$^c$ and R$^d$ is attached is R. In another aspect of this embodiment, R$^4$ is phenyl wherein said phenyl is optionally substituted with one or more halo, hydroxy, CN, N$_3$, N(R$^a$)$_2$, NH(R$^a$), NH$_2$, C(O)N(R$^a$)$_2$, C(O)NH(R$^a$), C(O)NH$_2$, OC(O)N(R$^a$)$_2$, OC(O)NH(R$^a$), OC(O)NH$_2$, C(O)OR$^a$, OC(O)OR$^a$, C(O)R$^a$, OC(O)R$^a$, S(O)$_n$R$^a$, S(O)$_2$N(R$^a$)$_2$, S(O)$_2$NH(R$^a$), S(O)$_2$NH$_2$, OR$^a$ or R$^a$. In another aspect of this embodiment, the chirality at phosphorus is S. In another aspect of this embodiment, the chirality at phosphorus is R. In another aspect of this embodiment, each

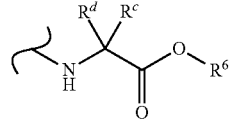

comprises a nitrogen-linked naturally occurring α-amino acid ester.

In another embodiment of Formula III, R$^8$ is NH$_2$, R$^9$ is H, R$^1$ is (C$_1$-C$_8$)alkyl and one of W$^1$ or W$^2$ is OR$^4$ and the other of W$^1$ or W$^2$ is

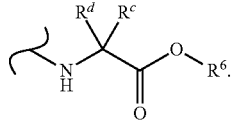

In another aspect of this embodiment, R$^2$ is OH. In another aspect of this embodiment, R$^2$ is OH and R$^3$ is (C$_1$-C$_8$)alkyl. In another aspect of this embodiment, R$^6$ is (C$_1$-C$_8$)alkyl. In another aspect of this embodiment, R$^6$ is secondary alkyl. In another aspect of this embodiment, one of R$^c$ or R$^d$ is H and the other of R$^c$ or R$^d$ is methyl. In another aspect of this embodiment, one of R$^c$ or R$^d$ is H and the other of R$^c$ or R$^d$ is methyl wherein the chirality of the carbon to which said R$^c$ and R$^d$ is attached is S. In another aspect of this embodiment, one of R$^c$ or R$^d$ is H and the other of R$^c$ or R$^d$ is methyl wherein the chirality of the carbon to which said R$^c$ and R$^d$ is attached is R. In another aspect of this embodiment, R$^4$ is phenyl wherein said phenyl is optionally substituted with one or more halo, hydroxy, CN, N$_3$, N(R$^a$)$_2$, NH(R$^a$), NH$_2$, C(O)N(R$^a$)$_2$, C(O)NH(R$^a$), C(O)NH$_2$, OC(O)N(R$^a$)$_2$, OC(O)NH(R$^a$), OC(O)NH$_2$, C(O)OR$^a$, OC(O)OR$^a$, C(O)R$^a$, OC(O)R$^a$, S(O)$_n$R$^a$, S(O)$_2$N(R$^a$)$_2$, S(O)$_2$NH(R$^a$), S(O)$_2$NH$_2$, OR$^a$ or R$^a$. In another aspect of this embodiment, the chirality at phosphorus is S. In another aspect of this embodiment, the chirality at phosphorus is R. In another aspect of this embodiment, each

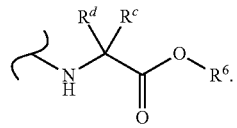

comprises a nitrogen-linked naturally occurring α-amino acid ester.

In another embodiment of Formula III, R$^8$ is NH$_2$ and R$^9$ is NH$_2$.

In another embodiment of Formula III, R$^8$ is OH and R$^9$ is NH$_2$.

In another embodiment of Formula III, R$^8$ is OH and R$^9$ is OH.

In another embodiment of Formula III, R$^8$ is OH and R$^9$ is OH.

An embodiment of the current invention is a compound, its stereoisomer, salt, hydrate, solvate, or crystalline or polymorphic form thereof, represented by formula III:

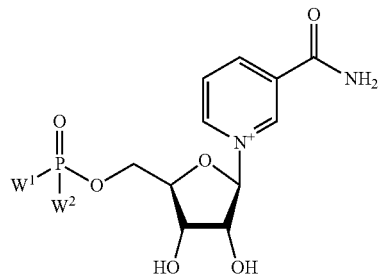

III wherein W$^1$ and W$^2$ are independently selected from the group consisting of the substituents in Table 1. Synthesis and general descriptions of representative substituents can be found, for instance, in U.S. Pat. No. 8,318,682, incorporated herein by reference. The variables used in Table 1 (e.g., W$^{23}$, R$^{21}$, etc.) pertain only to Table 1, unless otherwise indicated.

The variables used in Table 1 have the following definitions:

each R$^{21}$ is independently H or (C$_1$-C$_8$)alkyl;

each R$^{22}$ is independently H, R$^{21}$, R$^{23}$ or R$^{24}$ wherein each R$^{24}$ is independently substituted with 0 to 3 R$^{23}$;

each R$^{23}$ is independently R$^{23a}$, R$^{23b}$, R$^{23c}$ or R$^{23d}$, provided that when R$^{23}$ is bound to a heteroatom, then R$^{23}$ is R$^{23c}$ or R$^{23d}$;

each R$^{23a}$ is independently F, Cl, Br, I, —CN, N$_3$ or —NO$_2$;

each R$^{23b}$ is independently Y$^{21}$;

each R$^{23c}$ is independently —R$^{2x}$, —N(R$^{2x}$)(R$^{2x}$), —SR$^{2x}$, —S(O)R$^{2x}$; —S(O)$_2$R$^{2x}$, —S(O)(OR$^{2x}$), —S(O)$_2$(OR$^{2x}$), —OC(=Y$^{21}$)R$^{2x}$, —OC(=Y$^{21}$)OR$^{2x}$, —OC(=Y$^{21}$)(N(R$^{2x}$)(R$^{2x}$)); —SC(=Y$^{21}$)R$^{2x}$; —SC(=Y$^{21}$)OR$^{2x}$, —SC(=Y$^{21}$)(N(R$^{2x}$)(R$^{2x}$)), —N(R$^{2x}$)C(=Y$^{21}$)R$^{2x}$, —N(R$^{2x}$)C(=Y$^{21}$)OR$^{2x}$, or —N(R$^{2x}$)C(=Y$^{21}$)(N(R$^{2x}$)(R$^{2x}$));

each $R^{23d}$ is independently —C(=$Y^{21}$)$R^{2x}$; —C(=$Y^{21}$)O$R^{2x}$ or —C(=$Y^{21}$)(N($R^{2x}$)($R^{2x}$));

each $R_{2x}$ is independently H, ($C_1$-$C_8$)alkyl, ($C_2$-$C_8$)alkenyl, ($C_2$-$C_8$)alkynyl, aryl, heteroaryl; or two $R^{2x}$ taken together with a nitrogen to which they are both attached form a 3 to 7 membered heterocyclic ring wherein any one carbon atom of said heterocyclic ring can optionally be replaced with —O—, —S— or —N$R^{21}$—; and wherein one or more of the non-terminal carbon atoms of each said ($C_1$-$C_8$)alkyl may be optionally replaced with —O—, —S— or —N$R^{21}$—;

each $R^{24}$ is independently ($C_1$-$C_8$)alkyl, ($C_2$-$C_8$)alkenyl, or ($C_2$-$C_8$)alkynyl;

each $R^{25}$ is independently $R^{24}$ wherein each $R^{24}$ is substituted with 0 to 3 $R^{23}$ groups;

each $R^{25a}$ is independently ($C_1$-$C_8$)alkylene, ($C_2$-$C_8$)alkenylene, or ($C_2$-$C_8$)alkynylene any one of which said ($C_1$-$C_8$)alkylene, ($C_2$-$C_8$)alkenylene, or ($C_2$-$C_8$)alkynylene is substituted with 0-3 $R^{23}$ groups;

each $W^{23}$ is independently $W^{24}$ or $W^{25}$;

each $W^{24}$ is independently $R^{25}$, —C(=$Y^{21}$)$R^{25}$, —C(=$Y^{21}$)$W^{25}$, —$SO_2R^{25}$, or —$SO_2W^{25}$;

each $W^{25}$ is independently carbocycle or heterocycle wherein $W^{25}$ is independently substituted with 0 to 3 $R^{22}$ groups; and each $Y^{21}$ is independently O or S.

TABLE 1

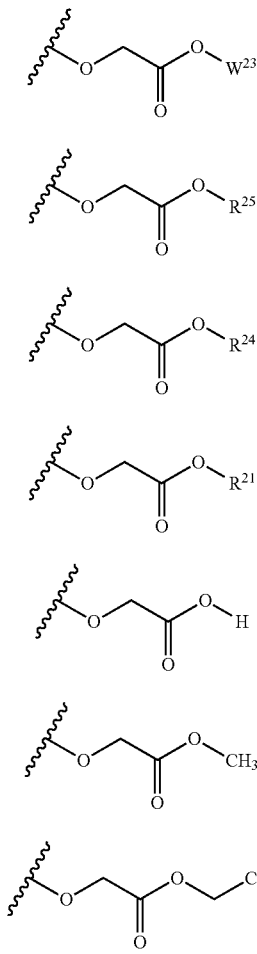

TABLE 1-continued

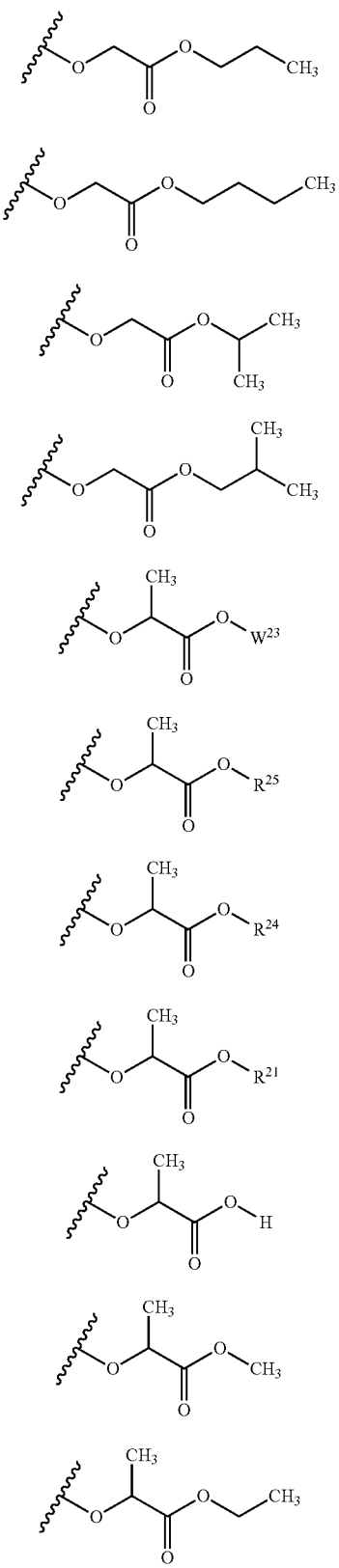

TABLE 1-continued

W¹ and W² Substituents (Structures 19–38 depicting various ester/acid substituents)

TABLE 1-continued

W¹ and W² Substituents

| | |
|---|---|
| (structure 39) | 39 |
| (structure 40) | 40 |
| (structure 41) | 41 |
| (structure 42) | 42 |
| (structure 43) | 43 |
| (structure 44) | 44 |
| (structure 45) | 45 |
| (structure 46) | 46 |
| (structure 47) | 47 |
| (structure 48) | 48 |
| (structure 49) | 49 |
| (structure 50) | 50 |
| (structure 51) | 51 |
| (structure 52) | 52 |
| (structure 53) | 53 |
| (structure 54) | 54 |
| (structure 55) | 55 |
| (structure 56) | 56 |
| (structure 57) | 57 |
| (structure 58) | 58 |
| (structure 59) | 59 |
| (structure 60) | 60 |
| (structure 61) | 61 |

TABLE 1-continued
W$^1$ and W$^2$ Substituents
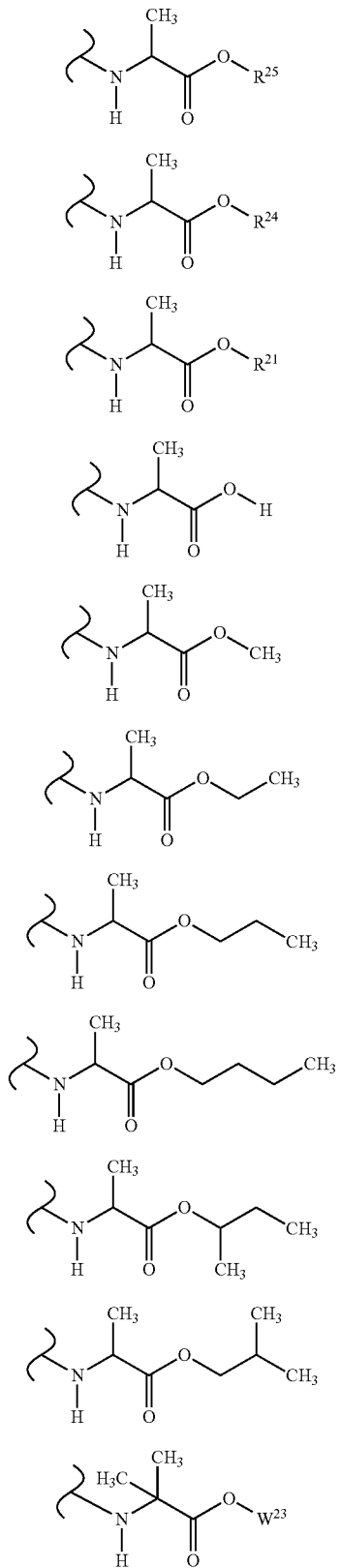
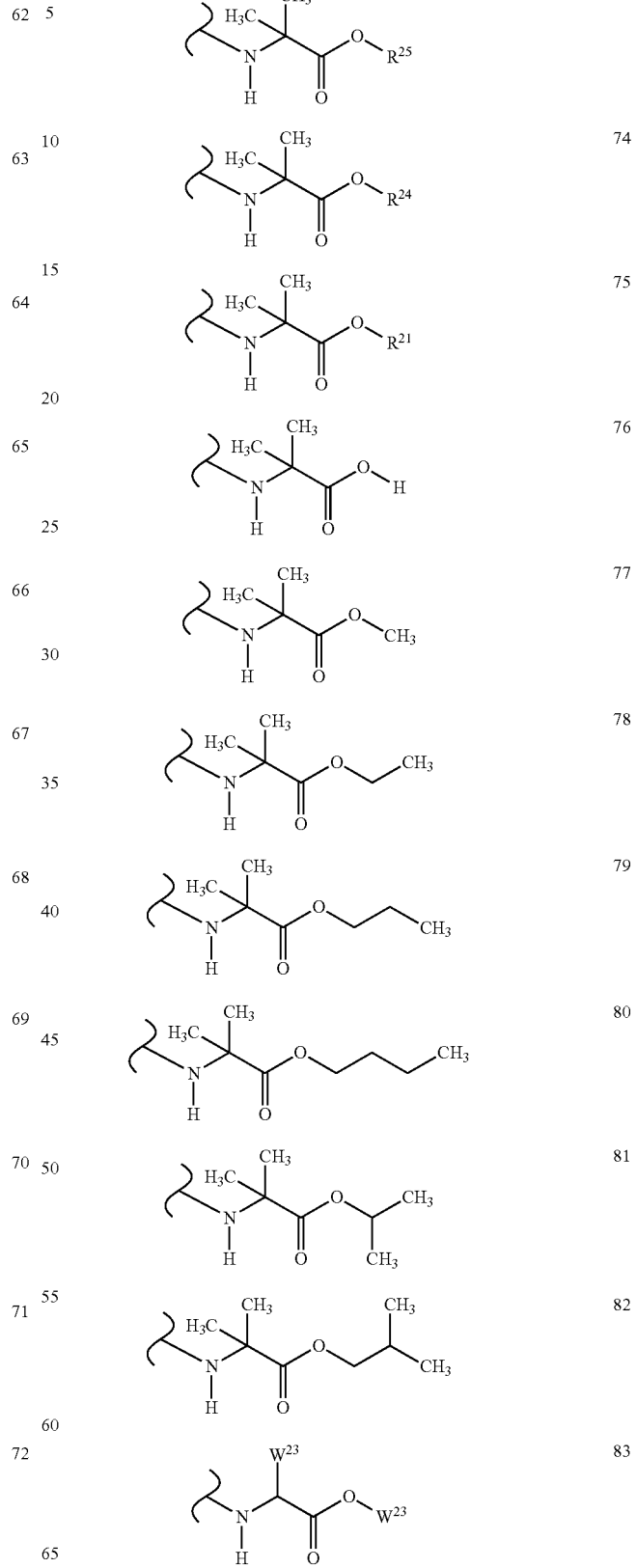

TABLE 1-continued
W¹ and W² Substituents
| | |
|---|---|
| 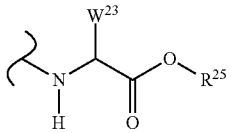 | 84 |
| 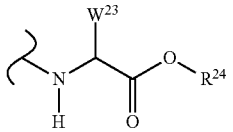 | 85 |
| 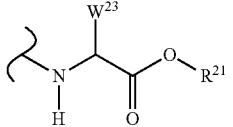 | 86 |
| 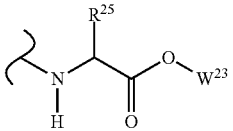 | 87 |
| 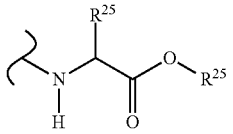 | 88 |
| 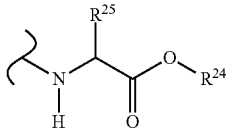 | 89 |
| 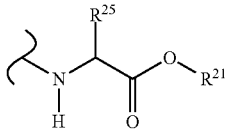 | 90 |
| 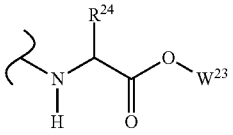 | 91 |
| 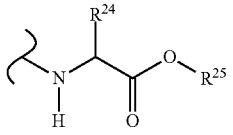 | 92 |
| 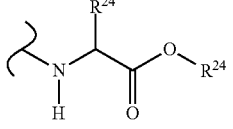 | 93 |
| 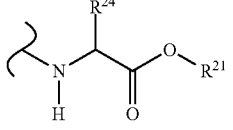 | 94 |
| 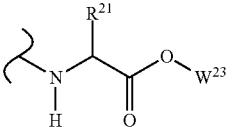 | 95 |
| 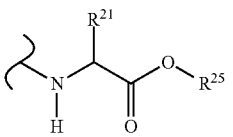 | 96 |
| 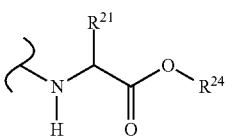 | 97 |
| 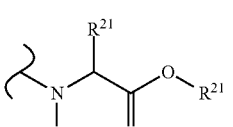 | 98 |
| 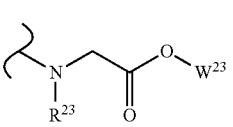 | 99 |
| 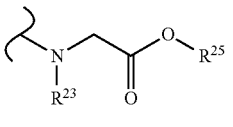 | 100 |
| 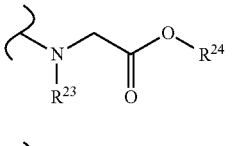 | 101 |
| 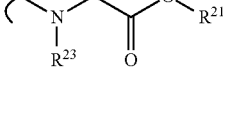 | 102 |
| 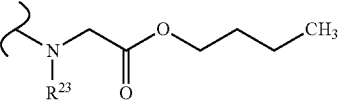 | 107 |
| 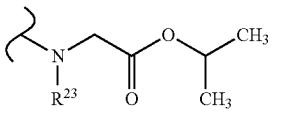 | 108 |
| 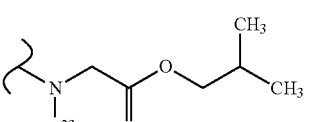 | 109 |

TABLE 1-continued
W¹ and W² Substituents
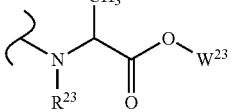 110
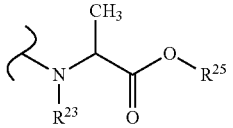 111
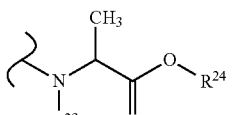 112
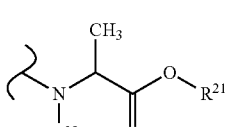 113
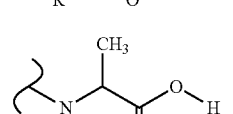 114
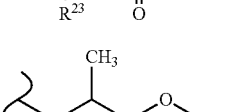 115
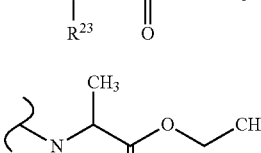 116
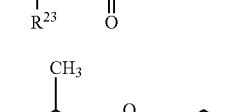 117
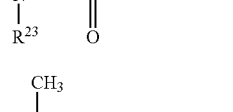 118
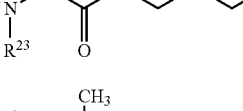 119
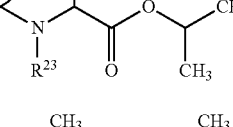 120
TABLE 1-continued
W¹ and W² Substituents
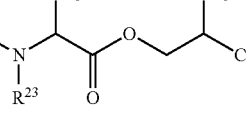 121
 122
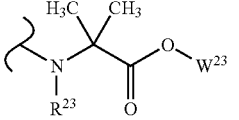 123
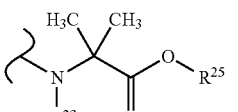 124
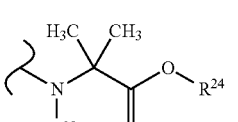 125
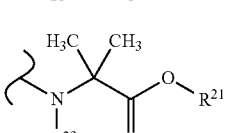 126
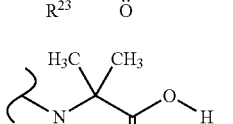 127
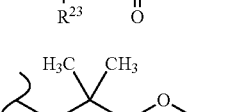 128
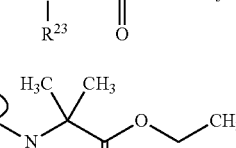 129
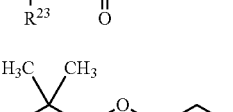 130
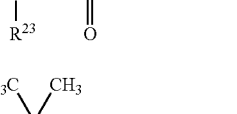 131

TABLE 1-continued

W¹ and W² Substituents

| Structure | No. |
|---|---|
| N(R²³)-CH(W²³)-C(O)-O-W²³ | 132 |
| N(R²³)-CH(W²³)-C(O)-O-R²⁵ | 133 |
| N(R²³)-CH(W²³)-C(O)-O-R²⁴ | 134 |
| N(R²³)-CH(W²³)-C(O)-O-R²¹ | 135 |
| N(R²³)-CH(R²⁵)-C(O)-O-W²³ | 136 |
| N(R²³)-CH(R²⁵)-C(O)-O-R²⁵ | 137 |
| N(R²³)-CH(R²⁵)-C(O)-O-R²⁴ | 138 |
| N(R²³)-CH(R²⁵)-C(O)-O-R²¹ | 139 |
| N(R²³)-CH(R²⁴)-C(O)-O-W²³ | 140 |
| N(R²³)-CH(R²⁴)-C(O)-O-R²⁵ | 141 |
| N(R²³)-CH(R²⁴)-C(O)-O-R²⁴ | 142 |
| N(R²³)-CH(R²⁴)-C(O)-O-R²¹ | 143 |
| N(R²³)-CH(R²¹)-C(O)-O-W²³ | 144 |
| N(R²³)-CH(R²¹)-C(O)-O-R²⁵ | 145 |
| N(R²³)-CH(R²¹)-C(O)-O-R²⁴ | 146 |
| N(R²³)-CH(R²¹)-C(O)-O-R²¹ | 147 |
| W²³ | 148 |
| R²⁵ | 149 |
| R²⁴ | 150 |
| R²¹ | 151 |
| H | 152 |
| R²³ | 153 |
| O-W²³ | 154 |
| O-R²⁵ | 155 |
| O-R²⁴ | 156 |
| O-R²¹ | 157 |

TABLE 1-continued
W¹ and W² Substituents
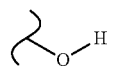 158
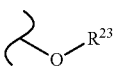 159
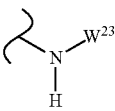 160
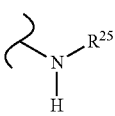 161
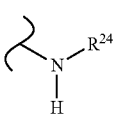 162
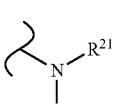 163
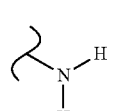 164
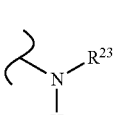 165
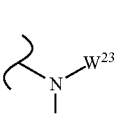 166
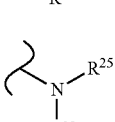 167
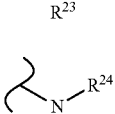 168
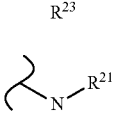 169
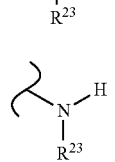 170
TABLE 1-continued
W¹ and W² Substituents
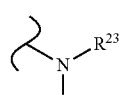 171
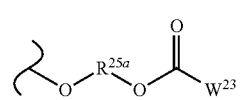 172
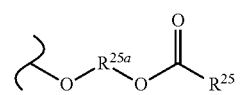 173
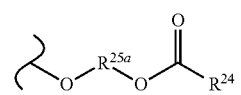 174
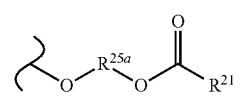 175
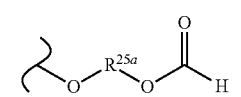 176
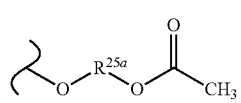 177
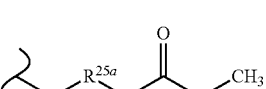 178
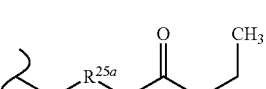 179
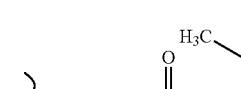 180
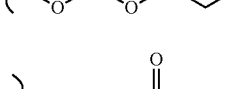 181
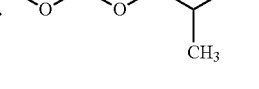 182
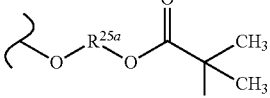 183

TABLE 1-continued

W¹ and W² Substituents

| Structure | # |
|---|---|
| ⟩–O–R²⁵ᵃ–O–C(=O)–C₆H₅ | 184 |
| ⟩–O–R²⁵ᵃ–O–C(=O)–CH₂–C₆H₅ | 185 |
| ⟩–O–CH₂–O–C(=O)–W²³ | 186 |
| ⟩–O–CH₂–O–C(=O)–R²⁵ | 187 |
| ⟩–O–CH₂–O–C(=O)–R²⁴ | 188 |
| ⟩–O–CH₂–O–C(=O)–R²¹ | 189 |
| ⟩–O–CH₂–O–C(=O)–H | 190 |
| ⟩–O–CH₂–O–C(=O)–CH₃ | 191 |
| ⟩–O–CH₂–O–C(=O)–CH₂CH₃ | 192 |
| ⟩–O–CH₂–O–C(=O)–CH₂CH₂CH₃ | 193 |
| ⟩–O–CH₂–O–C(=O)–CH₂CH₂CH₂CH₃ | 194 |
| ⟩–O–CH₂–O–C(=O)–CH(CH₃)₂ | 195 |
| ⟩–O–CH₂–O–C(=O)–C(CH₃)₃ | 196 |
| ⟩–O–CH₂–O–C(=O)–CH₂CH(CH₃)₂ | 197 |
| ⟩–O–CH₂–O–C(=O)–C₆H₅ | 198 |
| ⟩–O–CH₂–O–C(=O)–CH₂–C₆H₅ | 199 |
| ⟩–O–R²⁵ᵃ–O–C(=O)–O–W²³ | 200 |
| ⟩–O–R²⁵ᵃ–O–C(=O)–O–R²⁵ | 201 |
| ⟩–O–R²⁵ᵃ–O–C(=O)–O–R²⁴ | 202 |
| ⟩–O–R²⁵ᵃ–O–C(=O)–O–R²¹ | 203 |
| ⟩–O–R²⁵ᵃ–O–C(=O)–O–H | 204 |
| ⟩–O–R²⁵ᵃ–O–C(=O)–O–CH₃ | 205 |
| ⟩–O–R²⁵ᵃ–O–C(=O)–O–CH₂CH₃ | 206 |
| ⟩–O–R²⁵ᵃ–O–C(=O)–O–CH₂CH₂CH₃ | 207 |
| ⟩–O–R²⁵ᵃ–O–C(=O)–O–CH₂CH₂CH₂CH₃ | 208 |
| ⟩–O–R²⁵ᵃ–O–C(=O)–O–CH(CH₃)₂ | 209 |
| ⟩–O–R²¹ᵃ–O–C(=O)–O–C(CH₃)₃ | 210 |
| ⟩–O–R²⁵ᵃ–O–C(=O)–O–CH₂CH(CH₃)₂ | 211 |

TABLE 1-continued
W¹ and W² Substituents
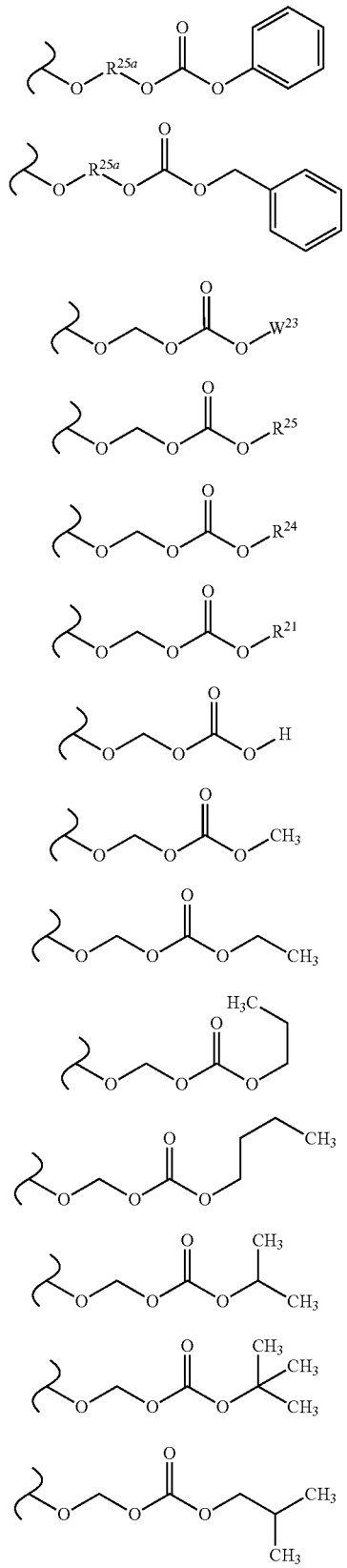
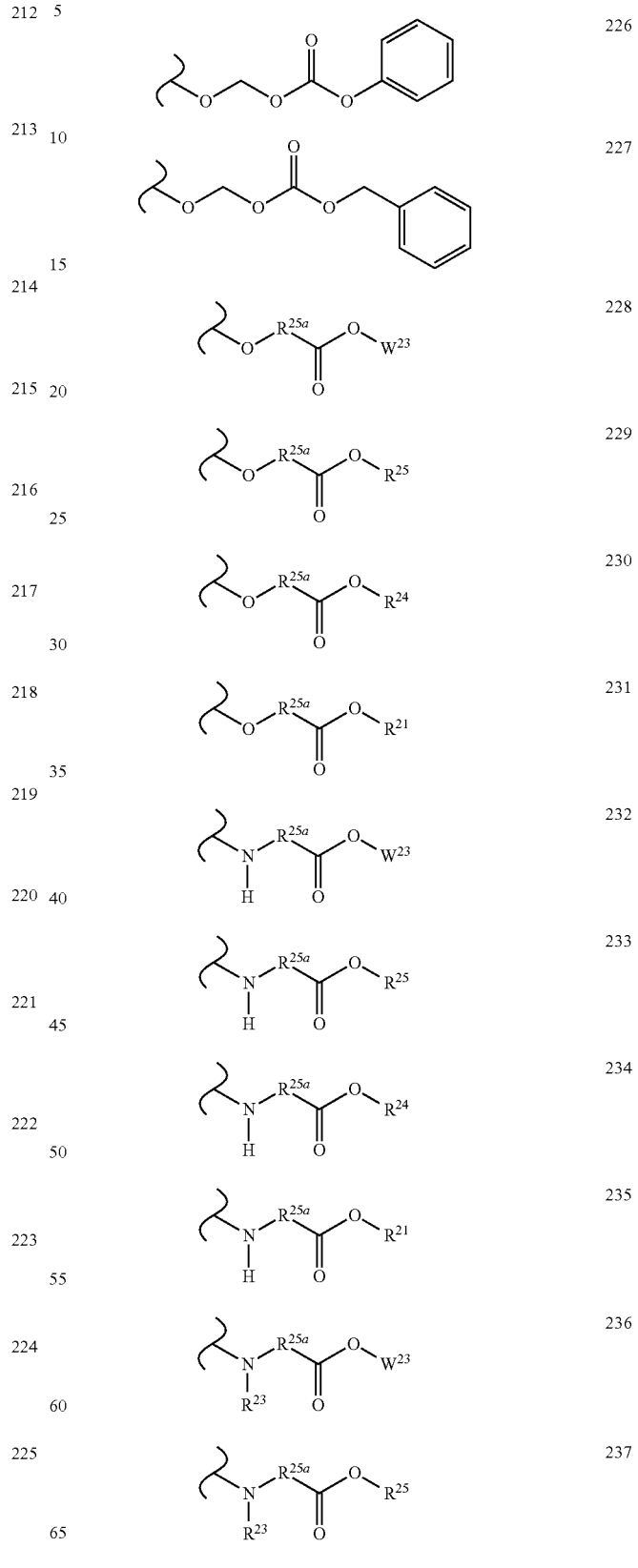

TABLE 1-continued
W¹ and W² Substituents
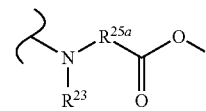

TABLE 1-continued

W¹ and W² Substituents

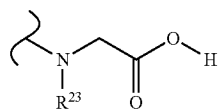

103

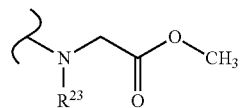

104

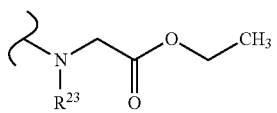

105

Another embodiment of the invention is a method of treatment in a subject in need thereof, which comprises: administering a therapeutically effective amount of the compound represented by formula I to the subject; wherein the compound or its stereoisomer, salt, hydrate, solvate, or crystalline or polymorphic form thereof represented by formula III:

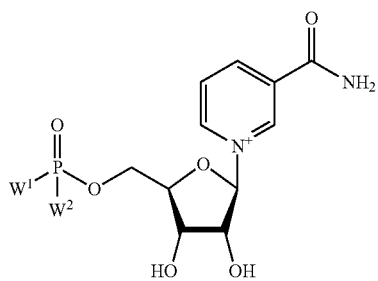

III wherein W¹ and W² are independently selected from the group consisting of the substituents in Table 1.

Another embodiment of the invention is a method of treatment, wherein the compound, its stereoisomer, salt, hydrate, solvate, or crystalline or polymorphic form thereof, wherein the compound is selected from the group consisting of

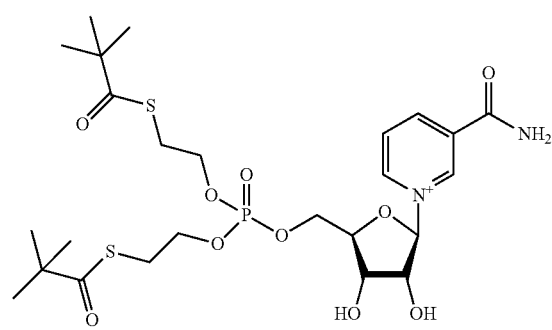

or

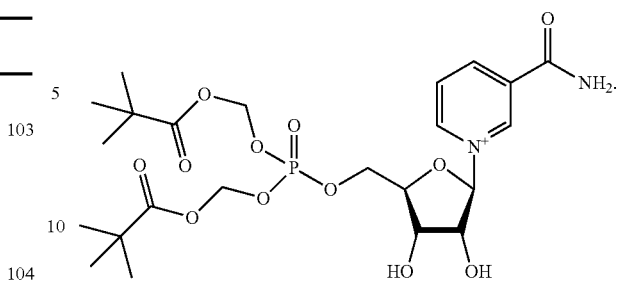

Another embodiment of the present invention is a compound, its stereoisomer, salt, hydrate, solvate, or crystalline or polymorphic form thereof, represented by formula I:

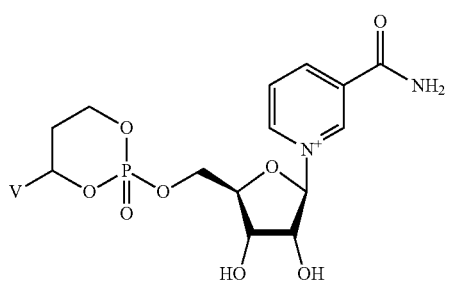

I wherein V is selected from the group consisting of phenyl and monocyclic heteroaryl, wherein (i) each said monocyclic heteroaryl contains five or six ring atoms of which 1 or 2 ring atoms are heteroatoms selected from the group consisting of N, S, and O, and the remainder of the ring atoms are carbon, and (ii) each said phenyl or monocyclic heteroaryl is unsubstituted or is substituted by one or two groups selected from halogen, trifluoromethyl, $C_1$-$C_6$ alkyl, $C_1$-$C_6$ alkoxy, and cyano.

In another embodiment of Formula I, a compound, its stereoisomer, salt, hydrate, solvate, or crystalline or polymorphic form thereof, represented by formula I:

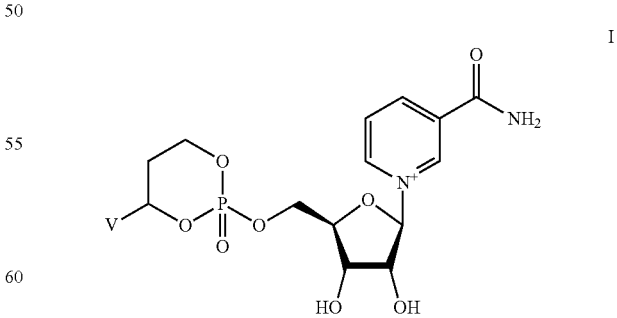

I wherein V is selected from the group consisting of the substituents in Table 2. Synthesis and general descriptions of representative substituents can be found, for instance, in U.S. Pat. No. 8,063,025, incorporated herein by reference.

TABLE 2
| V Substituents | |
|---|---|
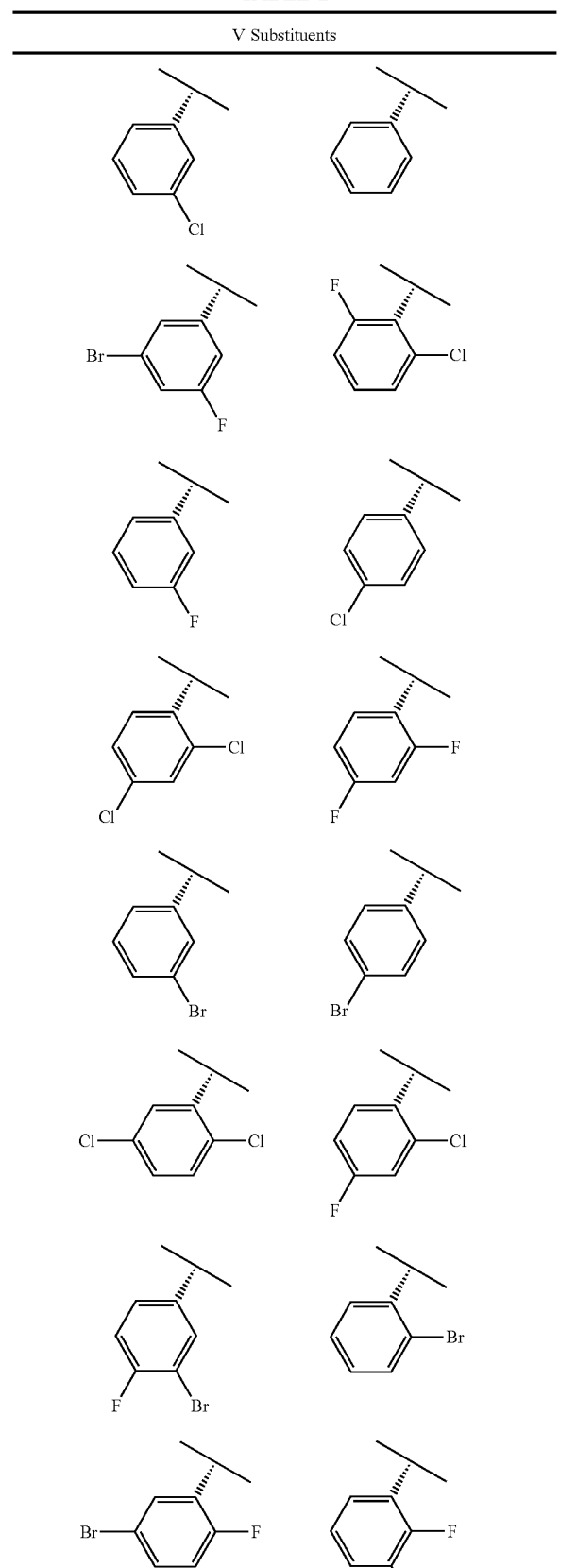
TABLE 2-continued
| V Substituents | |
|---|---|
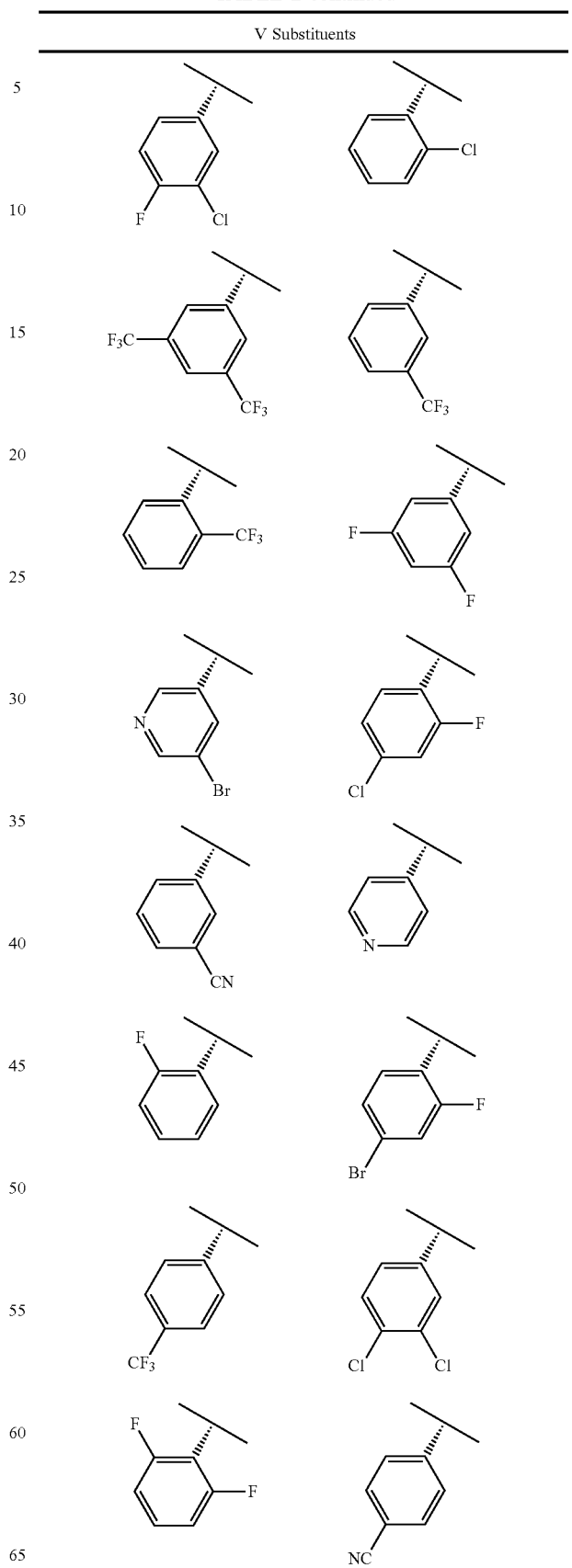

TABLE 2-continued

V Substituents

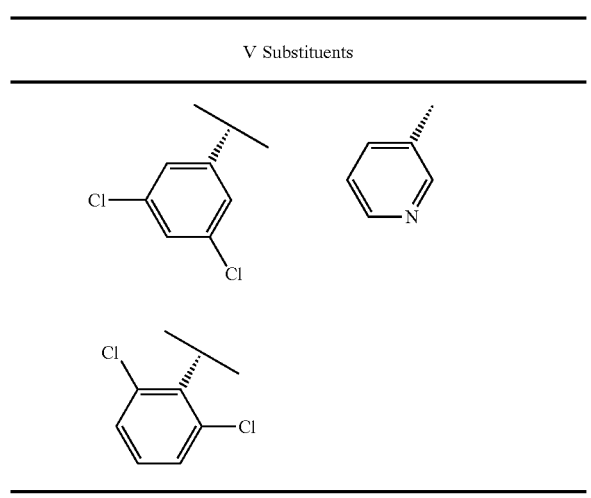

In another embodiment of Formula I, the compound, its stereoisomer, salt, hydrate, solvate, or crystalline or polymorphic form thereof, wherein the compound is selected from the group consisting of

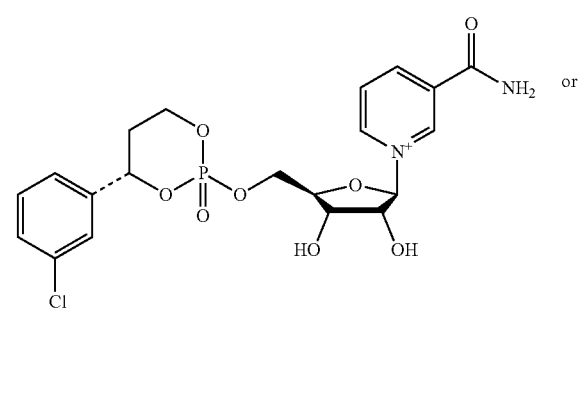

or

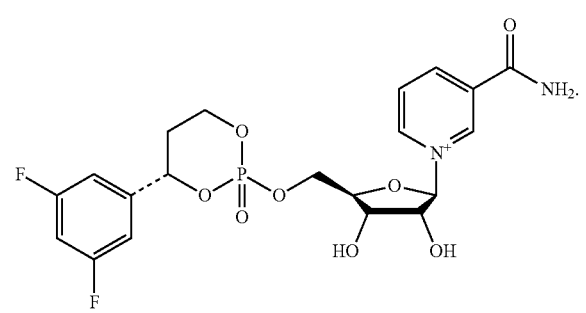

Another embodiment of the present invention is a composition for the treatment and/or prophylaxis of any of the diseases disclosed herein said composition comprising a pharmaceutically acceptable medium selected from among an excipient, carrier, diluent, and equivalent medium and a compound, its stereoisomer, salt, hydrate, solvate, or crystalline or polymorphic form thereof, represented by formula I:

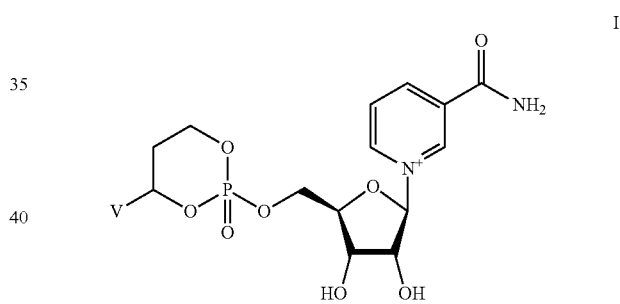

wherein V is selected from the group consisting of phenyl and monocyclic heteroaryl, wherein (i) each said monocyclic heteroaryl contains five or six ring atoms of which 1 or 2 ring atoms are heteroatoms selected from the group consisting of N, S, and O, and the remainder of the ring atoms are carbon, and (ii) each said phenyl or monocyclic heteroaryl is unsubstituted or is substituted by one or two groups selected from halogen, trifluoromethyl, $C_1$-$C_6$ alkyl, $C_1$-$C_6$ alkoxy, and cyano.

In yet another embodiment of the present invention, a composition for the treatment and/or prophylaxis of any of the diseases disclosed herein said composition comprising a pharmaceutically acceptable medium selected from among an excipient, carrier, diluent, and equivalent medium and a compound, its stereoisomer, salt, hydrate, solvate, or crystalline or polymorphic form thereof, represented by formula I:

I

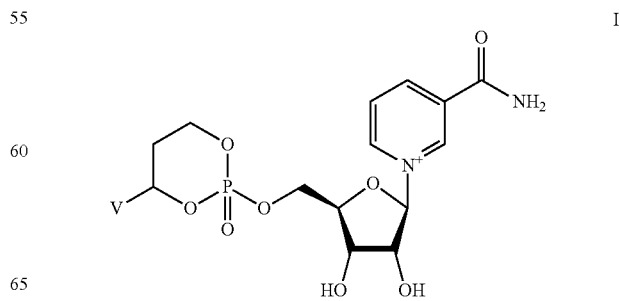

wherein V is selected from the group consisting of the substituents in Table 2.

Another embodiment is a method of treatment in a subject in need thereof, which comprises: administering a therapeutically effective amount of the compound represented by formula I to the subject; wherein the compound or its stereoisomer, salt, hydrate, solvate, or crystalline or polymorphic form thereof represented by formula I:

I wherein V is selected from the group consisting of phenyl and monocyclic heteroaryl, wherein (i) each said monocyclic heteroaryl contains five or six ring atoms of which 1 or 2 ring atoms are heteroatoms selected from the group consisting of N, S, and O, and the remainder of the ring atoms are carbon, and (ii) each said phenyl or monocyclic heteroaryl is unsubstituted or is substituted by one or two groups selected from halogen, trifluoromethyl, $C_1$-$C_6$ alkyl, $C_1$-$C_6$ alkoxy, and cyano.

Another alternative embodiment is a method of treatment in a subject in need thereof, which comprises: administering a therapeutically effective amount of the compound represented by formula I to the subject; wherein the compound or its stereoisomer, salt, hydrate, solvate, or crystalline or polymorphic form thereof represented by formula I:

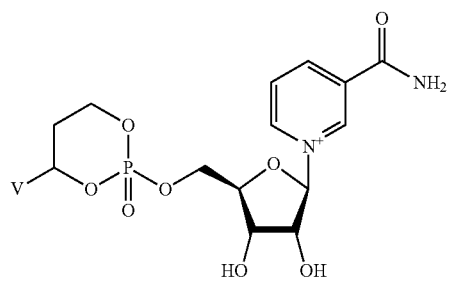

wherein V is selected from the group consisting of the substituents in Table 2. In another embodiment of the current invention, the compound, its stereoisomer, salt, hydrate, solvate, or crystalline or polymorphic form thereof, wherein the compound is selected from the group consisting of

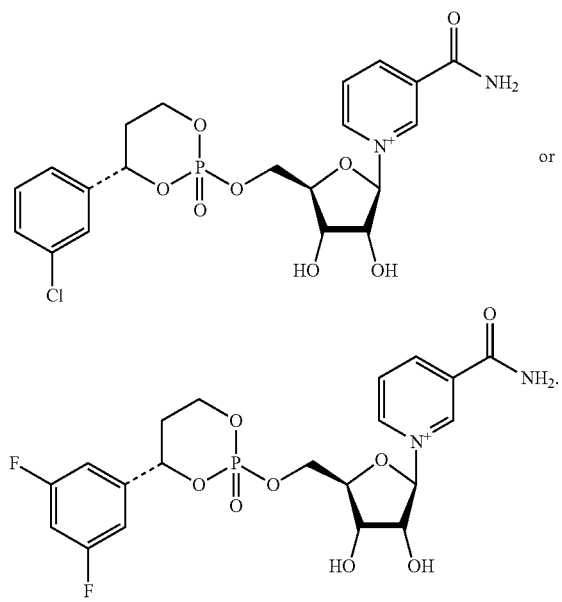

Synthetic schemes for preparing compounds of Formula I, Formula II and Formula III can be found, for instance, in the following references incorporated herein by reference. Nicotinamide Riboside and intermediates of nicotinamide riboside with protected functionalities and well established leaving groups that could be used in the synthesis of compounds of the present invention see for instance Milburn et al. (US2006/0229265) as well as Sauve et al. (U.S. Pat. No. 8,106,184). Synthetic schemes and characterization of intermediates necessary for compounds of Formula I can be found, for instance, in Heckler et al. (U.S. Pat. No. 8,063,025); Heckler et al. (U.S. application Ser. No. 12/745,419); Butler et al. (U.S. Pat. No. 8,318,682); Cho et al. (U.S. Pat. No. 8,415,308); Ross et al. (U.S. application Ser. No. 13/732,725); and Ross et al. (U.S. application Ser. No. 13/076,842). Protecting groups and/or Leaving Groups useful for synthesis of the compounds of the present invention can be found, for instance, in Ross et al. (U.S. application Ser. No. 13/076,842).

Definitions:

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The terms "optional" or "optionally" as used herein means that a subsequently described event or circumstance may but need not occur, and that the description includes instances where the event or circumstance occurs and instances in which it does not. For example, "optional bond" means that the bond may or may not be present, and that the description includes single, double, or triple bonds.

The term "P*" means that the phosphorus atom is chiral and that it has a corresponding Cahn-Ingold-Prelog designation of "R" or "S" which have their accepted plain meanings.

The term "purified," as described herein, refers to the purity of a given compound. For example, a compound is "purified" when the given compound is a major component of the composition, i.e., at least 50% w/w pure. Thus, "purified" embraces at least 50% w/w purity, at least 60% w/w purity, at least 70% purity, at least 80% purity, at least 85% purity, at least 90% purity, at least 92% purity, at least 94% purity, at least 96% purity, at least 97% purity, at least 98% purity, at least 99% purity, at least 99.5% purity, and at least 99.9% purity, wherein "substantially pure" embraces at least 97% purity, at least 98% purity, at least 99% purity, at least 99.5% purity, and at least 99.9% purity The term "metabolite," as described herein, refers to a compound produced in vivo after administration to a subject in need thereof.

The term "about" means that the recited numerical value is part of a range that varies within standard experimental error.

The term "substantially anhydrous" means that a substance contains at most 10% by weight of water, preferably at most 1% by weight of water, more preferably at most 0.5% by weight of water, and most preferably at most 0.1% by weight of water.

A solvent or anti-solvent (as used in reactions, crystallization, etc. or lattice and/or adsorbed solvents) includes at least one of a $C_1$ to $C_8$ alcohol, a $C_2$ to $C_8$ ether, a $C_3$ to $C_7$ ketone, a $C_3$ to $C_7$ ester, a $C_1$ to $C_2$ chlorocarbon, a $C_2$ to $C_7$ nitrile, a miscellaneous solvent, a $C_5$ to $C_{12}$ saturated hydrocarbon, and a $C_6$ to $C_{12}$ aromatic hydrocarbon.

The $C_1$ to $C_8$ alcohol refers to a straight/branched and/or cyclic/acyclic alcohol having such number of carbons. The $C_1$ to $C_8$ alcohol includes, but is not limited to, methanol, ethanol, n-propanol, isopropanol, isobutanol, hexanol, and cyclohexanol.

The $C_2$ to $C_8$ ether refers to a straight/branched and/or cyclic/acyclic ether having such number of carbons. The $C_2$ to $C_8$ ether includes, but is not limited to, dimethyl ether, diethyl ether, di-isopropyl ether, di-n-butyl ether, methyl-t-butyl ether (MTBE), tetrahydrofuran, and dioxane The $C_3$ to $C_7$ ketone refers to a straight/branched and/or cyclic/acyclic ketone having such number of carbons. The $C_3$ to $C_7$ ketone includes, but is not limited to, acetone, methyl ethyl ketone, propanone, butanone, methyl isobutyl ketone, methyl butyl ketone, and cyclohexanone.

The $C_3$ to $C_7$ ester refers to a straight/branched and/or cyclic/acyclic ester having such number of carbons. The $C_3$ to $C_7$ ester includes, but is not limited to, ethyl acetate, propyl acetate, n-butyl acetate, etc.

The $C_1$ to $C_2$ chlorocarbon refers to a chlorocarbon having such number of carbons. The $C_1$ to $C_2$ chlorocarbon includes, but is not limited to, chloroform, methylene chloride (DCM), carbon tetrachloride, 1,2-dichloroethane, and tetrachloroethane.

A $C_2$ to $C_7$ nitrile refers to a nitrile have such number of carbons. The $C_2$ to $C_7$ nitrile includes, but is not limited to, acetonitrile, propionitrile, etc.

A miscellaneous solvent refers to a solvent commonly employed in organic chemistry, which includes, but is not limited to, diethylene glycol, diglyme (diethylene glycol dimethyl ether), 1,2-dimethoxy-ethane, dimethylformamide, dimethylsulfoxide, ethylene glycol, glycerin, hexamethylphsphoramide, hexamethylphosphorous triame, N-methyl-2-pyrrolidinone, nitromethane, pyridine, triethyl amine, and acetic acid.

The term $C_5$ to $C_{12}$ saturated hydrocarbon refers to a straight/branched and/or cyclic/acyclic hydrocarbon. The $C_5$ to $C_{12}$ saturated hydrocarbon includes, but is not limited to, n-pentane, petroleum ether (ligroine), n-hexane, n-heptane, cyclohexane, and cycloheptane.

The term $C_6$ to $C_{12}$ aromatic refers to substituted and unsubstituted hydrocarbons having a phenyl group as their backbone. Preferred hydrocarbons include benzene, xylene, toluene, chlorobenzene, o-xylene, m-xylene, p-xylene, xylenes, with toluene being more preferred.

The term "halo" or "halogen" as used herein, includes chloro, bromo, iodo and fluoro.

The term "blocking group" refers to a chemical group which exhibits the following characteristics. The "group" is derived from a "protecting compound." Groups that are selective for primary hydroxyls over secondary hydroxyls that can be put on under conditions consistent with the stability of the phosphoramidate (pH 2-8) and impart on the resulting product substantially different physical properties allowing for an easier separation of the 3'-phosphoramidate-5'-new group product from the unreacted desired compound. The group must react selectively in good yield to give a protected substrate that is stable to the projected reactions (see *Protective Groups in Organic Synthesis*, 3.sup.nd ed. T. W. Greene and P. G. M. Wuts, John Wiley & Sons, New York, N.Y., 1999). Examples of groups include, but are not limited to: benzoyl, acetyl, phenyl-substituted benzoyl, tetrahydropyranyl, trityl, DMT (4,4'-dimethoxytrityl), MMT (4-monomethoxytrityl), trimethoxytrityl, pixyl (9-phenylxanthen-9-yl) group, thiopixyl (9-phenylthioxanthen-9-yl) or 9-(p-methoxyphenyl)xanthine-9-yl (MOX), etc.; C(O)-alkyl, C(O)Ph, C(O)aryl, $CH_2O$-alkyl, $CH.sub.2O$-aryl, $SO_2$-alkyl, $SO_2$-aryl, tert-butyldimethylsilyl, tert-butyl-diphenylsilyl. Acetals, such as MOM or THP and the like are considered possible groups. Fluorinated compounds are also contemplated in so far that they can be attached to the compound and can be selectively removed by passing through a fluorous solid phase extraction media (Fluoro-Flash™). A specific example includes a fluorinated trityl analog, trityl analog 1-[4-(1H,1H,2H,2H-perfluorodecyl) phenyl)-1,1-diphenylmethanol. Other fluorinated analogs of trityl, BOC, FMOC, CBz, etc. are also contemplated. Sulfonyl chlorides like p-toluenesulfonyl chloride can react selectively on the 5' position. Esters could be formed selectively such as acetates and benzoates. Dicarboxylic anhydrides such as succinic anhydride and its derivatives can be used to generate an ester linkage with a free carboxylic acid, such examples include, but are not limited to oxalyl, malonyl, succinyl, glutaryl, adipyl, pimelyl, superyl, azelayl, sebacyl, phthalyl, isophthalyl, terephthalyl, etc. The free carboxylic acid increases the polarity dramatically and can also be used as a handle to extract the reaction product into mildly basic aqueous phases such as sodium bicarbonate solutions. The phosphoramidate group is relatively stable in acidic media, so groups requiring acidic reaction conditions, such as, tetrahydropyranyl, could also be used.

The term "protecting group" which is derived from a "protecting compound," has its plain and ordinary meaning, i.e., at least one protecting or blocking group is bound to at least one functional group (e.g., —OH, —$NH_2$, etc.) that allows chemical modification of at least one other functional group. Examples of protecting groups, include, but are not limited to, benzoyl, acetyl, phenyl-substituted benzoyl, tetrahydropyranyl, trityl, DMT (4,4'-dimethoxytrityl), MMT (4-monomethoxytrityl), trimethoxytrityl, pixyl (9-phenylxanthen-9-yl) group, thiopixyl (9-phenylthioxanthen-9-yl) or 9-(p-methoxyphenyl)xanthine-9-yl (MOX), etc.; C(O)-alkyl, C(O)Ph, C(O)aryl, C(O)O(lower alkyl), C(O)O (lower alkylene)aryl (e.g., —C(O)OCH$_2$Ph), C(O)Oaryl, $CH_2O$-alkyl, $CH_2O$-aryl, $SO_2$-alkyl, $SO_2$-aryl, a protecting group comprising at least one silicon atom, such as, tert-butyldimethylsilyl, tert-butyldiphenylsilyl, Si(lower alkyl)$_2$OSi(lower alkyl)$_2$OH (such as, —Si($^i$Pr)$_2$OSi($^i$Pr)$_2$OH.

The term "protecting compound," as used herein and unless otherwise defined, refers to a compound that contains a "protecting group" and that is capable of reacting with a compound that contains functional groups that are capable of being protected.

The term "leaving group", as used herein, has the same meaning to the skilled artisan (*Advanced Organic Chemistry*: reactions, mechanisms and structure—Fourth Edition by Jerry March, John Wiley and Sons Ed.; 1992 pages 351-357) and represents a group which is part of and attached to a substrate molecule; in a reaction where the substrate molecule undergoes a displacement reaction (with for example a nucleophile), the leaving group is then displaced. Examples of leaving groups include, but are not limited to: halogen (F, Cl, Br, and I), preferably Cl, Br, or I; tosylate, mesylate, triflate, acetate, camphorsulfonate, aryloxide, and aryloxide substituted with at least one electron withdrawing group (e.g., p-nitrophenoxide, 2-chlorophenoxide, 4-chlorophenoxide, 2,4-dinitrophenoxide, pentafluorophenoxide, etc.), etc. The term "electron withdrawing group" is accorded its plain meaning here. Examples of electron withdrawing groups include, but are not limited to, a halogen, —NO2, —C(O)(lower alkyl), —C(O)(aryl), —C(O)O (lower alkyl), —C(O)O(aryl), etc.

The term "basic reagent", as used herein, means a compound that is capable of deprotonating a hydroxyl group. Examples of basic reagents include, but are not limited to, a (lower alk)oxide ((lower alkyl)OM) in combination with an alcoholic solvent, where (lower alk)oxides include, but are not limited to, MeO$^-$, EtO$^-$, $^n$PrO$^-$, $^i$PrO$^-$, $^t$BuO$^-$, $^i$AmO- (iso-amyloxide), etc., and where M is an alkali metal cation, such as Li$^+$, Na$^+$, K$^+$, etc. Alcoholic solvents include (lower alkyl)OH, such as, for example, MeOH, EtOH, $^n$PrOH, $^i$PrOH, $^t$BuOH, $^i$AmOH, etc. Non-alkoxy bases can also be used such as sodium hydride, sodium hexamethyldisilazane, lithium hexamethyldisilazane, lithium diisopropylamide, calcium hydride, sodium carbonate, potassium carbonate, cesium carbonate, DBU, DBN, Grignard reagents, such as (lower alkyl)Mg(halogen), which include but are not limited to MeMgCl, MeMgBr, $^t$BuMgCl, $^t$BuMgBr, etc.

The term "base" embraces the term "basic reagent" and is meant to be a compound that is capable of deprotonating a proton containing compound, i.e., a Bronsted base. In addition to the examples recited above, further examples of a base include, but are not limited to pyridine, collidine, 2,6-(loweralkyl)-pyridine, dimethyl-aniline, imidazole, N-methyl-imidazole, pyrazole, N-methyl-pyrazole, triethyl-amine, di-isopropylethylamine, etc.

The term "electron withdrawing group" is accorded its plain meaning Examples of electron withdrawing groups include, but are not limited to, a halogen (F, Cl, Br, or I), —$NO_2$, —C(O)(lower alkyl), —C(O)(aryl), —C(O)O (lower alkyl), —C(O)O(aryl), etc.

The term "salts," as described herein, refers to a compound comprising a cation and an anion, which can produced by the protonation of a proton-accepting moiety and/or deprotonation of a proton-donating moiety. It should be noted that protonation of the proton-accepting moiety results in the formation of a cationic species in which the charge is balanced by the presence of a physiological anion, whereas deprotonation of the proton-donating moiety results in the formation of an anionic species in which the charge is balanced by the presence of a physiological cation.

The phrase "pharmaceutically acceptable salt" means a salt that is pharmaceutically acceptable. Examples of pharmaceutically acceptable salts include, but are not limited to: (1) acid addition salts, formed with inorganic acids such as hydrochloric acid, hydrobromic acid, sulfuric acid, nitric acid, phosphoric acid, and the like; or formed with organic acids such as glycolic acid, pyruvic acid, lactic acid, malonic acid, malic acid, maleic acid, fumaric acid, tartaric acid, citric acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, lauryl sulfuric acid, gluconic acid, glutamic acid, salicylic acid, muconic acid, and the like or (2) basic addition salts formed with the conjugate bases of any of the inorganic acids listed above, wherein the conjugate bases comprise a cationic component selected from among $Na^+$, $K^+$, $Mg^{2+}$, $Ca^{2+}$, $NH_gR'''^{4-g+}$, in which R''' is a $C_{1-3}$ alkyl and g is a number selected from among 0, 1, 2, 3, or 4. It should be understood that all references to pharmaceutically acceptable salts include solvent addition forms (solvates) or crystal forms (polymorphs) as defined herein, of the same acid addition salt.

The term "alkyl" refers to an unbranched or branched chain, saturated, monovalent hydrocarbon residue containing 1 to 30 carbon atoms. The term "C.sub.1-M alkyl" refers to an alkyl comprising 1 to M carbon atoms, where M is an integer having the following values: 2, 3, 4, 5, 6, 7, 8, 9, 10, 11, 12, 13, 14, 15, 16, 17, 18, 19, 20, 21, 22, 23, 24, 25, 26, 27, 28, 29, or 30. The term "$C_{1-4}$ alkyl" refers to an alkyl containing 1 to 4 carbon atoms. The term "lower alkyl" denotes a straight or branched chain hydrocarbon residue comprising 1 to 6 carbon atoms. "$C_{1-20}$ alkyl" as used herein refers to an alkyl comprising 1 to 20 carbon atoms. "$C_{1-10}$ alkyl" as used herein refers to an alkyl comprising 1 to 10 carbons. Examples of alkyl groups include, but are not limited to, lower alkyl groups include methyl, ethyl, propyl, i-propyl, n-butyl, i-butyl, t-butyl or pentyl, isopentyl, neopentyl, hexyl, heptyl, and octyl. The term (ar)alkyl or (heteroaryl)alkyl indicate the alkyl group is optionally substituted by an aryl or a heteroaryl group respectively.

The term "alkenyl" refers to an unsubstituted hydrocarbon chain radical having from 2 to 10 carbon atoms having one or two olefinic double bonds, preferably one olefinic double bond. The term "$C_{2-N}$ alkenyl" refers to an alkenyl comprising 2 to N carbon atoms, where N is an integer having the following values: 3, 4, 5, 6, 7, 8, 9, or 10. The term "$C_{2-10}$ alkenyl" refers to an alkenyl comprising 2 to 10 carbon atoms. The term "$C_{2-4}$ alkenyl" refers to an alkenyl comprising 2 to 4 carbon atoms. Examples include, but are not limited to, vinyl, 1-propenyl, 2-propenyl (allyl) or 2-butenyl (crotyl).

The term "aryl," as used herein, and unless otherwise specified, refers to substituted or unsubstituted phenyl (Ph), biphenyl, or naphthyl, preferably the term aryl refers to substituted or unsubstituted phenyl. The aryl group can be substituted with one or more moieties selected from among hydroxyl, F, Cl, Br, I, amino, alkylamino, arylamino, alkoxy, aryloxy, nitro, cyano, sulfonic acid, sulfate, phosphonic acid, phosphate, and phosphonate, either unprotected, or protected as necessary, as known to those skilled in the art, for example, as taught in T. W. Greene and P. G. M. Wuts, *Protective Groups in Organic Synthesis*, 3rd ed., John Wiley & Sons, 1999.

The term "aryloxide," as used herein, and unless otherwise specified, refers to substituted or unsubstituted phenoxide (PhO—), p-phenyl-phenoxide (p-Ph-PhO—), or naphthoxide, preferably the term aryloxide refers to substituted or unsubstituted phenoxide. The aryloxide group can be substituted with one or more moieties selected from among hydroxyl, F, Cl, Br, I, —C(O)(lower alkyl), —C(O)O(lower alkyl), amino, alkylamino, arylamino, alkoxy, aryloxy, nitro, cyano, sulfonic acid, sulfate, phosphonic acid, phosphate, and phosphonate, either unprotected, or protected as necessary, as known to those skilled in the art, for example, as taught in T. W. Greene and P. G. M. Wuts, *Protective Groups in Organic Synthesis*, 3rd ed., John Wiley & Sons, 1999.

The term "preparation" or "dosage form" is intended to include both solid and liquid formulations of the active compound and one skilled in the art will appreciate that an active ingredient can exist in different preparations depending on the desired dose and pharmacokinetic parameters.

The term "excipient" as used herein refers to a compound that is used to prepare a pharmaceutical composition, and is generally safe, non-toxic and neither biologically nor otherwise undesirable, and includes excipients that are acceptable for veterinary use as well as human pharmaceutical use.

"Nicotinamide", which corresponds to the following structure,

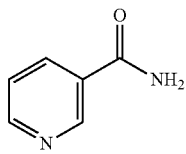

is one of the two principal forms of the B-complex vitamin niacin. The other principal form of niacin is nicotinic acid; nicotinamide, rather than nicotinic acid, however, is the major substrate for nicotinamide adenine dinucleotide (NAD) biosynthesis in mammals, as discussed in detail herein. Nicotinamide, in addition to being known as niacinamide, is also known as 3-pyridinecarboxamide, pyridine-3-carboxamide, nicotinic acid amide, vitamin B3, and vitamin PP. Nicotinamide has a molecular formula of $C_6H_6N_2O$ and its molecular weight is 122.13 Daltons. Nicotinamide is commercially available from a variety of sources.

"Nicotinamide Riboside" (NR), which corresponds to the following structure,

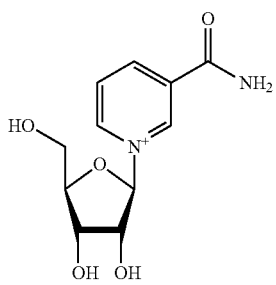

is characterized and a synthesized as described in, for instance, U.S. Pat. No. 8,106,184.

"Nicotinamide Mononucleotide" (NMN), which corresponds to the following structure,

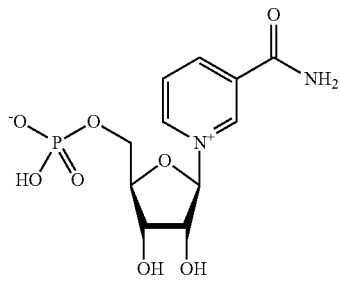

is produced from nicotinamide in the NAD biosynthesis pathway, a reaction that is catalyzed by Nampt. NMN is further converted to NAD in the NAD biosynthesis pathway, a reaction that is catalyzed by NMNAT. Nicotinamide mononucleotide (NMN) has a molecular formula of $C_{11}H_{15}N_2O_8P$ and a molecular weight of 334.22. Nicotinamide mononucleotide (NMN) is commercially available from such sources as Sigma-Aldrich (St. Louis, Mo.).

"Nicotinamide Adenine Dinucleotide" (NAD), which corresponds to the following structure,

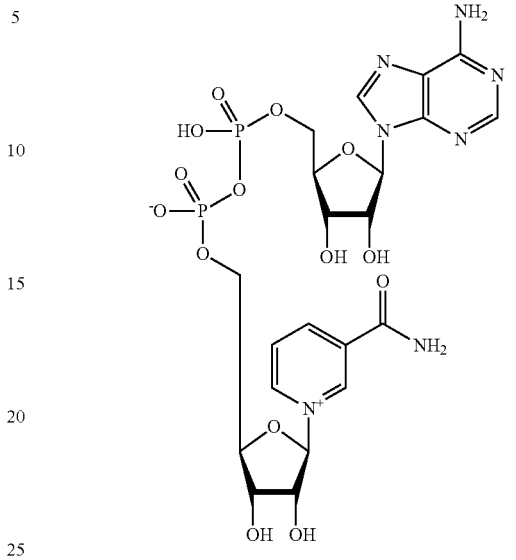

is produced from the conversion of nicotinamide to NMN, which is catalyzed by Nampt, and the subsequent conversion of NMN to NAD, which is catalyzed by NMNAT. Nicotinamide adenine dinucleotide (NAD) has a molecular formula of $C_{21}H_{27}N_7O_{14}P_2$ and a molecular weight of 663.43. Nicotinamide adenine dinucleotide (NAD) is commercially available from such sources as Sigma-Aldrich (St. Louis, Mo.).

Pharmaceutical Compositions

In certain embodiments the instant invention relates to a composition, e.g., a pharmaceutical composition, containing at least one agent or nicotinamide mononucleotide, analog and derivatives thereof, described herein together with a pharmaceutically acceptable carrier. In one embodiment, the composition includes a combination of multiple (e.g., two or more) agents of the invention.

As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; or (3) in a drink form, or sachet, that is mixed prior to ingestion.

Methods of preparing these formulations or compositions include the step of bringing into association an agent described herein with the carrier and, optionally, one or more accessory ingredients. In general, the formulations are prepared by uniformly and intimately bringing into association an agent described herein with liquid carriers, or finely divided solid carriers, or both, and then, if necessary, shaping the product.

Pharmaceutical compositions of this invention suitable for parenteral administration comprise one or more agents described herein in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Regardless of the route of administration selected, the agents of the present invention, which may be used in a suitable hydrated form, and/or the pharmaceutical compositions of the present invention, are formulated into pharmaceutically-acceptable dosage forms by conventional methods known to those of skill in the art.

4. Therapeutic Methods and Uses

Provided herein are methods of recovering from, treating, and preventing cancer, aging, cell death, radiation damage, radiation exposure, chemotherapy-induced damage, cellular senescence, among others, improving DNA repair, cell proliferation, cell survival, among others, and increasing the life span of a cell or protect it against certain stresses, among others by providing nicotinamide mononucleotides, encompassing analogs and derivatives thereof (e.g., NAD+) as set forth in sections 3 and 4 above. In some embodiments, the methods involve increasing the level or activity of nicotinamide dinucleotides (e.g., NAD+, NMN; NAD+ precursor pathways, such as a protein selected from the group consisting of NPT1, PNC1, NMA1 and NMA2; or NAD+ biosynthesis, such as enzymes selected from NMNAT-1, -2, and/or -3 or NAMPT).

The level of protein can be increased in a cell, e.g., by introducing into the cell a nucleic acid encoding the protein operably linked to a transcriptional regulatory sequence directing the expression of the protein in the cell. Methods for expressing nucleic acids in cells and appropriate transcriptional regulatory elements for doing so are well known in the art. Alternatively, a protein can be introduced into a cell, usually in the presence of a vector facilitating the entry of the protein into the cells, e.g., liposomes. Proteins can also be linked to transcytosis peptides for that purpose. Yet in other methods, an agent that stimulates expression of the endogenous gene is contacted with a cell. Such agents can be identified as further described herein.

It will be apparent to a person of skill in the art that a full length protein or nucleic acid encoding such or a portion thereof can be used according to the methods described herein. A portion of a protein is preferably a biologically active portion thereof. Portions that are biologically active can be identified according to methods known in the art and using an assay that can monitor the activity of the particular protein. Assays for determining the activity of any of the aforementioned protein are described, e.g., in Pescanglini et al. (1994) *Clin. Chim. Acta* 229: 15-25 and Sestini et al. (2000) *Archives of Biochem. Biophys.* 379:277. Alternatively, the activity of such a protein can be tested in an assay in which the life span of a cell is determined. For example, a cell is transfected with a nucleic acid comprising one or more copies of a sequence encoding a portion of an NPT1, PNC1, NMA1, NMA2, NMNAT-1, -2, and/or -3, or NAMPT protein or a control nucleic acid, and the life span of the cells is compared. A longer life span of a cell transfected with a portion of one of the proteins indicates that the portion of the protein is a biologically active portion. Assays for determining the life span of a cell are known in the art and are also further described herein. In particular, assays for determining the life span of a mammalian cell can be conducted as described, e.g., in *Cell Growth, Differentiation and Senescence: A Practical Approach*. George P. Studzinski (ed.). Instead of measuring the life span, one can also measure the resistance of a transfected cell to certain stresses, e.g., heatshock, for determining whether a portion of a protein is a biologically active portion. Methods for measuring resistance to certain stresses are known in the art and are also further described herein. In particular, assays for determining the resistance of a mammalian cell to heatshock can be conducted as described, e.g., in Bunelli et al. (1999) *Exp. Cell Res.* 262: 20.

In addition to portions of NPT1, PNC1, NMA1, NMA2, NMNAT-1, -2, and/or -3, or NAMPT proteins, other variants, such as proteins containing a deletion, insertion or addition of one or more amino acids can be used, provided that the protein is biologically active. Exemplary amino acid changes include conservative amino acid substitutions. Other changes include substitutions for non-naturally occurring amino acids. Proteins encoded by nucleic acids that hybridize to a nucleic acid encoding NPT1, PNC1, NMA1, NMA2, NMNAT-1, -2, and/or -3, or NAMPT under high or medium stringency conditions and which are biologically active can also be used. For example, nucleic acids that hybridize under high stringency conditions of 0.2 to 1×SSC at 65° C. followed by a wash at 0.2×SSC at 65° C. to a gene encoding NPT1, PNC1, NMA1, NMA2, NMNAT-1, -2, and/or -3, or NAMPT can be used. Nucleic acids that hybridize under low stringency conditions of 6×SSC at room temperature followed by a wash at 2×SSC at room temperature to a gene encoding NPT1, PNC1, NMA1, NMA2, NMNAT-1, -2, and/or -3, or NAMPT can be used. Other hybridization conditions include 3×SSC at 40 or 50° C., followed by a wash in 1 or 2×SSC at 20, 30, 40, 50, 60, or 65° C. Hybridizations can be conducted in the presence of formaldehyde, e.g., 10%, 20%, 30% 40% or 50%, which further increases the stringency of hybridization. Theory and practice of nucleic acid hybridization is described, e.g., in S. Agrawal (ed.) Methods in Molecular Biology, volume 20; and Tijssen (1993) *Laboratory Techniques in biochemistry and molecular biology-hybridization with nucleic acid probes*, e.g., part I chapter 2 "Overview of principles of hybridization and the strategy of nucleic acid probe assays," Elsevier, New York provide a basic guide to nucleic acid hybridization.

Exemplary proteins may have at least about 50%, 70%, 80%, 90%, preferably at least about 95%, even more preferably at least about 98% and most preferably at least 99% homology or identity with a wild-type NPT1, PNC1, NMA1, NMA2, NMNAT-1, -2, and/or -3, or NAMPT protein or a domain thereof, e.g., the catalytic domain. Other exemplary proteins may be encoded by a nucleic acid that is at least about 90%, preferably at least about 95%, even more preferably at least about 98% and most preferably at least 99% homology or identity with a wild-type NPT1, PNC1, NMA1, NMA2, NMNAT-1, -2, and/or -3, or NAMPT nucleic acid, e.g., those described herein.

In other embodiments proteins are fusion proteins, e.g., proteins fused to a transcytosis peptide. Fusion proteins may also comprise a heterologous peptide that can be used to purify the protein and/or to detect it.

In other embodiments, non-naturally occurring protein variants are used. Such variants can be peptidomimetics.

In yet other embodiments, the activity of one or more proteins selected from the group consisting of NPT1, PNC1, NMA1, NMA2, NMNAT-1, -2, and/or -3 or NAMPT is enhanced or increased. This can be achieved, e.g., by contacting a cell with a compound that increases the activity, e.g., enzymatic activity, of one of these proteins. Assays for identifying such compounds are further described herein.

Any means for the introduction of polynucleotides into mammals, human or non-human, or cells thereof may be adapted to the practice of this invention for the delivery of the various constructs of the invention into the intended recipient. In one embodiment of the invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., *Ann NY Acad Sci* 126-139, 1995). Formulation of DNA, e.g. with various lipid or liposome materials, may then be effected using known methods and materials and delivered to the recipient mammal. See, e.g., Canonico et al, *Am J Respir Cell Mol Biol* 10:24-29, 1994; Tsan et al, *Am J Physiol* 268; Alton et al., *Nat Genet.* 5:135-142, 1993 and U.S. Pat. No. 5,679,647 by Carson et al.

The expression of a protein, e.g., a protein selected from the group consisting of NPT1, PNC1, NMA1, NMA2, NMNAT-1, -2, and/or -3, or NAMPT or a biologically active variant thereof in cells of a subject to whom, e.g., a nucleic acid encoding the protein was administered, can be determined, e.g., by obtaining a sample of the cells of the patient and determining the level of the protein in the sample, relative to a control sample.

In another embodiment, a protein or biologically active variant thereof, is administered to the subject such that it reaches the target cells, and traverses the cellular membrane. Polypeptides can be synthesized in prokaryotes or eukaryotes or cells thereof and purified according to methods known in the art. For example, recombinant polypeptides can be synthesized in human cells, mouse cells, rat cells, insect cells, yeast cells, and plant cells. Polypeptides can also be synthesized in cell free extracts, e.g., reticulocyte lysates or wheat germ extracts. Purification of proteins can be done by various methods, e.g., chromatographic methods (see, e.g., Robert K Scopes *Protein Purification: Principles and Practice* Third Ed. Springer-Verlag, N.Y. 1994). In one embodiment, the polypeptide is produced as a fusion polypeptide comprising an epitope tag consisting of about six consecutive histidine residues. The fusion polypeptide can then be purified on a $Ni^{++}$ column. By inserting a protease site between the tag and the polypeptide, the tag can be removed after purification of the peptide on the $Ni^{++}$ column. These methods are well known in the art and commercial vectors and affinity matrices are commercially available.

Administration of polypeptides can be done by mixing them with liposomes, as described above. The surface of the liposomes can be modified by adding molecules that will target the liposome to the desired physiological location.

In one embodiment, a protein is modified so that its rate of traversing the cellular membrane is increased. For example, the polypeptide can be fused to a second peptide which promotes "transcytosis," e.g., uptake of the peptide by cells. In one embodiment, the peptide is a portion of the HIV transactivator (TAT) protein, such as the fragment corresponding to residues 37-62 or 48-60 of TAT, portions which are rapidly taken up by cell in vitro (Green and Loewenstein, (1989) *Cell* 55:1179-1188). In another embodiment, the internalizing peptide is derived from the *Drosophila* antennapedia protein, or homologs thereof. The 60 amino acid long homeodomain of the homeo-protein antennapedia has been demonstrated to translocate through biological membranes and can facilitate the translocation of heterologous polypeptides to which it is couples. Thus, polypeptides can be fused to a peptide consisting of about amino acids 42-58 of *Drosophila* antennapedia or shorter fragments for transcytosis. See for example Derossi et al. (1996) *J Biol Chem* 271:18188-18193; Derossi et al. (1994) *J Biol Chem* 269: 10444-10450; and Perez et al. (1992) *J Cell Sci* 102:717-722.

In another embodiment, the amount of nicotinamide is decreased in a cell. This can be achieved, e.g., by inhibiting the expression of genes of the NAD+ salvage pathway or other pathway that produce nicotinamide. Inhibition of the genes can be conducted, e.g., as further described herein, such as by performing RNAi on the NAD+ salvage pathway genes that produce nicotinamide. One can also inhibit genes that are involved in the de novo synthesis of nicotinamide. For example, nicotinamide levels in cells can be regulated by regulating the level or activity of poly(adenosine diphosphate-ribose) polymerase-1 (PARP). In particular, nicotinamide levels can be reduced by reducing the level or activity of PARP, since this enzyme generates nicotinamide. Nicotinamide levels may also be decreased in cells by reducing the level or activity of glycohydrolases (e.g., human CD38, an ectoenzyme that is expressed on the surface of immune cells, such as neutrophils; gi:4502665 and GenBank Accession No. NP_001766), which cleave NAD to nicotinamide.

Nicotinamide levels may also be decreased by inhibiting the de novo nicotinamide synthesis pathway. Genes involved in this pathway include the BNA genes in *S. cerevisiae* (BNA1-6). Alternatively, poly(adenosine diphosphate-ribose) polymerase (PARP) family members, e.g., PARP-1 and PARPv and tankyrase can also be inhibited to decrease nicotinamide levels.

It is also possible to reduce the level or activity of nicotinamide transporters to reduce the level of nicotinamide that is imported into cells. For example, in yeast, nicotinic acid is transported by the Tna1 (nicotinate/nicotinamide mononucleotide transport) protein. Human homologues of yeast TNA1 have the following GenBank Accession numbers: gi:9719374 and AAF97769; gi:6912666 and NP_036566; gi:18676562 and AB84933; gi:12718201 and CAC28600; gi:19263934 and AAH25312; gi:9966811 and NP_065079; and gi:22761334 and BAC11546. Other nucleoside transporters that can be modulated include bacterial and fly nucleoside transporter and the following human genes that are homologous thereto: gi:8923160 and NP_060164; gi:14336678 and AAK61212; gi: 22749231 and NP_689812; and gi: 18603939 and XP_091525.

Alternatively, nicotinamide levels can be decreased or nicotinamide inactivated, e.g., by stimulating the activity or increase the level of enzymes that metabolize, degrade or inhibit nicotinamide, e.g., nicotinamide N-methyl transferase, also referred to as nicotinamide methyltransferase (NNMT; EC 2.1.1.1; CAS registry number 9029-74-7). This enzyme catalyzes the reaction S-adenosyl-L-methionine+nicotinamide=S-adenosyl-L-homocysteine+1-methylnicotinamide and promotes excretion of nicotinamide from the cell (see also, Cantoni (1951) *J. Biol. Chem.* 203-216). The human enzyme is referred to as NNMT and its complete sequence can be found at GenBank Accession number U08021 and as SEQ ID NO: 9 for the nucleotide sequence and SEQ ID NO: 10 for the protein (Aksoy et al. (1994) *J. Biol. Chem.* 269:14835). The yeast version of this enzyme is referred to as NNT1 (also referred to as YLR258w).

Yet another enzyme that metabolizes nicotinamide and thereby reduces the level of nicotinamide is nicotinamide phosphribosyltransferase (NAMPRT; E.C.2.4.2.12). The human gene is also referred to as pre-B-cell colony enhancing factor (PBEF), and its sequence is available under GenBank Accession numbers NP_005737; NM_005746; AAH20691; and BC020691. The nucleotide and amino acid sequences of human NAMPRT (BC020691) are set forth as SEQ ID NOs: 11 and 12, respectively. In yeast and human cells, the level of NPT1 or human homolog thereof, respectively, can be increased to reduce nicotinamide levels.

Another enzyme that metabolizes nicotinamide and may thereby modulate, e.g., reduce, the level of nicotinamide is nicotinamide mononucleotide (NMN) adenylyltransferase in human cells. The human enzyme is referred to as NMNAT-1 (E.C.2.7.7.18). The following GenBank Accession numbers are provided for the human enzyme: NP_073624; NM_022787; AAL76934; AF459819; and NP_073624; AF314163. A variant of this gene is NMNAT-2 (KIAA0479), the human version of which can be found under GenBank Accession numbers NP_055854 and NM_015039 (Raffaelli et al. (2002) Biochem Biophys Res Commun 297:835). In yeast cells, the equivalent enzymes in the NAD+ salvage pathway are nicotinate mononucleotide adenyltransferase 1 and 2 (NMA1 and NMA2, respectively) (E.C. 2.7.7.1). Another variant is NMNAT-3, the human version of which can be found under GenBank Accession numbers NP_001186976.1, NP_001307439.1, NP_001307440.1, NP_001307441.1, NP_001307442.1, NP_835471.1. In some embodiments of the present invention, the NMNAT-2 and NMNAT-3 are nuclear targeted.

Yet another enzyme that may be increased to decrease nicotinamide levels is phosphoribosyl pyrophosphate (PRPP) synthase (PRPS), which converts ribose 5-phosphate to PRPP, the substrate of NPT1. There are several related enzymes, having the following GenBank Accession numbers: gi:4506127 and NP_002755 (Prps1); gi:4506129 and NP_002756 (Prps2); gi:20539448; gi:4506133 and NP_002758 (Prps associated protein 2); gi:24418495 and Q14558 (Prps associated protein 1); gi:17644236 and CAD18892; gi:2160401 and BAA05675 (Prps isoform 1); and gi:2160402 and BAA05676 (Prps isoform 2).

Reducing nicotinamide levels in cells may also provide other advantages, such as stimulating DNA break repair. Indeed, PARP is regulated by nicotinamide (nicotinamide negatively regulates PARP). Thus, regulating the level of nicotinamide in cells, e.g., as further described herein, will regulate the activity of PARP. Accordingly, since PARP is involved in numerous cellular functions, such as DNA break repair, telomere-length regulation, and histone modification, modulating nicotinamide levels will modulate these activities. For example, reducing nicotinamide levels in cells will increase the activity of PARP and thereby further enhance the DNA break repair mechanism of cells.

In addition to applying the methods of the invention in eukaryotic cells, such as mammalian cells and yeast cells, the methods can also be applied to plant cells. Accordingly, the invention also provides methods for extending the life span of plants and plant cells and for rendering the plant and plant cells more resistant to stress, e.g., excessive salt conditions. This can be achieved, e.g., by modulating the level or activity of proteins in the plant cells that are essentially homologous to the proteins described herein in the yeast and mammalian systems as increasing the life span and/or the stress resistance of cells. Alternatively, the level of nicotinamide in plant cells can be reduced, in particular, as described herein for modulating their level in other eukaryotic cells. Nucleic acids can be introduced into plant cells according to methods known in the art.

For example, the following are genes form *Arabidopsis thalainia* that are homologous to the genes described above that can be modulated to modulate the pathways leading to NAD+ or reduction of nicotinamide levels in cells. Homologues of yeast PNC1: gi 18401044 NP_566539.1 (a putative hydrolase); gi 15237256 NP_1977131; and gi 15237258 NP_197714.1. Homologues of yeast NPT1: gi 2026021 AAM13003.1; gi 15234571 NP_195412.1; gi 25054896 AAN71931.1; and gi 15227832 NP_179923.1. Homologues of yeast NMA1/2: gi 22327861 NP_200392.2 and gi 9758615 BAB09248.1. Homologues of yeast NNT1 (YL285W): gi 20197178 AAC14529; gi 22325900 NP_565619.2; gi 15219438 NP_177475.1 (a Tumor related Protein); gi 12324311 AA652120.1; gi:22330409 NP_683465; gi:15240506 NP_199767; gi 8778835 AAF79834.1; and gi 15231011 NP_188637. Homologue of human NNMT: gi 15238203 NP_196623. Homologue of yeast QNS1 (gene downstream of NMA1/2 in the NAD+ salvage pathway): gi:15221990 NP_175906. Homologues of yeast BNA6: gi:18379203 NP_565259 and gi:21555686 AAM63914.

In some embodiments, the invention relates to the use of a nicotinamide mononucleotide based derivative to prevent adverse effects and protect cells from toxicity. Toxicity may be an adverse effect of radiation or external chemicals on the cells of the body. Examples of toxins are pharmaceuticals, drugs of abuse, and radiation, such as UV or X-ray light. Both radiative and chemical toxins have the potential to damage biological molecules such as DNA. This damage typically occurs by chemical reaction of the exogenous agent or its metabolites with biological molecules, or indirectly through stimulated production of reactive oxygen species (eg, superoxide, peroxides, hydroxyl radicals). Repair systems in the cell excise and repair damage caused by toxins.

Enzymes that use NAD+ play a part in the DNA repair process. Specifically, the poly(ADP-ribose) polymerases (PARPs), particularly PARP-1, are activated by DNA strand breaks and affect DNA repair. The PARPs consume NAD+ as an adenosine diphosphate ribose (ADPR) donor and synthesize poly(ADP-ribose) onto nuclear proteins such as histones and PARP itself. Although PARP activities facilitate DNA repair, overactivation of PARP can cause significant depletion of cellular NAD+, leading to cellular necrosis. The apparent sensitivity of NAD+ metabolism to genotoxicity has led to pharmacological investigations into the inhibition of PARP as a means to improve cell survival. Numerous reports have shown that PARP inhibition increases NAD+ concentrations in cells subject to genotoxicity, with a resulting decrease in cellular necrosis. Nevertheless, cell death from toxicity still occurs, presumably because cells are able to complete apoptotic pathways that are activated by genotoxicity. Thus, significant cell death is still a consequence of DNA/macromolecule damage, even with inhibition of PARP. This consequence suggests that improvement of NAD+ metabolism in genotoxicity can be partially effective in improving cell survival but that other players that modulate apoptotic sensitivity, such as sirtuins, may also play important roles in cell responses to genotoxins.

Physiological and biochemical mechanisms that determine the effects of chemical and radiation toxicity in tissues are complex, and evidence indicates that NAD+ metabolism is an important player in cell stress response pathways. For example, upregulation of NAD+ metabolism, via nicotinamide/nicotinic acid mononucleotide (NMNAT-1, -2, and/or -3) overexpression, has been shown to protect against neuron axonal degeneration, and nicotinamide used pharmacologically has been recently shown to provide neuron protection in a model of fetal alcohol syndrome and fetal ischemia. Such protective effects could be attributable to upregulated NAD+ biosynthesis, which increases the available NAD+ pool subject to depletion during genotoxic stress. This depletion of NAD+ is mediated by PARP enzymes, which are activated by DNA damage and can deplete cellular NAD+, leading to necrotic death. Another mechanism of enhanced cell protection that could act in concert with upregulated NAD+ biosynthesis is the activation of cell protection transcriptional programs regulated by sirtuin enzymes.

In one embodiment, the invention provides a method extending the lifespan of a cell, extending the proliferative capacity of a cell, slowing aging of a cell, promoting the survival of a cell, delaying cellular senescence in a cell, mimicking the effects of calorie restriction, increasing the resistance of a cell to stress, or preventing apoptosis of a cell, by contacting the cell with a nicotinamide mononucleotide based derivative compound. In an exemplary embodiment, the methods comprise contacting the cell with a nicotinamide mononucleotide based derivative to thereby bind and modulate the activity of a biologically active polypeptide comprising a Nudix homology domain (NHD), or fragment thereof, or a nucleic acid encoding same.

The methods described herein may be used to increase the amount of time that cells, particularly primary cells (i.e., cells obtained from an organism, e.g., a human), may be kept alive in a cell culture. Embryonic stem (ES) cells and pluripotent cells, and cells differentiated therefrom, may also be treated with nicotinamide mononucleotide based or derivative compound to keep the cells, or progeny thereof, in culture for longer periods of time. Such cells can also be used for transplantation into a subject, e.g., after ex vivo modification.

In one embodiment, cells that are intended to be preserved for long periods of time may be treated with a nicotinamide mononucleotide based derivative compound. The cells may be in suspension (e.g., blood cells, serum, biological growth media, etc.) or in tissues or organs. For example, blood collected from an individual for purposes of transfusion may be treated with a nicotinamide mononucleotide based derivative compound to preserve the blood cells for longer periods of time. Additionally, blood to be used for forensic purposes may also be preserved using a nicotinamide mononucleotide based derivative compound. Other cells that may be treated to extend their lifespan or protect against apoptosis include cells for consumption, e.g., cells from non-human mammals (such as meat) or plant cells (such as vegetables).

Nicotinamide mononucleotide based derivative compounds may also be applied during developmental and growth phases in mammals, plants, insects or microorganisms, in order to, e.g., alter, retard or accelerate the developmental and/or growth process.

In another embodiment, a nicotinamide mononucleotide based derivative compounds may be used to treat cells useful for transplantation or cell therapy, including, for example, solid tissue grafts, organ transplants, cell suspensions, stem cells, bone marrow cells, etc. The cells or tissue may be an autograft, an allograft, a syngraft or a xenograft. The cells or tissue may be treated with the nicotinamide mononucleotide based derivative compound prior to administration/implantation, concurrently with administration/implantation, and/or post administration/implantation into a subject. The cells or tissue may be treated prior to removal of the cells from the donor individual, ex vivo after removal of the cells or tissue from the donor individual, or post implantation into the recipient. For example, the donor or recipient individual may be treated systemically with a nicotinamide mononucleotide based derivative compound or may have a subset of cells/tissue treated locally with a nicotinamide mononucleotide based derivative compound. In certain embodiments, the cells or tissue (or donor/recipient individuals) may additionally be treated with another therapeutic agent useful for prolonging graft survival, such as, for example, an immunosuppressive agent, a cytokine, an angiogenic factor, etc.

In yet other embodiments, cells may be treated with a nicotinamide mononucleotide based derivative compound that increases the level of NAD+ in vivo, e.g., to increase their lifespan or prevent apoptosis. For example, skin can be protected from aging (e.g., developing wrinkles, loss of elasticity, etc.) by treating skin or epithelial cells with a nicotinamide mononucleotide based derivative compound or cream that increases the level intracellular NAD+. In an exemplary embodiment, skin is contacted with a cream, pharmaceutical or cosmetic composition comprising a nicotinamide mononucleotide based derivative compound that increases the level of intracellular NAD+. Exemplary skin afflictions or skin conditions that may be treated in accordance with the methods described herein include disorders or diseases associated with or caused by inflammation, sun damage or natural aging. For example, the compositions find utility for sunburn prevention, recovery from sunburn, and in the prevention or treatment of contact dermatitis (including irritant contact dermatitis and allergic contact dermatitis), atopic dermatitis (also known as allergic eczema), actinic keratosis, keratinization disorders (including eczema), epidermolysis bullosa diseases (including penfigus), exfoliative dermatitis, seborrheic dermatitis, erythemas (including erythema multiforme and erythema nodosum), damage caused by the sun or other light sources, discoid lupus erythematosus, dermatomyositis, psoriasis, skin cancer and the effects of natural aging. In another embodiment, a nicotinamide mononucleotide based derivative compound that increases the level of intracellular NAD+ may be used for the treatment of wounds and/or burns to promote healing, including, for example, first-, second- or third-degree burns and/or thermal, chemical or electrical burns. The formulations may be administered topically, to the skin or mucosal tissue, as an ointment, lotion, cream, microemulsion, gel, solution or the like, as further described herein, within the context of a dosing regimen effective to bring about the desired result.

Topical formulations comprising one or more a nicotinamide mononucleotide based derivative compound that increases the level of intracellular NAD+ may also be used as preventive, e.g., chemopreventive, compositions. When used in a chemopreventive method, susceptible skin is treated prior to any visible condition in a particular individual.

In another embodiment, a nicotinamide mononucleotide based derivative compound that increases the level of intracellular NAD+ may be used for recovering from, treating, or preventing a disease or condition induced or exacerbated by cellular senescence in a subject; methods for decreasing the rate of senescence of a subject, e.g., after onset of senescence; methods for extending the lifespan of a subject; methods for recovering from, treating or preventing a disease or condition relating to lifespan; methods for recovering from, treating or preventing a disease or condition relating to the proliferative capacity of cells; and methods for recovering from, treating or preventing a disease or condition resulting from cell damage or death. In certain embodiments, the method does not act by decreasing the rate of occurrence of diseases that shorten the lifespan of a subject. In certain embodiments, a method does not act by reducing the lethality caused by a disease, such as cancer.

In yet another embodiment, a nicotinamide mononucleotide based derivative compound that increases the level of intracellular NAD+ may be administered to a subject in order to generally increase the lifespan of its cells and to protect its cells against stress and/or against apoptosis. It is believed that treating a subject with a compound described herein is similar to subjecting the subject to hormesis, i.e., mild stress that is beneficial to organisms and may extend their lifespan.

A nicotinamide mononucleotide based derivative compound that increases the level of intracellular NAD+ can also be administered to subjects for treatment of diseases, e.g., chronic diseases, associated with cell death, in order to protect the cells from cell death. Exemplary diseases include those associated with neural cell death, neuronal dysfunction, or muscular cell death or dysfunction, such as Parkinson's disease, Alzheimer's disease, multiple sclerosis, amyotropic lateral sclerosis, and muscular dystrophy; AIDS; fulminant hepatitis; diseases linked to degeneration of the brain, such as Creutzfeld-Jakob disease, retinitis pigmentosa and cerebellar degeneration; myelodysplasis such as aplastic anemia; ischemic diseases such as myocardial infarction and stroke; hepatic diseases such as alcoholic hepatitis, hepatitis B and hepatitis C; joint-diseases such as osteoarthritis; atherosclerosis; alopecia; damage to the skin due to UV light; lichen planus; atrophy of the skin; cataract; and graft rejections. Cell death can also be caused by surgery, drug therapy, chemical exposure or radiation exposure.

A nicotinamide mononucleotide based derivative compound that increases the level of intracellular NAD+ can also be administered to a subject suffering from an acute disease, e.g., damage to an organ or tissue, e.g., a subject suffering from stroke or myocardial infarction or a subject suffering from a spinal cord injury. A nicotinamide mononucleotide based derivative compound that increases the level of intracellular NAD+ may also be used to repair an alcoholic's liver.

In one embodiment, modulating NHD through NAD$^+$ may directly regulate protein-protein interactions, the modulation of which may be useful in methods of recovering from, treating and preventing cancer, aging, cell death, radiation damage, radiation exposure, among others, may improve DNA repair, cell proliferation, cell survival, among others, and may increase the life span of a cell or protect it against certain stresses, among others. For example, cells in culture can be treated as described herein, such as to keep them proliferating longer. This is particularly useful for primary cell cultures (i.e., cells obtained from an organism, e.g., a human), which are known to have only a limited life span in culture. Treating such cells according to methods of the invention, e.g., by integrating one or more additional copies of one or more genes selected from the group consisting of NPT1, PNC1, NMA1, NMA2, nicotinamide N-methyl transferase (NNMT and NNT1), nicotinamide phosphoribosyltransferase (NAMPRT), and optionally human nicotinamide mononucleotide adenylyltransferase (NMNAT, NMAT-1, -2, and/or -3), will result in increasing the amount of time that the cells are kept alive in culture. Embryonic stem (ES) cells and pluripotent cells, and cells differentiated therefrom, can also be modified according to the methods of the invention such as to keep the cells or progeny thereof in culture for longer periods of time. Primary cultures of cells, ES cells, pluripotent cells and progeny thereof can be used, e.g., to identify compounds having particular biological effects on the cells or for testing the toxicity of compounds on the cells (i.e., cytotoxicity assays).

In other embodiments, cells that are intended to be preserved for long periods of time are treated as described herein. The cells can be cells in suspension, e.g., blood cells, or tissues or organs. For example, blood collected from an individual for administering to an individual can be treated according to the invention, such as to preserve the blood cells for longer periods of time. Other cells that one may treat for extending their lifespan and/or protect them against certain types of stresses include cells for consumption, e.g., cells from non-human mammals (such as meat), or plant cells (such as vegetables).

In another embodiment, cells obtained from a subject, e.g., a human or other mammal, are treated according to the methods of the invention and then administered to the same or a different subject. Accordingly, cells or tissues obtained from a donor for use as a graft can be treated as described herein prior to administering to the recipient of the graft. For example, bone marrow cells can be obtained from a subject, treated ex vivo to extend their life span and protect the cells against certain types of stresses and then administered to a recipient. In certain embodiments, the cells of the graft, e.g., bone marrow, are transfected with one or more copies of one or more genes selected from the group consisting of NPT1, PNC1, NMA1, NMA2, NMNAT-1, -2, and/or -3, NNT1, NAMPRT, and optionally NMAT-1 or 2. The graft can be an organ, a tissue or loose cells.

In yet other embodiments, cells are treated in vivo to increase their life span and/or protect them against certain types of stresses. For example, skin can be protected from aging, e.g., developing wrinkles, by treating skin, e.g., epithelial cells, as described herein. In an exemplary embodiment, skin is contacted with a pharmaceutical or cosmetic composition comprising a compound that is capable of increasing the transcription of one or more genes selected from the group consisting of NPT1, PNC1, NMA1, NMA2, NMNAT-1, -2, and/or -3, NNT1, NAMPRT, and optionally NMAT-1 or 2. In another embodiment, skin cells are contacted with a composition comprising a protein selected from the group consisting of NPT1, PNC1, NMA1, NMA2, NMNAT-1, -2, and/or -3, NNT1, NAMPRT, and optionally NMAT-1 or 2, or a nucleic acid encoding such, and a vehicle for delivering the nucleic acid or protein to the cells.

Compounds, nucleic acids and proteins can also be delivered to a tissue or organ within a subject, such as by injection, to extend the life span of the cells or protect the cells against certain stresses.

In yet another embodiment, an agent of the invention is administered to subjects, such as to generally increase the life span of its cells and protect its cells against certain types of stresses. For example, an agent can be taken by subjects as food supplements. In one embodiment, such an agent is a component of a multi-vitamin complex.

Agents that extend the life span of cells and protect them from stress can also be administered to subjects for treatment of diseases, e.g., chronic diseases, associated with cell death, such as to protect the cells from cell death, e.g., diseases associated with neural cell death or muscular cell death. Exemplary diseases include Parkinson's disease, Alzheimer's disease, multiple sclerosis, amniotropic lateral sclerosis, and muscular dystrophy. In such cases, the agent may be administered in the tissue or organ likely to encounter cell death.

Such agents can also be administered to a subject suffering from an acute damage to an organ or tissue, e.g., a subject suffering from stroke or myocardial infarction or a subject suffering from a spinal cord injury. Agents can also be used to repair an alcoholic's liver.

Since DNA repair is also inhibited by nicotinamide, agents that reduce nicotinamide levels in cells can be used to promote DNA repair in cells. Accordingly, cells exposed to conditions that may trigger DNA damage, e.g., U.S. radiation and ethidium bromide, may be protected by contacting them before, during and/or after exposure to the DNA damaging agent, with an agent that reduces nicotinamide levels in the cell.

In other embodiments, the methods of the invention are applied to yeast cells. Situations in which it may be desirable to extend the life span of yeast cells and to protect them against certain types of stress include any process in which yeast is used, e.g., the making of beer, yogurt, and bakery, e.g., making of bread. Use of yeast having an extended life span can result in using less yeast or in having the yeast be active for longer periods of time.

The invention also provides methods for reducing the life span of a cell or rendering it more susceptible to certain stresses, e.g., heatshock, radioactivity, osmotic stress, DNA damage, e.g., from U.V. Such methods can be used whenever it is desired to reduce the life span of a cell. Exemplary methods include decreasing the level or activity of a protein selected from the group consisting of NPT1, PNC1, NMA1, NMA2, NMNAT-1, -2, and/or -3, NNT1, NAMPRT, and optionally NMAT-1 or 2.

Another method includes increasing the level of nicotinamide in the cell, e.g., by contacting the cell with nicotinamide, or by increasing the level or activity of an enzyme stimulating nicotinamide biosynthesis or decreasing the level or activity of an enzyme inhibiting or degrading nicotinamide, e.g., by decreasing the level or activity of NPT1, PNC1, NMA1, NMA2, NMNAT-1, -2, and/or -3, NNT1, NAMPRT, and optionally NMAT-1 or 2. Exemplary situations in which one may wish to reduce the life span of a cell or render it more susceptible to certain stresses include treatment of cancer, autoimmune diseases or any other situation in which it is desirable to eliminate cells in a subject. Nicotinamide or other compounds or agents of the invention can be administered directly to the area containing the underirable cells, e.g., in a tumor. These methods can also be used to eliminate cells or prevent further proliferation of undesirable cells of non-malignant tumors, e.g., warts, beauty spots and fibromas. For example, nicotinamide can be injected into a wart, or alternatively be included in a pharmaceutical composition for applying onto the wart.

Methods for decreasing the life span of cells or increasing their susceptibility to certain stresses can be applied to yeast, e.g., yeast infecting subjects. Accordingly, a composition comprising an agent, e.g., nicotinamide, can be applied to the location of the yeast infection.

Subjects that may be treated as described herein include eukaryotes, such as mammals, e.g., humans, ovines, bovines, equines, porcines, canines, felines, non-human primate, mice, and rats. Cells that may be treated include eukaryotic cells, e.g., from a subject described above, or plant cells, yeast cells and prokaryotic cells, e.g., bacterial cells.

The compound or composition disclosed herein can be used for recovering from, treating, mitigating, or ameliorating various conditions pertaining to DNA repair deficiency disorder. For example, the compound or composition disclosed herein can be used for mitigation, treatment, or amelioration of a DNA repair deficiency disorder.

The invention method of use generally comprises administering to a subject (e.g., a human being) a compound or a composition disclosed herein. Such administering can be local administration or systemic administration, which administering can be achieved by, for example, oral administration, subcutaneous injection, intravenous injection, topical administration, or implant.

Examples of conditions related to DNA repair deficiency disorders include, but are not limited to, Ataxia Telangiectasia (A-T), Xeroderma Pigmentosum (XP), Fanconi's Anemia (FA), Li Fraumeni syndrome, Nijmegen breakage syndrome (NBS), A-T-like disorder (ATLD), Werner's syndrome, Bloom's syndrome, Rothmund-Thompson syndrome, Cockayne's syndrome (CS), Trichothiodystrophy, ATR-Seckel syndrome, LIG4 syndrome, Human immunodeficiency with microcephaly, Spinocerebellar ataxia with axonal neuropathy, Ataxia with oculomotor apraxia 1, Ataxia with oculomotor apraxia 2, Diamond-Blackfan anemia, Rapadilino syndrome, Turcot Syndrome, Seckle Syndrome, Lynch syndrome, NBS-like syndrome, and RIDDLE Syndrome and others like those.

In some embodiments, the methods include administering to the subject an effective amount of an agent that inhibits NHD complex formation.

In some embodiments, the methods further comprise administering to the subject an effective amount of an agent that increases the levels of NAD+ in the subject. Examples of such agents include NAD+ precursor, such as nicotinic acid, nicotinamide, nicotinamide mononucleotide (NMN), nicotinamide riboside (NR), or a salt thereof or prodrug thereof, including crystalline and polymorphic forms. In some embodiments, such an agent is administered at a dose of between 0.5-5 grams per day. In some embodiments, NMN is orally administered in doses of between 250 mg-5 grams per day. NAD+ levels also can be increased by increasing the activity of enzymes (or enzymatically active fragments thereof) involved in NAD+ biosynthesis (de novo synthesis or salvage pathways). Enzymes involved in NAD+ biosynthesis such as nicotinate phosphoribosyl transferase 1 (NPT1), pyrazinamidase/nicotinamidase 1 (PNC1), nicotinic acid mononucleotide adenylyltransf erase 1 (NMA1), nicotinic acid mononucleotide adenylyltransferase 2 (NMA2), nicotinamide N-methyltransferase (NNMT), nicotinamide phosphoribosyl transferase (NAMPT or NAM-PRT), nicotinate/nicotinamide mononucleotide adenylyl transferase 1 (NMNAT-1), and nicotinamide mononucleotide adenylyl transferase 2 (NMNAT-2); are described in U.S. Pat. No. 7,977,049, which is incorporated by reference herein. The NHD inhibitor and agent that increases the levels of NAD+ can be administered simultaneously (e.g., as a single formulation) or sequentially (e.g., as separate formulations).

In some embodiments, the methods include administering to a subject an effective amount of an agent that increases the levels of NAD+, without administering an inhibitor of NHD.

Aspects of the invention thus relate to compositions of matter including NAD+ precursors, such as NMN or a salt thereof or prodrug thereof, including crystalline and polymorphic forms. Further aspects of the invention relate to compositions of matter including an enzyme involved in NAD+ biosynthesis, such as NMNAT-1, -2, and/or -3, or NAMPT, or an enzymatically active fragment thereof, or a nucleic acid encoding an enzyme involved in NAD+ biosynthesis, or an enzymatically active fragment thereof. In some embodiments, compositions include conjugates of agents described herein, such as fish oil conjugates.

In one embodiment, the invention provides a method for recovering from, treating, or preventing a disease or condition induced or exacerbated by cellular senescence in a subject; methods for decreasing the rate of senescence of a subject, e.g., after onset of senescence; methods for extending the lifespan of a subject; methods for recovering from, treating, or preventing a disease or condition relating to lifespan; methods for recovering from, treating, or preventing a disease or condition relating to the proliferative capacity of cells; and methods for recovering from, treating, or preventing a disease or condition resulting from cell damage or death. In certain embodiments, the disease or condition does not result from oxidative stress. In certain embodiments, a method does not significantly increase the resistance of the subject to oxidative stress. In certain embodiments, the method does not act by decreasing the rate of occurrence of diseases that shorten the lifespan of a subject. In certain embodiments, a method does not act by reducing the lethality caused by a disease, such as cancer.

In yet another embodiment, any of the compositions described herein is administered to a subject, such as to generally increase the lifespan of its cells and to protect its cells against stress and/or against apoptosis. It is believed that treating a subject with a composition described herein is similar to subjecting the subject to hormesis, i.e., mild stress that is beneficial to organisms and may extend their lifespan. For example, a composition can be taken by subjects as a food or dietary supplement. In one embodiment, such a composition is a component of a multi-vitamin complex. Compositions can also be added to existing formulations that are taken on a daily basis, e.g., statins and aspirin. Compositions may also be used as food additives.

Compositions described herein could also be taken as one component of a multi-drug complex or as a supplement in addition to a multi-drug regimen. In one embodiment, this multi-drug complex or regimen would include drugs or compositions for the treatment or prevention of aging-related diseases, e.g., stroke, heart disease, arthritis, high blood pressure, Alzheimer's. In another embodiment, this multi-drug regimen would include chemotherapeutic drugs for the treatment of cancer. In a specific embodiment, a composition could be used to protect non-cancerous cells from the effects of chemotherapy or for recovering from, treating, or preventing chemotherapy-induced damage.

Chemotherapeutic agents that may be coadministered with compositions described herein as having anti-cancer activity include: aminoglutethimide, amsacrine, anastrozole, asparaginase, bcg, bicalutamide, bleomycin, buserelin, busulfan, camptothecin, capecitabine, carboplatin, carmustine, chlorambucil, cisplatin, cladribine, clodronate, colchicine, cyclophosphamide, cyproterone, cytarabine, dacarbazine, dactinomycin, daunorubicin, dienestrol, diethylstilbestrol, docetaxel, doxorubicin, epirubicin, estradiol, estramustine, etoposide, exemestane, filgrastim, fludarabine, fludrocortisone, fluorouracil, fluoxymesterone, flutamide, gemcitabine, genistein, goserelin, hydroxyurea, idarubicin, ifosfamide, imatinib, interferon, irinotecan, irinotecan, letrozole, leucovorin, leuprolide, levamisole, lomustine, mechlorethamine, medroxyprogesterone, megestrol, melphalan, mercaptopurine, mesna, methotrexate, mitomycin, mitotane, mitoxantrone, nilutamide, nocodazole, ocreotide, oxaliplatin, paclitaxel, pamidronate, pentostatin, plicamycin, porfimer, procarbazine, raltitrexed, rituximab, streptozocin, suramin, tamoxifen, temozolomide, teniposide, testosterone, thioguanine, thiotepa, titanocene dichloride, topotecan, trastuzumab, tretinoin, vinblastine, vincristine, vindesine, and vinorelbine.

These chemotherapeutic agents may be categorized by their mechanism of action into, for example, following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disrupters such as taxane (paclitaxel, docetaxel), vincristin, vinblastin, nocodazole, epothilones and navelbine, epidipodophyllotoxins (teniposide), DNA damaging agents (actinomycin, amsacrine, anthracyclines, bleomycin, busulfan, camptothecin, carboplatin, chlorambucil, cisplatin, cyclophosphamide, cytoxin, dactinomycin, daunorubicin, docetaxel, doxorubicin, epirubicin, hexamethylmelamineoxaliplatin, iphosphamide, melphalan, mechlorethamine, mitomycin, mitoxantrone, nitrosourea, paclitaxel, plicamycin, procarbazine, teniposide, triethiylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, COX-2 inhibitors, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compositions (TNP-470, genistein) and growth factor inhibitors (vascular endothelial growth factor (VEGF) inhibitors, fibroblast growth factor (FGF) inhibitors, epidermal growth factor (EGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylprednisolone, prednisone, and prednisolone); growth factor signal transduction kinase inhibitors; mitochondrial dysfunction inducers and caspase activators; chromatin disrupters.

These chemotherapeutic agents may be used by themselves with a composition described herein as inducing cell death or reducing lifespan or increasing sensitivity to stress and/or in combination with other chemotherapeutics agents. Many combinatorial therapies have been developed, including but not limited to, those listed in Table 5.

TABLE 5

Exemplary conventional combination cancer chemotherapy

| Name | Therapeutic agents |
| --- | --- |
| ABV | Doxorubicin, Bleomycin, Vinblastine |
| ABVD | Doxorubicin, Bleomycin, Vinblastine, Dacarbazine |
| AC (Breast) | Doxorubicin, Cyclophosphamide |
| AC (Sarcoma) | Doxorubicin, Cisplatin |
| AC (Neuroblastoma) | Cyclophosphamide, Doxorubicin |
| ACE | Cyclophosphamide, Doxorubicin, Etoposide |
| ACe | Cyclophosphamide, Doxorubicin |
| AD | Doxorubicin, Dacarbazine |
| AP | Doxorubicin, Cisplatin |
| ARAC-DNR | Cytarabine, Daunorubicin |
| B-CAVe | Bleomycin, Lomustine, Doxorubicin, Vinblastine |
| BCVPP | Carmustine, Cyclophosphamide, Vinblastine, Procarbazine, Prednisone |
| BEACOPP | Bleomycin, Etoposide, Doxorubicin, Cyclophosphamide, Vincristine, Procarbazine, Prednisone, Filgrastim |
| BEP | Bleomycin, Etoposide, Cisplatin |
| BIP | Bleomycin, Cisplatin, Ifosfamide, Mesna |
| BOMP | Bleomycin, Vincristine, Cisplatin, Mitomycin |
| CA | Cytarabine, Asparaginase |
| CABO | Cisplatin, Methotrexate, Bleomycin, Vincristine |
| CAF | Cyclophosphamide, Doxorubicin, Fluorouracil |
| CAL-G | Cyclophosphamide, Daunorubicin, Vincristine, Prednisone, Asparaginase |
| CAMP | Cyclophosphamide, Doxorubicin, Methotrexate, Procarbazine |
| CAP | Cyclophosphamide, Doxorubicin, Cisplatin |
| CaT | Carboplatin, Paclitaxel |
| CAV | Cyclophosphamide, Doxorubicin, Vincristine |
| CAVE ADD | CAV and Etoposide |
| CA-VP16 | Cyclophosphamide, Doxorubicin, Etoposide |
| CC | Cyclophosphamide, Carboplatin |
| CDDP/VP-16 | Cisplatin, Etoposide |
| CEF | Cyclophosphamide, Epirubicin, Fluorouracil |
| CEPP(B) | Cyclophosphamide, Etoposide, Prednisone, with or without/Bleomycin |
| CEV | Cyclophosphamide, Etoposide, Vincristine |
| CF | Cisplatin, Fluorouracil or Carboplatin Fluorouracil |
| CHAP | Cyclophosphamide or Cyclophosphamide, Altretamine, Doxorubicin, Cisplatin |
| ChlVPP | Chlorambucil, Vinblastine, Procarbazine, Prednisone |
| CHOP | Cyclophosphamide, Doxorubicin, Vincristine, Prednisone |
| CHOP-BLEO | Add Bleomycin to CHOP |
| CISCA | Cyclophosphamide, Doxorubicin, Cisplatin |
| CLD-BOMP | Bleomycin, Cisplatin, Vincristine, Mitomycin |
| CMF | Methotrexate, Fluorouracil, Cyclophosphamide |
| CMFP | Cyclophosphamide, Methotrexate, Fluorouracil, Prednisone |
| CMFVP | Cyclophosphamide, Methotrexate, Fluorouracil, Vincristine, Prednisone |
| CMV | Cisplatin, Methotrexate, Vinblastine |
| CNF | Cyclophosphamide, Mitoxantrone, Fluorouracil |
| CNOP | Cyclophosphamide, Mitoxantrone, Vincristine, Prednisone |
| COB | Cisplatin, Vincristine, Bleomycin |
| CODE | Cisplatin, Vincristine, Doxorubicin, Etoposide |
| COMLA | Cyclophosphamide, Vincristine, Methotrexate, Leucovorin, Cytarabine |
| COMP | Cyclophosphamide, Vincristine, Methotrexate, Prednisone |
| Cooper Regimen | Cyclophosphamide, Methotrexate, Fluorouracil, Vincristine, Prednisone |
| COP | Cyclophosphamide, Vincristine, Prednisone |
| COPE | Cyclophosphamide, Vincristine, Cisplatin, Etoposide |
| COPP | Cyclophosphamide, Vincristine, Procarbazine, Prednisone |
| CP(Chronic lymphocytic leukemia) | Chlorambucil, Prednisone |

TABLE 5-continued

Exemplary conventional combination cancer chemotherapy

| Name | Therapeutic agents |
|---|---|
| CP (Ovarian Cancer) | Cyclophosphamide, Cisplatin |
| CT | Cisplatin, Paclitaxel |
| CVD | Cisplatin, Vinblastine, Dacarbazine |
| CVI | Carboplatin, Etoposide, Ifosfamide, Mesna |
| CVP | Cyclophosphamide, Vincristine, Prednisome |
| CVPP | Lomustine, Procarbazine, Prednisone |
| CYVADIC | Cyclophosphamide, Vincristine, Doxorubicin, Dacarbazine |
| DA | Daunorubicin, Cytarabine |
| DAT | Daunorubicin, Cytarabine, Thioguanine |
| DAV | Daunorubicin, Cytarabine, Etoposide |
| DCT | Daunorubicin, Cytarabine, Thioguanine |
| DHAP | Cisplatin, Cytarabine, Dexamethasone |
| DI | Doxorubicin, Ifosfamide |
| DTIC/Tamoxifen | Dacarbazine, Tamoxifen |
| DVP | Daunorubicin, Vincristine, Prednisone |
| EAP | Etoposide, Doxorubicin, Cisplatin |
| EC | Etoposide, Carboplatin |
| EFP | Etoposie, Fluorouracil, Cisplatin |
| ELF | Etoposide, Leucovorin, Fluorouracil |
| EMA 86 | Mitoxantrone, Etoposide, Cytarabine |
| EP | Etoposide, Cisplatin |
| EVA | Etoposide, Vinblastine |
| FAC | Fluorouracil, Doxorubicin, Cyclophosphamide |
| FAM | Fluorouracil, Doxorubicin, Mitomycin |
| FAMTX | Methotrexate, Leucovorin, Doxorubicin |
| FAP | Fluorouracil, Doxorubicin, Cisplatin |
| F-CL | Fluorouracil, Leucovorin |
| FEC | Fluorouracil, Cyclophosphamide, Epirubicin |
| FED | Fluorouracil, Etoposide, Cisplatin |
| FL | Flutamide, Leuprolide |
| FZ | Flutamide, Goserelin acetate implant |
| HDMTX | Methotrexate, Leucovorin |
| Hexa-CAF | Altretamine, Cyclophosphamide, Methotrexate, Fluorouracil |
| ICE-T | Ifosfamide, Carboplatin, Etoposide, Paclitaxel, Mesna |
| IDMTX/6-MP | Methotrexate, Mercaptopurine, Leucovorin |
| IE | Ifosfamide, Etoposie, Mesna |
| IfoVP | Ifosfamide, Etoposide, Mesna |
| IPA | Ifosfamide, Cisplatin, Doxorubicin |
| M-2 | Vincristine, Carmustine, Cyclophosphamide, Prednisone, Melphalan |
| MAC-III | Methotrexate, Leucovorin, Dactinomycin, Cyclophosphamide |
| MACC | Methotrexate, Doxorubicin, Cyclophosphamide, Lomustine |
| MACOP-B | Methotrexate, Leucovorin, Doxorubicin, Cyclophosphamide, Vincristine, Bleomycin, Prednisone |
| MAID | Mesna, Doxorubicin, Ifosfamide, Dacarbazine |
| m-BACOD | Bleomycin, Doxorubicin, Cyclophosphamide, Vincristine, Dexamethasone, Methotrexate, Leucovorin |
| MBC | Methotrexate, Bleomycin, Cisplatin |
| MC | Mitoxantrone, Cytarabine |
| MF | Methotrexate, Fluorouracil, Leucovorin |
| MICE | Ifosfamide, Carboplatin, Etoposide, Mesna |
| MINE | Mesna, Ifosfamide, Mitoxantrone, Etoposide |
| mini-BEAM | Carmustine, Etoposide, Cytarabine, Melphalan |
| MOBP | Bleomycin, Vincristine, Cisplatin, Mitomycin |
| MOP | Mechlorethamine, Vincristine, Procarbazine |
| MOPP | Mechlorethamine, Vincristine, Procarbazine, Prednisone |
| MOPP/ABV | Mechlorethamine, Vincristine, Procarbazine, Prednisone, Doxorubicin, Bleomycin, Vinblastine |
| MP (multiple myeloma) | Melphalan, Prednisone |
| MP (prostate cancer) | Mitoxantrone, Prednisone |
| MTX/6-MO | Methotrexate, Mercaptopurine |
| MTX/6-MP/VP | Methotrexate, Mercaptopurine, Vincristine, Prednisone |
| MTX-CDDPAdr | Methotrexate, Leucovorin, Cisplatin, Doxorubicin |
| MV (breast cancer) | Mitomycin, Vinblastine |
| MV (acute myelocytic leukemia) | Mitoxantrone, Etoposide |
| M-VAC Methotrexate | Vinblastine, Doxorubicin, Cisplatin |
| MVP Mitomycin | Vinblastine, Cisplatin |
| MVPP | Mechlorethamine, Vinblastine, Procarbazine, Prednisone |
| NFL | Mitoxantrone, Fluorouracil, Leucovorin |
| NOVP | Mitoxantrone, Vinblastine, Vincristine |
| OPA | Vincristine, Prednisone, Doxorubicin |
| OPPA | Add Procarbazine to OPA. |
| PAC | Cisplatin, Doxorubicin |
| PAC-I | Cisplatin, Doxorubicin, Cyclophosphamide |
| PA-CI | Cisplatin, Doxorubicin |

TABLE 5-continued

Exemplary conventional combination cancer chemotherapy

| Name | Therapeutic agents |
|---|---|
| PC | Paclitaxel, Carboplatin or Paclitaxel, Cisplatin |
| PCV | Lomustine, Procarbazine, Vincristine |
| PE | Paclitaxel, Estramustine |
| PFL | Cisplatin, Fluorouracil, Leucovorin |
| POC | Prednisone, Vincristine, Lomustine |
| ProMACE | Prednisone, Methotrexate, Leucovorin, Doxorubicin, Cyclophosphamide, Etoposide |
| ProMACE/cytaBOM | Prednisone, Doxorubicin, Cyclophosphamide, Etoposide, Cytarabine, Bleomycin, Vincristine, Methotrexate, Leucovorin, Cotrimoxazole |
| PRoMACE/MOPP | Prednisone, Doxorubicin, Cyclophosphamide, Etoposide, Mechlorethamine, Vincristine, Procarbazine, Methotrexate, Leucovorin |
| Pt/VM | Cisplatin, Teniposide |
| PVA | Prednisone, Vincristine, Asparaginase |
| PVB | Cisplatin, Vinblastine, Bleomycin |
| PVDA | Prednisone, Vincristine, Daunorubicin, Asparaginase |
| SMF | Streptozocin, Mitomycin, Fluorouracil |
| TAD | Mechlorethamine, Doxorubicin, Vinblastine, Vincristine, Bleomycin, Etoposide, Prednisone |
| TCF | Paclitaxel, Cisplatin, Fluorouracil |
| TIP | Paclitaxel, Ifosfamide, Mesna, Cisplatin |
| TTT | Methotrexate, Cytarabine, Hydrocortisone |
| Topo/CTX | Cyclophosphamide, Topotecan, Mesna |
| VAB-6 | Cyclophosphamide, Dactinomycin, Vinblastine, Cisplatin, Bleomycin |
| VAC | Vincristine, Dactinomycin, Cyclophosphamide |
| VACAdr | Vincristine, Cyclophosphamide, Doxorubicin, Dactinomycin, Vincristine |
| VAD | Vincristine, Doxorubicin, Dexamethasone |
| VATH | Vinblastine, Doxorubicin, Thiotepa, Flouxymesterone |
| VBAP | Vincristine, Carmustine, Doxorubicin, Prednisone |
| VBCMP | Vincristine, Carmustine, Melphalan, Cyclophosphamide, Prednisone |
| VC | Vinorelbine, Cisplatin |
| VCAP | Vincristine, Cyclophosphamide, Doxorubicin, Prednisone |
| VD | Vinorelbine, Doxorubicin |
| VelP | Vinblastine, Cisplatin, Ifosfamide, Mesna |
| VIP | Etoposide, Cisplatin, Ifosfamide, Mesna |
| VM | Mitomycin, Vinblastine |
| VMCP | Vincristine, Melphalan, Cyclophosphamide, Prednisone |
| VP | Etoposide, Cisplatin |
| V-TAD | Etoposide, Thioguanine, Daunorubicin, Cytarabine |
| 5 + 2 | Cytarabine, Daunorubicin, Mitoxantrone |
| 7 + 3 | Cytarabine with/, Daunorubicin or Idarubicin or Mitoxantrone |
| "8 in 1" | Methylprednisolone, Vincristine, Lomustine, Procarbazine, Hydroxyurea, Cisplatin, Cytarabine, Dacarbazine |

In addition to conventional chemotherapeutics, the compositions described herein as capable of inducing cell death or reducing lifespan can also be used with antisense RNA, RNAi or other polynucleotides to inhibit the expression of the cellular components that contribute to unwanted cellular proliferation that are targets of conventional chemotherapy. Such targets are, merely to illustrate, growth factors, growth factor receptors, cell cycle regulatory proteins, transcription factors, or signal transduction kinases.

The methods may be advantageous over combination therapies known in the art because they may allow conventional chemotherapeutic agents to exert greater effect at lower dosage. In a preferred embodiment, the effective dose ($ED_{50}$) for a chemotherapeutic agent or combination of conventional chemotherapeutic agents when used in combination with a composition described herein is at least 2 fold less than the ED50 for the chemotherapeutic agent alone, and even more preferably at 5 fold, 10 fold or even 25 fold less. Conversely, the therapeutic index (TI) for such chemotherapeutic agent or combination of such chemotherapeutic agent when used in combination with a composition described herein can be at least 2 fold greater than the TI for conventional chemotherapeutic regimen alone, and even more preferably at 5 fold, 10 fold or even 25 fold greater.

Other combination therapies include conjoint administration with nicotinamide, NAD+ or salts thereof, or other Vitamin B3 analogs. Carnitines, such as L-carnitine, may also be co-administered, particularly for recovering from, treating, or preventing cerebral stroke, loss of memory, pre-senile dementia, Alzheimer's disease or preventing or treating disorders elicited by the use of neurotoxic drugs. Cyclooxygenase inhibitors, e.g., a COX-2 inhibitor, may also be co-administered for recovering from, treating, or preventing certain conditions described herein, such as an inflammatory condition or a neurologic disease.

Pharmaceutical Compositions

Compounds, nucleic acids, proteins, antibodies cells and other compositions can be administered to a subject according to methods known in the art. For example, nucleic acids encoding a protein or an antisense molecule can be administered to a subject as described above, e.g., using a viral vector. Cells can be administered according to methods for administering a graft to a subject, which may be accompanied, e.g., by administration of an immunosuppressant drug, e.g., cyclosporin A. For general principles in medicinal formulation, the reader is referred to *Cell Therapy: Stem Cell Transplantation, Gene Therapy, and Cellular Immunotherapy*, by G. Morstyn & W. Sheridan eds, Cambridge University Press, 1996; and *Hematopoietic Stem Cell Therapy*, E. D. Ball, J. Lister & P. Law, Churchill Livingstone, 2000.

The compounds of this invention are formulated with conventional carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. All formulations will optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10. While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof. The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth (such as oral mucositis, gum disease, periodontal disease, tooth decay) and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween™ 60, Span™ 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a combination according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 .mu.g of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of HCV infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active viral infection, the method of delivery, and the pharmaceutical formulation, and will be determined by the clinician using conventional dose escalation studies. It can be expected to be from about 0.0001 to about 100 mg/kg body weight per day; typically, from about 0.01 to about 10 mg/kg body weight per day; more typically, from about 0.01 to about 5 mg/kg body weight per day; most typically, from about 0.05 to about 0.5 mg/kg body weight per day. For example, the daily candidate dose for an adult human of approximately 70 kg body weight will range from 1 mg to 1000 mg, preferably between 5 mg and 500 mg, and may take the form of single or multiple doses.

One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual*, $2^{nd}$ Ed., ed. by Sambrook, Fritsch and Maniatis (Cold Spring Harbor Laboratory Press: 1989); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); Transcription And Translation (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, Methods In Enzymology (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); *Manipulating the Mouse Embryo*, (Cold Spring Harbor Laboratory Press, Cold Spring Harbor, N.Y., 1986).

As can be appreciated from the disclosure above, the present invention has a wide variety of applications. The invention is further illustrated by the following examples, which are only illustrative and are not intended to limit the definition and scope of the invention in any way.

EXAMPLES

Example 1: Materials and Methods

1. Chemical Reagents

All chemicals were purchased from Sigma Aldrich, with the following exceptions: PJ34 (Orchid Pharmaceuticals), 3-AB (Calbiochem) and EX-527 (Tocris Bioscience). NR and carba-NAD were synthesized and provided by Sirtris, a GSK company.

2. Constructs/Mutagenesis

The constructs used for stable expression of full-length and truncated human Flag-DBC1, have been previously described (24). The transient expression plasmids for human pcDNA 3.1 V5/His-DBC1 were constructed by cloning human DBC1 cDNA into pcDNA3.1 vector. Myc-DDK-tagged human PARP1 (Flag-PARP1) was purchased from OriGene (RC207085). Point mutants or deletion mutants for Flag-DBC1, V5/His-DBC1 or Flag-PARP1 were generated using Quickchange II XL Site Directed Mutagenesis kit (Stratagene), and verified by DNA sequencing (Dana-Farber/Harvard Cancer Center DNA Resource Core, Boston, MA). The constructs overexpressing mouse NMNAT1: pEGFP-N1 vector and pEGFP-N2-NMNAT1, were gifts from Dr. Shin-Ichiro Imai, Washington University School of Medicine (25). The constructs overexpressing the rat BRCT domain of PARP1 was a gift from Dr. Robert London, National Institute of Environmental Health (26). The construct overexpressing human MACROD1 was purchased from Addgene (#39041). The constructs overexpressing the catalytic domain of human PARP1 was a gift from Dr. Lee Kraus, University of Texas Southwest Medical Center (27). The shRNA constructs for SIRT1 (TRCN0000018979, TRCN0000018983) and DBC1 (TRCN0000053723 and TRCN0000053725) were both in pLKO.1 vector and purchased from Open Biosystems. The control shRNA for both SIRT1 and DBC1 was a TRC lentiviral pLKO.1 vector (#RHS4080). The siRNAs for human DBC1 (sc-72274), human PARP1 (sc-29437) and control siRNA (sc-36869) were from Santa Cruz.

3. Cell Culture, Transfection and Infection

293T, MCF-7, DBC1 wild type and knockout MEFs (a gift from Dr. Eduardo N. Chini from Mayo Clinic) were cultured in Dulbecco's modified Eagle's medium (DMEM, Mediatech, Inc., Herndon, VA) supplemented with 10% fetal bovine serum (Gemini Bio-products, Woodland, CA) with the presence of penicillin and streptomycin (Corning, Manassas, VA). Retroviruses expressing wild-type or mutant Flag-DBC1 proteins were produced by transfecting 293T cells with plasmids encoding VSV-G, Gag-Pol, and pMSCVpuro-Flag-DBC1 constructs using Lipofectamine® 2000 according to the manufacturer's instructions. Media was changed the day after transfection, and virus-containing media was harvested between 48 and 72 hours post-transfection and filtered through a 0.45 mm filter (Corning, Manassas, VA). The filtered media was incubated with the target cells in the presence of 5 µg/mL polybrene (Sigma) and selection started using puromycin (2 µg/mL) 48 hrs post-infection. Lentivirus for knocking down DBC1 or SIRT1 was produced by transfecting 293T with psPAX2 (Addgene plasmid #12260), pMD2.G (Addgene plasmid #12259) and shRNA constructs using Lipofectamine® 2000. The virus harvest, infection and selection were same as described for retrovirus production. The transfections of siRNA were performed using Lipofectamine® RNAiMAX, according to the manufacturer's instructions.

The human primary fibroblast cells were cultured in Dulbecco's modified Eagle's medium supplemented with 15% fetal bovine serum in a low oxygen incubator (3% oxygen, 5% $CO_2$, 37° C.).

4. Immunoprecipitation

Protein extracts from 293T or mouse liver tissues were lysed in ice-cold buffer (150 mM NaCl, 1 mM EDTA, 1 mM EGTA, 1% Triton X-100, 0.5% NP-40, 10 mM Tris HCl, pH 7.4) supplemented with protease inhibitors cocktail cOmplete tablets (Roche) and phosphatase inhibitor cocktail 2 and 3 (Sigma). Protein concentrations were determined by the Bradford protein assay (Bio-rad). Flag-M2 agarose beads or anti-V5 agarose affinity gel (Sigma) were mixed with the lysate supernatant. Immunoprecipitation was allowed to proceed for 2 hours up to overnight at 4° C. with gentle rotation. After 4 washes with lysis buffer, proteins were either directly boiled in SDS-PAGE sample buffer or eluted from the agarose beads using 3×FLAG peptides (Sigma).

5. Immunoblotting

Cell lysates or Co-IP samples were run on homemade 10% or 4-20% gradient pre-cast SDS-PAGE gels (Bio-Rad) under reducing conditions, and then transferred to a polyvinylidene difluoride (PVDF) membrane (Millipore). Membranes were blocked with 5% non-fat dry milk in TBS-Tween (10 mM Tris HCl, pH 7.5, 150 mM NaCl, and 0.1% Tween-20). Antibodies were used at the following concentrations: anti-SIRT1 (Santa Cruz, SC-15404) at 1:500, anti-DBC1 (Bethyl Laboratories, A300-434A) at 1:1000, anti-PARP1 (Cell Signaling, #9542L) at 1:1000, anti-γH2AX (Abcam, ab2893) at 1:1000, anti-H2AX (Abcam, ab11175) at 1:1000, anti-NMNAT1 (Abcam, ab45548) at 1:1000, anti-GAPDH (Millipore, MAB374) at 1:3000, anti-V5 (Invitrogen, R960-25) at 1:3000, anti-beta-tubulin (Upstate, 05-661) at 1:1000, anti-α-actin (Millipore, MAB1501R) at 1:2000, anti-Flag (Sigma, F7425) at 1:3000, anti-PARG (Abcam, ab16060) at 1:1000, p53 (Calbiochem, OP43) at 1:1000, RAD51 (Calbiochem, PC130) at 1:1000, p21 (Neomarker-Labvision-Thermal Fisher, RB-032-P1) at 1:1000, SIRT6 (Cell signaling, D8D12) at 1:1000, Streptavidin-HRP at 1:1000 (Trevigen #4800-30-06), anti-PAR (Trevigen, #4335-MC-100; Abcam, ab14459) at 1:1000 and anti-PARP2 (Santa Cruz, SC-393310) at 1:200 overnight at 4° C. The antibodies ATM, ATR, BRCA1, Chk1, Chk2, DNA-PKs and XRCC1 were all from the Bethyl Laboratories. Phospho-Chk1, phospho-Chk2 and phosphor-p53 antibodies were from a DNA Damage Antibody Sampler Kit (Cell Signaling #9947). Secondary antibodies were horseradish peroxidase-coupled sheep anti-mouse IgG (GE Healthcare, UK), donkey anti-rabbit IgG (GE Healthcare, UK). Amersham™ ECL and Amersham Select ECL western blotting detection systems (GE Healthcare, UK) were used to develop signals. Quantifications of images from western blot films were performed using ImageJ (National Institutes of Health, Bethesda, MD).

6. PARP1-DBC1 Dissociation Assays

Equal aliquots of 293T cell lysates with over-expressing Flag-DBC1 were immunoprecipitated using Flag-M2 agarose beads as described above. After four brief washes with lysis buffer, the beads aliquots were incubated with the freshly dissolved $NAD^+$ or other chemicals for 1 hr at 4° C. with gentle rotation then centrifuged (5000 rpm, 5 min). After completely removing supernatant, the beads were boiled in SDS loading buffer, analyzed by SDS-PAGE, and probed with antibodies.

7. $NAD^+$ Quantification $NAD^+$ quantification was conducted with an NAD/NADH Quantification Kit (Biovision, Milpitas, CA) following the manufacturer's instructions and normalized to soluble protein content.

8. $^{32}P$-$NAD^+$ Binding Assays

Empty vector (6 µg), wild type, $DBC1_{Q391A}$ and $DBC1_{A354-396}$ (pcDNA 3.1 vector with V5/his tag) were transfected into 293T cells in 15 cm petri dishes separately, followed by IP using anti-V5 agarose gel as described above. After immunoprecipitation, ⅛ of the purified DBC1 protein bound to beads was boiled in SDS loading buffer and assessed for protein input by dot blotting. The remainder of the protein was incubated with cold $NAD^+$ (1 µM), 8 µCi $^{32}P$ $NAD^+$ (PerkinElmer) in 50 µl incubation buffer (50 mM Tris HCl, 150 mM NaCl and 10 mM DTT, pH7.4) for 2 hrs at 4° C. with gentle rotation. Beads were then washed in 1 ml of the same incubation buffer 3 times, centrifuged, and eluted in 25 µl of incubation buffer with 10 µg/ml V5 peptides on ice for 30 min with occasional shaking. Each elutant (5 µl) was spotted on filter paper and assessed by autoradiography.

9. Biotin-$NAD^+$ Binding Assays

Lysates of 293T cells expressing Flag-DBC1 or V5/his-DBC1 were prepared as described above and bound to an anti-Flag high sensitivity M2 coated 96-well plate (Sigma) or His-Select® high sensitivity nickel coated 96-well plate (Sigma) by incubating for 3-4 hrs at 4° C., then washed three times with lysis buffer. Biotin-$NAD^+$ (Trevigen), or specified molecules were incubated in the plates overnight at 4° C. After washing twice with PBS (pH 7.4) and twice with PBS-T (0.1% Triton X-100), streptavidin-HRP (Trevigen, 1:500) in PBS-T was added to each well and incubated for 1 hr at room temperature. After washing twice with PBS (pH 7.4) and twice with PBS-T, 100 μl of PeroxyGlow™ A and B chemiluminescent substrates (Trevigen) mixture (1:1) was added into each well for 1 min followed by immediate quantification of chemiluminescence on a EnSpire 2300 Multi-label reader (Perkin Elmer). Binding curves were calculated using the "one site, specific binding" formula of GraphPad.

10. Cell Survival

The CellTiter 96® Aqueous One Solution Cell Proliferation Assay (MTS) kit from Promega was used to measure cell survival after treating cells with paraquat for 24 hrs, according to manufacturer's instructions. The absorbance was measured using an EnSpire 2300 Multi-label reader (Perkin Elmer).

11. PARP1 Activity Assay

PARP1 was immunoprecipitated from cell or tissue extracts and activity was determined by a Universal Chemiluminescent PARP Assay Kit (Trevigen, #4676-096-K) that is based on HRP-streptavidin-mediated detection of biotin-labelled PAR. Luminescence was measured on an EnSpire 2300 Multi-label reader (Perkin Elmer).

12. Comet Assay

The CometAssay® kit (Trevigen) was used to detect DNA fragmentation in DBC1 knockdown 293T cells. After treatment with paraquat for 24 hrs, the cells were gently harvested and embedded in an agarose layer on microscope slides provided by the kit. Cells were lysed and DNA was electrophoresed for 30 min at 1 Volt/cm in alkaline conditions. Tails were visualized at a magnification of 200× using a Nikon Eclipse Ti microscope. The comet analysis open software casp_1.2.3b1 was used (casplab.com) to analyze randomly chosen nuclei (n>50) per group.

13. 8-OHdG DNA Damage Quantification

The OxiSelect™ oxidative DNA damage Elisa kit (Cell Biolabs) was used to detect 8-OHdG in mice livers after irradiation. Genomic DNA was extracted from liver using a DNeasy blood and tissue kit (Qiagen).

14. Gene Expression Analysis

MCF-7 Cells were trypsinized and washed in PBS before RNA was extracted using an RNeasy Mini Kit (Qiagen) and quantified using a NanoDrop 1000 spectrophotometer (Thermo Scientific). The cDNA synthesis was performed with iScript™ cDNA Synthesis Kit (Bio-Rad). Quantitative RT-PCR reactions were performed using LightCycler® 480 SYBR Green Master (Roche) on a LightCycler® 96 Real-Time PCR System (Roche). Calculations were performed using GeneEx qPCR data analysis software from Bio-Rad. Gene expression was normalized to housekeeping gene HPRT. Primers used for qPCR:

```
HPRT:
TGCTGAGGATTTGGAAAGGG
and

ACAGAGGGCTACAATGTGATG;

ABHD2:
CACCTCTCTGAGCCTGTTCC
and

CGCAGATGTTCAGCAATGTT;

TMSNB:
TCCCAACAGCAGATTTCGAC
and

GCCAGGGAACATAGGTGAGA;
```

```
PEG10:
CAAGCCACCACCAGGTAGAT
and

GAGGCACAGGTTCAGCTTTC;

NELL2:
TGAAGGGAACCACCTACC
and

ATTTGCCATCCACATACG.
```

15. Mouse Handling and Treatment

C57BL/6J mice were obtained from the National Institutes of Aging (Bethesda, MD) or The Jackson Laboratory (Bar Harbor, ME). Treatment with PBS, NMN (i.p. 500 mg/kg/day) or Olaparib (i.p. 100 mg/kg/day) has been described previously (28). Olaparib (Selleckchem) was first dissolved in DMSO as a stock solution and diluted to final concentrations with the vehicle 10% w/v 2-hydroxypropyl-b-cyclodextrin in PBS prior to injection (Sigma, H107-5G). Mice were allowed to acclimatize to the facility for at least three weeks and all animal procedures were in accordance with the animal care and use policies of the IACUC committee at Harvard Medical School.

16. Protein Sequence Analysis, Structural Modeling and Docking

Iterative profile searches with the PSI-BLAST program (29) were used to retrieve homologous sequences from the protein non-redundant (NR) database at National Center for Biotechnology Information (NCBI). Multiple sequence alignments were built using the Kalign (30) and Promals (31) programs, followed by careful manual adjustments based on profile-profile alignment derived using the HHpred program (32), secondary structure prediction using the Jpred program (33) and using structural alignments. The Modeller9v11 program (34) was utilized for homology modeling the 3-dimensional structure of DBC1-NHD by using multiple PDB templates including *Shewanella oneidensis* NrtR (3gz5), *Aquifex* aeolicus Nudix hydrolase (2yyh), *Caenorhabditis elegans* AP4A hydrolase (1ktg), *Mycobacterium tuberculosis* ADPr pyrophosphatase (1mk1), and *Escherichia coli* GDP mannose hydrolase (1rya). In these low-sequence-identity cases, sequence alignment is the most important factor affecting the quality of the model (35). Alignments were therefore carefully built and cross-validated on the basis of information from HHpred and DaliLite programs, then edited manually using secondary structure information. The model was further refined using KoBaMIN (36). Autodock Vina was implemented in PyRx (http://pyrx.sorceforge.net) for molecular docking analysis, followed by a docked configuration that was based on the known nucleotide binding modes of Nudix enzyme-substrate complexes.

17. Immunohistochemistry and Immunofluorescence

The fresh frozen tissues were sectioned on a Minotome Cryostat (International Equipment Co. USA), fixed in pre-cooled acetone (−20° C.) for 10 min, rinsed in ice-cold PBS buffer (pH 7.4) 3 times for 5 min, then incubated in $H_2O_2$ solution in PBS (0.3% v/v) at room temperature for 10 min to block endogenous peroxidase activity, followed by rinsing in PBS 3 times for 5 min. After incubating with blocking buffer (1% fetal bovine serum in PBS with 0.05% Tween 20) in a humidified chamber at room temperature for 1 hr, the slides were incubated with 7-H2AX antibody (1:200 dilution, Cell signaling, #2577) in blocking buffer for 1 hr at room temperature, rinsed with PBS for 3 times for 5 min.

Anti-rabbit-Horseradish Peroxidase (GE Healthcare, #NA934) was applied as secondary antibody (1:500 diluted in blocking buffer) at room temperature for 1 hr in a humidified chamber. After rinsing with PBS for 3 times for 5 min, freshly made DAB substrate was applied (Thermo Scientific, #34002, USA) for 5 min, followed by counter-staining using Hematoxylin (Mayer's Hematoxylin, Sigma #26043-05) for 2 min and then rinsing in tap water for 15 min before mounting. For immunofluorescence, nuclei were detected by DAPI (Vectashield from Vector Lab, #H-1200) and the 7-H2AX antibody (Cell signaling, #2577) was applied at a 1:200 dilution, then detected using an Alexa Flour® 488 conjugated goat anti-rabbit secondary antibody (Life technology, #A-11034, 1:500 dilution).

18. Blue Native PAGE

The human PARP1-ACAT (residue 1 to 654) and human DBC1-NHD (residue 239 to 553) sequences were cloned into a modified pET19 vector and expressed as fusion proteins containing a N-terminal $His_{x6}$-SUMO tag in *E. coli* Codon+ using an auto-induction method overnight at 20° C. in TB medium supplemented with lactose (0.2% v/v). Both proteins were purified by affinity chromatography (His-Trap column, GE Healthcare) and size-exclusion chromatography (Superdex 200, GE Healthcare). For DBC1, the N-terminal tag was digested with SUMO protease at a protein/protein ratio of 1/100 (w/w) overnight at 4° C. and a second affinity chromatography was performed to separate the SUMO tag and protease from the target protein. Purified PARP1-ACAT and DBC1-NHD proteins were incubated for 30 min on ice prior to addition of glycerol (20% v/v final concentration) and loaded on a two-layer blue native page (5% and 12.5% acrylamide for the stacking and resolving layers, respectively). The blue native PAGE was then run at 4° C. for 2-3 hours at 200V. Marker bands at 240, 67 and 45 kDa corresponding to catalase, bovine serum albumin, and albumin from chicken egg white, respectively, were used to assess molecular weights.

19. DNA Repair Reporter Assays and FACS Analysis

In vivo DNA repair efficiency was measured as described (37). Reporter plasmids for measuring NHEJ or HR repair efficiency were linearized by HindIII (NEB) and purified using QIAquick gel extraction kit (Qiagen). Linearized reporter plasmids (0.5 µg) were co-transfected with pDsRed-express-DR (1.5 µg) using Lipofectamin 2000. Cells were treated with paraquat or 3-AB in 24 hrs post-transfection.

Example 2: A Conserved NAD+ Binding Pocket that Regulates Protein-Protein Interactions During Aging The protein Deleted in Breast Cancer 1 (DBC1) is one of the most abundant, yet enigmatic proteins in mammals (M. Wang et al. *Proteomics* 15, 3163-3168 (2015); S. M. Armour et al. *Mol. Cell. Biochem.* 33, 1487-1502 (2013)), with a conserved domain similar to Nudix hydrolases that hydrolyze nucleoside diphosphates but lacking catalytic activity due to the absence of key catalytic residues (V. Anantharaman et al. *Cell cycle* 7, 1467-1472 (2008); A. S. Mildvan et al. *Arch. Biochem. Biophys.* 433, 129-143 (2005); J. P. Gagne et al. *Nucleic Acids Res.* 36, 6959-6976 (2008)).

Figure 5A:
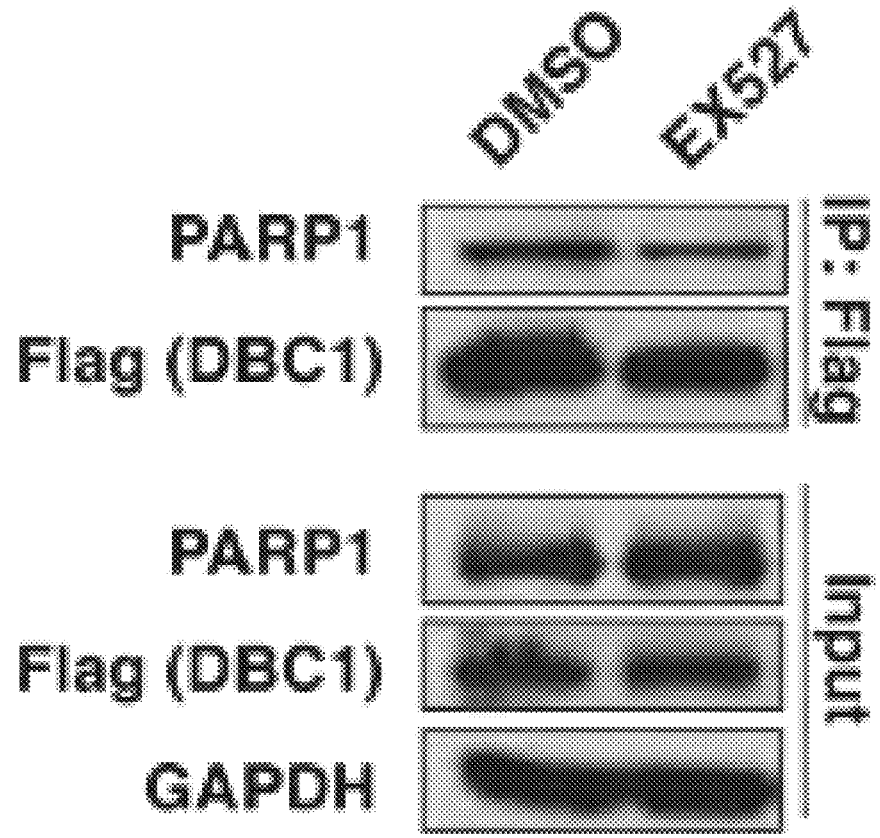
FIG. 5A-FIG. 5E shows that PARP1-DBC1 complex formation is independent of SIRT1 or PARP1 activity.
Figure 5B:
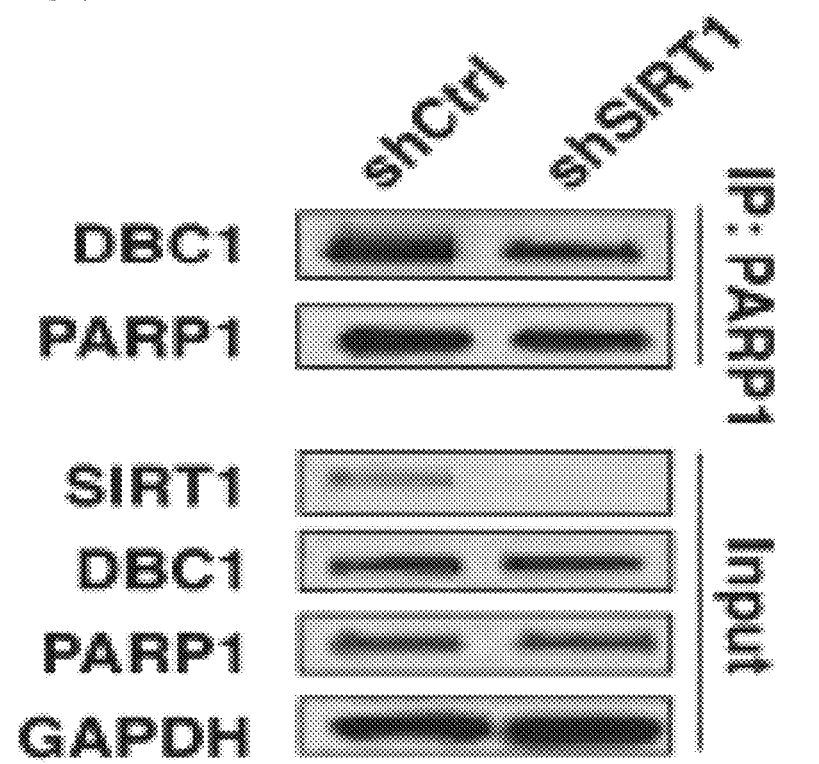
Figure 5C:
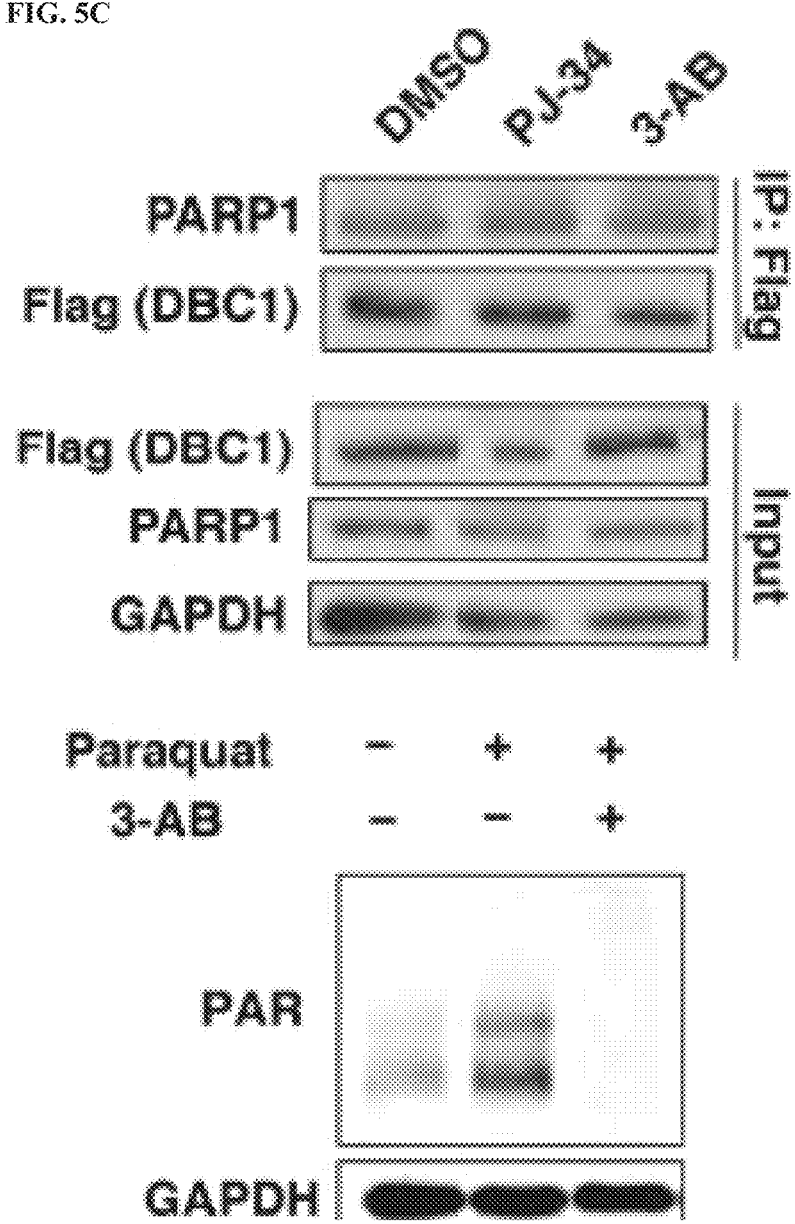
Figure 5D:
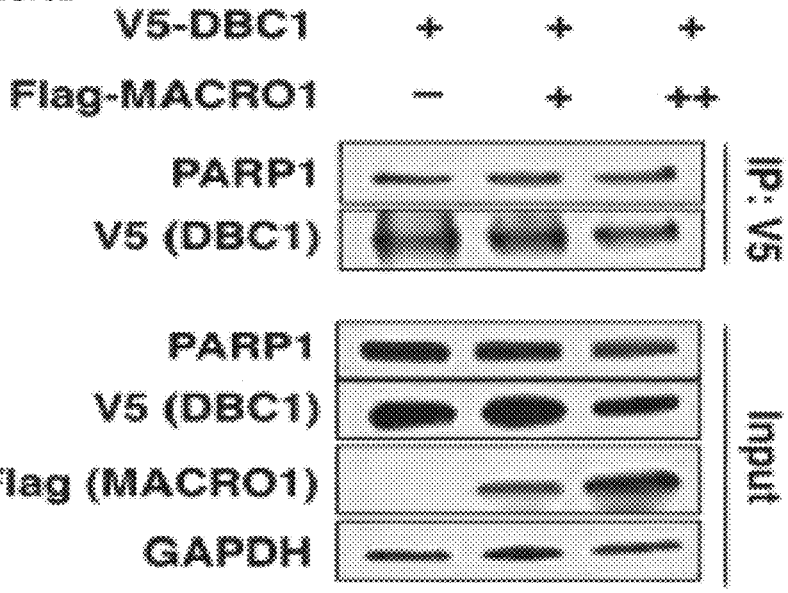
Figure 5E:
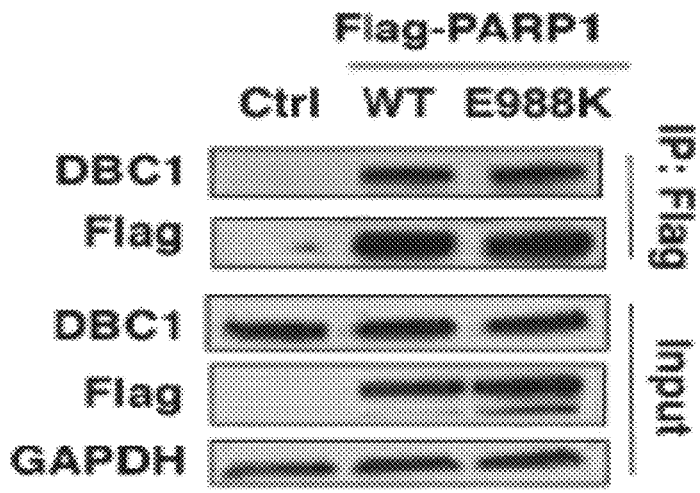
Figure 5E:
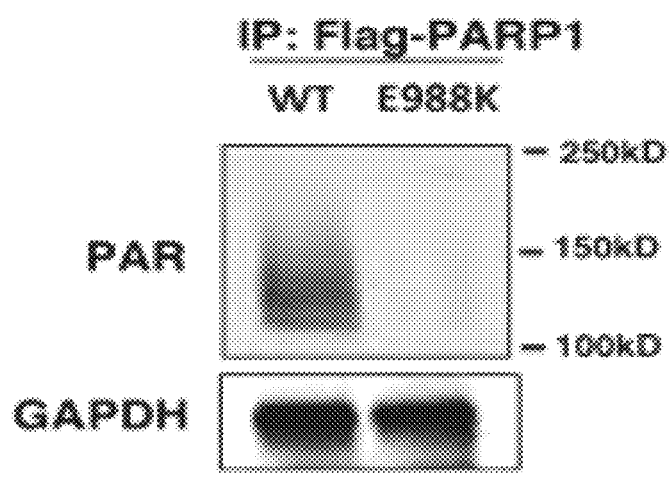

DBC1 is known to inhibit SIRT1 (J. E. Kim et al. *Nature* 451, 583-586 (2008)). Thus, it was tested whether DBC1 might also inhibit PARP1 as a way to co-regulate these two major $NAD^+$-responsive pathways. In human embryonic kidney 293T (293T) cells, a SIRT1-independent interaction between DBC1 and PARP1 was detected (FIG. 1A and FIG. 5A and FIG. 5B). The PARP1 inhibitors PJ-34 or 3-aminobenzamide (3-AB) had no effect on the interaction (FIG. 5C), nor did over-expression of the ADP-ribose hydrolase MACRO Domain containing 1 (MACROD1) (FIG. 5D), or the PARP1 catalytic mutant, PARP1-E988K (FIG. 5E). Thus, PARP1-DBC1 binding is independent of PARP1 catalytic activity.

Figure 1B:
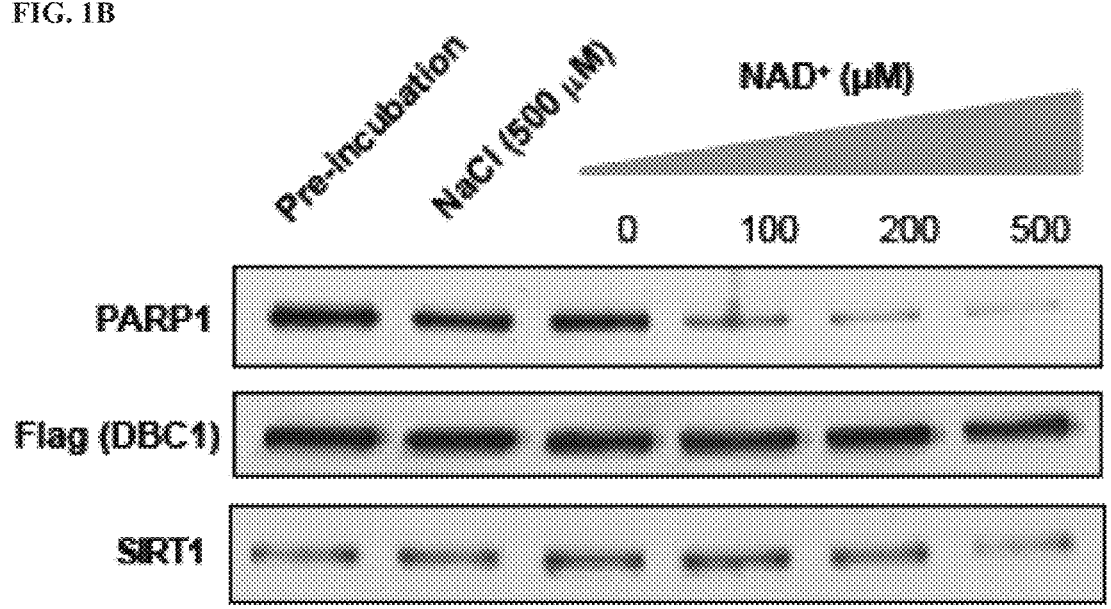
Figure 1C:
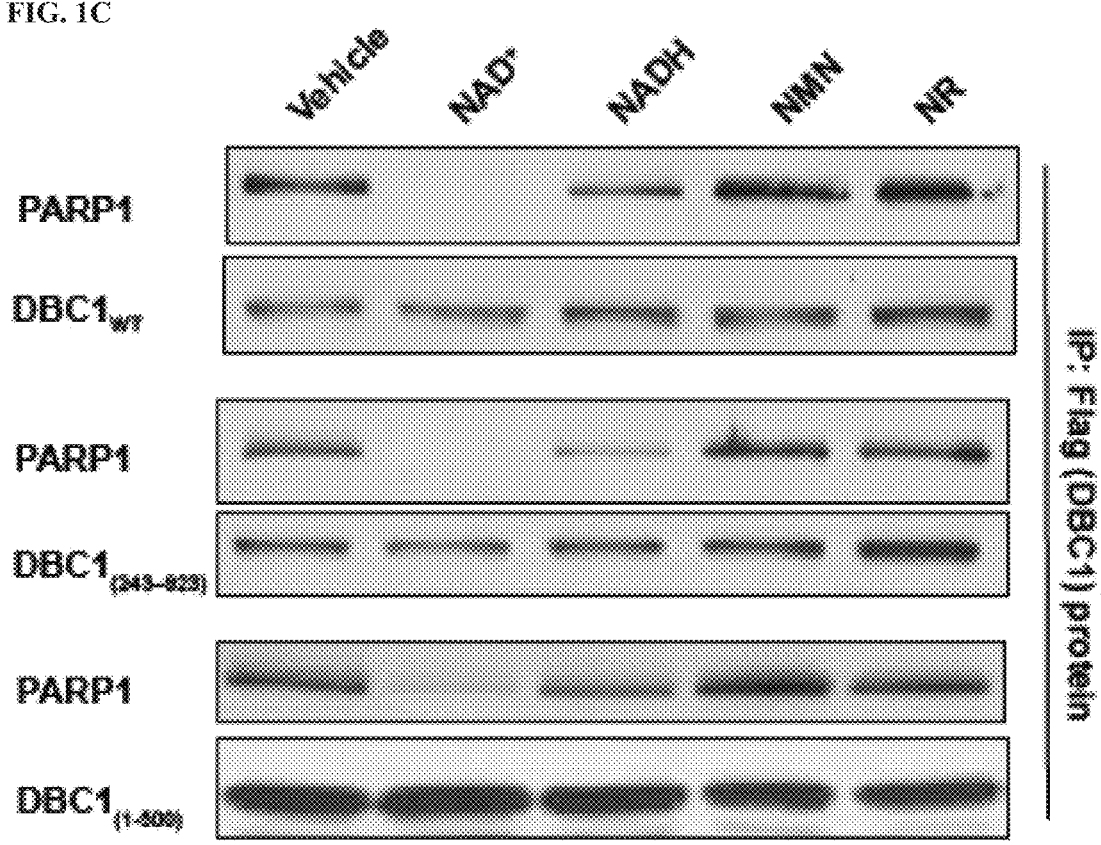
Figure 6A:
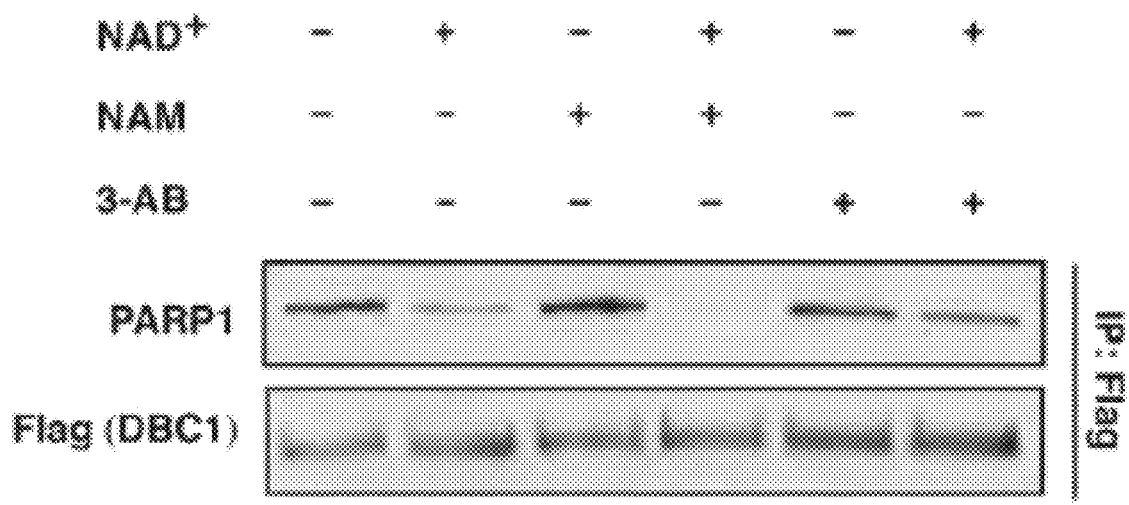
FIG. 6A-FIG. 6F shows the effect of NAD$^+$ on the PARP1-DBC1 complex.
Figure 6B:
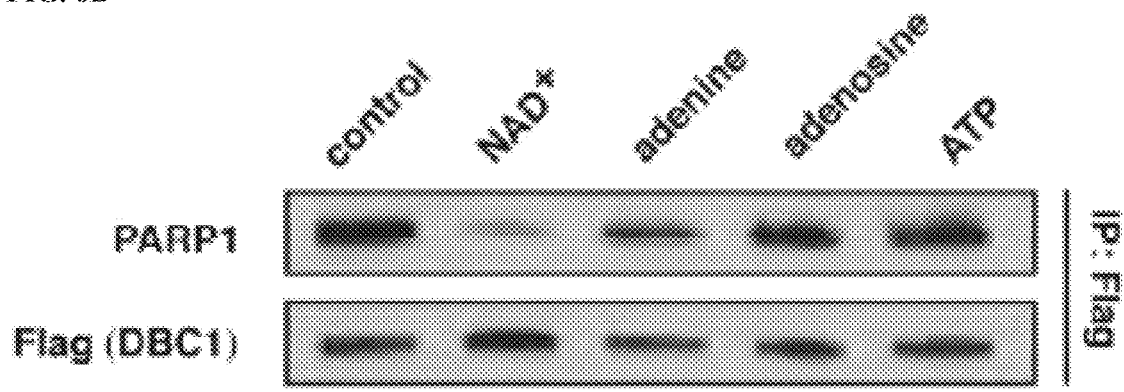
Figure 6C:
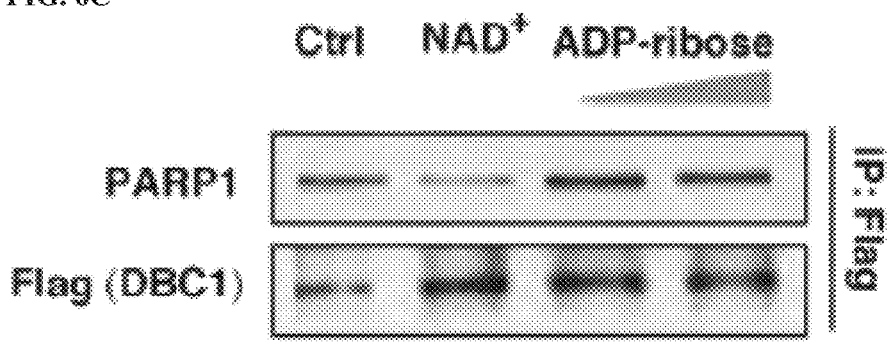

The PARP1-DBC1 complex was abrogated by $NAD^+$ in a concentration-dependent manner, whereas the SIRT1-DBC1 interaction was unaffected within physiological ranges of $NAD^+$ (H. Yang et al., *Cell* 130, 1095-1107 (2007)) except at 500 µM (FIG. 1B). This effect was surprisingly specific: 200 µM of nicotinamide mononucleotide (NMN), nicotinamide riboside (NR), adenosine, adenosine triphosphate (ATP), ADP-ribose (ADPr) or 500 µM of nicotinamide (NAM) and its structural analogue 3-AB (2 mM), had no effect on the PARP1-DBC1 complex, and NADH (200 µM) or adenine (200 µM), were less effective than $NAD^+$ (FIG. 1C and FIG. 6A and FIG. 6C).

Figure 6D:
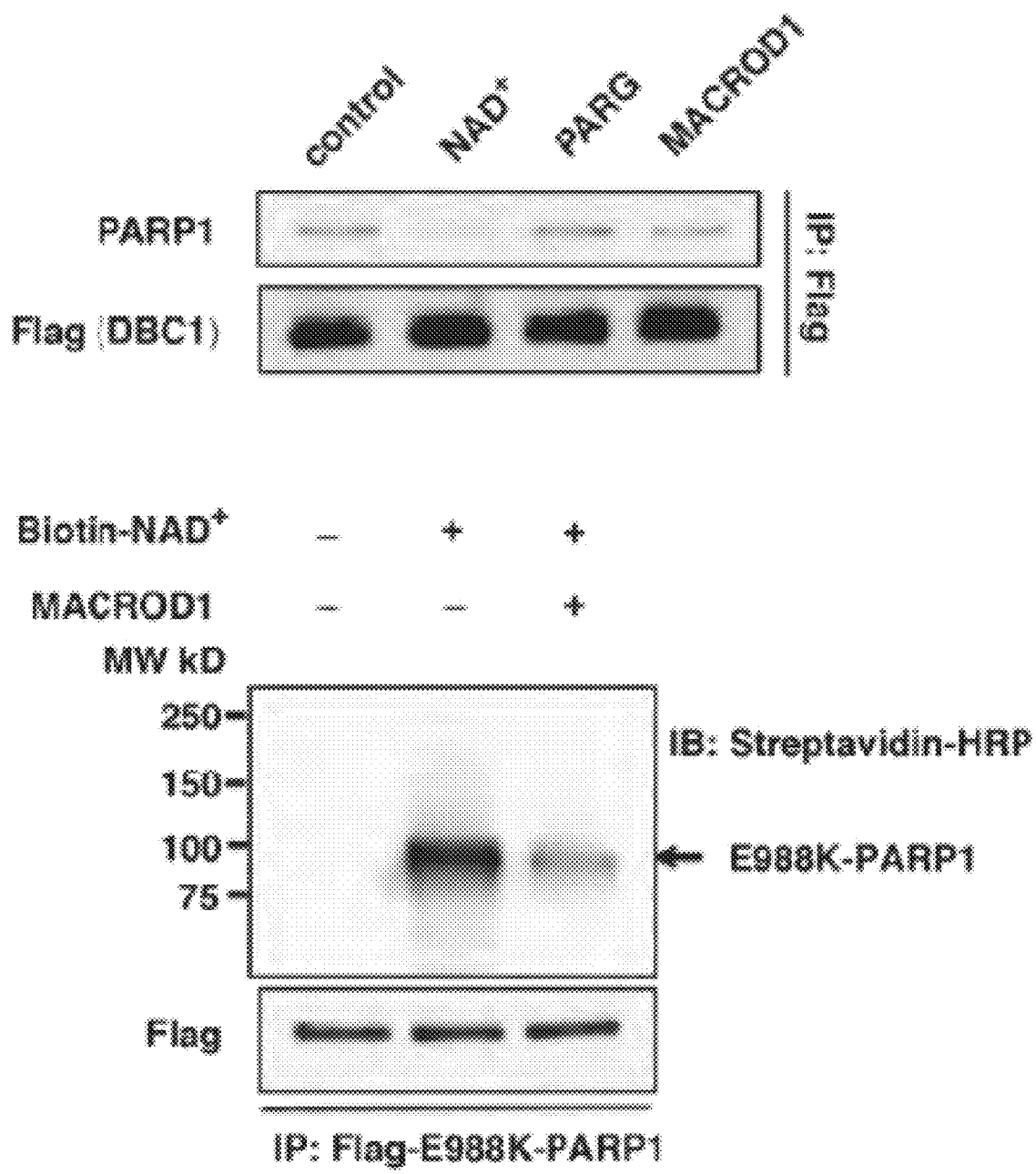
Figure 6E:
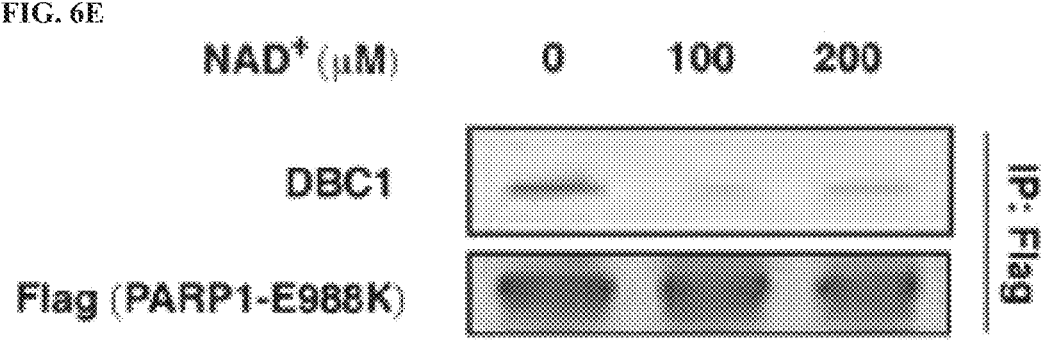
Figure 6F:
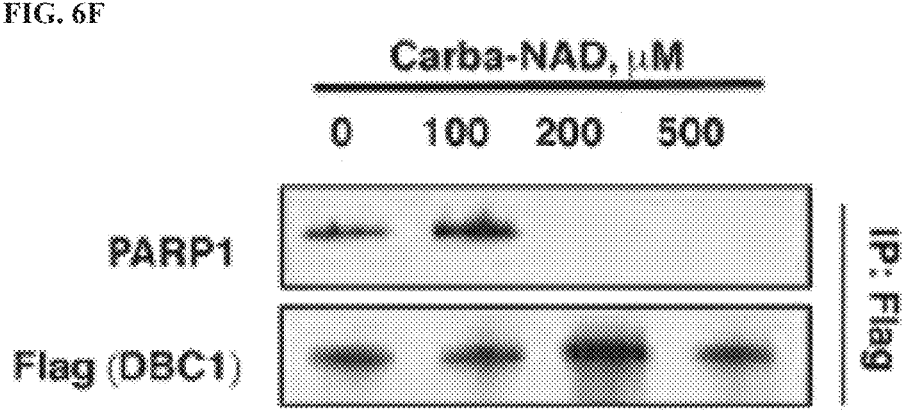

DBC1 mutants lacking regions outside the NHD ($DBC1_{1-500}$ and $DBC1_{243-923}$) behaved similarly to full-length (FIG. 1C), while MACROD1, poly-ADP-ribose glycohydrolase (PARG) (FIG. 6D), or PARP1 inhibitors (FIG. 5C) had no effect. PARP1-E988K behaved similarly to the wild-type (FIG. 5E and FIG. 6E). Carbanicotinamide adenine dinucleotide (Carba-NAD), a non-reactive PARP1 substrate, abrogated the complex (FIG. 6F). Thus, disruption of the PARP1-DBC1 complex by $NAD^+$ does not require $NAD^+$ cleavage or a covalently attached ADP-ribose.

Figure 1D:
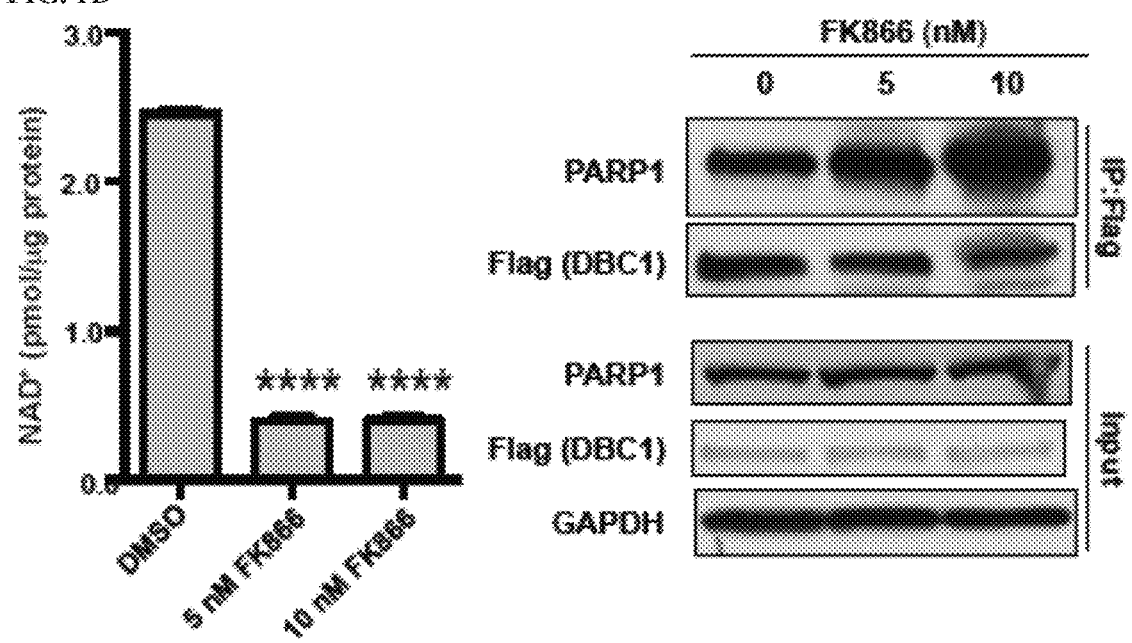
Figure 1E:
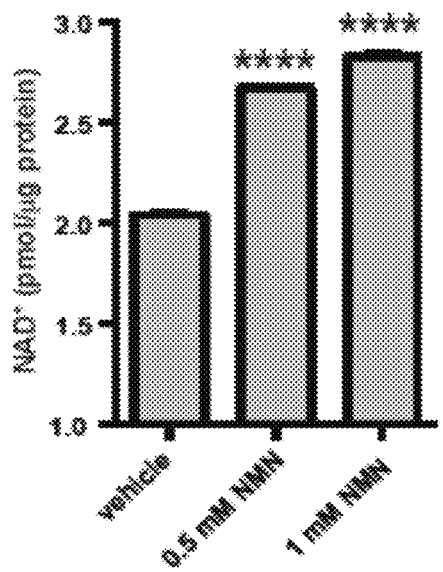
Figure 1E:
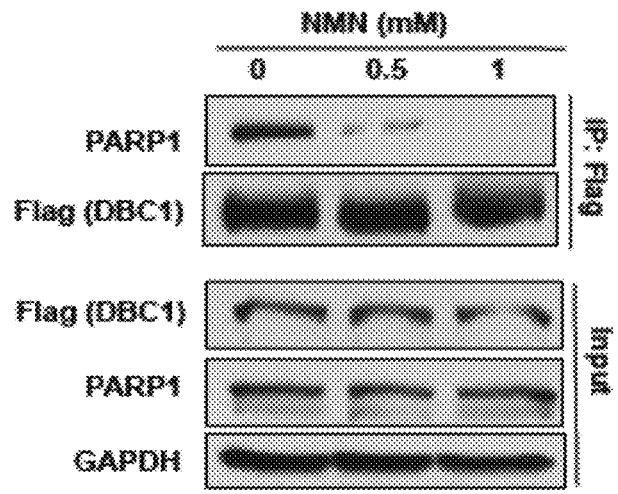
Figure 1F:
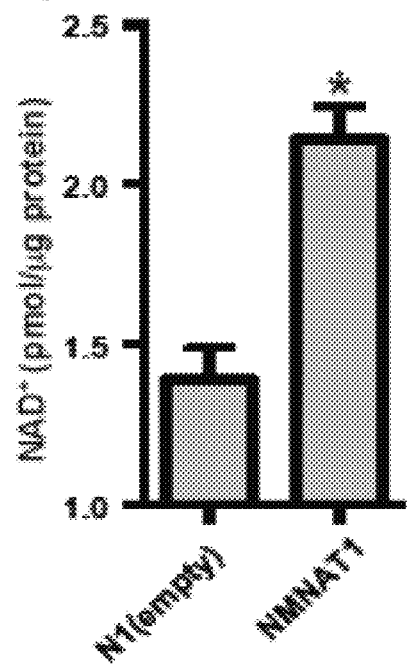
Figure 1F:
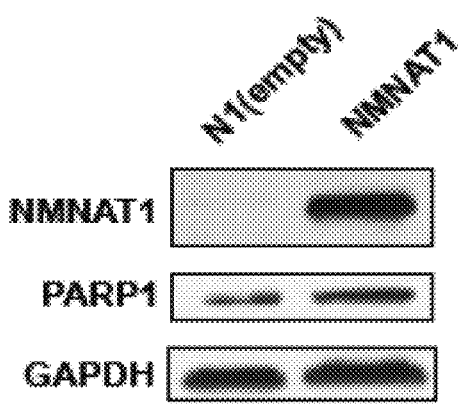
Figure 1F:
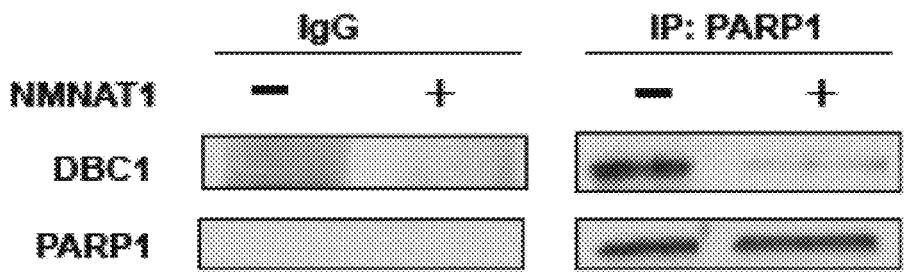
Figure 7A:
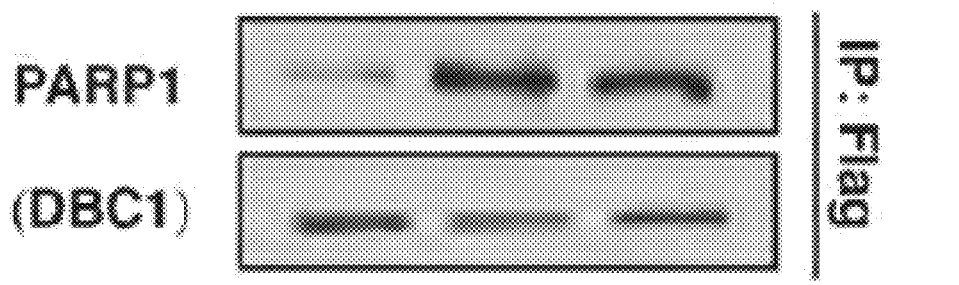
FIG. 7A-FIG. 7C shows the effects of NAD$^+$ levels and DNA damage on the interactions of DBC1 with PARP1.
Figure 7B:
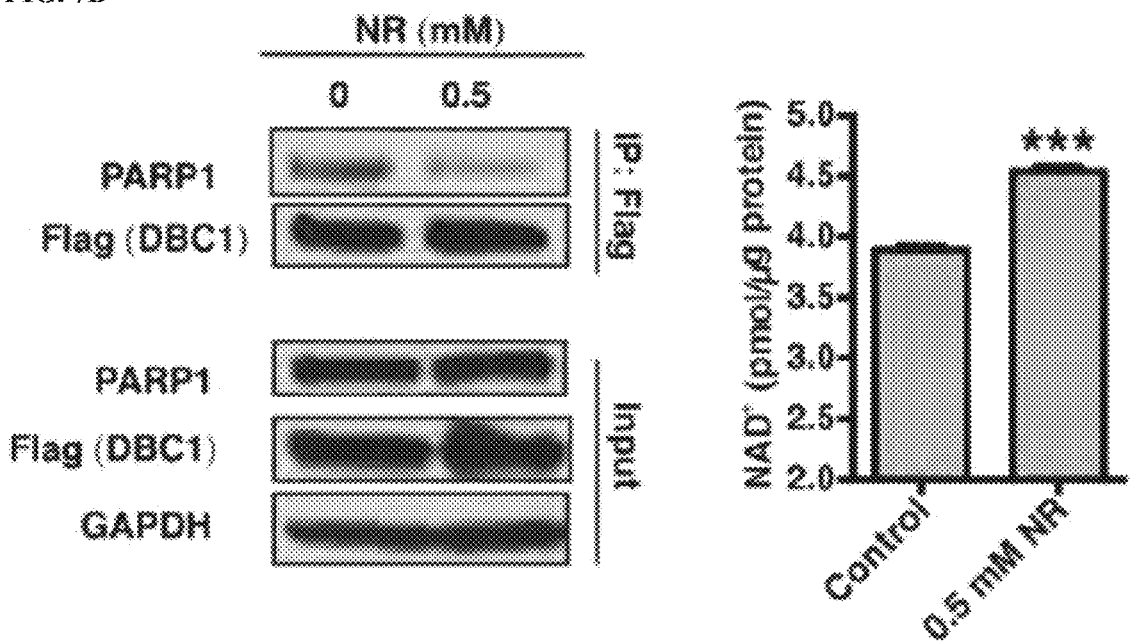
Figure 7C:
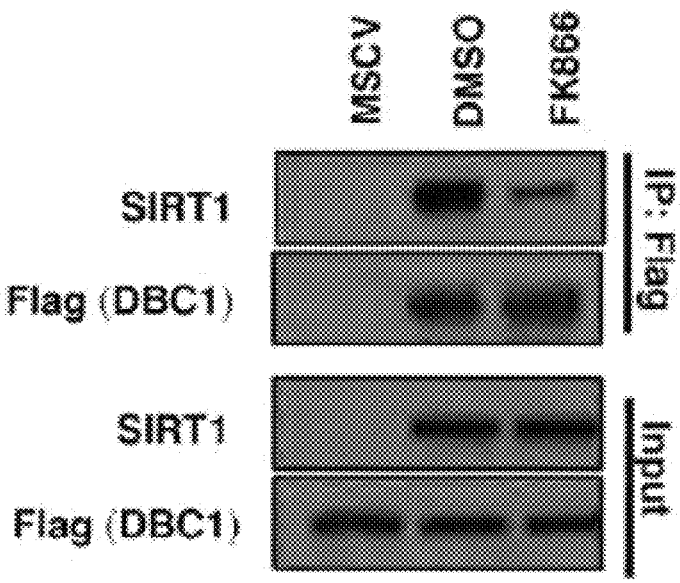

In HEK293T cells, FK866, an inhibitor of $NAD^+$ biosynthesis (M. Hasmann et al. *Cancer Res.* 63, 7436-7442 (2003)), increased the PARP1-DBC1 interaction (FIG. 1D), as did depletion of $NAD^+$ by genotoxic stress (FIG. 7A). Interventions that increased $NAD^+$ abundance (J. Yoshino et al. *Cell Metab.* 14, 528-536 (2011); F. Berger et al. *J. Biol. Chem.* 280, 36334-36341 (2005)) decreased the PARP1-DBC1 interaction (FIG. 1E and FIG. 1F and FIG. 7B). The SIRT1-DBC1 interaction was slightly diminished by FK866, possibly through the sequestration of DBC1 by PARP1 (FIG. 7B). Together, these data indicate that $NAD^+$ inhibits PARP1-DBC1 complex formation in cells.

Figure 8A:
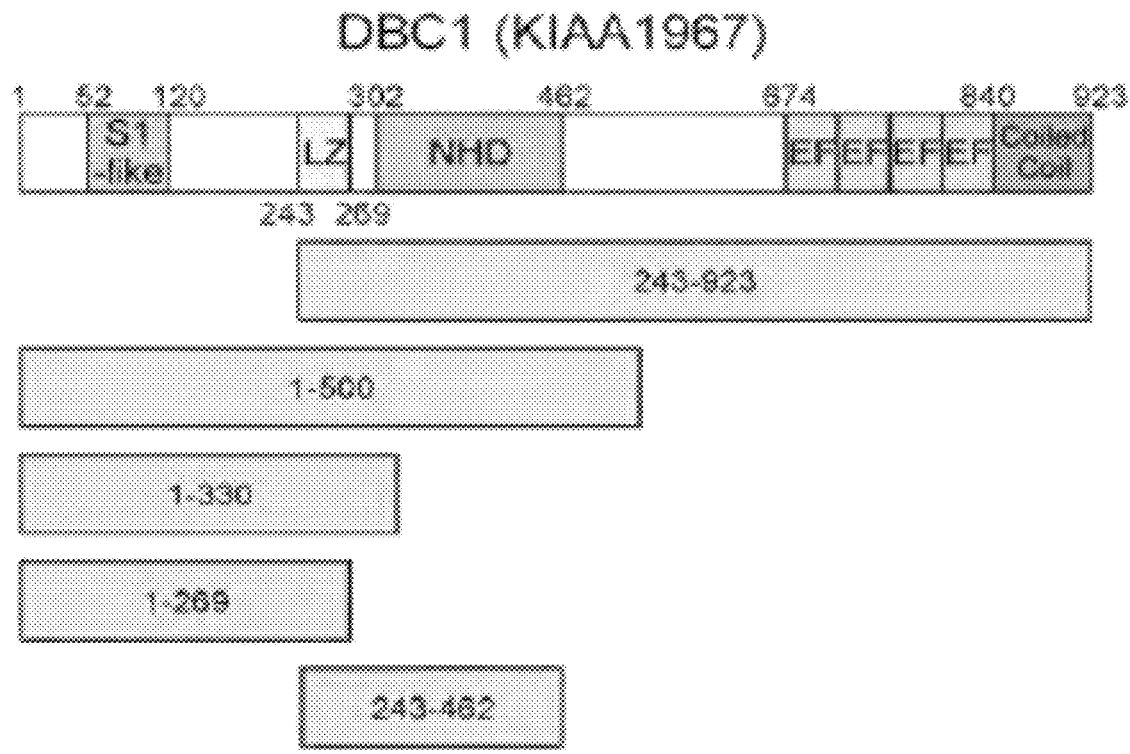
FIG. 8A-FIG. 8D shows that the PARP1-DBC1 interaction requires the NHD.
Figure 8B:
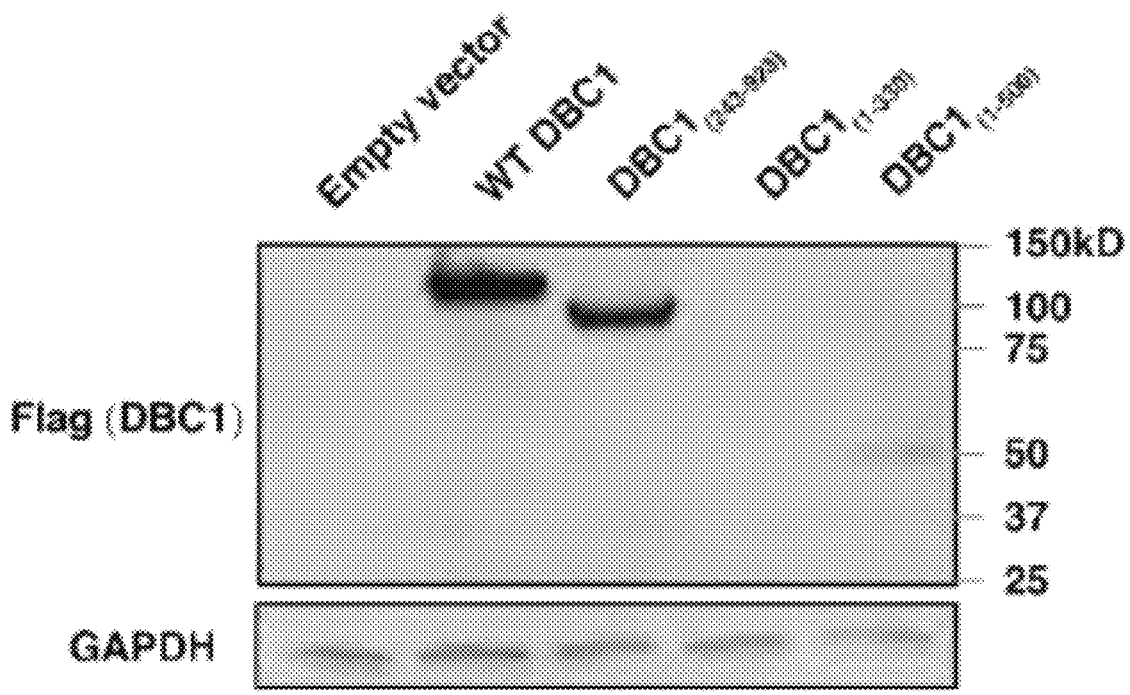
Figure 8C:
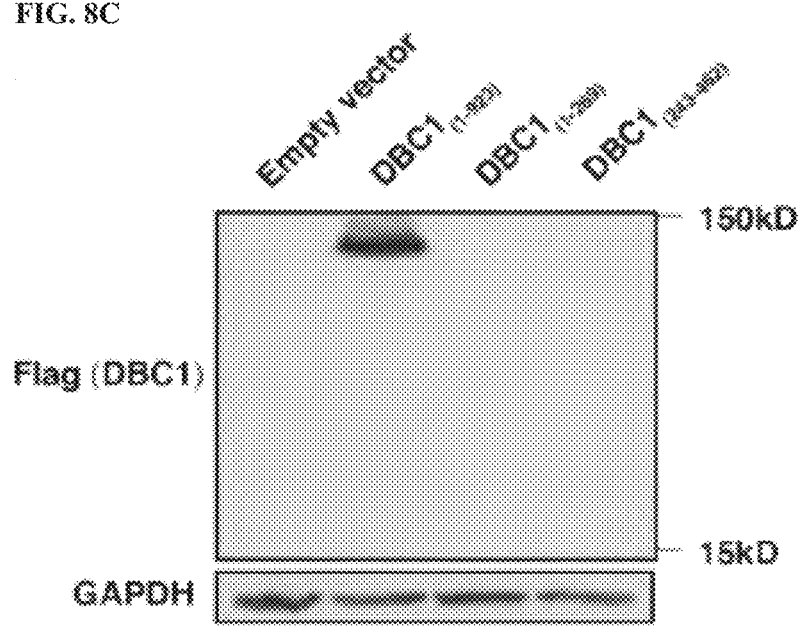
Figure 8D:
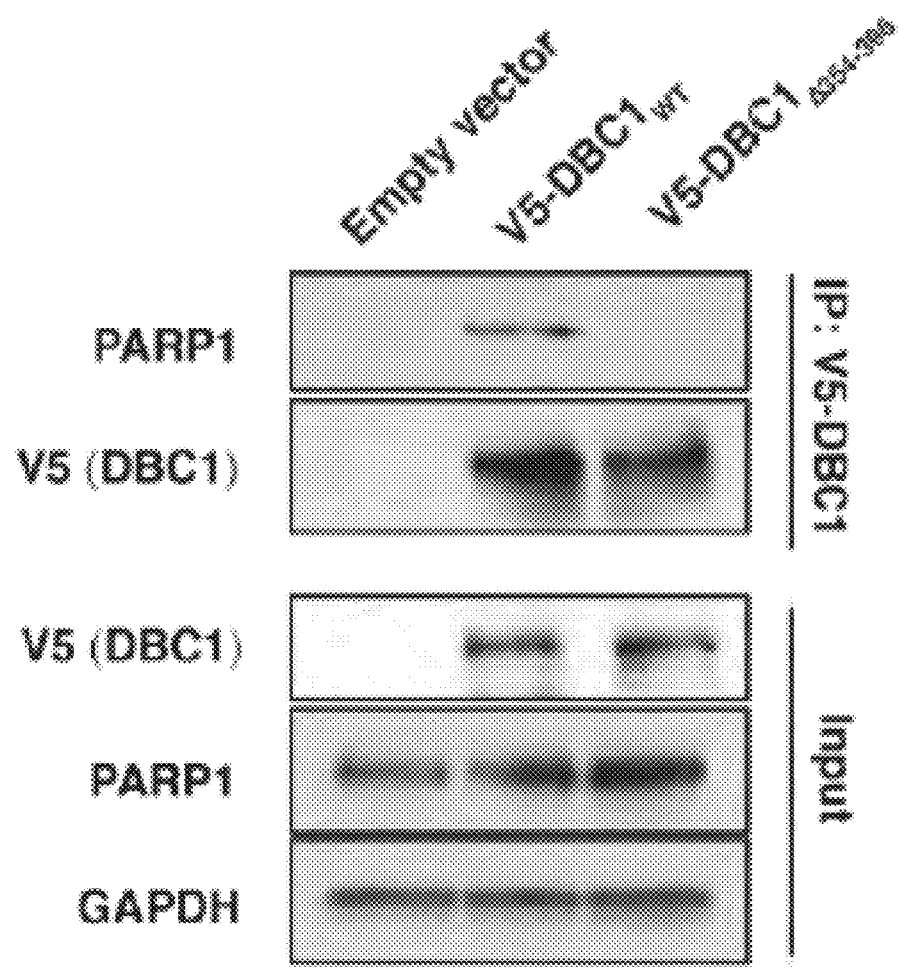
Figure 9A:
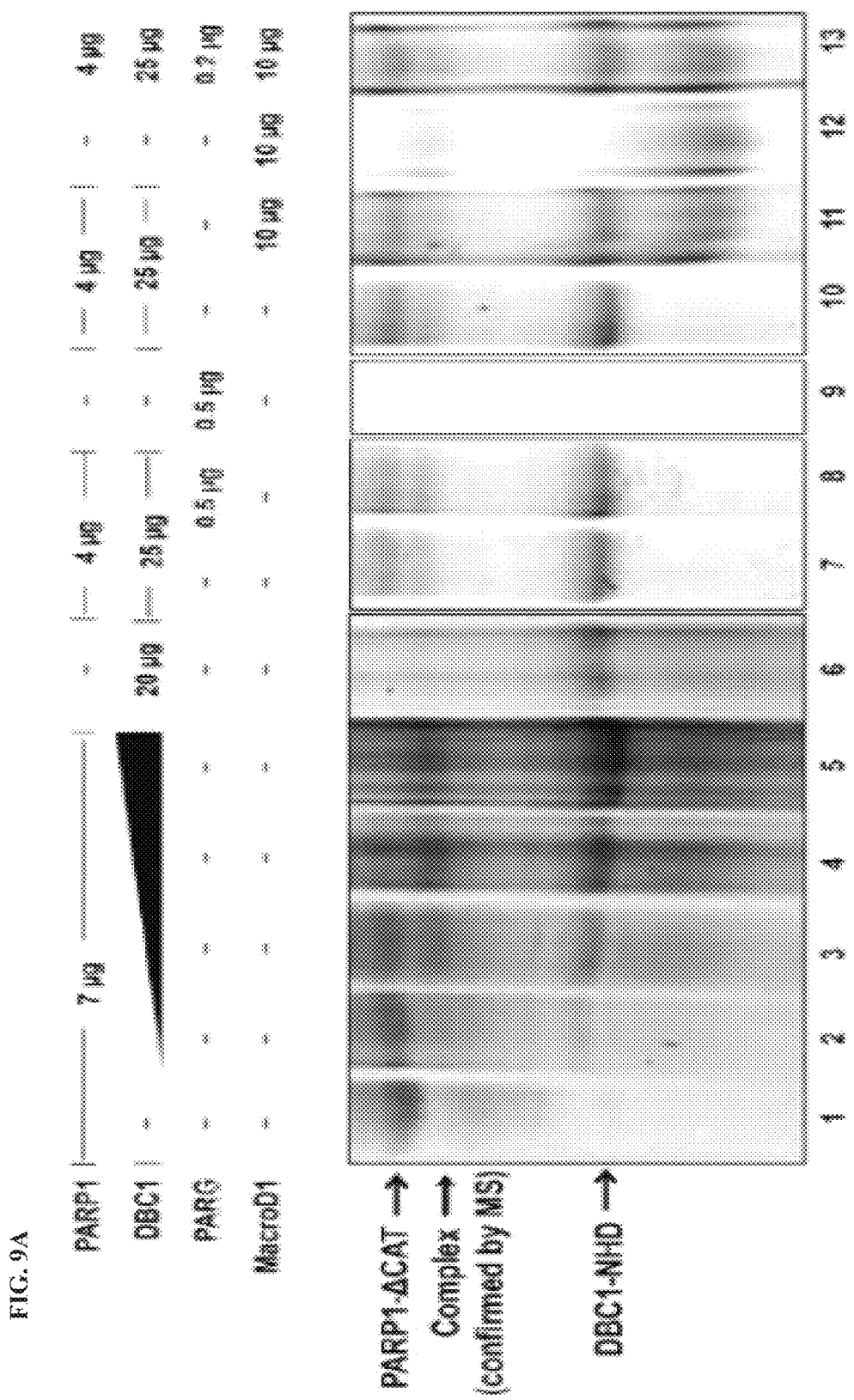

To better understand the mechanism by which $NAD^+$ inhibits complex formation, the DBC1 domain necessary for interaction with PARP1 was identified. A truncated version of DBC1 lacking an NHD conserved region ($DBC1_{\Delta354-396}$) had impaired PARP1 binding in cells (FIG. 8A and FIG. 8D), whereas a recombinant DBC1 mutant covering NHD domain (DBC1-NHD, residues 243-553) bound to a truncated PARP1 lack of catalytic domain (PARP1-ΔCAT, residues 1-654) (FIG. 9A and FIG. 9B) and was not abrogated by $NAD^+$, indicating that residues outside the minimal NHD domain may be necessary for $NAD^+$ to dissociate the complex.

Figure 10A:
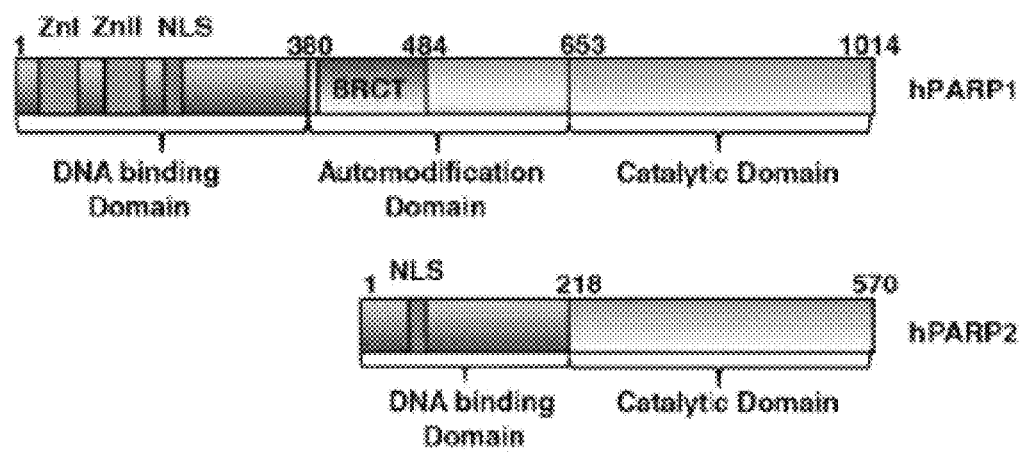
FIG. 10A-FIG. 10F shows that the PARP1-DBC1 interaction requires the BRCT domain of PARP1.
Figure 10B:
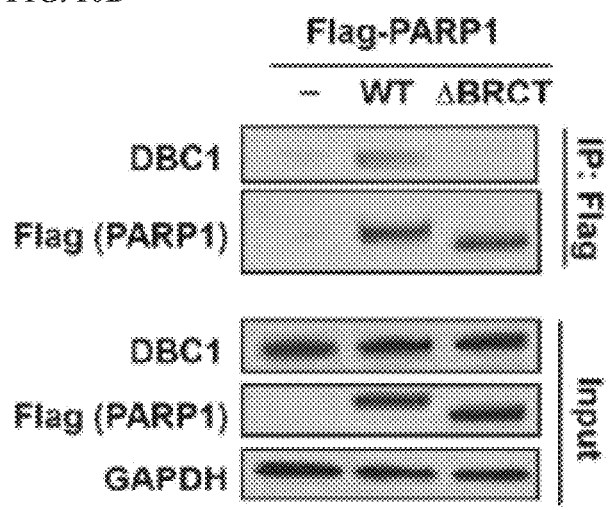
Figure 10C:
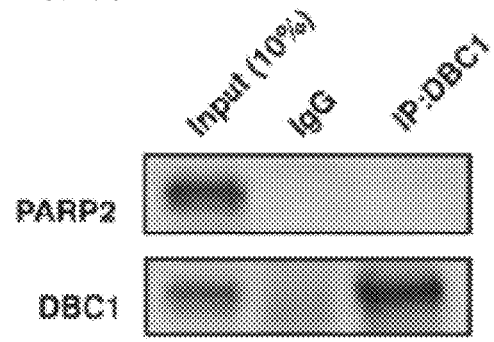
Figure 10D:
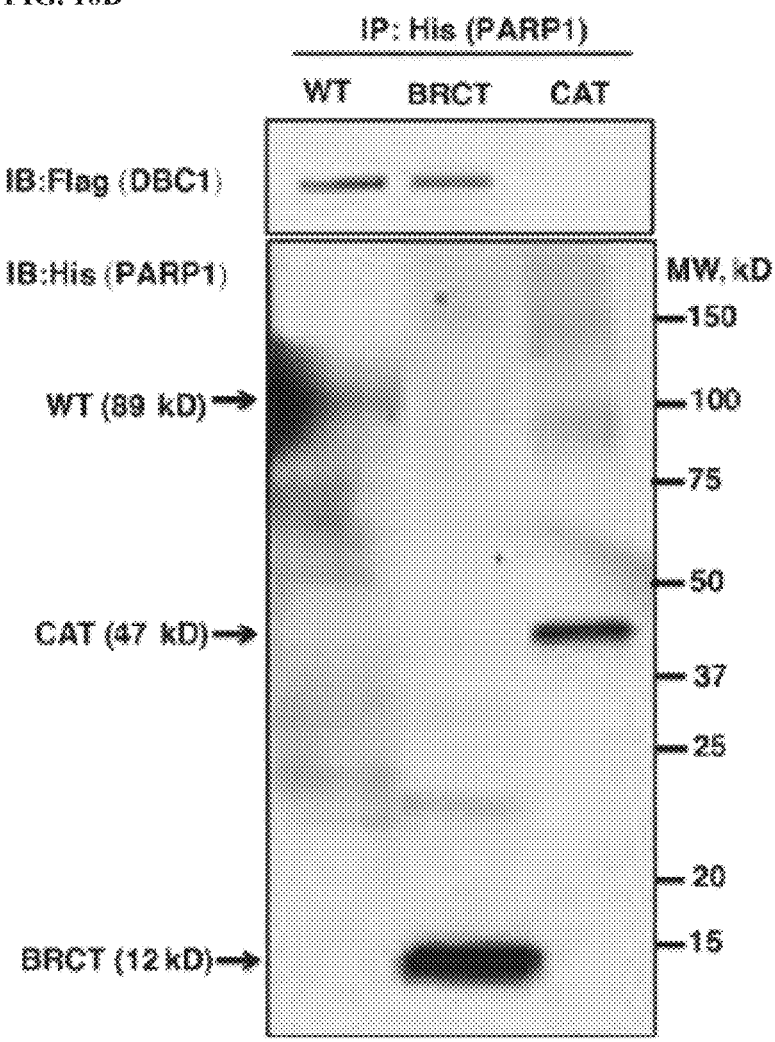
Figure 10E:
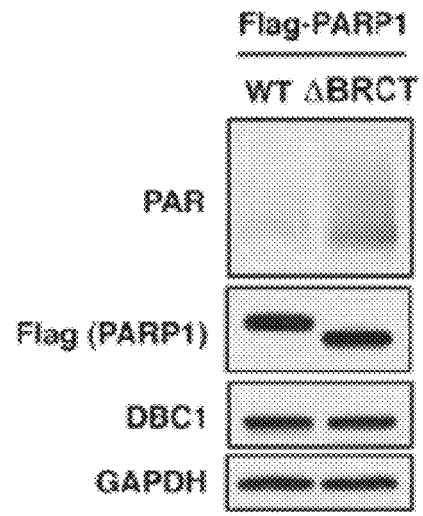
Figure 10F:
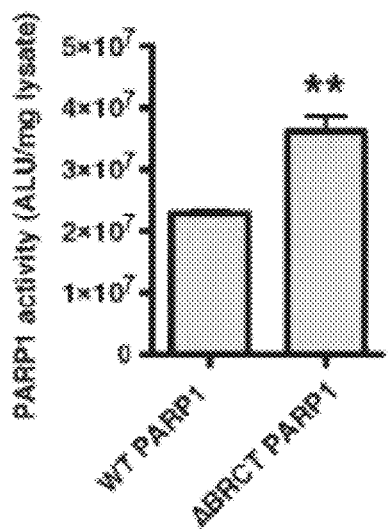

DBC1 interacted with the Breast Cancer 1 (BRCA1)C-Terminal (BRCT) domain of PARP1 (FIG. 10A) (P. Bork et al. *FASEB J.* 11, 68-76 (1997)) but not with the PARP1 catalytic domain or PARP2, which lacks a BRCT domain (FIG. 10B and FIG. 10D). A BRCT-deficient PARP1 has higher activity than wild-type (FIG. 10E and FIG. 10F), together indicating PARP1-DBC1 is mediated by contacts between the NHD and PARP1-BRCT.

Figure 2A:
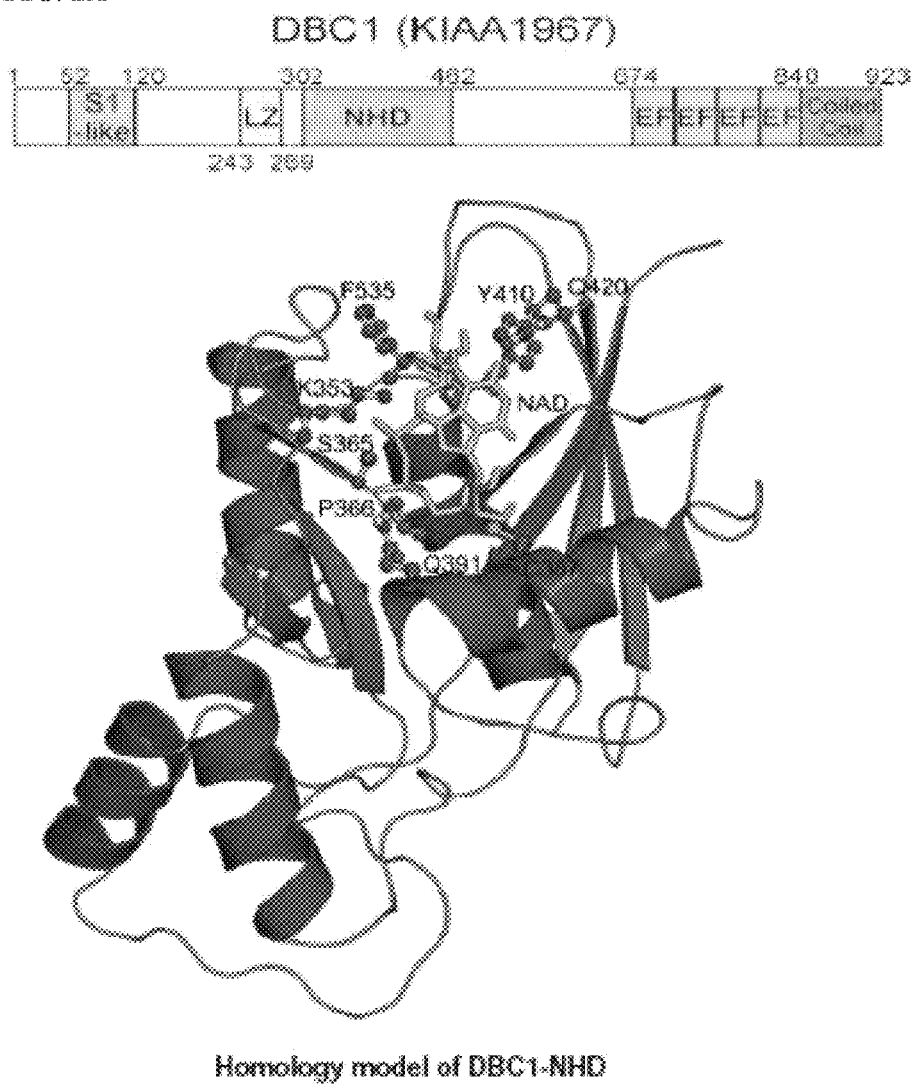
FIG. 2A-FIG. 2E depicts binding of the Nudix homology domain (NHD) of DBC1 to NAD$^+$ and PARP1.
Figure 2B:
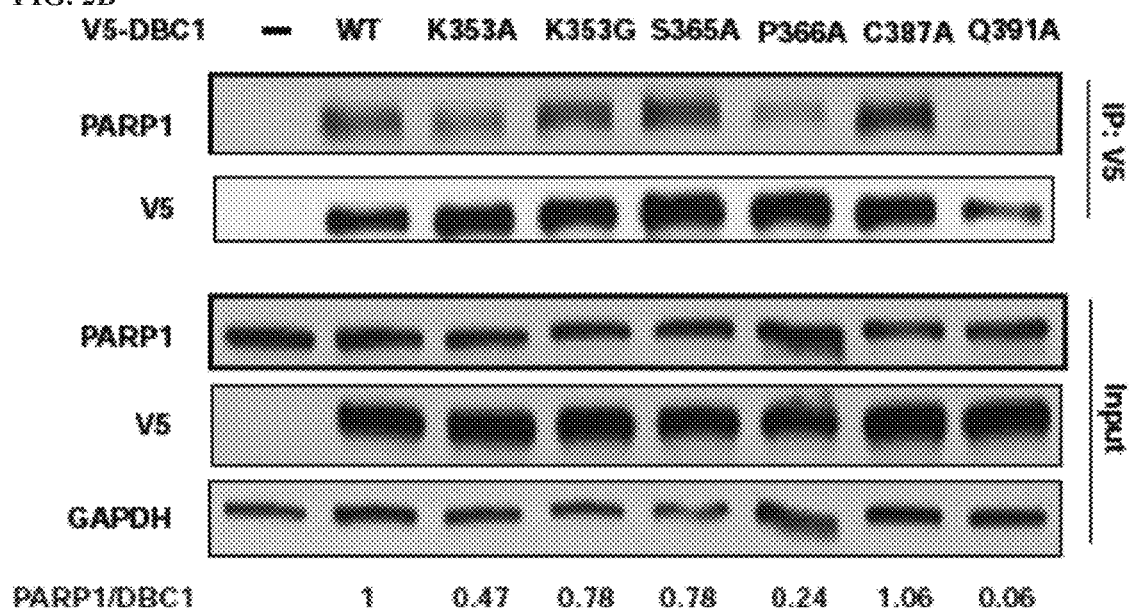

An atomic resolution homology model was generated for the human DBC1-NHD based on five known crystal structures of Nudix domains from other proteins (FIG. 2A FIG. 11 and Methods). $NAD^+$ had the best fit of all riboside nucleotides. Substitutions of the amino acids predicted to alter $NAD^+$ binding inhibited PARP1-DBC1 binding either slightly (K353A and P366A) or dramatically (Q391A) (FIG.

Figure 2C:
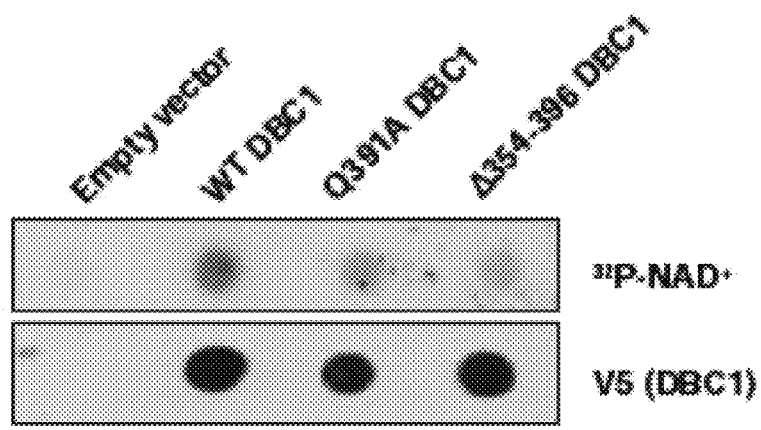
Figure 2D:
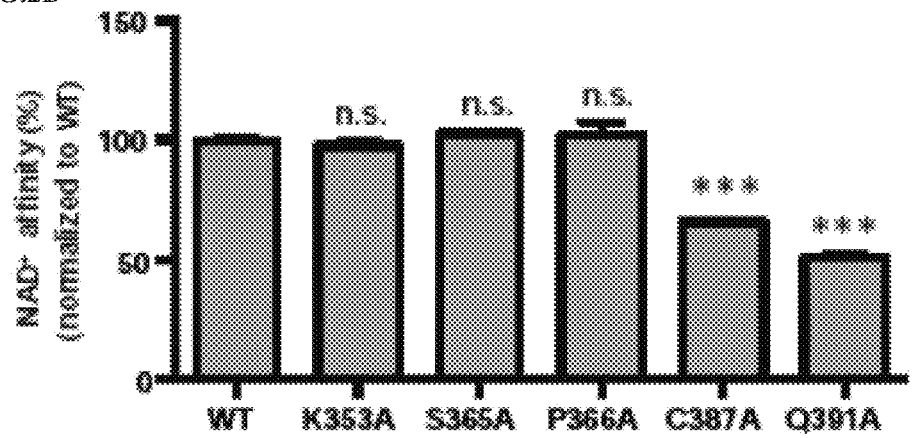
Figure 2E:
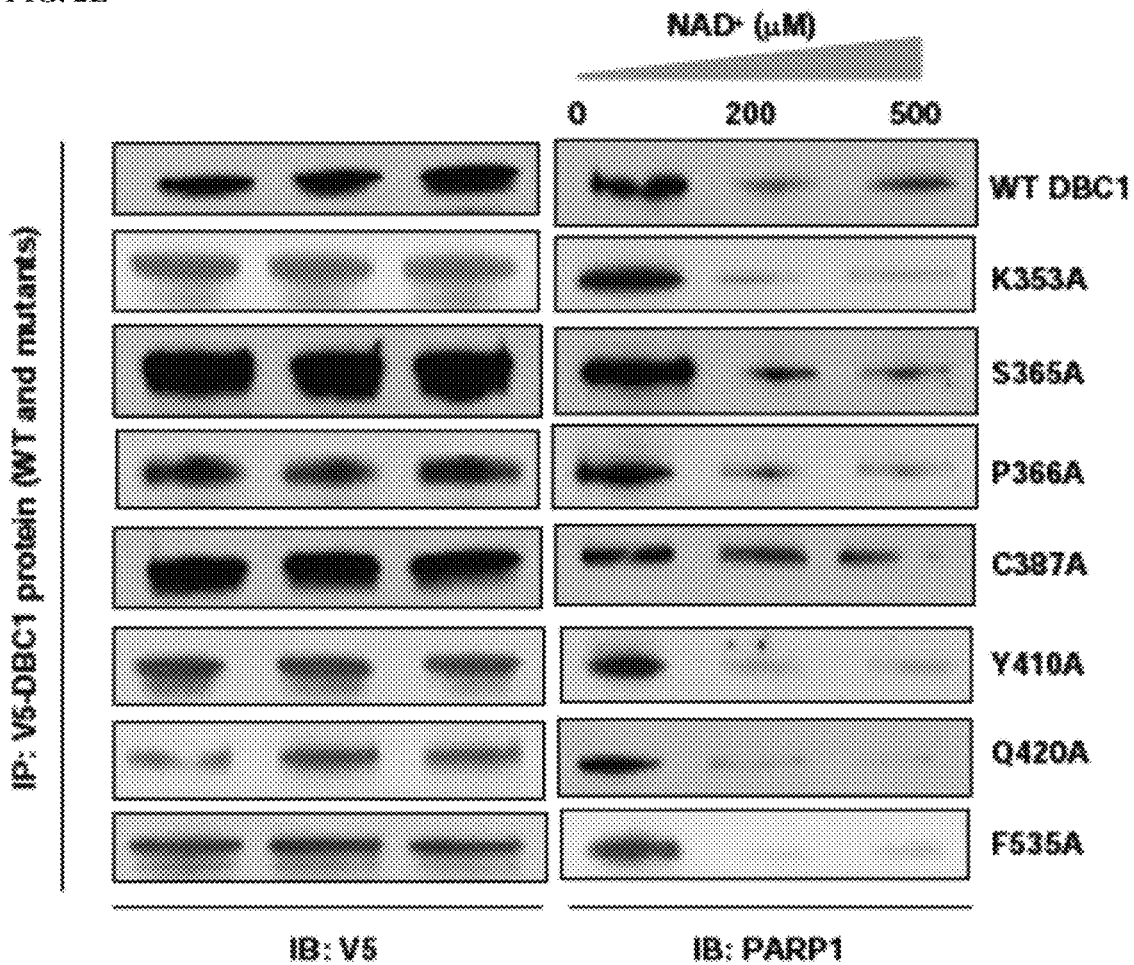
Figure 12A:
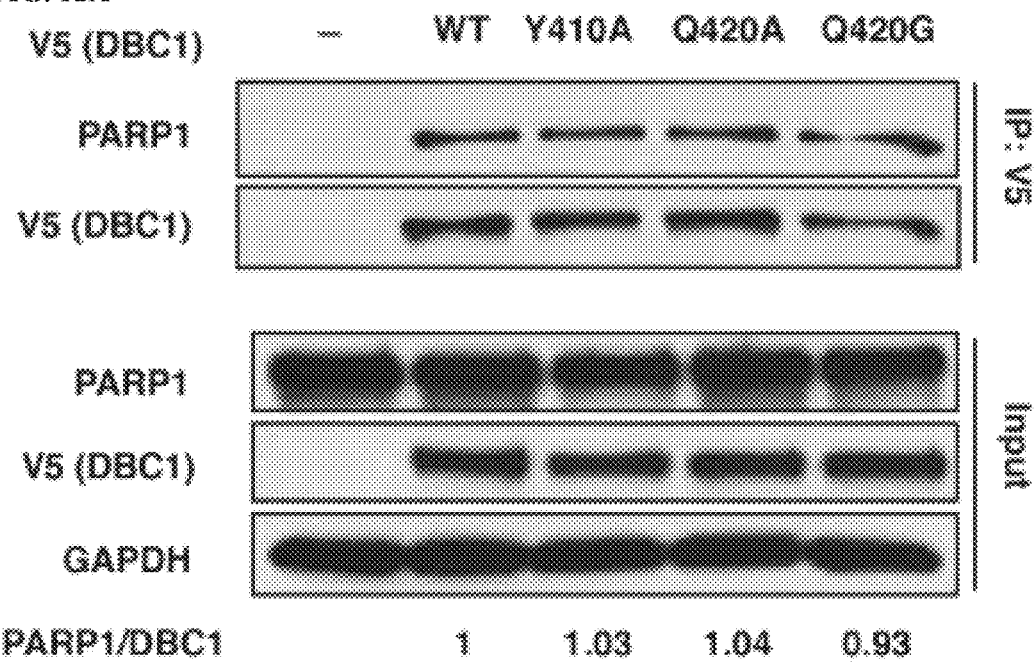
FIG. 12A-FIG. 12B shows representative interactions of DBC1-NHD mutants with PARP1 (continued after FIG. 2B). The effects of mutating Y410 or Q420 (FIG. 12A), or F535 (FIG. 12B) on the PARP1-DBC1 interaction. DBC1 was immunoprecipitated using an anti-V5 antibody agarose beads and probed by western blotting for PARP1. Ratio listed below images was determined from band intensities quantified using Image J.
Figure 12B:
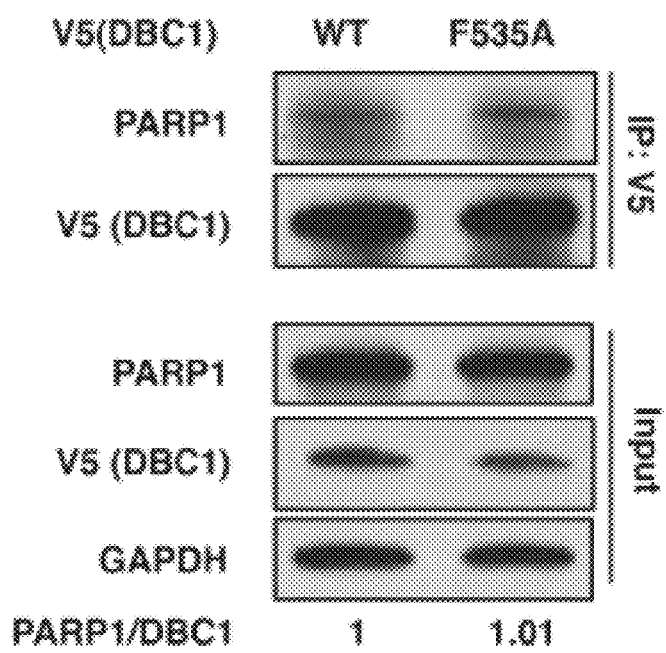
Figure 13A:
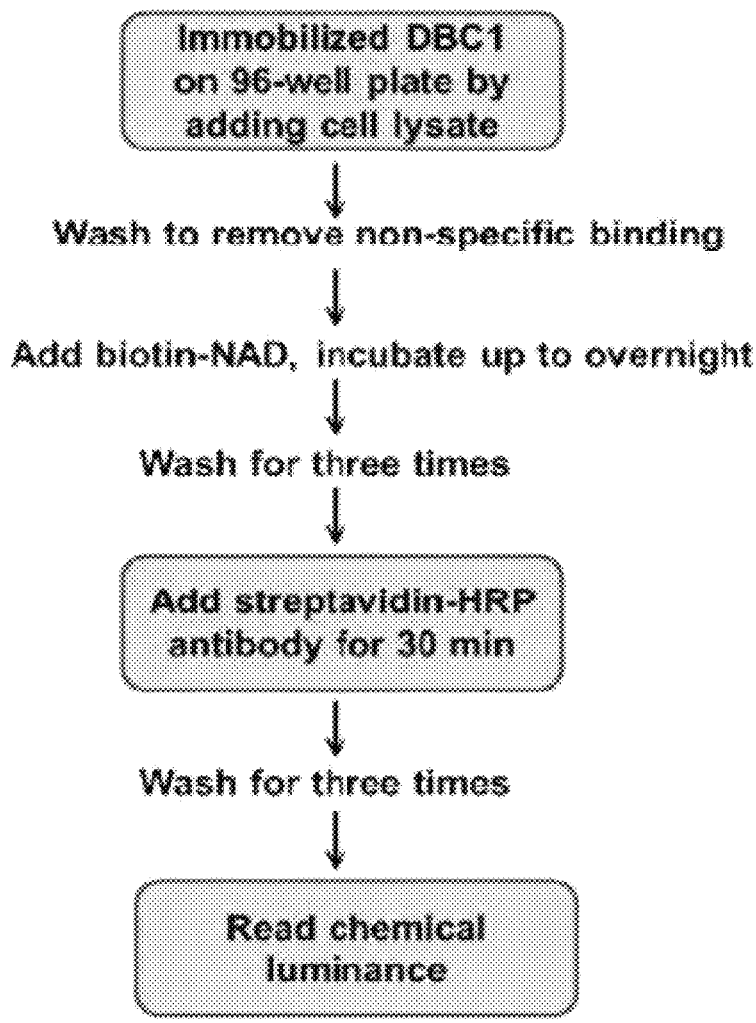
Figure 13B:
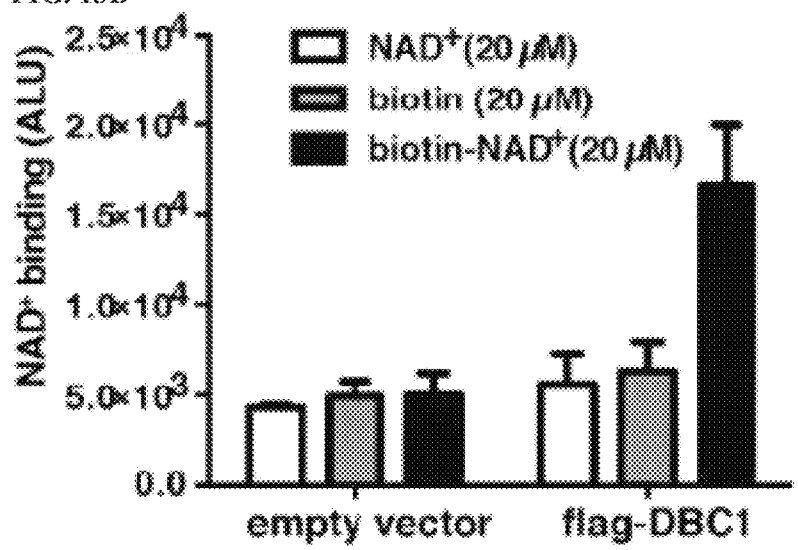
Figure 13C:
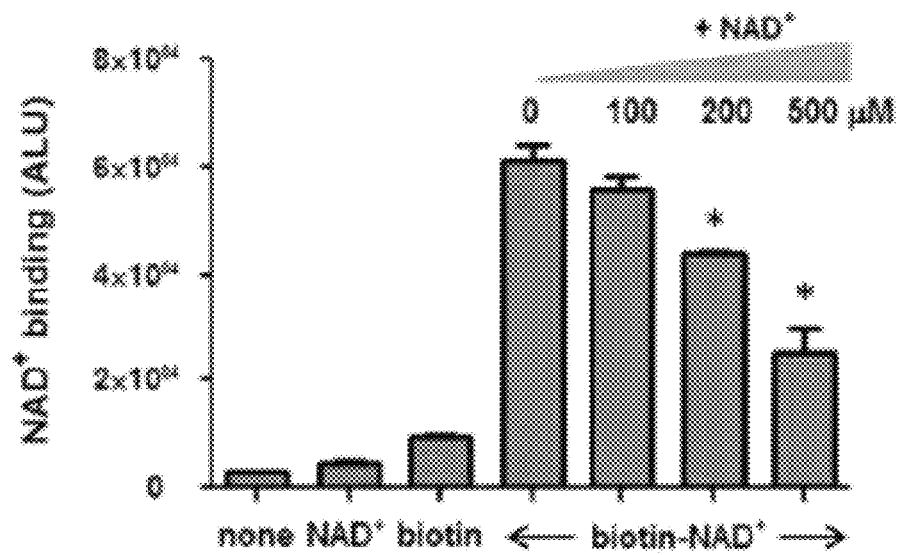
Figure 13D:
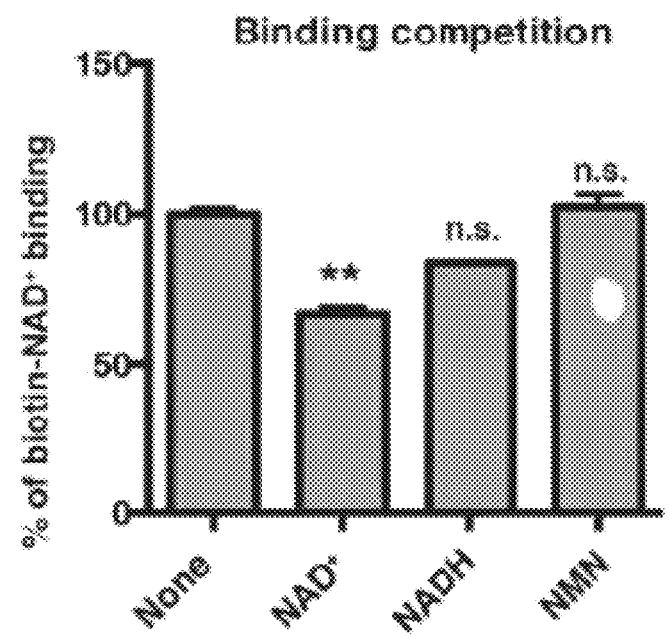

2B and FIG. 12A and FIG. 12B). Radio-labeled or biotin-labeled NAD+ directly bound to DBC1 (FIG. 2C and FIG. 2D) and was competed off with unlabeled NAD+. Partial deletion of the NHD (DBC1$_{\Delta 354-396}$) or Q391A (DBC1$^{Q391A}$) reduced NAD+ binding, whereas N-terminal and C-terminal truncations did not (FIG. 2C and FIG. 2D, and FIG. 13E). Mutation of $C_{387}$, a residue close to Q391 on the same helix (FIG. 2A), also decreased NAD+ binding (FIG. 2D) and reduced the responsiveness of the PARP1-DBC1 complex to NAD+ (FIG. 2E).

Figure 3A:
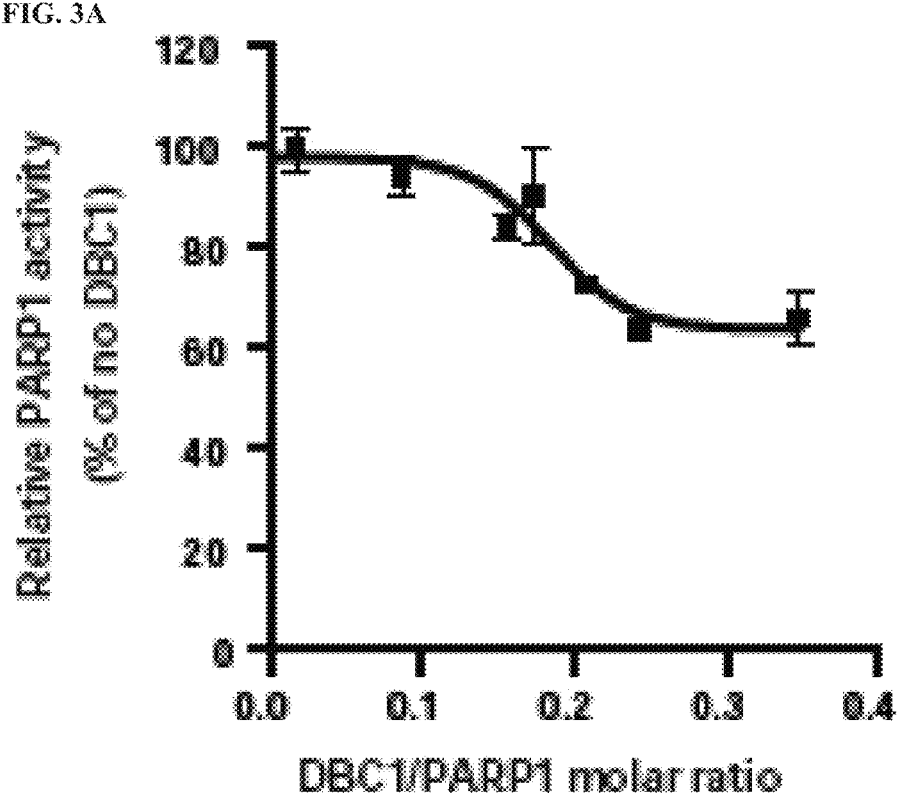
FIG. 3A-FIG. 3G depicts DBC1 inhibits PARP1 activity and DNA repair.
Figure 3B:
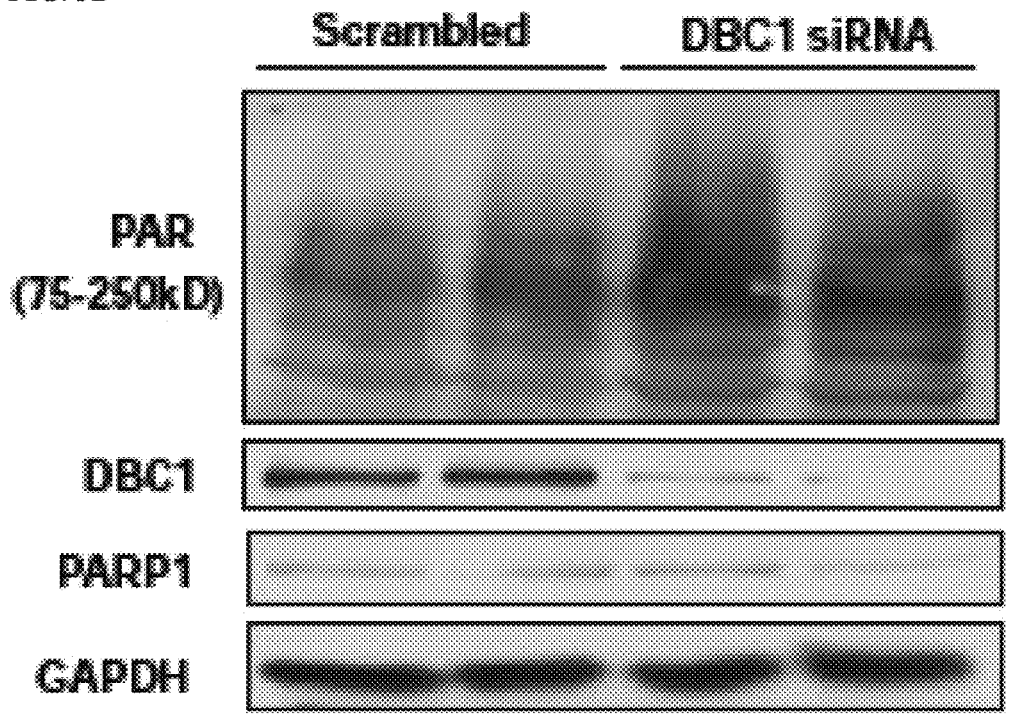
Figure 3C:
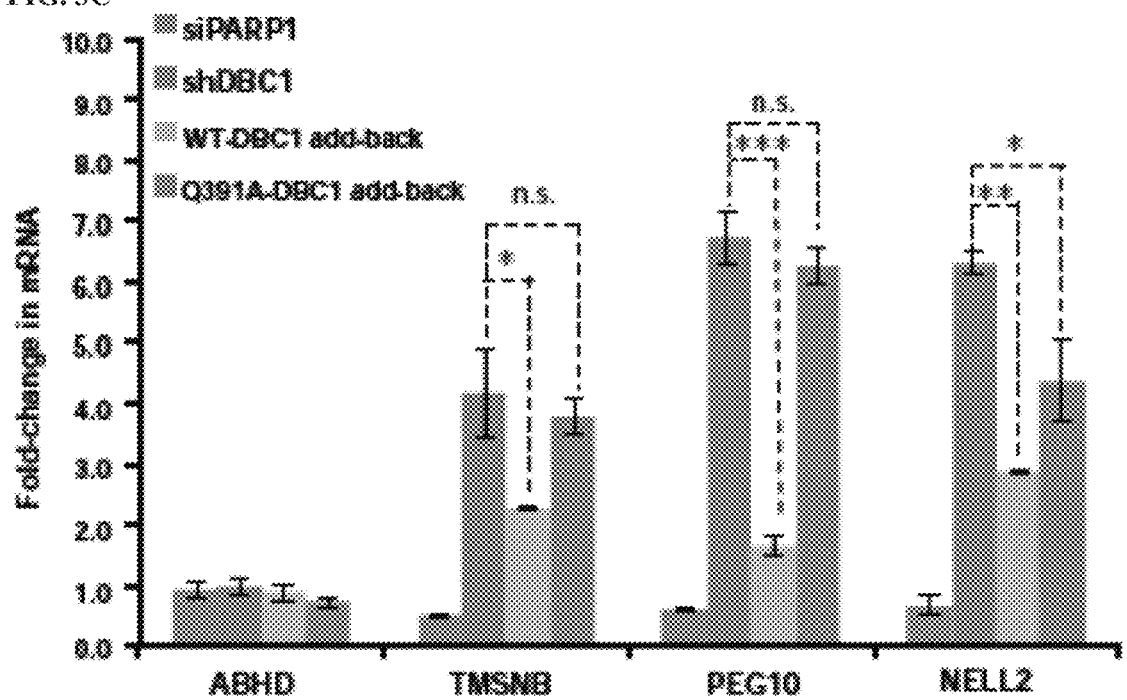
Figure 3D:
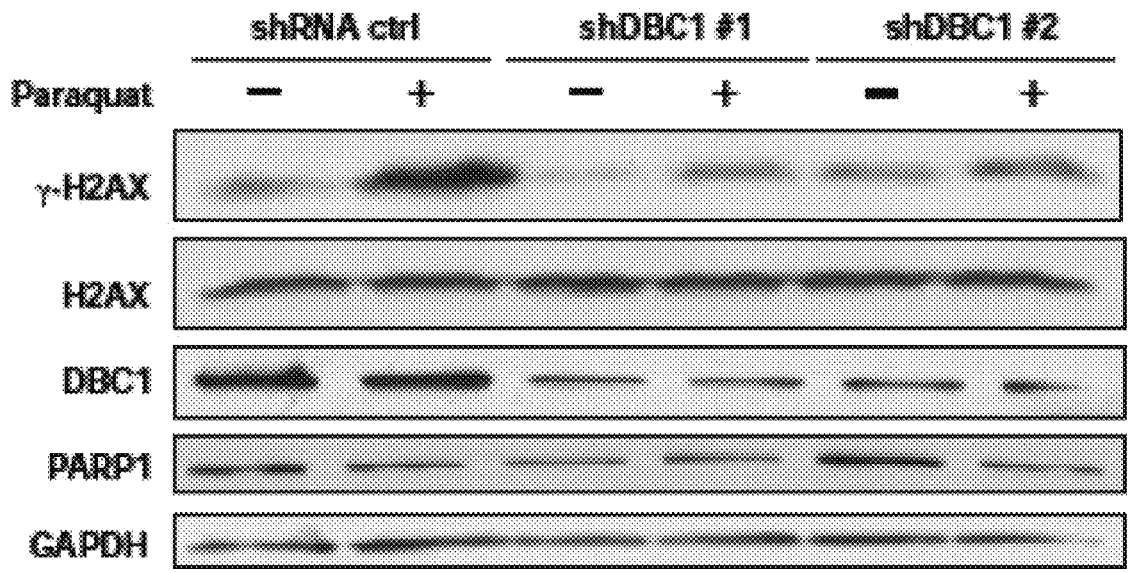
Figure 3E:
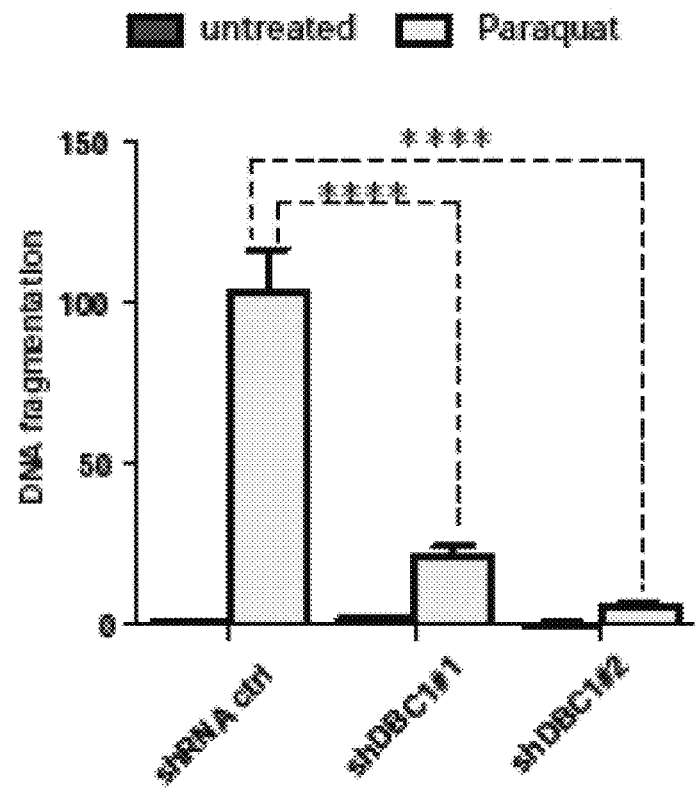
Figure 3F:
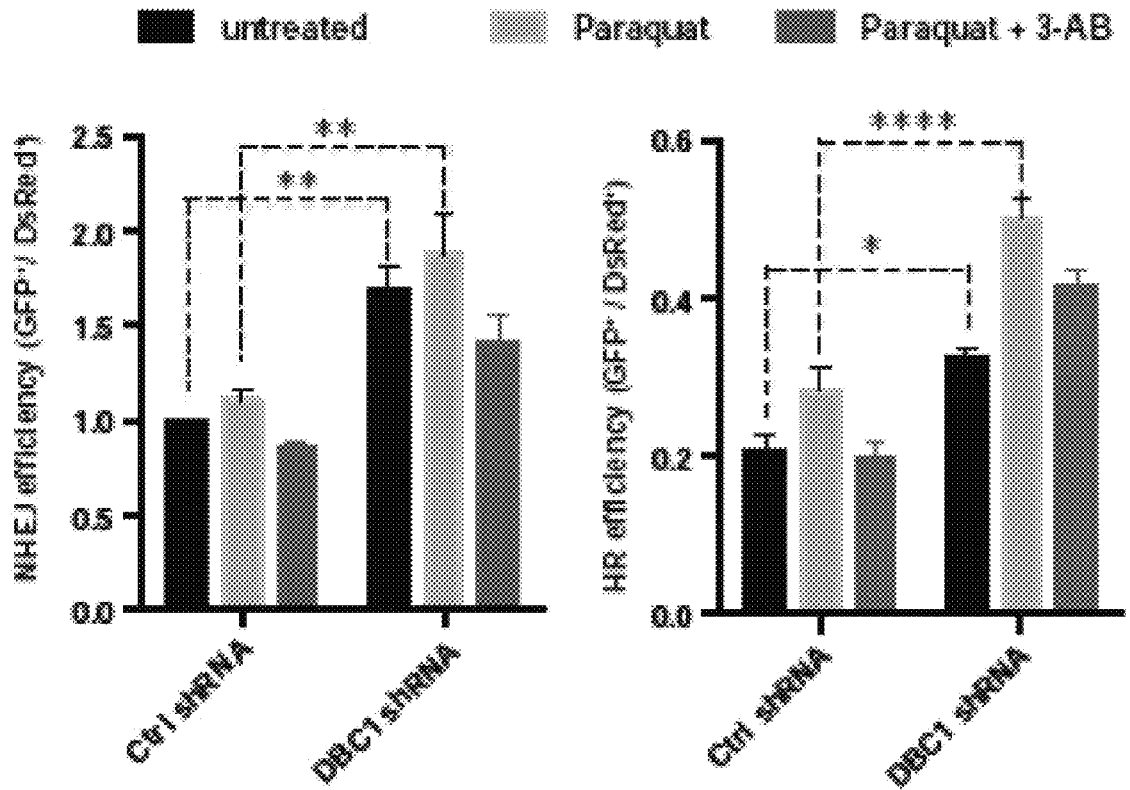
Figure 3G:
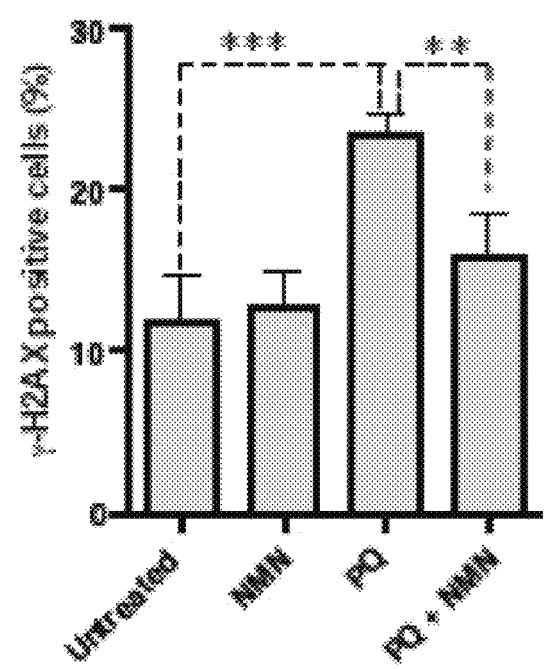
Figure 14A:
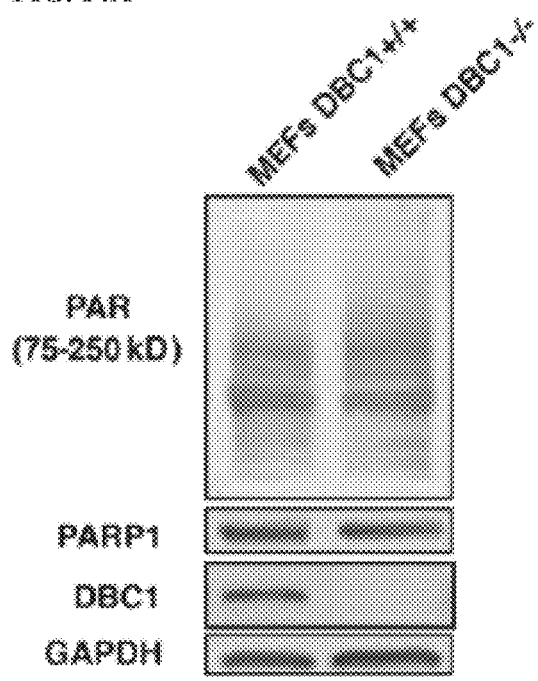
FIG. 14A-FIG. 14F shows that DBC1 inhibits PARP1 activity in the presence and absence of genotoxic stresses.
Figure 14B:
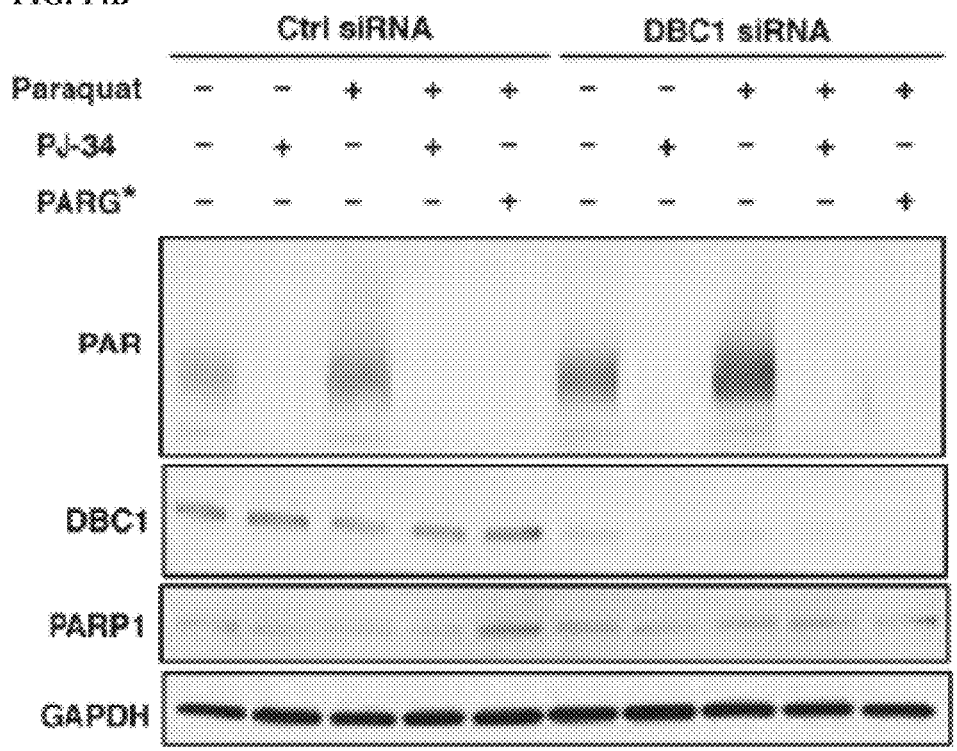
Figure 14C:
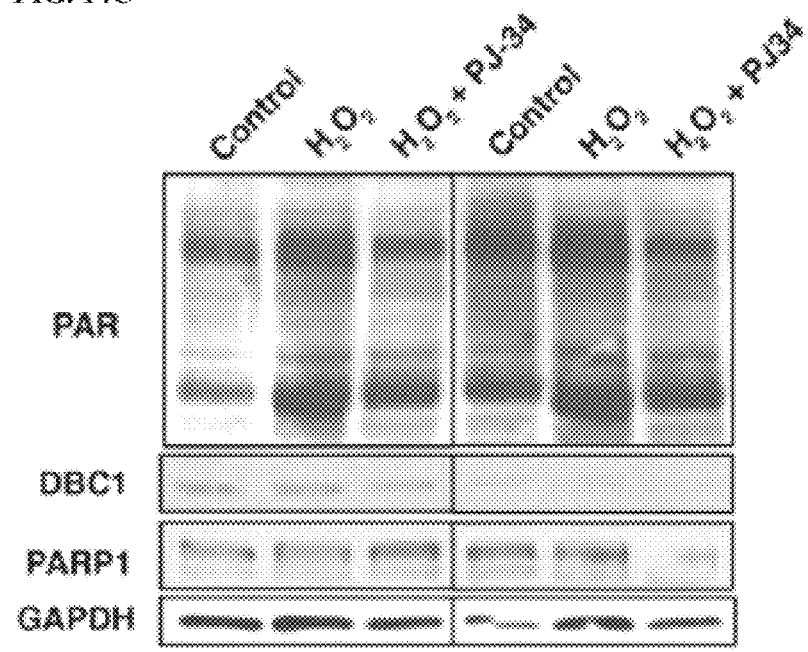
Figure 14D:
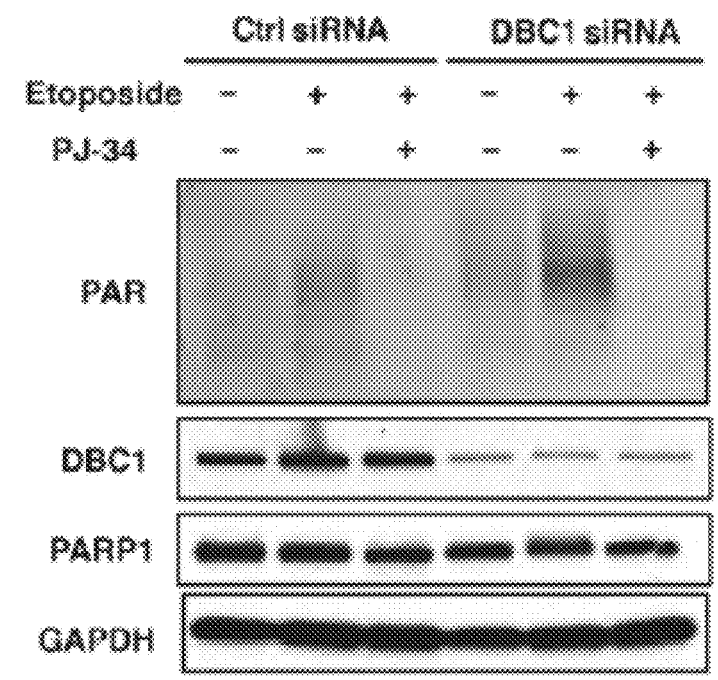
Figure 14E:
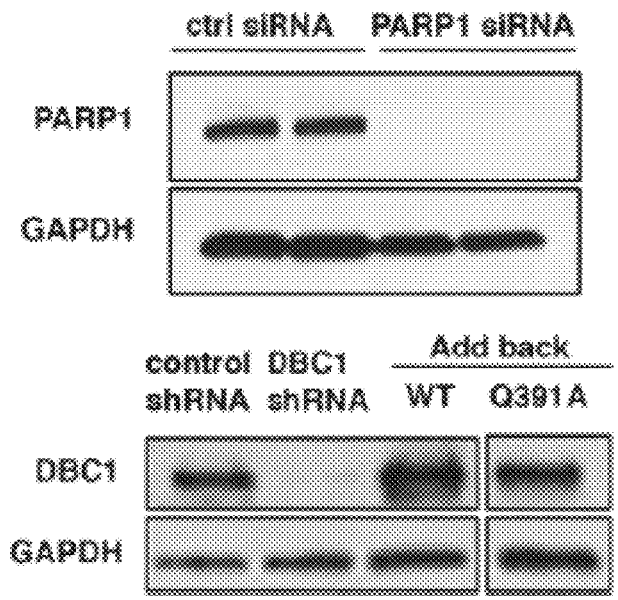
Figure 14F:
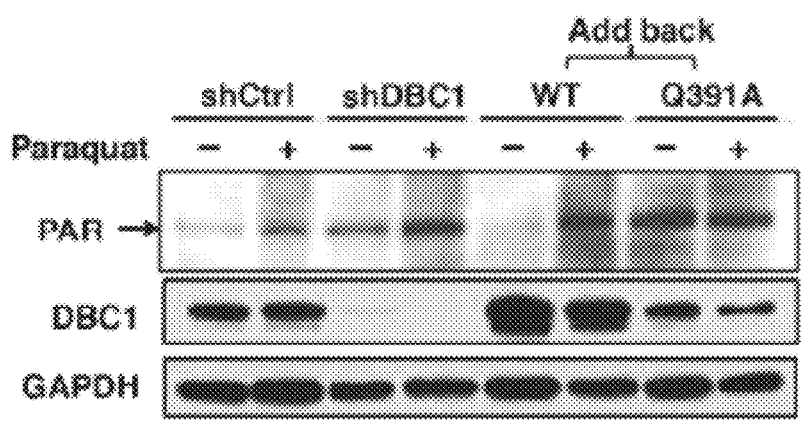
Figure 15A:
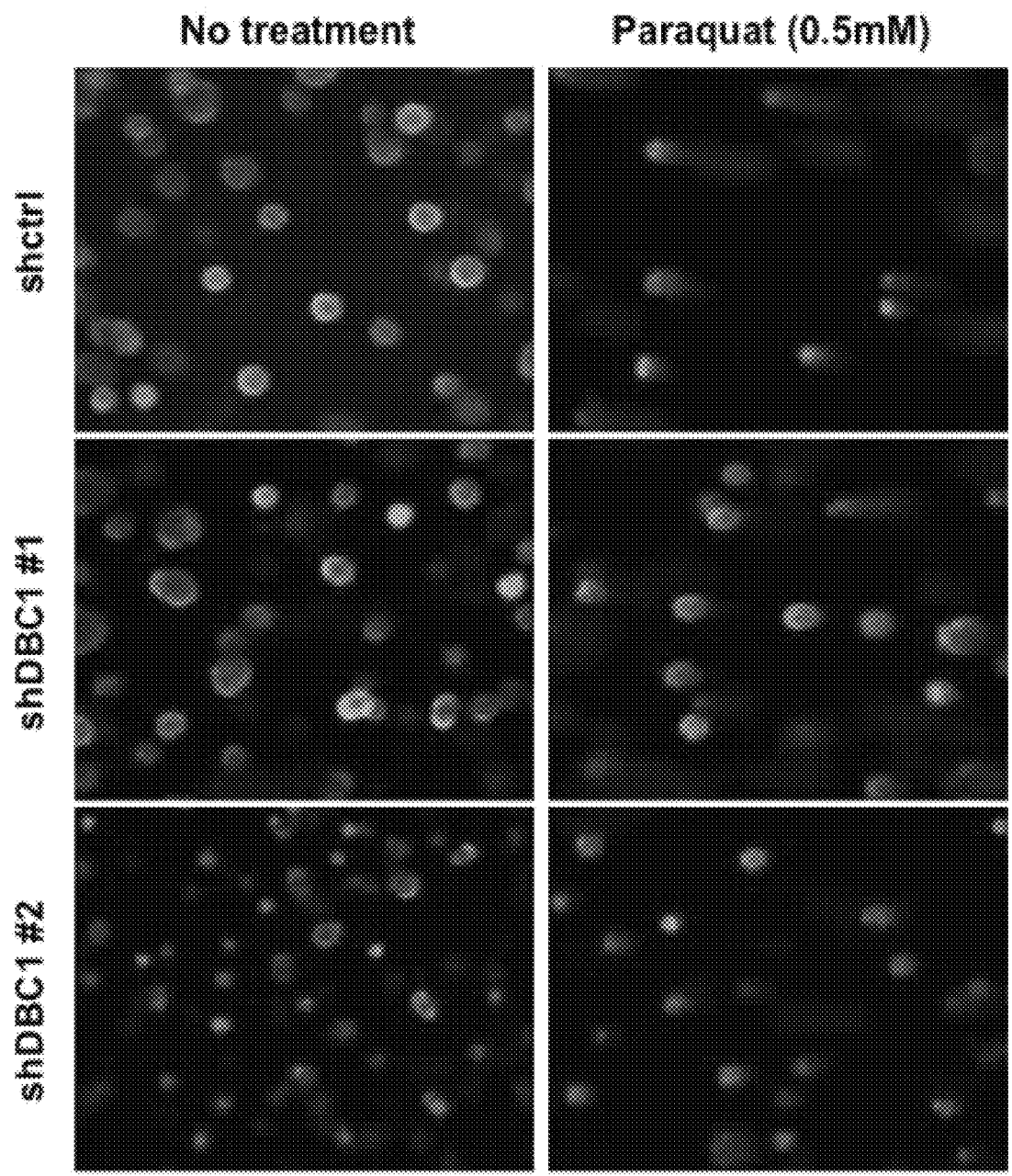
FIG. 15A-FIG. 15C shows that DBC1 knockdown protects cells from DNA damage by activating DNA repair.
Figure 15B:
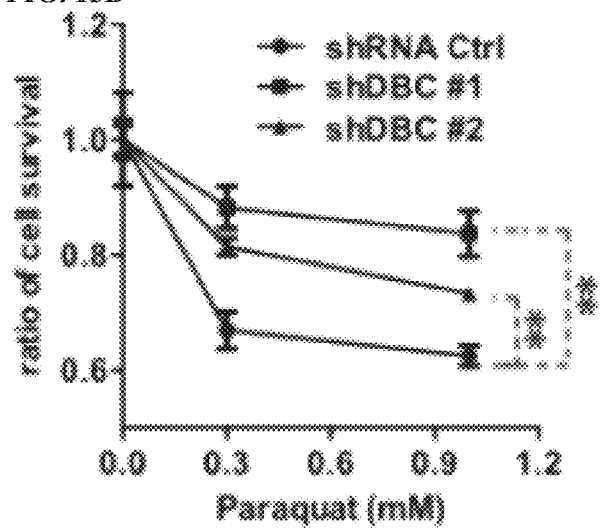
Figure 15C:
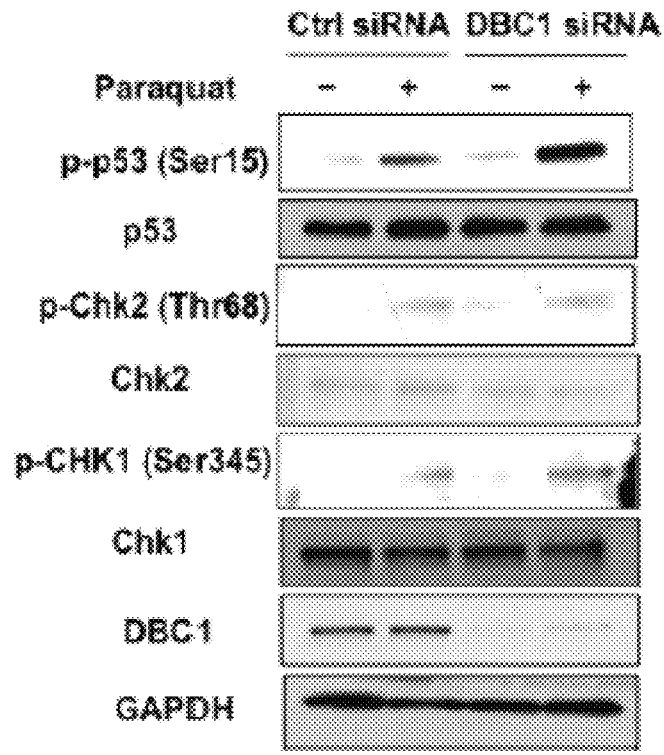
Figure 16:
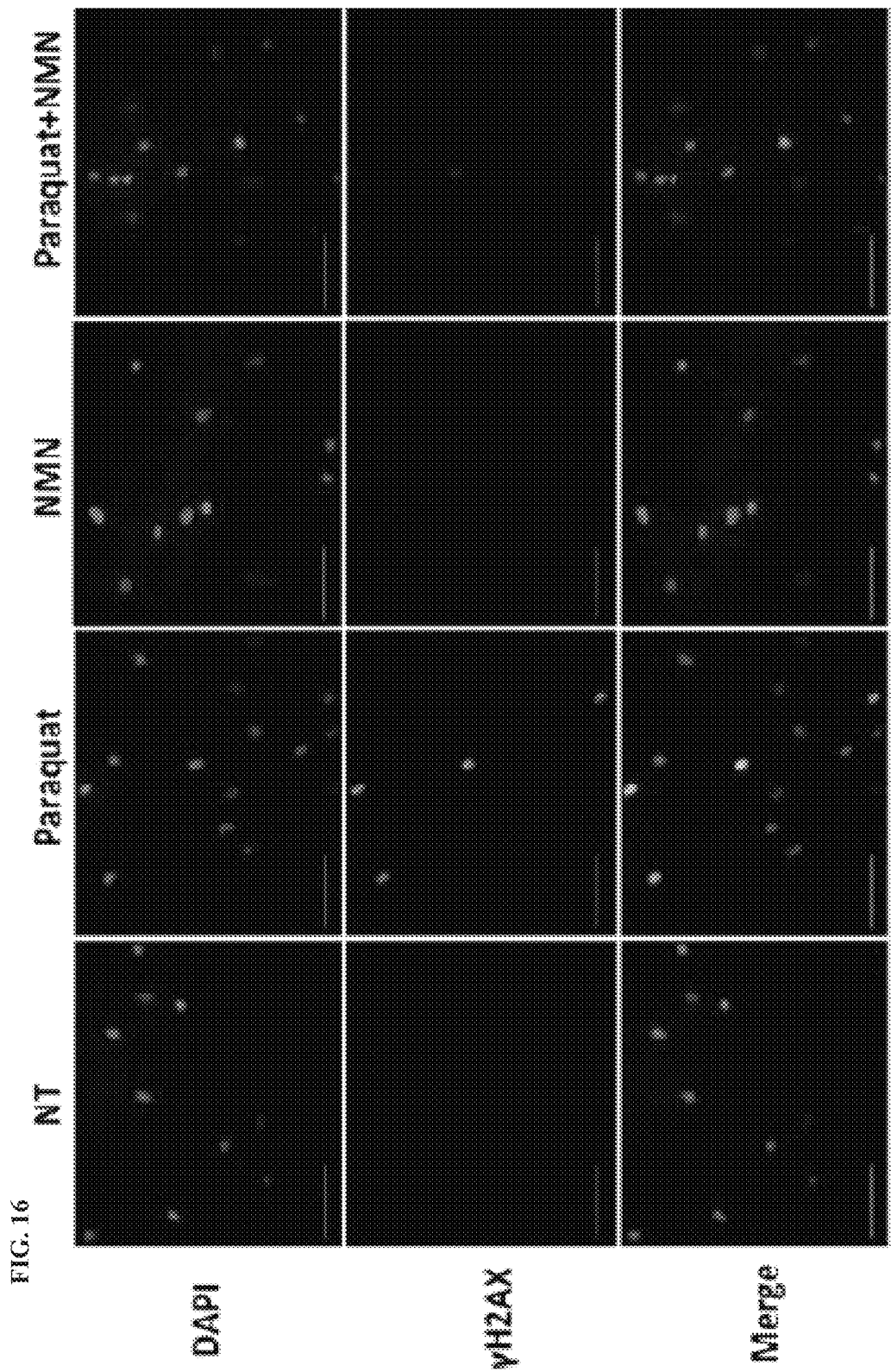
FIG. 16 shows that NMN reduces DNA damage in primary human fibroblasts. Representative images of the immunofluorescence experiment in FIG. 3G. Scale=50 μM. Two fibroblasts cell lines from 94- and 57-year old males (Coriell Institute, #AG08433 and #AG13145) were treated with NMN (500 μM), paraquat (300 μM), or both for 24 hrs at passages 12-13 and immunostained for γH2AX.
Figure 17A:
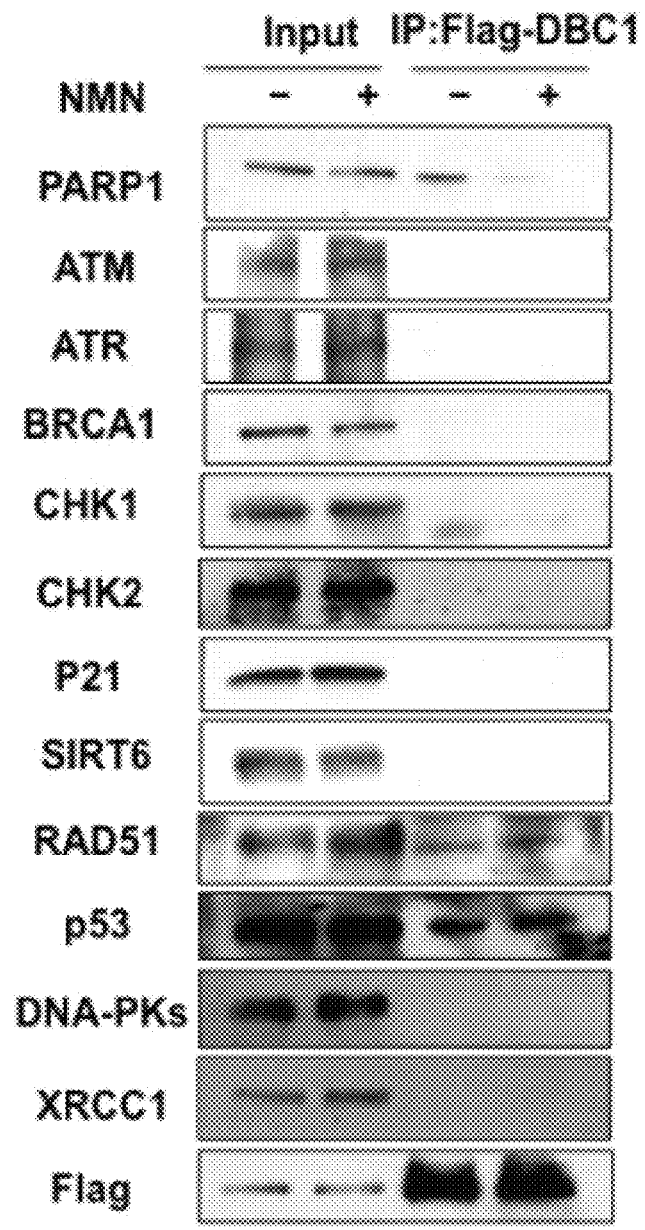
FIG. 17A-FIG. 17B shows that DNA damage and NAD$^+$ levels do not change the interaction of major DNA repair proteins with the PARP1-DBC1 complex. 293T cells overexpressing Flag-DBC1 were treated with (FIG. 17A) NMN (0.5 mM) or (FIG. 17B) paraquat (0.5 mM) for 24 hrs. Flag-DBC1 was immunoprecipitated and DNA repair proteins were assessed by western blotting as indicated. Both p53 and RAD51 were pulled down with Flag-DBC1 and the interaction did not change with treatment of NMN or paraquat.
Figure 17B:
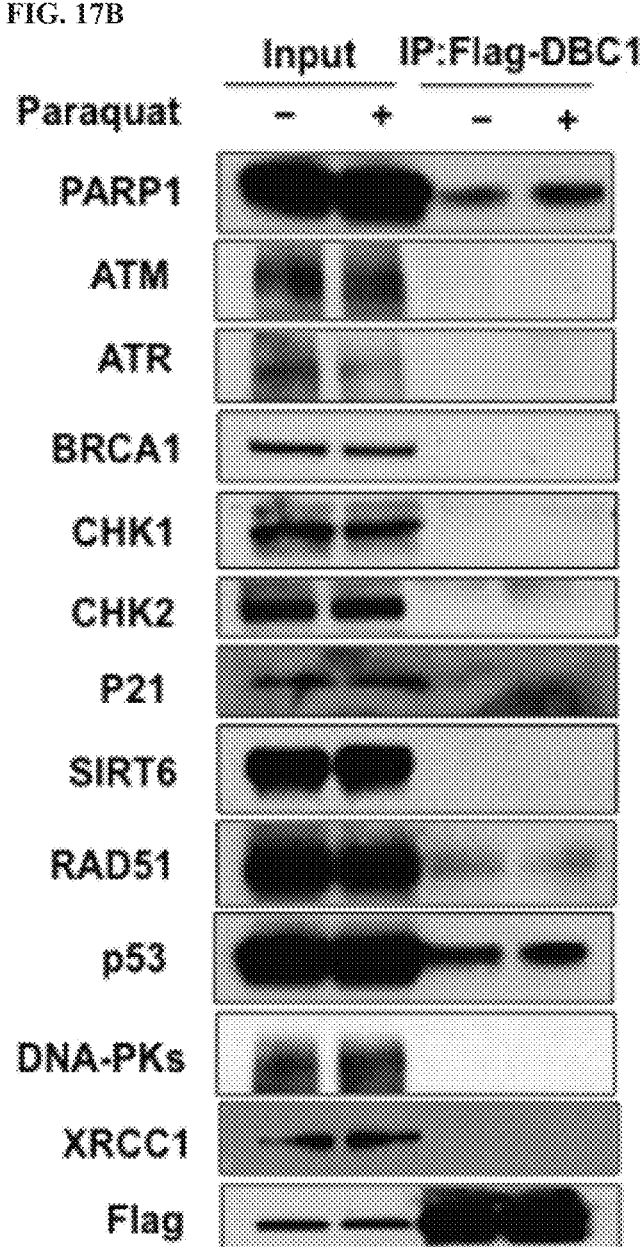

PARP1 activity was inhibited by DBC1 in vitro (FIG. 3A). In cells, knocking down DBC1 increased both PAR concentrations before and after exposure to paraquat, $H_2O_2$, or etoposide (FIG. 3B and FIG. 14A and FIG. 14D) and the abundance of mRNAs positively regulated by PARP1 (T. Zhang et al. *J. Biol. Chem.* 287, 12405-12416 (2012); R. Krishnakumar et al. *Mol. Cell* 39, 736-749 (2010)). Reintroduction of wild-type DBC1 reduced PARP1 activity and partially restored gene expression whereas DBC1$_{Q391A}$ had no effect (FIG. 3C and FIG. 14E and FIG. 14F). Reducing DBC1 lowered the abundance of the phosphorylated form of histone H2AX (γ-H2AX) (FIG. 3D), reduced DNA fragmentation (FIG. 3E and FIG. 15A), increased cell survival post-paraquat (FIG. 15B), and increased both non-homologous end-joining (NHEJ) and homologous recombination (HR) pathways in a PARP1-dependent manner (FIG. 3F) and FIG. 15C). Similarly, NMN treatment reduced the number of γH2AX foci in paraquat-treated primary human fibroblasts (FIG. 3G) and FIG. 16). No other major DNA repair proteins appeared to change their interactions with PARP1-DBC1 complex in the presence of NMN or DNA damage (FIG. 17A) to (FIG. 17B), though other interactions cannot be ruled out. These results are consistent with a model in which binding of NAD+ to the DBC1 NHD regulates the two major pathways of DNA repair.

Figure 4A:
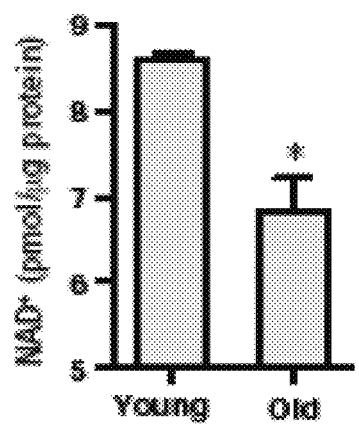
FIG. 4A-FIG. 4J depicts increases in the PARP1-DBC1 complex and DNA damage with age are reversed by NMN, a precursor to NAD$^+$.
Figure 4B:
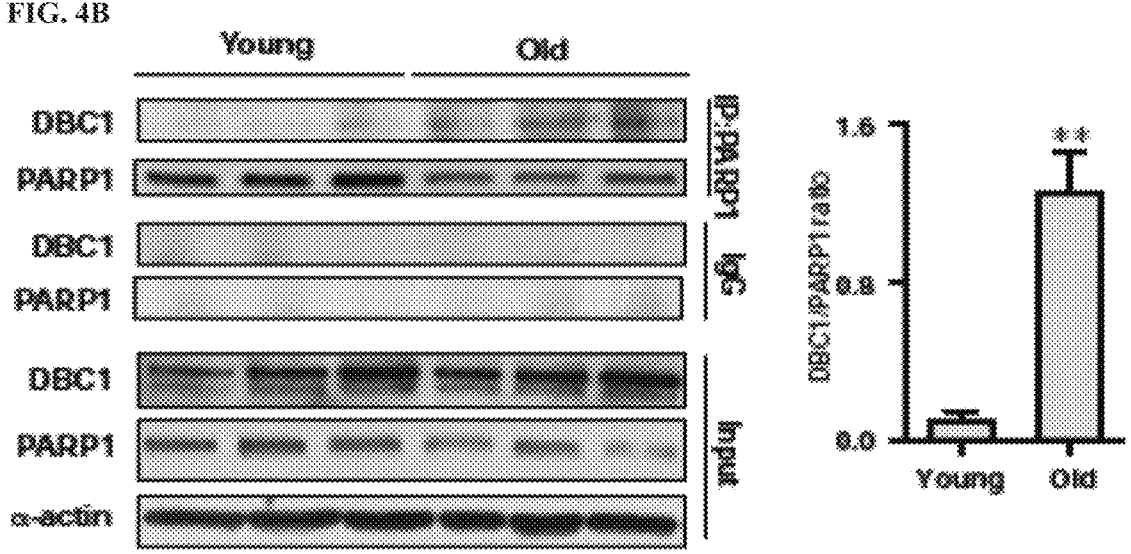
Figure 4C:
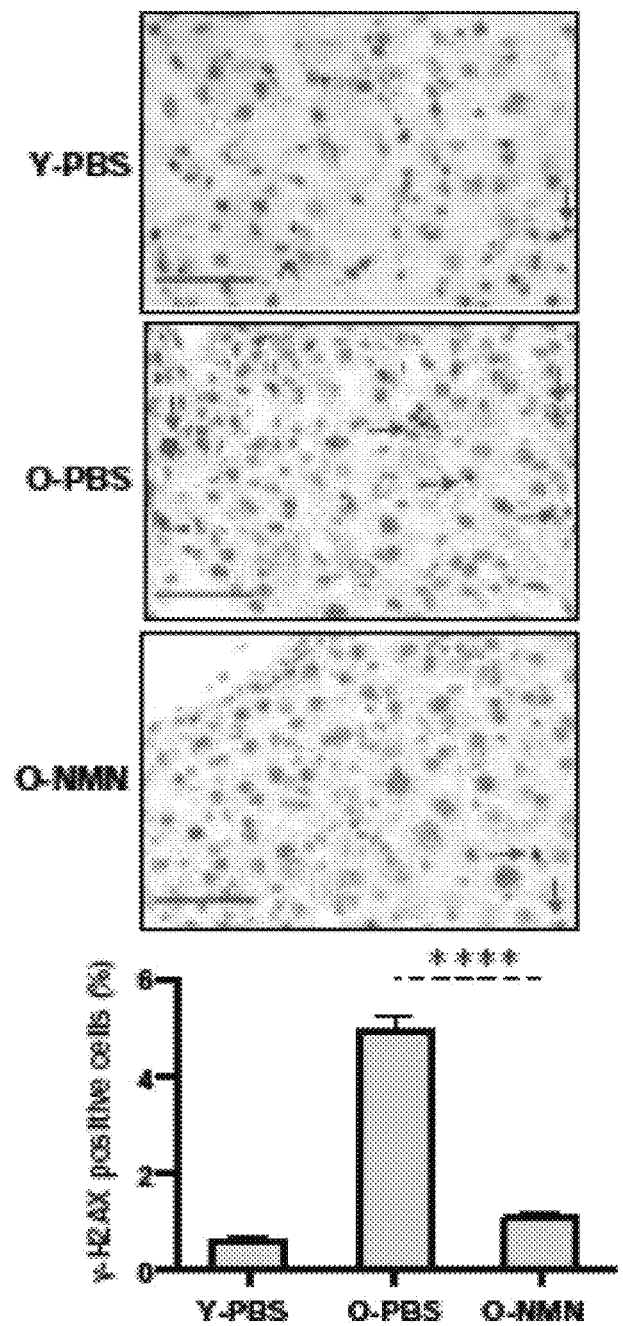
Figure 4D:
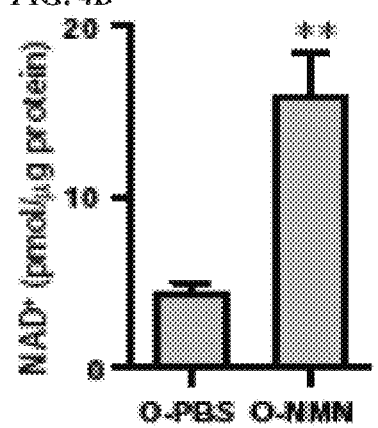
Figure 4E:
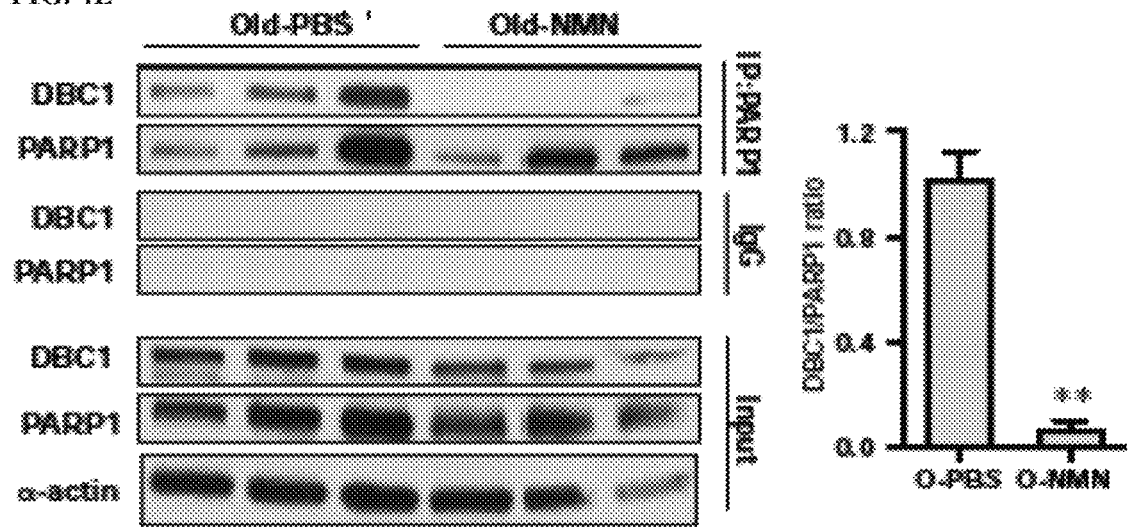
Figure 4F:
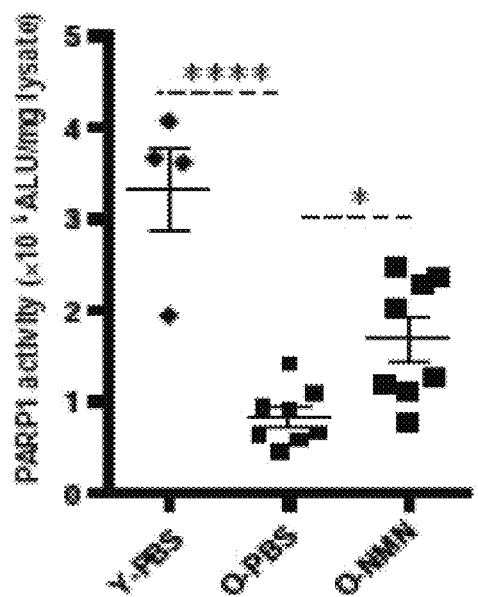
Figure 18:
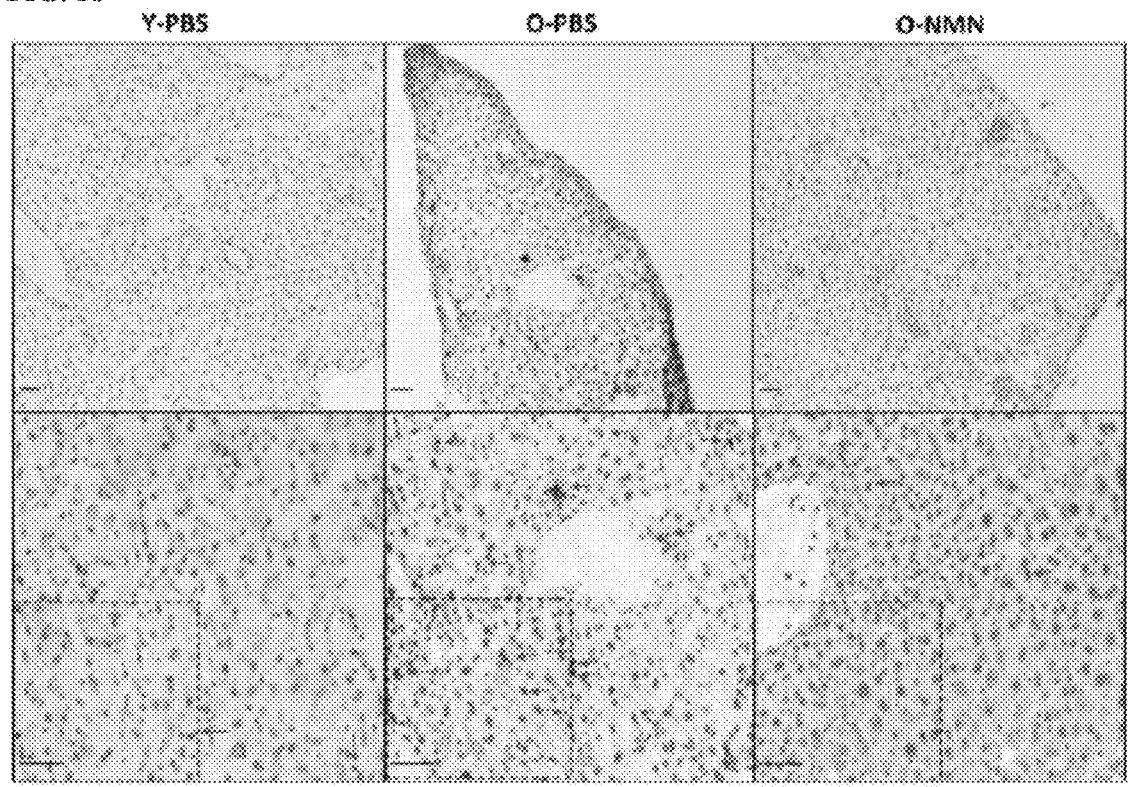
FIG. 18 depicts that NMN treatment decreases DNA damage in livers of old mice. Spontaneous DNA damage in the livers of young and old mice treated with PBS or NMN as in FIG. 4E. γH2AX-positive cells were detected by DAB-immunohistochemistry. Foci indicated by red arrows. Young (Y)=6 months, n=4; old (O)=30 months; n=3. Images in upper and lower rows are 100× and 200× magnification, respectively. Scale=50 μM. Insets are representative images shown in FIG. 4E.
Figure 19A:
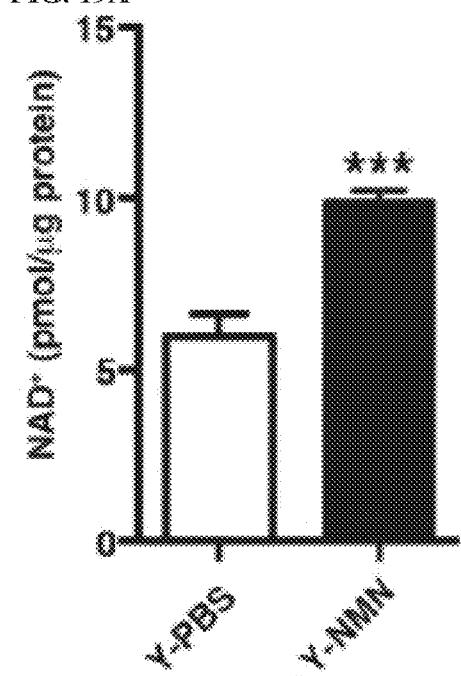
FIG. 19A-FIG. 19B shows that PARP1-DBC1 interaction in 6-month old mice is reduced by NMN. Increased relative NAD$^+$ levels (n=4/group) (FIG. 19A) and reduced PARP1-DBC1 interaction (FIG. 19B) in the livers of 6-month old mice treated by daily intraperitoneal injections of PBS (Y-PBS) or NMN (Y-NMN) for one week (500 mg/kg/day), mean±SEM, unpaired two-tailed t-test *p<0.05, ***p<0.001.
Figure 19B:
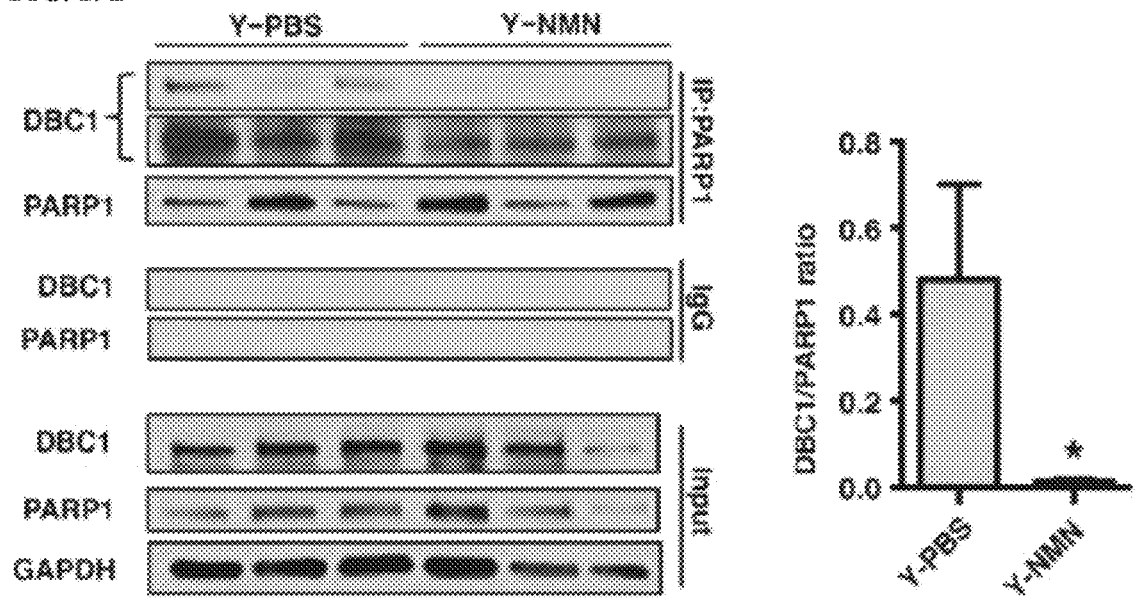

DNA repair declines with age (V. Gorbunova et al. *Nucleic Acids Res.* 35, 7466-7474 (2007)) in concert with lower PARP1 activity (K. Grube et al. *Proc. Natl. Acad. Sci. U.S.A.* 89, 11759-11763 (1992)). The data presented herein indicated a cause may be increased binding of DBC1 to PARP1 as NAD+ levels decline during aging. To test this, the effect of NMN treatment was examined on young and old mice. Hepatic NAD+ concentrations were lower in old mice (FIG. 4A), coincident with a higher amount of the DBC1-PARP1 complex (FIG. 4B) and an increase in γH2AX staining (FIG. 4C), and FIG. 18). A week of NMN treatment (i.p. 500 mg/kg/d) increased hepatic NAD+ concentrations, disrupted the PARP1-DBC1 complex in young (FIG. 19A) to (FIG. 19B) and old mice (FIG. 4D) to (FIG. 4E), and reduced the abundance of γH2AX in old mice (FIG. 4C and FIG. 18).

Figure 4G:
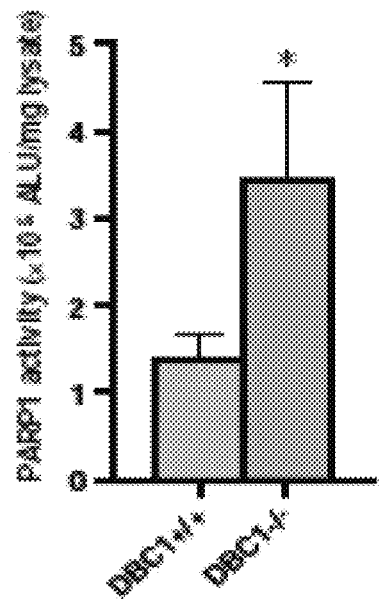
Figure 4H:
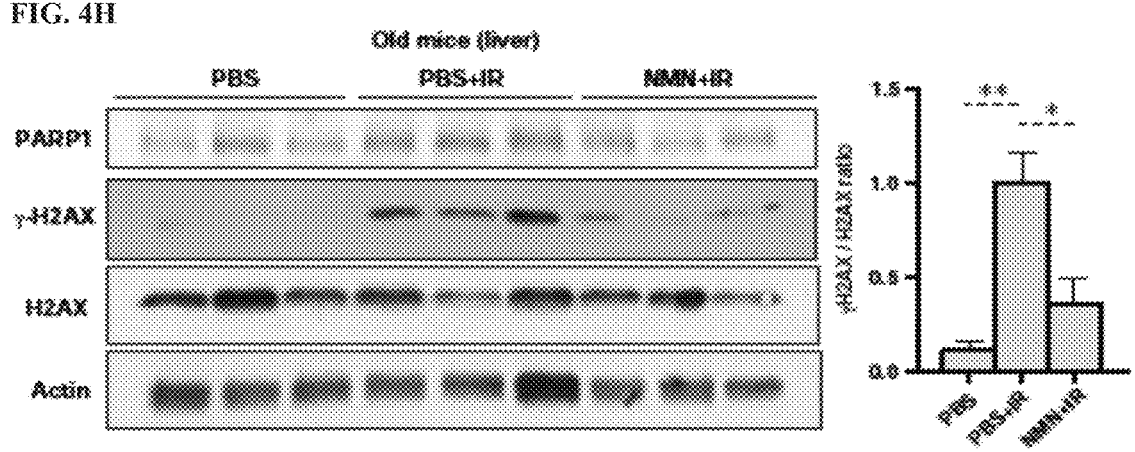
Figure 4I:
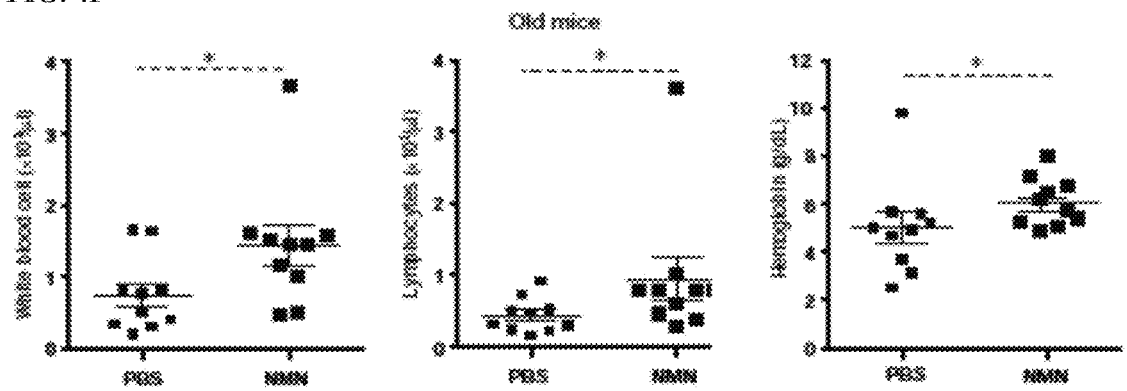
Figure 4J:
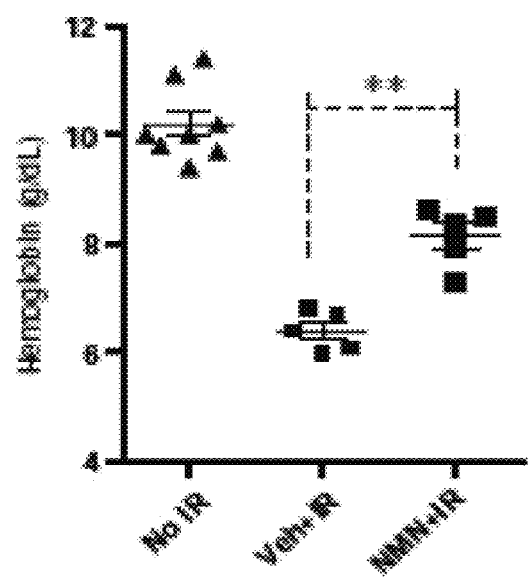
Figure 20A:
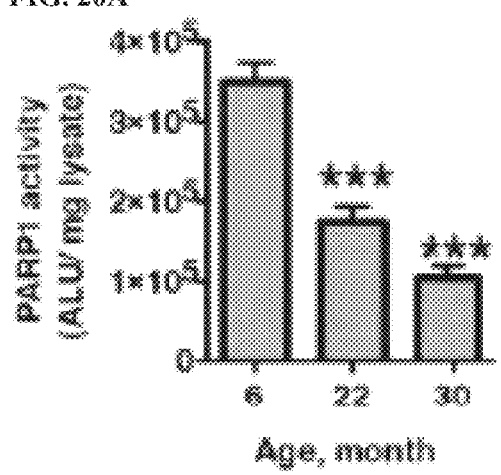
Figure 20B:
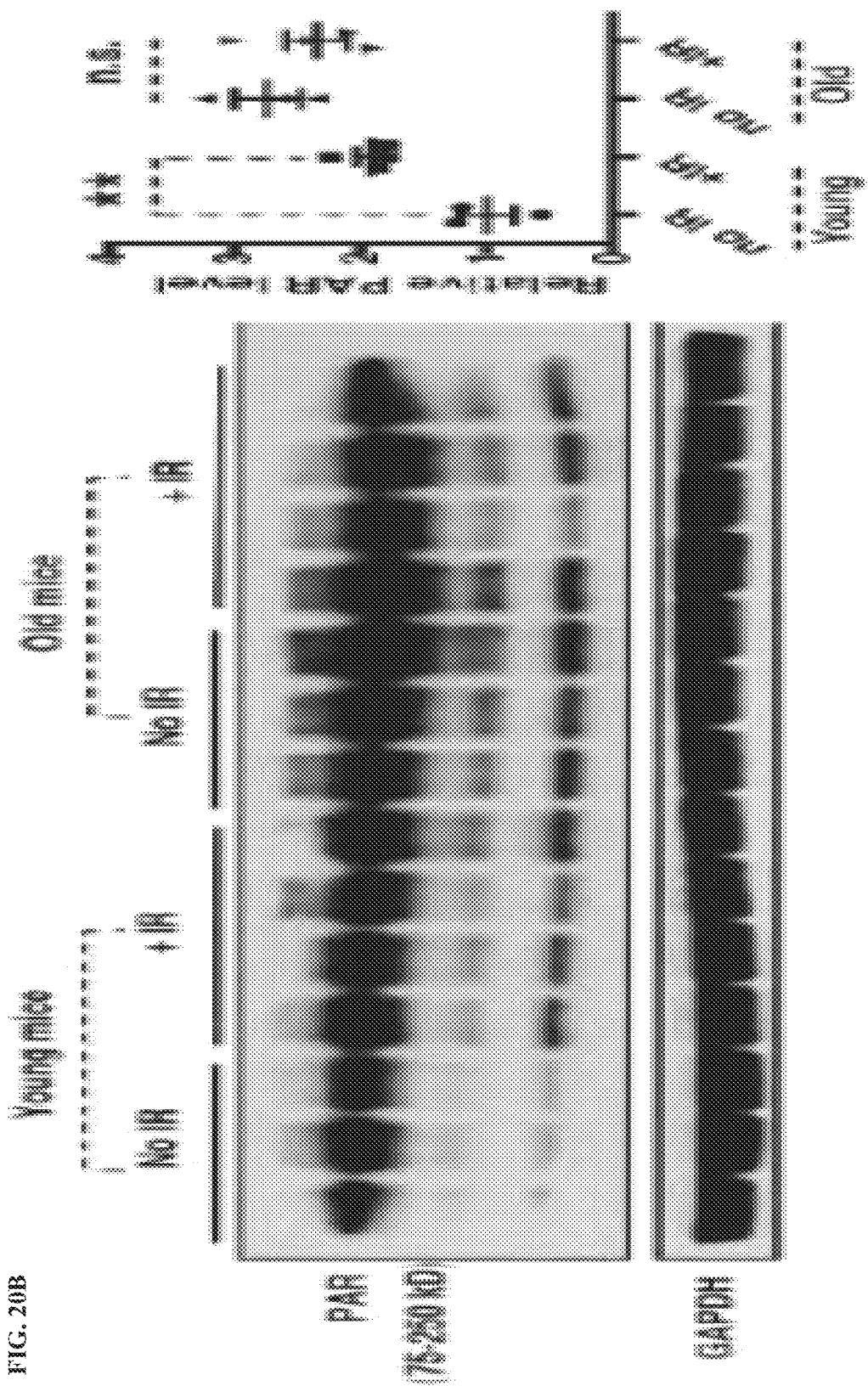
Figure 20C:
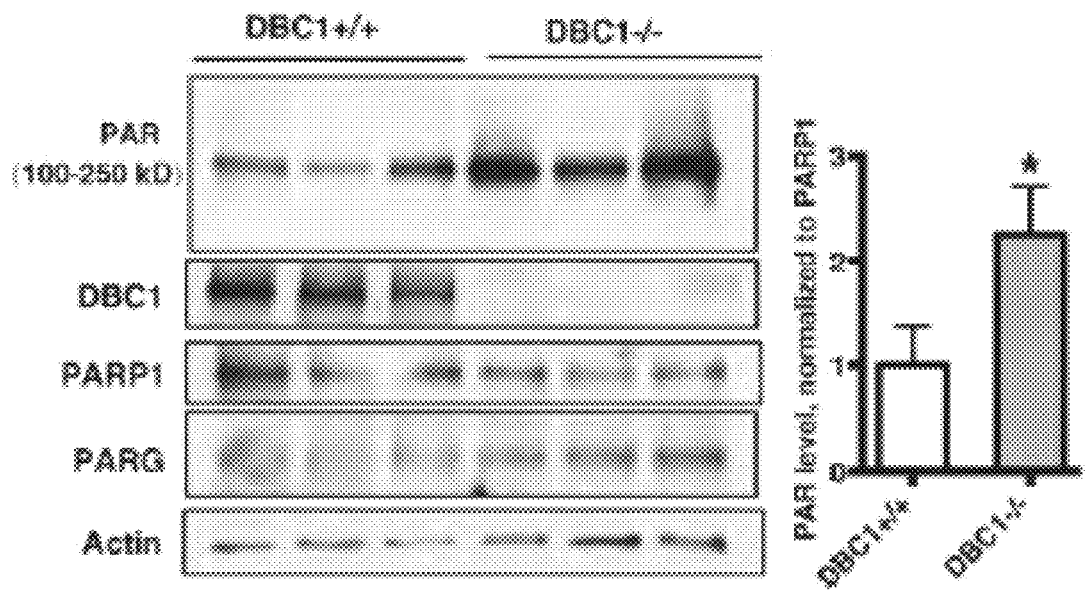
Figure 20D:
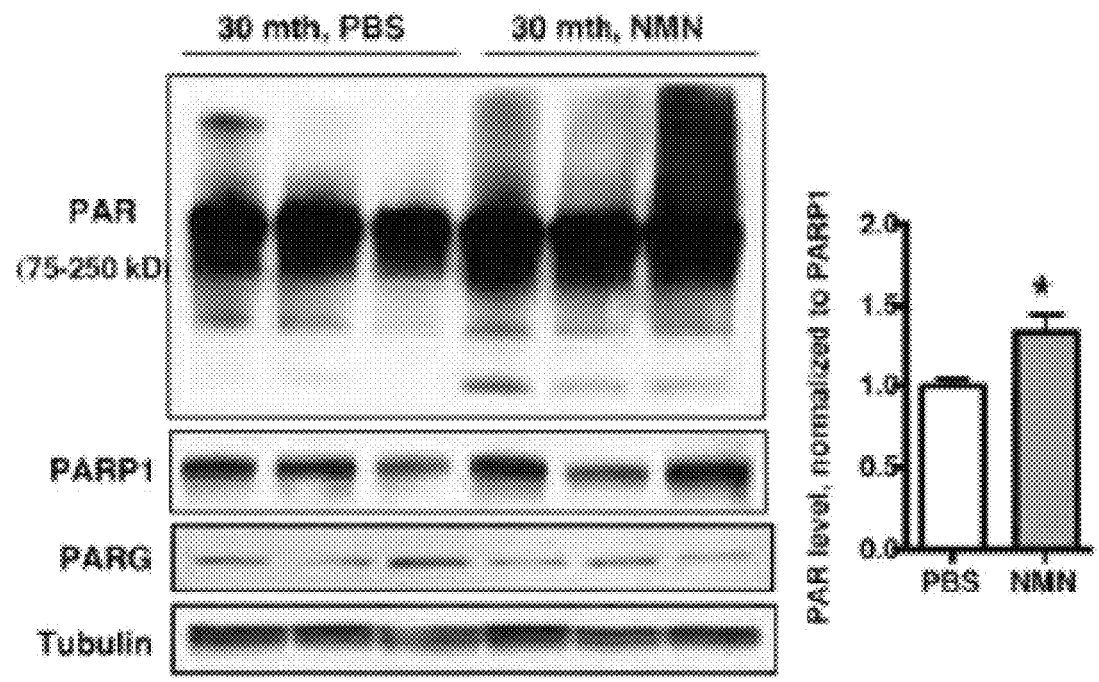
Figure 20F:
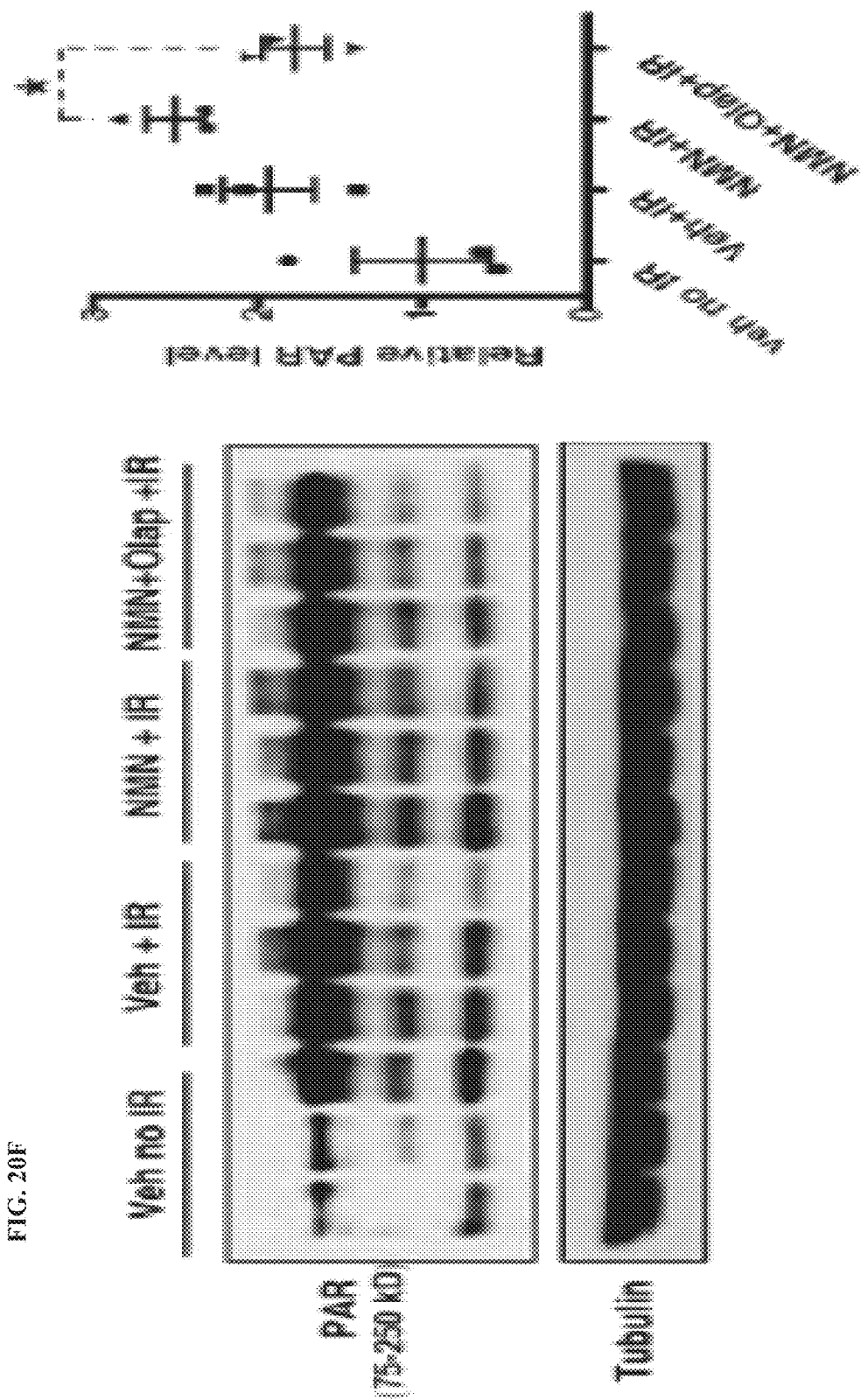
Figure 21A:
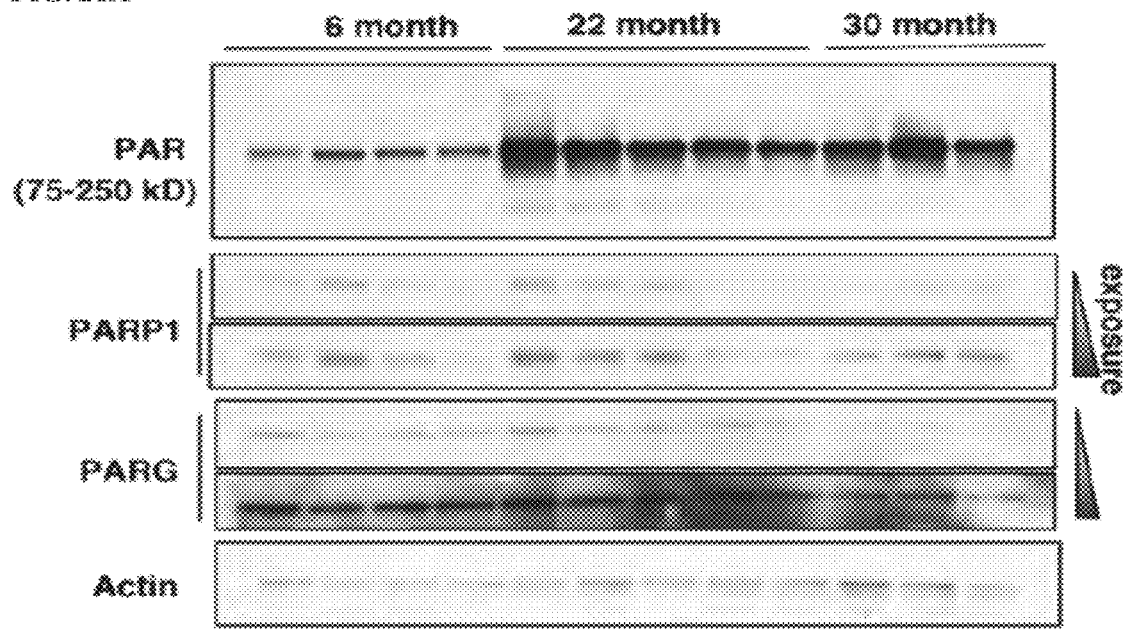
FIG. 21A-FIG. 21C shows that NMN treatment reduces oxidative DNA damage.
Figure 21B:
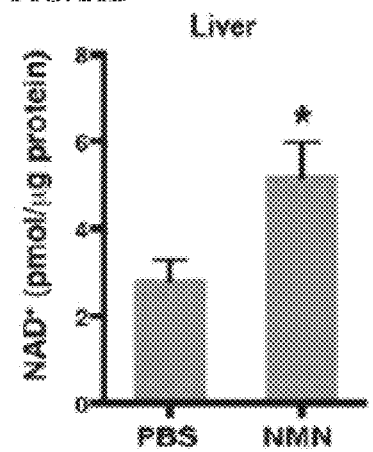
Figure 21C:
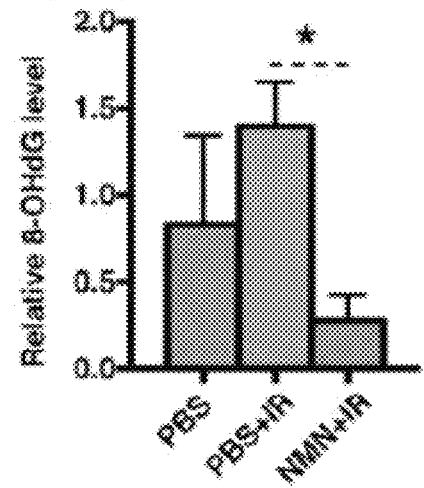
Figure 22A:
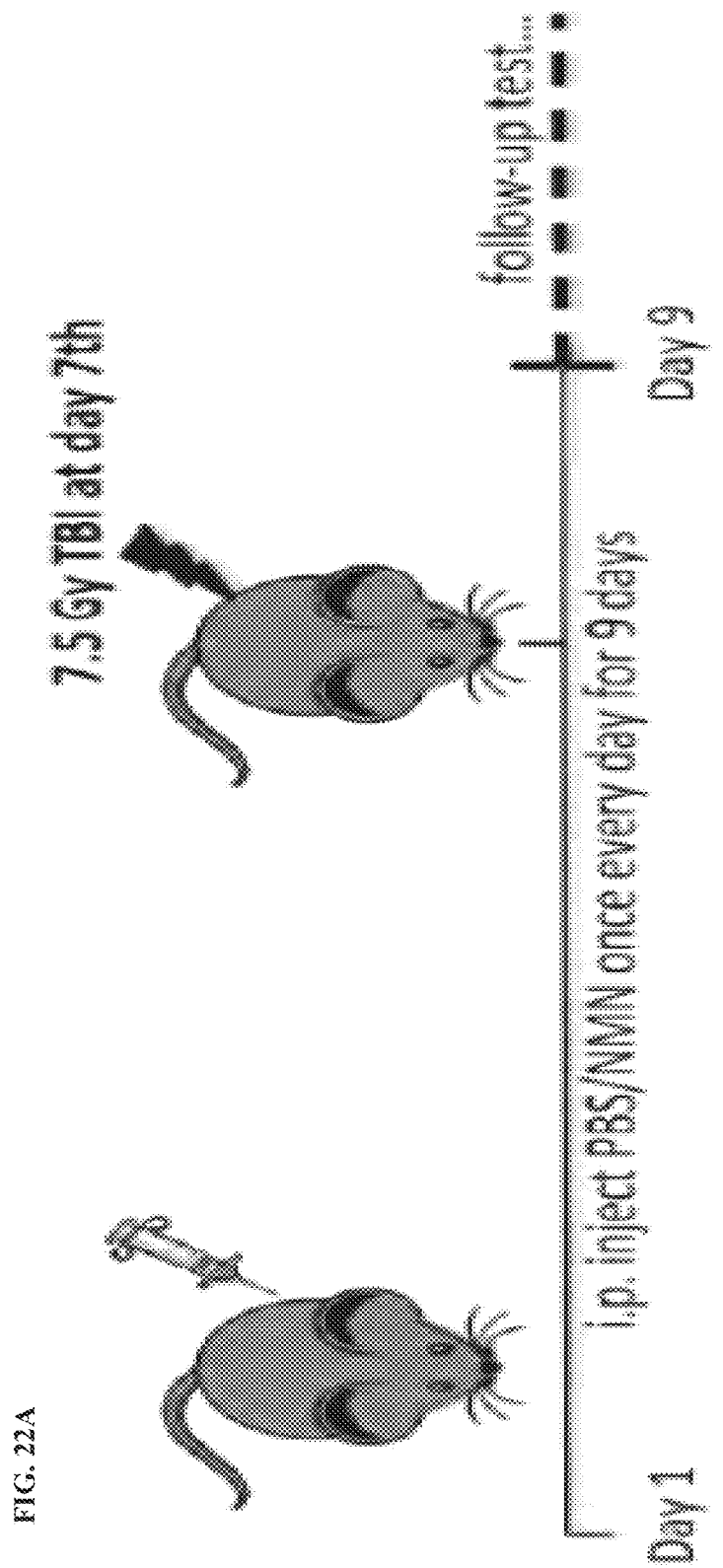
FIG. 22A-FIG. 22C shows depicts additional blood metrics and body weight measurements in mice treated with NMN.
Figure 22B:
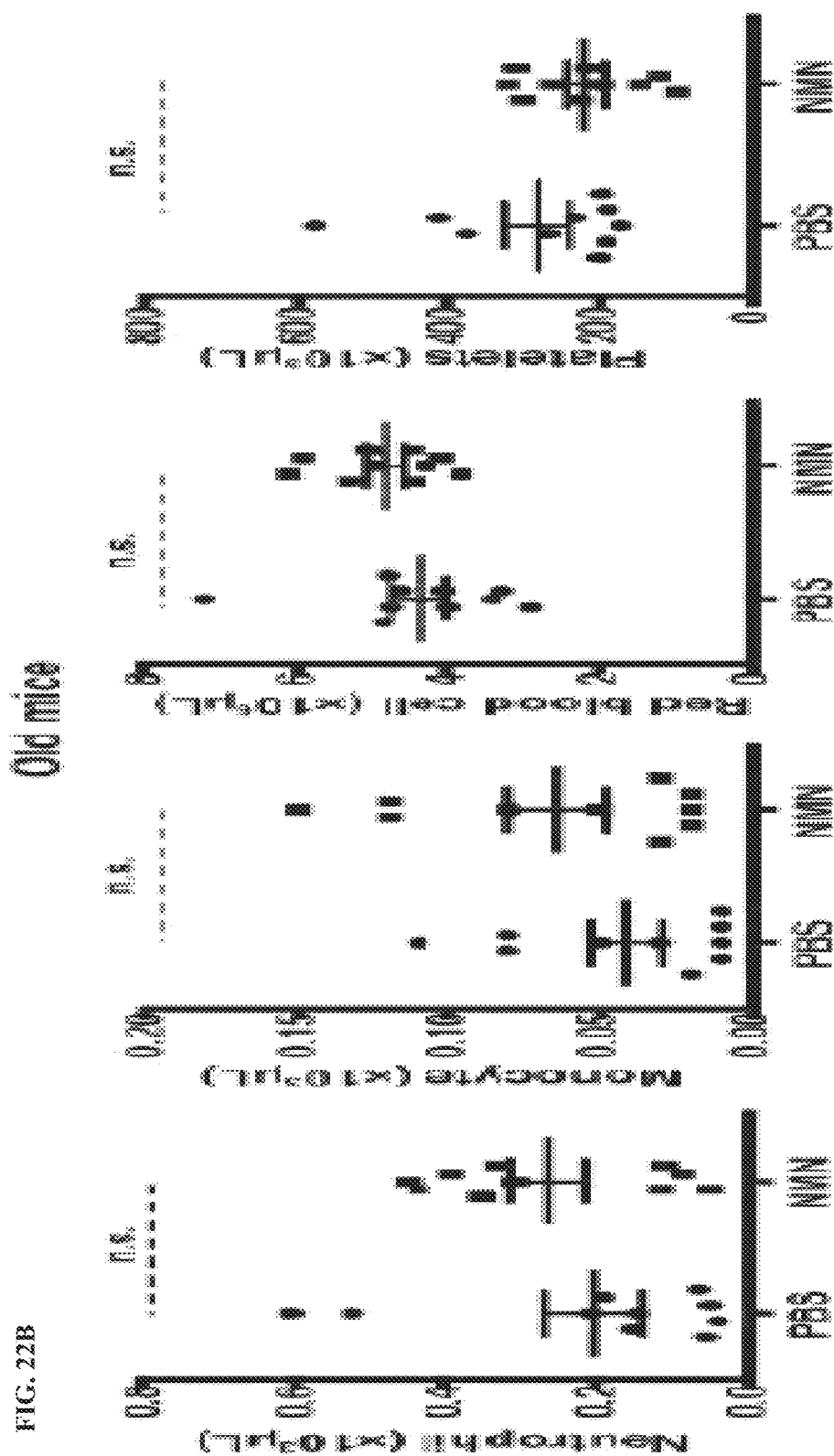
Figure 22C:
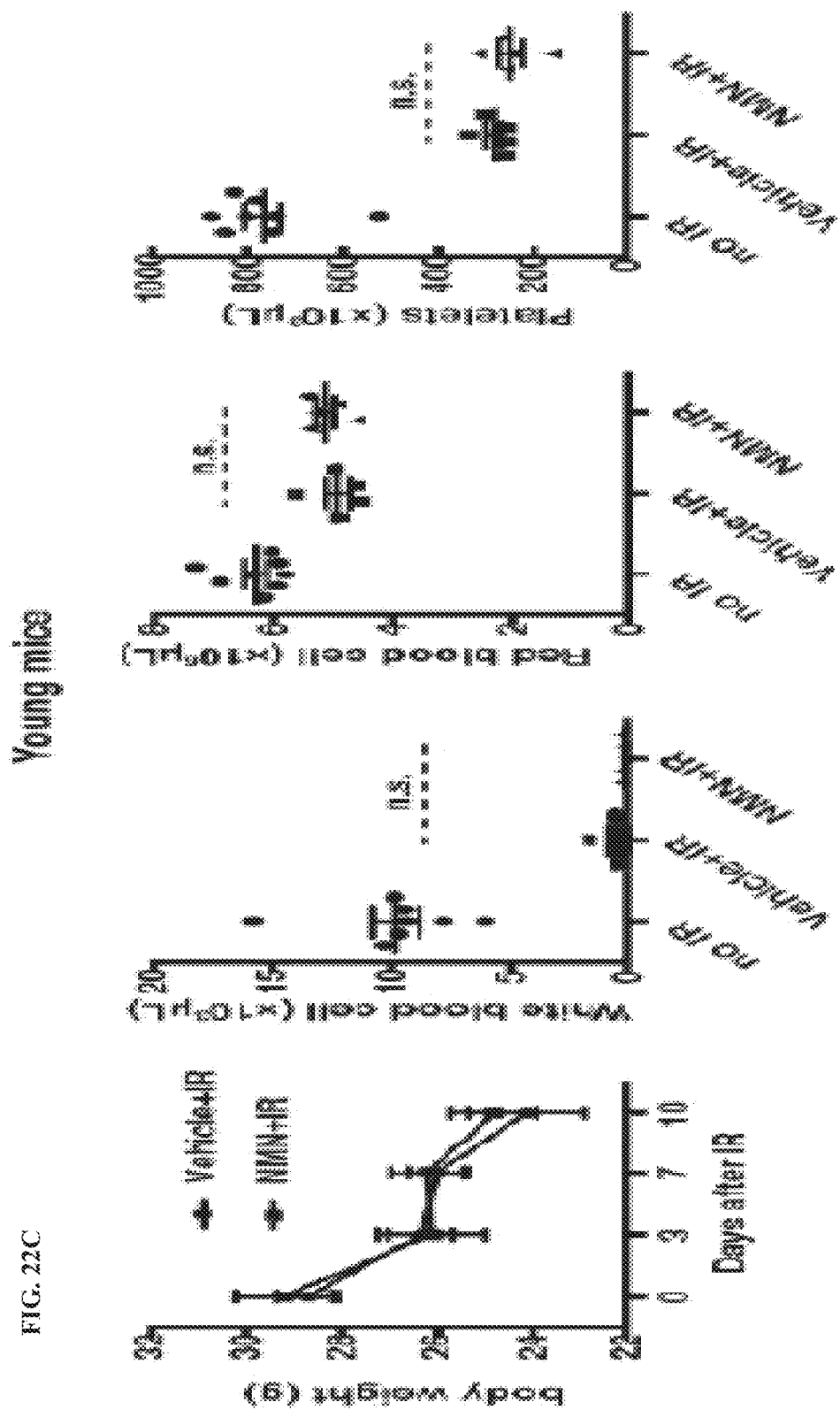

In old mice, the low levels of PARP1 activity (FIG. 4F), and FIG. 20A) and poor response to DNA damage (FIG. 20B). Knockout of DBC1 increased PARP1 activity (FIG. 4G and FIG. 20C). The reduced PARP1 activity in the old mice was restored by NMN (FIG. 4F), and FIG. 20D) but not if PARP1 activity was inhibited (FIG. 20E and FIG. 20F). Total amounts of PARylation increased with age in the liver (L. Mouchiroud et al, *Cell* 154, 430-441 (2013)), possibly due to reduced PARG abundance (FIG. 21A). These data indicate that the decline in NAD+ during aging promotes binding of DBC1 to PARP1, which inhibits PARP1's ability to mediate DNA repair. Similar studies were conducted on old mice exposed to gamma irradiation. NMN treatment (FIG. 4E) reduced DNA damage (FIG. 4H and FIG. 21B to C) and protected against alterations in white blood cell counts, lymphocytes, and hemoglobin, even when given after irradiation (FIG. 4I and FIG. 4J, FIG. 22A to FIG. 22C).

Figure 23:
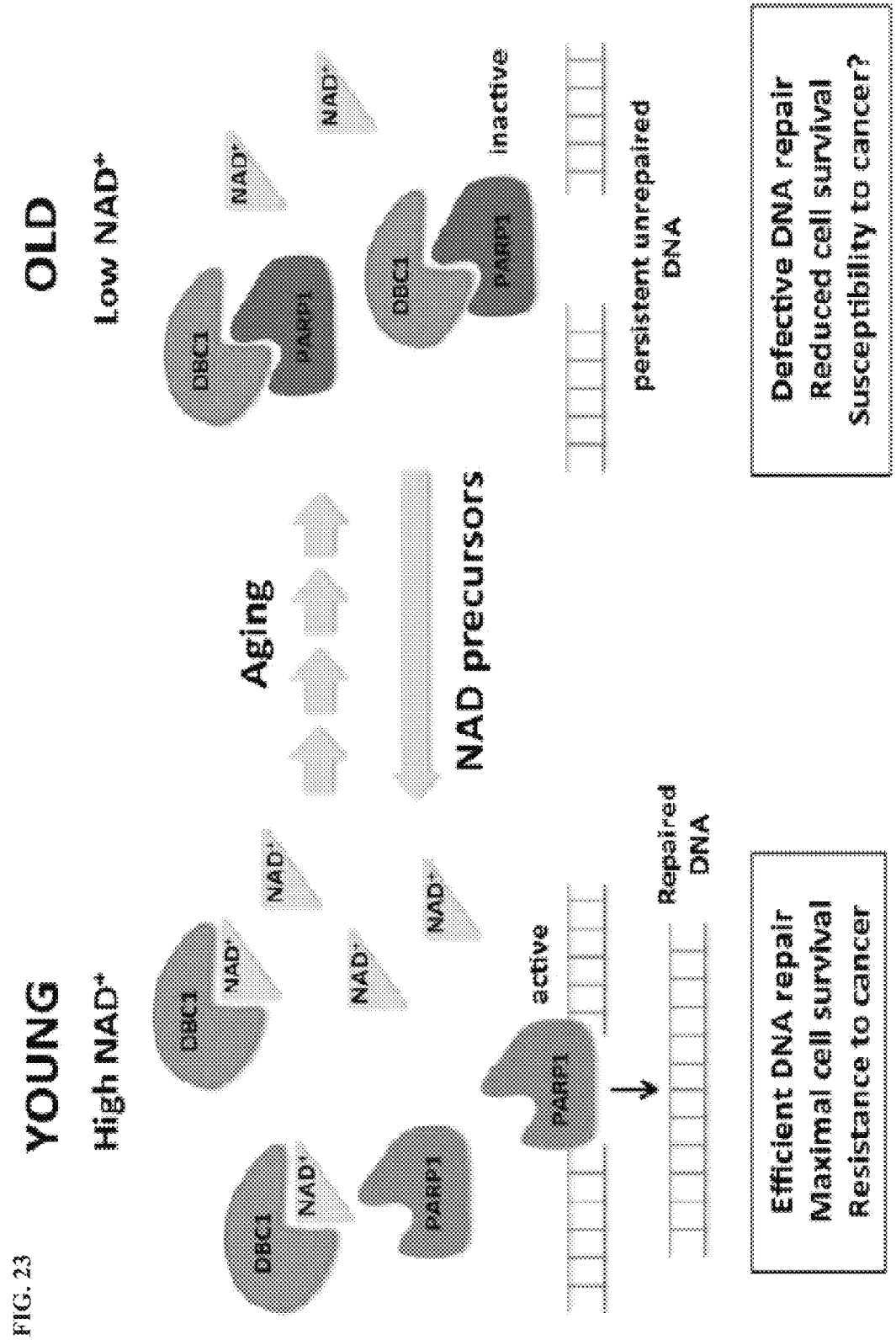
FIG. 23 depicts a model for the regulation of PARP1-DBC1 complex during aging. Relatively high $NAD^+$ levels in youth maintain optimal PARP1 activity by limiting the PARP1-DBC1 complex, allowing free PARP1 to facilitate DNA repair and promote cell survival. The regulation of PARP1 by $NAD^+$ may serve as a negative-feedback loop to limit the consumption of $NAD^+$ by PARP1 when levels fall below the threshold of cell viability, thereby allowing other modes of DNA repair to take over until $NAD^+$ levels are restored. As $NAD^+$ levels decline with aging, PARP1 is increasingly bound to DBC1, resulting in reduced PARP1 and DNA repair activity. Raising $NAD^+$ levels liberates PARP1 from DBC1 and restores PARP1 and DNA repair activities.

These data show that NAD+ has a third function in cells: to directly regulate protein-protein interactions. It was speculated that this mechanism evolved to allow a cell to adapt to fluctuations in NAD+ abundance without degrading it and, in the case of DBC1, to serve as a negative-feedback loop to prevent PARP1 from depleting NAD+ down to lethal levels during DNA damage (H. Yang et al. *Cell* 130, 1095-1107 (2007)) (FIG. 23). The data also provide an explanation for why DBC1 mutations are associated with cancers (M. Hamaguchi et al. *Proc. Natl. Acad. Sci. U.S.A.* 99, 13647-13652 (2002)) and indicate that assessing DBC1 status in tumors will help inform ongoing clinical trials of PARP1 inhibitors for treating cancer (M. W. Audeh et al. *Lancet* 376, 245-251 (2010)). Although it is unclear why NAD+ declines with age, this work provides a plausible explanation for why DNA repair capacity declines as mammals age (D. B. Lombard et al. *Cell* 120, 497-512 (2005)), pointing to NAD+ replenishment as a means of reducing the side effects of chemotherapy, protecting against radiation exposure, and slowing the natural decline in DNA repair capacity during aging.

INCORPORATION BY REFERENCE

All publications, including but not limited to patents and patent applications, cited in this specification, to the extent that they provide exemplary procedural or other details supplementary to those set forth herein, are specifically incorporated herein by reference as if each individual publication were specifically and individually indicated to be incorporated by reference herein as though fully set forth.

EQUIVALENTS

Those skilled in the art will recognize, or be able to ascertain using no more than routine experimentation, many equivalents of the specific embodiments of the invention described herein. Such equivalents are intended to be encompassed by the following claims.

The invention claimed is:

1. A method for recovering from, treating, or preventing cancer in a subject in need thereof comprising
   i) assessing protein-protein complexes in a sample from said subject, wherein said protein-protein complexes are between a first protein containing a Nudix Homology Domain (NHD) and a second protein which is different from the first protein and interacts with the NHD;
   ii) administering to the subject an effective amount of
      a) nicotinamide mononucleotide (NMN), or an analog or derivative thereof; or
      b) an agent that is not NMN or an analog or derivative thereof, wherein the agent increases the level of nicotinamide mononucleotide, or an analog or derivative thereof; or
      c) both a) and b); or
      d) an NHD-modulating agent that is not a) or b), wherein said NHD-modulating agent modulates protein-protein complex forming activity of the Nudix Homology Domain of said first protein in step (i).

2. A method for recovering from, treating, or preventing aging or cell death in a subject in need thereof comprising
   i) assessing protein-protein complexes in a sample from said subject, wherein said protein-protein complexes are between a first protein containing a Nudix Homology Domain (NHD) and a second protein which is different from the first protein and interacts with the NHD;
   ii) administering to the subject an effective amount of
      a) nicotinamide mononucleotide (NMN), or an analog or derivative thereof; or
      b) an agent that is not NMN or an analog or derivative thereof, wherein the agent increases the level of nicotinamide mononucleotide, or an analog or derivative thereof; or
      c) both a) and b); or
      d) an NHD-modulating agent that is not a) or b), wherein said NHD-modulating agent modulates protein-protein complex forming activity of the Nudix Homology Domain of said first protein in step (i).

3. A method for recovering from, treating, or preventing radiation damage or radiation exposure, recovering from, treating, or preventing chemotherapy-induced damage or cellular senescence, modulating DNA repair, or modulating cell proliferation or cell survival in a subject in need thereof comprising
   i) assessing protein-protein complexes in a sample from said subject, wherein said protein-protein complexes are between a first protein containing a Nudix Homology Domain (NHD) and a second protein which is different from the first protein and interacts with the NHD;
   ii) administering to the subject an effective amount of
      a) nicotinamide mononucleotide (NMN), or an analog or derivative thereof; or
      b) an agent that is not NMN or an analog or derivative thereof, wherein the agent increases the level of nicotinamide mononucleotide, or an analog or derivative thereof; or
      c) both a) and b); or
      d) an NHD-modulating agent that is not a) or b), wherein said NHD-modulating agent modulates protein-protein complex forming activity of the Nudix Homology Domain of said first protein in step (i).

4. The method of claim 1, comprising administering a) nicotinamide mononucleotide (NMN), or an analog, or derivative thereof, wherein the nicotinamide mononucleotide, or an analog or derivative thereof is nicotinamide adenine dinucleotide (NAD+).

5. The method of claim 1, wherein said first protein of step (i) is selected from Deleted Breast Cancer 1 (DBC1), CCAR2, or CCAR1.

6. The method of claim 1, wherein said second protein of step (i) is selected from PARP1, HNRPLL, SON, SUGP2, WDR33, TH005, PUS1, SYMPK, THOC2, SART3, LSM4, PLRG1, SF3B2, SNRNP40, XAB2, ZCCHC8, PRPF8, PRPF4, POLR3B, POLR1A, POLR2D, POLR2A, SUPT5H, SUPT6H, GT3C4, EXOSC7, EIF4H, GTF3C5, MRPS23, SEP15, FKBP5, MRPS34, TPX2, TRIM27, USP7, UBE2K, STAG2, PDSSB, SMC4, PDSSA, NCAPG2, AKAP8, NUMA1, CEP170, POGZ, CTR9, TBLXR1, G3BP1, TLE1, SPIN1, COPS3, TLE3, GPS1, CSNK2A1, PRKDC, MSH3, MSH6, POLA1, TMPO, FEN1, PRIM2, CHTF18, AKAP8L, MLF2, SPATA5, ZMPSTE24, SMARCA2, SIRT1, SMARCA4, ARID1A, SMARCC2, KDM3B, ADNP, HDAC3, VPRBP, LCP1, KPNA3, TOMM40, IPO9, TIMM13, COBRA1, SAFB2, PELP1, TCEB2, CDK9, TROVE2, SRRT, PSPC1, FAM98B, GK, TXNRD1, NADKD1, NDUFS2, PCK2, CISD1, CYC1, UQCRFS1, MATR3, SRRT, NOP56, RIP1L1, UPF1, ZC3H14, HNRNPA0, LRPPRC, FARSA, EIF3D, MRPS22, NOP2, DNAJA2, NSUN2, DNAJA3, DDX5, DHX9, SFPQ, PPP1CB, PPP2R1A, BUB3, ILF3, ADAR, ISG15, NUP155, ZFR, ZC3H11A, KPNA4, KPNA1, KPNA3, KPNA6, ZNF326, SKIV2L2, SON, SUGP2, WTAP, PTBP1, PTBP3, CPSF1, RBM4, HNRNPUL2, SF1, SF3B1, PNN, ZCCHC8, SF3B3, CDCSL, PRPF8, SNRNP200, SAFB, PRMT5, WDR77, SUPT16H, SIRT1, SAP18, IKZF1, HCFC1, HDAC3, ZNF281, ZNF318, GIGYF2, RBM14, SAFB2, SPIN1, GTF21, MCM3, AKAP8L, TRIM28, PSMA2, PSME3, PSMB3, p53, USP11, SLC25A6, PFAS, CAD, SLC25A3, PFKL, ACLY, PPHLN1, RBM12B, or FLNA, or biologically active fragments thereof.

7. The method of claim 1, wherein said second protein of step (i) is PARP1.

8. The method of claim 1, wherein said second protein of step (i) is selected from the group consisting of HNRPLL, SON, SUGP2, WDR33, THOC5, PUS1, SYMPK, THOC2, SART3, LSM4, PLRG1, SF3B2, SNRNP40, XAB2, ZCCHC8, PRPF8, PRPF4, POLR3B, POLR1A, POLR2D, POLR2A, SUPT5H, SUPT6H, GT3C4, EXOSC7, EIF4H, GTF3C5, MRPS23, SEP15, FKBP5, MRPS34, TPX2, TRIM27, USP7, UBE2K, STAG2, PDSSB, SMC4, PDSSA, NCAPG2, AKAP8, NUMA1, CEP170, POGZ, CTR9, TBLXR1, G3BP1, TLE1, SPIN1, COPS3, TLE3, GPS1, CSNK2A1, PRKDC, MSH3, MSH6, POLA1, TMPO, FEN1, PRIM2, CHTF18, AKAP8L, MLF2, SPATA5, ZMPSTE24, SMARCA2, SIRT1, SMARCA4, ARID1A, SMARCC2, KDM3B, ADNP, HDAC3, VPRBP, LCP1, KPNA3, TOMM40, IPO9, TIMM13, COBRA1, SAFB2, PELP1, TCEB2, CDK9, TROVE2, SRRT, PSPC1, FAM98B, GK, TXNRD1, NADKD1, NDUFS2, PCK2, CISD1, CYC1, and UQCRFS1, or combination thereof.

9. The method of claim 1, wherein said second protein of step (i) is selected from the group consisting of MATR3, SRRT, NOP56, RIP1L1, UPF1, ZC3H14, HNRNPA0, LRPPRC, FARSA, EIF3D, MRPS22, NOP2, DNAJA2, NSUN2, DNAJA3, DDX5, DHX9, SFPQ, PPP1CB, PPP2R1A, BUB3, ILF3, ADAR, ISG15, NUP155, ZFR, ZC3H11A, KPNA4, KPNA1, KPNA3, KPNA6, ZNF326, SKIV2L2, SON, SUGP2, WTAP, PTBP1, PTBP3, CPSF1, RBM4, HNRNPUL2, SF1, SF3B1, PNN, ZCCHC8, SF3B3, CDCSL, PRPF8, SNRNP200, SAFB, PRMT5, WDR77, SUPT16H, SIRT1, SAP18, IKZF1, HCFC1, HDAC3, ZNF281, ZNF318, GIGYF2, RBM14, SAFB2, SPIN1, GTF21, MCM3, AKAP8L, TRIM28, PSMA2, PSME3, PSMB3, p53, USP11, SLC25A6, PFAS, CAD, SLC25A3, PFKL, ACLY, PPHLN1, RBM12B, and FLNA, or combination thereof.

10. The method of claim 1, comprising administering a) nicotinamide mononucleotide (NMN), or an analog, or derivative thereof, wherein the nicotinamide mononucleotide (NMN), or an analog, or derivative thereof is an NAD+precursor.

11. The method of claim 1, comprising administering a) nicotinamide mononucleotide (NMN), or an analog, or derivative thereof, wherein the nicotinamide mononucleotide (NMN), or an analog, or derivative thereof is nicotinamide mononucleotide (NMN).

12. The method of claim 1, comprising administering b) an agent that is not NMN or an analog or derivative thereof, wherein the agent increases the level of nicotinamide mononucleotide, or an analog or derivative thereof, and further wherein the agent increases the level or activity of an enzyme selected from mononucleotide adenylyl transferase (NMNAT) or nicotinamide phosphoribosyl transferase (NAMPT or NAMPRT).

13. The method of claim 1, comprising administering d) an NHD-modulating agent that is not a) or b), wherein the NHD-modulating agent is an inhibitor that blocks or prevents protein-protein interaction or binding of said first protein with said second protein of step (i).

14. The method of claim 10, wherein the NAD+precursor is administered at a dose of between 0.5-5 grams per day.

15. The method of claim 1, comprising administering d) an NHD-modulating agent that is not a) or b) wherein the NHD-modulating agent is an antibody to NHD.

* * * * *